(12) United States Patent
Rublee et al.

(10) Patent No.: US 8,048,623 B1
(45) Date of Patent: Nov. 1, 2011

(54) COMPOSITIONS, PRODUCTS, METHODS AND SYSTEMS TO MONITOR WATER AND OTHER ECOSYSTEMS

(75) Inventors: Parke A. Rublee, Greensboro, NC (US); Vincent C. Henrich, III, Greensboro, NC (US); Michael McClain Marshall, Greensboro, NC (US)

(73) Assignee: The University of North Carolina at Greensboro, Greensboro, NC (US)

( * ) Notice: Subject to any disclaimer, the term of this patent is extended or adjusted under 35 U.S.C. 154(b) by 354 days.

(21) Appl. No.: 12/221,541

(22) Filed: Aug. 4, 2008

Related U.S. Application Data

(60) Continuation-in-part of application No. 11/716,450, filed on Mar. 9, 2007, and a continuation-in-part of application No. 11/716,895, filed on Mar. 12, 2007, each which is a division of application No. 11/071,849, filed on Mar. 3, 2005, now Pat. No. 7,214,492, which is a continuation-in-part of application No. 10/131,618, filed on Apr. 24, 2002, now abandoned, and a continuation-in-part of application No. 11/527,129, filed on Sep. 26, 2006, which is a continuation of application No. 10/131,618, filed on Apr. 24, 2002, now abandoned.

(51) Int. Cl.
*C12Q 1/68* (2006.01)
*C12P 19/34* (2006.01)
*C12M 1/34* (2006.01)
*C07H 21/02* (2006.01)
*C07H 21/04* (2006.01)

(52) U.S. Cl. ....... 435/6; 435/91.2; 435/287.2; 536/23.1; 536/24.1

(58) Field of Classification Search ............ 435/6, 91.2, 435/287.2; 536/23.1, 24.1
See application file for complete search history.

(56) References Cited

U.S. PATENT DOCUMENTS
4,713,330 A  12/1987  McLoughlin
(Continued)

FOREIGN PATENT DOCUMENTS
CN  1396270  2/2003
(Continued)

OTHER PUBLICATIONS
King et al, Appl. Envir. Microbiol., vol. 66, pp. 2430-2437, Jun. 2000.*
(Continued)

*Primary Examiner* — Robert T. Crow
(74) *Attorney, Agent, or Firm* — Kilpatrick Townsend & Stockton LLP

(57) ABSTRACT

Disclosed are compositions, products, methods and systems for monitoring ecosystems, such as bodies of water, for a parameter of the ecosystems, such as the presence or absence of mercury. In one embodiment, the product may include a plurality of oligonucleotides immobilized at known locations on a substrate as an array, such that each location on the array is an oligonucleotide having a sequence derived from a single, predetermined operational taxonomic unit (OTU) and wherein at least one sequence on the array is associated with the presence or absence of mercury. The sequences immobilized on the array may be from known, or unknown organisms. Also disclosed are methods for identifying and isolating bioindicators diagnostic of ecosystem parameters, such as whether mercury is present. The compositions, products, methods and systems of the invention may be used for rapid, and continual monitoring of ecosystems for parameters of interest, such as the presence or absence of mercury.

10 Claims, 27 Drawing Sheets
(5 of 27 Drawing Sheet(s) Filed in Color)

U.S. PATENT DOCUMENTS

| | | | |
|---|---|---|---|
| 5,324,632 | A | 6/1994 | Weisburg et al. |
| 5,324,633 | A | 6/1994 | Fodor et al. |
| 5,429,807 | A | 7/1995 | Matson et al. |
| 5,466,577 | A | 11/1995 | Weisburg |
| 5,482,834 | A | 1/1996 | Gillespie |
| 5,496,706 | A | 3/1996 | Kuusela et al. |
| 5,498,392 | A | 3/1996 | Wilding et al. |
| 5,552,272 | A | 9/1996 | Bogart |
| 5,582,978 | A | 12/1996 | Shah |
| 5,589,585 | A | 12/1996 | Mabilat et al. |
| 5,667,667 | A | 9/1997 | Southern |
| 5,723,320 | A | 3/1998 | Dehlinger |
| 5,736,188 | A | 4/1998 | Alcock et al. |
| 5,770,367 | A | 6/1998 | Southern et al. |
| 5,837,832 | A | 11/1998 | Chee et al. |
| 5,851,767 | A | 12/1998 | Stanbridge et al. |
| 5,858,195 | A | 1/1999 | Ramsey |
| 5,869,288 | A | 2/1999 | Chapman et al. |
| 5,945,282 | A | 8/1999 | Rossau et al. |
| 6,033,546 | A | 3/2000 | Ramsey |
| 6,040,138 | A | 3/2000 | Lockhard et al. |
| 6,048,692 | A | 4/2000 | Maracas et al. |
| 6,051,388 | A | 4/2000 | Bodenhamer |
| 6,054,270 | A | 4/2000 | Southern |
| 6,074,725 | A | 6/2000 | Kennedy |
| 6,080,585 | A | 6/2000 | Southern et al. |
| 6,129,896 | A | 10/2000 | Noonan et al. |
| 6,141,097 | A | 10/2000 | Herman |
| 6,150,095 | A | 11/2000 | Southern et al. |
| 6,168,948 | B1 | 1/2001 | Anderson et al. |
| 6,187,530 | B1 | 2/2001 | Scholin et al. |
| 6,203,981 | B1 | 3/2001 | Ackley et al. |
| 6,225,067 | B1 | 5/2001 | Rogers |
| 6,228,575 | B1 | 5/2001 | Gingeras et al. |
| 6,307,039 | B1 | 10/2001 | Southern et al. |
| 6,309,822 | B1 | 10/2001 | Fodor et al. |
| 6,326,228 | B1 | 12/2001 | Hughes et al. |
| 6,338,820 | B1 | 1/2002 | Hubbard et al. |
| 6,355,420 | B1 | 3/2002 | Chan |
| 6,363,772 | B1 | 4/2002 | Berry |
| 6,537,801 | B1 | 3/2003 | Ida et al. |
| 6,808,879 | B1 | 10/2004 | Guillot et al. |
| 7,214,492 | B1 | 5/2007 | Rublee et al. |
| 2002/0065609 | A1 | 5/2002 | Ashby |

FOREIGN PATENT DOCUMENTS

| | | |
|---|---|---|
| EP | 0 950 720 A1 | 10/1999 |
| FR | 2844522 | 3/2004 |
| WO | WO 96/41893 | 12/1996 |
| WO | WO 97/22720 | 6/1997 |
| WO | WO 01/61038 A2 | 8/2001 |
| WO | WO 02/101094 A1 | 12/2002 |
| WO | WO 2004/104211 A2 | 12/2004 |

OTHER PUBLICATIONS

Office action mailed Jan. 29, 2010 for U.S. Appl. No. 11/716,450.
Office action mailed Feb. 4, 2010 for U.S. Appl. No. 11/716,895.
Dieffenbach, C. et al., "General Concepts for PCR Primer Design," Genome Res., 1993, 3:S30-S37.
Weisburg, W. et al., "16S Ribosomal DNA Amplification for Phylogenetic Study," J. Bacteriology, 1991, 173:697-703.
Office action mailed Jul. 6, 2009 for U.S. Appl. No. 11/527,129.
Office action mailed Jun. 23, 2010 corresponding to U.S. Appl. No. 11/527,129.
Office action mailed Aug. 11, 2010 corresponding to U.S. Appl. No. 11/716,895.
Adleman, L. M., "Molecular Computation of Solutions to Combinatorial Problems," Science, vol. 266, pp. 1021-1024, 1994.
Altschul, S.F. et al., "Basic Local Alignment Search Tool," J. Mol. Biol.,1990, vol. 215, 403-410.
Amos, R. N., "Aquatic Microorganisms: Exploring Prokaryotic Diversity and its Relationship to Water Quality using 16S rDNA Sequences." Masters Thesis, Directed by Drs. Parke A. Rublee and Vincent C. Henrich, University of North Carolina at Greensboro, 2002, 55pgs.
Anantharaman, V. et al., "TRAM, A Predicted RNA-Binding Domain, Common to tRNA Uracil Methylation and Adenine Thiolation Enzymes," FEMS Microbiology Letters, vol. 197, pp. 215-221, 2001.
Anantharaman, V. et al., "Regulatory Potential, Phyletic Distribution and Evolution of Ancient, Intracellular Small-Molecule-binding Domains," J. Mol. Biol., vol. 307, pp. 1271-1292, 2001.
Antolin, M. et al., "Genes, Description of," Encyclopedia of Biodiversity, vol. 3, 2001.
Aravind, L. et al., "The α/β Fold Uracil DNA Glycosylases: A Common Origin with Diverse Fates," Genome Biology, vol. 1, No. 4, pp. research0007.1-0007.8, 2000.
Ausubel, F. M. et al., Short Protocols in Molecular Biology, 4$^{th}$ Ed., Chapter 2, John Wiley and Sons, N.Y. 1999.
Balser, L. M., "Determining Small-Scale Spatial, Temporal and Replicate Variability of Microbial Eukaryotic rDNA Libraries in an Aquatic Community." Masters Thesis, Directed by Dr. Parke A. Rublee, University of North Carolina at Greensboro, Dec. 2003.
Bassett Jr., D. E. et al., "Gene Expression Informatics—It's All in your Mine," Nature Genetics Supplement, vol. 21, pp. 51-55, 1999.
Bavykin, S. et al., "Portable System for Microbial Sample Preparation and Oligonucleotide Microarray Analysis," Applied and Environmental Microbiology, vol. 67, p. 922-928, 2001.
Bej, A. K. et al., "Multiplex PCR Amplification and Immobilized Capture Probes for Detection of Bacterial Pathogens and Indicators in Water," Molecular and Cellular Probes, vol. 4, pp. 353-365, 1990.
Bernhard, A.E. et al., "Identification of Nonpoint Sources of Fecal Pollution in Coastal Waters by Using Host-Specific 16S Ribosomal DNA Genetic Markers from Fecal Anaerobes," Applied and Environmental Microbiology, 2000, vol. 66, No. 4, 1587-1594.
Bernhard, A.E. et al., "A PCR Assay to Discriminate Human and Ruminant Feces on the Basis of Host Differences in Bacteroides-Prevotella Genes Encoding 16S rRNA," Applied and Environmental Microbiology, 2000, vol. 66, No. 10, 4571-4574.
Blattner, F.R. et al., "The Complete Genome Sequence of Escherichia coli K-12," Science, 1997, vol. 277, 1453-1468.
Bowman, L., "Waterborne Illnesses on the Rise," Scripps-Howard News Service, Nov. 21, 2002, web site at http://www.shns.com/shns/g_index2.cfm?action=detail&pk=WATERDISEASE-11-21-02, as available via the Internet.
Bowtell, D. D. L., "Options Available—From Start to Finish—for Obtaining Expression Data by Microarray," Nature Genetics Supplement, vol. 21, pp. 25-32, 1999.
Brosius, J. et al., "Gene Organization and Primary Structure of a Ribosomal RNA Operon from Escherichia Coli," J. Mol. Biol., 1981, vol. 148, 107-127.
Bruce, K.D. et al., "Amplification of DNA from Native Populations of Soil Bacteria by Using the Polymerase Chain Reaction," Appl. Environ. Microbiol., 1992, vol. 58, No. 10, 3413-3416.
Call, D. et al., "Detecting and Genotyping Escherichia coli O157:H7 using Multiplexed PCR and Nucleic Acid Microarrays," International Journal of Food Microbiology, vol. 67, p. 71-80, 2001.
Campbell, Biology, Benjamin/Cummings, 1993, 3$^{rd}$ ed., p. 1053.
Castiglioni, B. et al., "Development of a Universal Microarray Based on the Ligation Detection Reaction and 16SrRNA Gene Polymorphism to Target Diversity of Cyanobacteria," Applied and Environmental Microbiology, vol. 70, No. 12, pp. 7161-7172, 2004.
Cheung, V. G. et al., "Making and Reading Microarrays," Nature Genetics Supplement, vol. 21, pp. 15-19, 1999.
Chizhikov, V. et al., "Microarray Analysis of Microbial Virulence Factors," Applied and Environmental Microbiology, vol. 67, No. 7, p. 3258-3263, 2001.
Delorenzo, M. E. et al., "Effects of the Agricultural Pesticides Atrazine, Deethylatrazine, Endosulfan, and Chlorpyrifos on an Estuarine Microbial Food Web," Environmental Toxicology and Chemistry, 1999, vol. 18, No. 12, 2824-2835.
Diez, B. et al., "Application of Denaturing Gradient Gel Electrophoresis (DGGE) to Study the Diversity of Marine Picoeukaryotic Assemblages and Comparison of DGGE with other Molecular Techniques," Appl. Environ. Microbiol., 2001, vol. 67, No. 7, 2942-2951.

Edwards, U. et al., "Isolation and Direct Complete Nucleotide Determination of Entire Genes. Characterization of a Gene Coding for 16S Ribosomal RNA," Nucleic Acids Res., 1989, vol. 17, No. 19, 7843-7853.

Farrelly, V. et al., "Effect of Genome Size and rrn Gene Copy Number on PCR Amplification of 16S rRNA Genes from a Mixture of Bacterial Species," Appl. Environ. Microbiol., 1995, vol. 61, No. 7, 2798-2801.

Finlay, B. J., "Global Dispersal of Free-Living Microbial Eukaryote Species," Science, 2002, vol. 296, 1061-1063.

Friend, S. et al., "The Magic of Microarrays," Scientific American, vol. 286, No. 2, p. 44-53, 2002.

Geourjon, C. et al., "Identification of Related Proteins with Weak Sequence Identity using Secondary Structure Information," Protein Science, vol. 10, pp. 788-797, 2001.

Gibson, G. et al., "Microarrays in Ecology and Evolution: a Preview," Molecular Ecology, vol. 11, p. 17-24, 2002.

Giovannoni, S. J. et al., "Genetic Diversity in Sargasso Sea Bacterioplankton," Nature, 1990, vol. 345, 60-63.

Grech, A. et al., "Complete Structural Characterisation of the Mammalian and Drosophila TRAF Genes: Implications for TRAF Evolution and the Role of RING Finger Splice Variants," Molecular Immunology, vol. 37, pp. 721-734, 2000.

Greer, C. et al., "Genomics Technologies for Environmental Science," Environmental Science and Technology, vol. 35, Issue 17, p. 360A-366A, 2001.

Grimes, D.J., "Ecology of Estuarine Bacteria Capable of Causing Human Disease: A Review," Estuaries, 1991, vol. 14, No. 4, 345-360.

Guschin, D. Y. et al., "Oligonucleotide Microchips as Genosensors for Determinative and Environmental Studies in Microbiology," Applied and Environmental Microbiology, vol. 63, No. 6, pp. 2397-2402, 1997.

Hacia, J. G. et al., "Strategies for Mutational Analysis of the Large Multiexon ATM Gene Using High-Density Oligonucleotide Arrays," Genome Research, vol. 8, pp. 1245-1258, 1998.

Haldeman, D. L. et al., "Changes in Bacteria Recoverable from Subsurface Volcanic Rock Samples during Storage at 4 C," Appl. Environ. Microbiol., 1994, vol. 60, No. 8, 2697-2703.

Henrich, V. C. et al., "Microarrays as Environmental Surveillance Tools in Aquatic Ecosystems: Microbial Community Detection from Lakewater Samples." 2004 ASLO Annual Meeting (Abstract and Slides).

Hiorns, W.D. et al., "Bacterial Diversity in Adirondack Mountain Lakes as Revealed by 16S rRNA Gene Sequences," Appl. Environ. Microbiol., 1997, vol. 63, No. 7, 2957-2960.

Hurlbert, S. H., "The Nonconcept of Species Diversity: A Critique and Alternative Parameters," Ecology, 1971, vol. 52, No. 4, 577-586.

Kaeberlein, T. et al., "Isolating "Uncultivable" Microorganisms in Pure Culture in a Simulated Natural Environment," Science, 2002, vol. 296, 1127-1129.

Kane, A. S. et al., "Fish Lesions in the Chesapeake Bay: Pfiesteria-like Dinoflagellates and other Etiologies," Maryland Medical Journal, 1998, vol. 47, No. 3, 106-112.

Kilham, P. et al., "Hypothesized Resource Relationships among African Planktonic Diatoms," Limnol. & Oceanogr., 1986, vol. 31, No. 6, 1169-1181.

Kitazoe, Y. et al., "A New Theory of Phylogeny Inference through Construction of Multidimensional Vector Space," Mol. Biol. Evol., vol. 18, No. 5, pp. 812-828, 2001.

Kopczysnski, E.D. et al., "Recognition of Chimeric Small-Subunit Ribosomal DNAs Composed of Genes from Uncultivated Microorganisms," Appl. Environ. Microbiol.,1994, vol. 60, No. 2, 746-748.

Leff, L.G. et al., "Identification of Aquatic Burkholderia (Pseudomonas) cepacia by Hybridization with Species-Specific rRNA Gene Probes," Appl. Environ. Microbiol.,1995, vol. 61, No. 4, 1634-1636.

Lemke, M. J. et al., "The Response of Three Bacterial Populations to Pollution in a Stream," Microb. Ecol., 1997, vol. 34, 224-231.

Liberles, D. A. et al., "The Adaptive Evolution Database (TAED)," Genome Biology, vol. 2, No. 4, pp. preprint0003.1-0003.18, 2001.

Lipp, E.K. et al., "Assessment and Impact of Microbial Fecal Pollution and Human Enteric Pathogens in a Coastal Community," Marine Pollution Bull., 2001, vol. 42, No. 4, 286-293.

Liu, Q. et al., "DNA Computing on Surfaces," Nature, vol. 403, pp. 175-179, 2000.

Lopez-Garcia, P. et al., "Unexpected Diversity of Small Eukaryotes in Deep-Sea Antarctic Plankton," Nature, 2001, vol. 409, 603-607.

Lucchini, S. et al., "Microarrays for Microbiologists," Microbiology, vol. 147, p. 1403-1414, 2001.

Mallin, M. A. et al., "North and South Carolina Coasts," Marine Pollution Bulletin, 2000, vol. 41, Nos. 1-6, 56-75.

Mallin, M. A., "Impacts of Industrial Animal Production on Rivers and Estuaries," American Scientist, 2000, vol. 88, Issue 1, 26-37, printed Jun. 9, 2005.

Mallin, M. A. et al., "Effect of Human Development on Bacteriological Water Quality in Coastal Watersheds," Ecological Applications, 2000, vol. 10, No. 4, 1047-1056.

Maniatis, T. et al., Molecular Cloning: A Laboratory Manual, Cold Spring Harbor Laboratory, 1982.

Maniatis, T. et al., DNA Cloning 3: A Practical Approach. (D. M. Glover ed.), 1995 (Table of Contents and Index only).

Marshall, M. "A Biological Approach to Water Quality Analysis Using 18S rDNA to Assess Aquatic Microbial Diversity across Spatial and Temporal Scales." Masters Thesis, Directed by Drs. Parke A. Rublee and Vincent C. Henrich, University of North Carolina at Greensboro, 2002, 52 pgs.

McCaig, A. E. et al., "Molecular Analysis of Bacterial Community Structure and Diversity in Unimproved and Improved Upland Grass Pastures," Appl. Environ. Microbiol., 1999, vol. 65, No. 4, 1721-1730.

Medlin, et al., "The Characterization of Enzymatically Amplified Eukaryotic 16S-like rRNA-Coding Regions," Gene, 1988, vol. 71, 491-499.

Methe, B. A. et al., "Diversity of Bacterial Communities in Adirondack Lakes: Do Species Assemblages Reflect Lake Water Chemistry?" Hydrobiologia, 1999, vol. 401, 77-96.

Moon-Van Der Staay, S. Y. et al., "Oceanic 18S rDNA Sequences from Picoplankton Reveal Unsuspected Eukaryotic Diversity," Nature, 2001, vol. 409, 607-610.

Muller, S. et al., "Defining the Ancestral Karyotype of All Primates by Multidirectional Chromosome Painting between Tree Shrews, Lemurs and Humans," Chromosoma, vol. 108, pp. 393-400, 1999.

Natale, D. A. et al., "Towards Understanding the First Genome Sequence of a Crenarchaeon by Genome Annotation using Clusters of Orthologous Groups of Proteins (COGs)," Genome Biology, vol. 1, No. 5, pp. research0009.1-0009.19, 2000.

Needleman, S.B. et al., "A General Method Applicable to the Search for Similarities in the Amino Acid Sequence of Two Proteins," J. Mol. Biol., 1970, vol. 48, 443-453.

Nubel, U. et al., "Quantifying Microbial Diversity: Morphotypes, 16S rRNA Genes, and Carotenoids of Oxygenic Phototrophs in Microbial Mats," Appl. Environ. Microbiol., 1999, vol. 65, No. 2, 422-430.

O'Brien, W. J. et al. "The Limnology of Toolik Lake," Freshwaters of Alaska-Ecological Syntheses, A. M. Milner and M. W. Oswood (eds), Springer-Verlag Publishers, New York, NY, 1997.

Oldach, D. W. et al., "Heteroduplex Mobility Assay-Guided Sequence Discovery: Elucidation of the Small Subunit (18S) rDNA Sequences of Pfiesteria Piscicida and Related Dinoflagellates from Complex Algal Culture and Environmental Sample DNA Pools," Proc. Natl. Acad. Sci. USA, 2000, vol. 97, No. 8, 4303-4308.

Oremland, R.S.et al., "The Ecology of Arsenic" Science, 2003, vol. 300, 939-943.

Pace, N. R. et al., "The Analysis of Natural Microbial Populations by Ribosomal RNA Sequences," Advances in Microbial Ecology, 1986, vol. 9, 1-55.

Paerl, H. W. et al., "Microbial Indicators of Aquatic Ecosystem Change: Current Applications to Eutrophication Studies," FEMS Microbiology Ecology, 2003, vol. 46, 233-246.

Pearson, W.R. et al., "Improved Tools for Biological Sequence Comparison," Proc. Natl. Acad. Sci. USA, 1988, vol. 85, 2444-2448.

Perez-Lopez, M. et al., "Assessment of Heavy Metal Contamination of Seawater and Marine Limpet, Patella Vulgata L., from Northwest Spain," Journal of Environmental Science and Health, Part A—Toxic/Hazardous Substances and Environmental Engineering, 2003, vol. A38, No. 12, 2845-2856.

Perna, et al., "Genome Sequence of Enterohaemorrhagic *Escherichia coli*0157:H7," Nature, 2001, vol. 409, 529-533.

Ramsay, G. et al., "DNA Chips: State-of-the-Art," Nature Biotechnology, vol. 16, pp. 40-44, 1998.

Reysenbach, A. L. et al., "Differential Amplification of rRNA Genes by Polymerase Chain Reaction," Appl. Environ. Microbiol., 1992, vol. 58, No. 10, 3417-3418.

Rublee, P. A. et al., "PCR and FISH Detection Extends the Range of *Pfiesteria piscicida* in Estuarine Waters," Va. J. Sci., 1999, vol. 50, No. 4, 325-335.

Rublee, P. A. et al., "Use of Molecular Probes to Access Geographic Distribution of Pfiesteria Species," Environ. Health Perspectives, 2001, vol. 109 (Supplement 5), 765-767.

Rublee, P. A. et al., "From Pfiesteria to Gene Arrays-Development Molecular Tools for Water Quality Assessment." EPA, Kansas City, MO. May 2002 (Abstract and Slides).

Rublee, P. A. et al., "Microarrays: New Tools for Water Surveillance." WRRI, Raleigh, NC, May 2003; Also presented at EPA, Research Triangle Park, NC, Mar. 2003 (Slides).

Rublee, P.A. et al., "Microarrays as Environmental Surveillance Tools in Aquatic Ecosystems: Will Nature Variation Preclude Practical Use?" 2004 ASLO Annual Meeting (Abstract and Slides).

Rubtsov, P.M. et al., "The Structure of the Yeast Ribosomal RNA Genes. The Complete Nucleotide Sequence of the 18S Ribosomal RNA Gene from Saccharomyces Cereviciae," Nucleic Acids Research, 1980, vol. 8, No. 23, 5779-5794.

Rudi, K. et al., "Application of Sequence-Specific Labeled 16S rRNA Gene Oligonucleotide Probes for Genetic Profiling of Cyanobacterial Abundance and Diversity by Array Hybridization," Appl. Environ. Microbiol., 2000, vol. 66, No. 9, 4004-4011.

Rushing et al., "Cloning and Characterization of the sigA Gene Encoding the Major Sigma Subunit of *Rhizobium meliloti*," J. Bacteriology, 1995, vol. 177, pp. 6952-6957.

Saghai-Maroof et al., "Ribosomal DNA spacer-lenth polymorphisms in barley: Mendelian inheritance, chromosomal location, and population dynamics," Proc. Natl. Acad. Sci. USA, 1984, vol. 81, pp. 8014-8018.

Sayada, C. et al., "Genomic Fingerprinting of *Yersinia enterocolitica* Species by Degenerate Oligonucleotide-Primed Polymerase Chain Reaction," Electrophoresis, vol. 15, pp. 562-565, 1994.

Schonfelder, I. et al., "Relationships between Littoral Diatoms and their Chemical Environment in Northeastern German Lakes and Rivers," J. Phycol., vol. 38, p. 66-82, 2002.

Schonhuber, W. et al., "In Situ Identification of Cyanobacteria with Horseradish Peroxidase-Labeled, rRNA-Targeted Oligonucleotide Probes," Appl. Environ. Microbiol., 1999, vol. 65, No. 3, 1259-1267.

Shubert, L.E. (ed), *Algae as Ecological Indicators*. 1984, Academic Press, N.Y., Chapters 4,5,8,& 9.

Shi, W. et al., "Association of Microbial Community Composition and Activity with Lead, Chromium, and Hydrocarbon Contamination," Appl. Environ. Microbiol., 2002, vol. 68, No. 8, 3859-3866.

Siver, P.A. et al., "Century Changes in Connecticut, U.S.A., Lakes as Inferred from Siliceous Algal Remains and Their Relationships to Land-Use Change," Limnol. Oceanograph, 1999, vol. 44, No. 8, 1928-1935.

Small, J. et al., "Direct Detection of 16S rRNA in Soil Extracts by Using Oligonucleotide Microarrays," Applied and Environmental Microbiology, vol. 67, No. 10, p. 4708-4716, 2001.

Smith, T.F. et al., "Comparison of Biosequences," Adv. Appl. Math., 1981, vol. 2, 482-489.

Sogin, M.L. et al., "Structural Diversity of Eukaryotic Small Subunit Ribosomal RNAs," Annals. NY Acad. Sci., 1987, vol. 503, 125-139.

Southern, E. et al., "Molecular Interactions on Microarrays," Nature Genetics Supplement, vol. 21, pp. 5-9, 1999.

Stine et al., "Characterization of Microbial Communities from Coastal Waters using Microarrays." Environmental Monitoring and Assessment, 2003, vol. 81, No. 1/3, 327-336 (Abstract).

Stoermer, et al., *The Diatoms: Applications for the Environmental and Earth Sciences*. 1999, Cambridge University Press, Cambridge, UK, Chapters 1-11, and 13-17.

Tatusov, R. et al., "A Genomic Perspective on Protein Families," Science, vol. 278, p. 631-637, 1997.

Tatusov, R. et al., "The COG Database: A Tool for Genome-Scale Analysis of Protein Functions and Evolution," Nucleic Acid Research, vol. 28, No. 1, p. 33-36, 2000.

Tatusov, R. et al., "The COG Database: New Developments in Phylogenetic Classification of Proteins from Complete Genomes," Nucleic Acids Research, vol. 29, No. 1, p. 22-28, 2001.

Thompson, J.D. et al., "Clustal W: Improving the Sensitivity of Progressive Multiple Sequence Alignment through Sequence Weighting, Position-Specific Gap Penalties and Weight Matrix Choice," Nucleic Acids Res., 1994, vol. 22, No. 22, 4673-4680.

Troesch, A. et al., "Mycobacterium Species Identification and Rifampin Resistance Testing with High-Density DNA Probe Arrays," J. Clin. Microbiol., 1999, vol. 37, No. 1, 49-55.

Venter, J. C. et al., "Environmental Genome Shotgun Sequencing of the Sargasso Sea," Science, 2004, vol. 304, 66-74.

Wang, G. et al., "Frequency of Formation of Chimeric Molecules as a Consequence of PCR Coamplification of 16S rRNA Genes from Mixed Bacterial Genomes," Appl. Environ. Microbiol., 1997, vol. 63, No. 12, 4645-4650.

Williams, R. B. et al., "Phytoplankton Production and Chlorophyll Concentration in the Beaufort Channel, North Carolina," Limnology and Oceanography, 1966, vol. 11, No. 1, 73-82.

Woese, C. R., "Interpreting the Universal Phylogenetic Tree," PNAS, vol. 97, No. 15, pp. 8392-8396, 2000.

Wu, L. et al., "Development and Evaluation of Functional Gene Arrays for Detection of Selected Genes in the Environment," Appl. Environ. Microbiol., 2001, vol. 67, No. 12, 5780-5790.

Xiao, L. et al., "Genetic Diversity within Cryptosporidium parvum and Related Cryptosporidum Species," Appl. Environ. Microbiol., 1999, vol. 65, No. 8, 3386-3391.

Ye, R. et al., "Applications of DNA Microarrays in Microbial Systems," Journal of Microbiological Methods, vol. 47, p. 257-272, 2001.

Yen-Lieberman, B. et al., "Nucleic Acid Amplification Techniques and Evaluation of RNA Quantitation Assays in HIV 1 Subtype B Virus," 1998 Conference on the Laboratory Science of HIV.

Entrez Nucleotide, NCBI Sequence, Accession No. V00348, (Definition)—*E. coli* ribosomal operon rmB encoding the 16S ribosomal RNA. Also transfer RNA specific for Glu, 23S ribosomal RNA and two unidentified open reading frames. This sequence was obtained from the transducing phage lambda-rif-d 18 (BAMHI fragment). *J. Mol. Biol. 148* (2), 107-127, 1981. NCBI web page at http://www.ncbi.nlm.nih.gov/entrez/viewer.fcgi?db=nucleotide&val=2073407, as available via the Internet and printed Mar. 10, 2005.

Entrez Nucleotide, NCBI Sequence, Accession No. AY351647, (Definition)—Acanthamoeba mauritaniensis 18S ribosomal RNA gene, complete sequence. *Submitted* (Jul. 25, 2003) *by Department of Parasitology, Kyungpook National University School of Medicine*, 101 Dongin-dong, Chung-gu, Taegu 700-422, Korea (unpublished). NCBI web page at http://www.ncbi.nlm.nih.gov/entrez/viewer.fcgi?db=nucleotide&val=34305120, as available via the Internet and printed Mar. 10, 2005.

Entrez Nucleotide, NCBI Sequence, Accession No. V01335, (Definition)—Yeast 18S ribosomal RNA. *Nucleic Acids Res.*, 8(23), 5779-5794, 1980. NCBI web page at http://www.ncbi.nlm.nih.gov/entrez/viewer.fcgi?db=nucleotide&val=4347, as available via the Internet and printed Mar. 10, 2005.

Entrez Nucleotide, NCBI Sequence, Accession No. AF111183, (Definition)—*Cyclospora cayetanensis* 18S ribosomal RNA gene, complete sequence. *Emerging Infect. Dis.* 5(5), 651-658, 1999. NCBI web page at http://www.ncbi.nlm.nih.gov/entrez/viewer.fcgi?db=nucleotide&val=4406385, as available via the Internet and printed Mar. 10, 2005.

Entrez Nucleotide, NCBI Sequence, Accession No. X65163, (Definition)—*E. histolytica* rRNA. *Nucleic Acids Res. 21*(8), 2011, 1993. NCBI web page at http://www.ncbi.nlm.nih.gov/entrez/viewer.fcgi?db=nucleotide&val=415339, as available via the Internet and printed Mar. 10, 2005.

Entrez Nucleotide, NCBI Sequence, Accession No. AF199449, (Definition)—*Giardia intestinalis* isolate Dog19 small subunit ribosomal RNA gene, partial sequence. *Parasitol. Today (Regul.Ed.)* 16(5), 210-213, 2000. NCBI web page at http://www.ncbi.nlm.nih.gov/entrez/viewer.fcgi?db=nucleotide&val=7008148, as available via the Internet and printed Mar. 10, 2005.

Entrez Nucleotide, NCBI Sequence, Accession No. AF106935,(Definition)—*Isospora belli* small subunit ribosomal RNA gene, complete sequence. *Parasitol. Res.* 86(8), 669-676, 2000, NCBI web page at http://www.ncbi.nlm.nih.gov/entrez/viewer.fcgi?db=nucleotide&val=4028606 as available via the Internet and printed Mar. 10, 2005.

Entrez Nucleotide, NCBI Sequence, Accession No. AY140647, (Definition)—*Microsporidium* sp. STF small subunit ribosomal RNA gene, partial sequence; internal transcribed spacer, complete sequence; and large subunit ribosomal RNA gene, partial sequence. Submitted (Aug. 14, 2000) *by Departement de Biologie, Universite de Fribourg, chemin du Musee 10, Fribourg 1700*, Switzerland (unpublished). NCBI web page at http://www.ncbi.nlm.nih.gov/entrez/viewer.fcgi?db=nucleotide&val=34391477, as available via the Internet and printed Mar. 10, 2005.

Entrez Nucleotide, NCBI Sequence, Accession No. AF338423, (Definition)—*Naegleria fowleri* 18S ribosomal RNA gene, partial sequence. *Dis. Aquat. Org.* 46(2), 115-121, 2001. NCBI web page at http://www.ncbi.nlm.nih.gov/entrez/viewer.fcgi?db=nucleotide&val=13398505 as available via the Internet and printed Mar. 10, 2005.

Entrez Nucleotide, NCBI Sequence, Accession No. AB116124, (Definition)—*Bacillus anthracis* gene for 16S ribosomal RNA, partial sequence, strain:S51. *Submitted* (Jul. 31, 2003) *by Akihiro Ohnishi, Tokyo University of Agriculture, Dept. of Fermentation Science*; Sakuragaoka 1-1-1, Setagaya-ku, Toyko 156-8502, Japan, (direct submission). NCBI web page at http://www.ncbi.nlm.nih.gov/entrez/viewer.fcgi?db=nucleotide&val=33468788, as available via the Internet and printed Mar. 10, 2005.
Entrez Nucleotide, NCBI Sequence, Accession No. AF220149, (Definition)—*Brucella melitensis* ribosomal RNA operon C, complete sequence, *Gene 255*(1), 117-126, 2000. NCBI web page at http://www.ncbi.nlm.nih.gov/entrez/viewer.fcgi?db=nucleotide &val=6979879, as available via the Internet and printed Mar. 10, 2005.
Entrez Nucleotide, NCBI Sequence, Accession No. AY305760, (Definition)—*Burkholderia mallei* strain 2000031063 16S ribosomal RNA gene, complete sequence. *J. Clin. Microbiol*., 41(10), 4647-4654, 2003. NCBI web page at http://www.ncbi.nlm.nih.gov/entrez/viewer.fcgi?db=nucleotide&val=33286643, as available via the internet and printed Mar. 10, 2005.
Entrez Nucleotide, NCBI Sequence, Accession No. AF550630, (Definition)—*Campylobacter jejuni* strain B99/206 16S ribosomal RNA gene, partial sequence. *J. Clin. Microbiol*., 41(6), 2537-2549, 2003. NCBI web page at http://www.ncbi.nlm.nih.gov/entrez/viewer.fcgi?db=nucleotide&val=25229129, as available via the Internet and printed Mar. 10, 2005.
Entrez Nucleotide, NCBI Sequence, Accession No. AY334530, (Definition)—*Chlamydophila psittaci* clone cvCps2 16S ribosomal RNA gene, partial sequence. *Res. Microbiol*., 153(9), 563-567, 2002. NCBI web page at http://www.ncbi.nlm.nih.gov/entrez/viewer.fcgi?db=nucleotide&val=33114016, as available via the Internet and printed Mar. 10, 2005.
Entrez Nucleotide, NCBI Sequence, Accession No. AY303799, (Definition)—*Clostridium botulinum* strain AIP 355.02 16S ribosomal RNA gene, partial sequence. *J. Clin. Microbiol*., 42(1), 484-486, 2004. NCBI web page at http://www.ncbi.nlm.nih.gov/entrez/viewer.fcgi?db=nucleotide&val=31790293, as available via the Internet and printed Mar. 10, 2005.
Entrez Nucleotide, NCBI Sequence, Accession No. Y11502, (Definition)—*C. bumetii* ribosomal RNA, strain Nine Mile. *FEMS Immunol. Med. Microbiol*., 20(2), 165-172, 1998. NCBI web page at http://www.ncbi.nlm.nih.gov/entrez/viewer.fcgi?db=nucleotide &val=1883009, as available via the Internet and printed Mar. 10, 2005.
Entrez Nucleotide, NCBI Sequence, Accession No. AB035920, (Definition)—*Escherichia coli* 0157:H7 hemG, rrsA, ileT, alaT, rrlA, rrfA, mobB, mobA genes for protoporphyrin oxidase protein, 16S rRNA, isoleucine tRNA 1, alanine tRNA 1B, 23S rRNA, 5S rRNA, molybdopterin-guanine dinucleotide biosynthesis protein B, molybdopterin-guanine dinucleotide biosynthesis protein A, complete and partial cds. *Syst. Appl. Microbiol*., 23(3), 315-324, 2000. NCBI web page at http://www.ncbi.nlm.nih.gov/entrez/viewer.fcgi?db=nucleotide&val=7415846, as available via the Internet and printed Mar. 10, 2005.
Entrez Nucleotide, NCBI Sequence, Accession No. X96964, (Definition)—*S. sonnei* 16S rRNA gene. *Mol. Cell. Probes*, 11(6), 427-432, 1997. NCBI web page at http://www.ncbi.nlm.nih.gov/entrez/viewer.fcgi?db=nucleotide&val=1255976, as available via the Internet and printed Mar. 10, 2005.
Entrez Nucleotide, NCBI Sequence, Accession No. AY243028, (Definition)—*Francisella tularensis* strain 3523 16S ribosomal RNA gene, partial sequence. J. Med. Microbiol., 52(9), 839-842, 2003. NCBI web page at http://www.ncbi.nlm.nih.gov/entrez/viewer.fcgi?db=nucleotide&val=29570257, as available via the Internet and printed Mar. 10, 2005.
Entrez Nucleotide, NCBI Sequence, Accession No. AJ496383, (Definition)—*Legionella pneumophila* serogroup 6 partial 16S rRNA gene, avirulent mutant. *Submitted* (Jul. 19, 2002) *by Bacteriology and Medical Micology, National Institute of Health, Viale Regina Elena*, 299, Rome 00161, Italy (unpublished). NCBI web page at http://www.ncbi.nlm.nih.gov/entrez/viewer.fcgi?db=nucleotide&val=22080754, as available via the Internet and printed Mar. 10, 2005.
Entrez Nucleotide, NCBI Sequence, Accession No. Z12817, (Definition)—*L. interrogans* 16S ribosomal RNA. Submitted (Jun. 19, 1992) by Hookey J. V., Public Health Laboratory Service, Leptospira Reference Laboratory, Stonebow Road, Hereford, Herefordshire, United Kingdom, HR1 2ER, (direct submission). NCBI web page at http://www.ncbi.nlm.nih.gov/entrez/viewer.fcgi?db=nucleotide &val=44003, as available via the Internet and printed Mar. 10, 2005.
Entrez Nucleotide, NCBI Sequence, Accession No. AB117953, (Definition)—*Pseudomonas aeruginosa* gene for 16S rRNA, strain:WatG. *Submitted* (Aug. 21, 2003) *by Isao Yumoto, National Institute of Advanced Industrial Science and Technology, Institute for Biological Resources and Functions*; 2-17-2-1, Tsukisamu-Higashi, Toyohira-ku, Sapporo, Hokkaido 062-8517, Japan, (unpublished). NCBI web page at http://www.ncbi.nlm.nih.gov/entrez/viewer.fcgi?db=nucleotide&val=34146778, as available via the Internet and printed Mar. 10, 2005.
Entrez Nucleotide, NCBI Sequence, Accession No. M21789, (Definition)—*Rickettsia prowazekii* 16S ribosomal RNA. *J. Bacteriol*. 171(8), 4202-4206, 1989. NCBI web page at http://www.ncbi.nlm.nih.gov/entrez/viewer.fcgi?db=nucleotide&val=152479, as available via the Internet and printed Mar. 10, 2005.
Entrez Nucleotide, NCBI Sequence, Accession No. Z49264, (Definition)—*S. typhimurium* gene for 16S ribosomal RNA. *Int. J. Syst. Bacteriol*., 47(4), 1253-1254, 1997. NCBI web page at http://www.ncbi.nlm.nih.gov/entrezJviewer.fcgi?db=nucleotide&val=2826774, as available via the Internet and printed Mar. 10, 2005.
Entrez Nucleotide, NCBI Sequence, Accession No. X76337, (Definition)—*V. cholerae* (CECT 514 T) 16S rRNA gene. *Int. J. Syst. Bacteriol*., 44(2), 330-337, 1994. NCBI web page at http://www.ncbi.nlm.nih.gov/entrez/viewer.fcgi?db=nucleotide&val=531549, as available via the Internet and printed Mar. 10, 2005.
Entrez Nucleotide, NCBI Sequence, Accession No. AF366383, (Definition)—*Yersinia pestis* 16S ribosomal RNA gene, partial sequence. *Antonie Van Leeuwenhoek*, 83(2), 125-133, 2003. NCBI web page at http://www.ncbi.nlm.nih.gov/entrez/viewer.fcgi?db=nucleotide&val=13991901, as available via the Internet and printed Mar. 10, 2005.
Entrez Nucleotide, NCBI Sequence, Accession No. AF406554, (Definition)—Arsenite-oxidizing bacterium MLHE-1 16S ribosomal RNA gene, partial sequence. *Appl. Environ. Microbiol*., 68(10), 4795-4802, 2002. NCBI web page at http://www.ncbi.nlm.nih.gov/entrez/viewer.fcgi?db=nucleotide&val=23451034, as available via the Internet and printed Mar. 10, 2005.
Entrez Nucleotide, NCBI Sequence, Accession No. U46506, (Definition)—*Thiomicrospira* sp. CVO 16S ribosomal RNA gene, partial sequence. *Appl. Environ. Microbiol*., 62(5), 1623-1629, 1996. NCBI web page at http://www.ncbi.nlm.nih.gov/entrez/viewer.fcgi?db=nucleotide&val=6995983, as available via the Internet and printed Mar. 10, 2005.
Entrez Nucleotide, NCBI Sequence, Accession No. Z24450, (Definition)—*D. longreachii* ribosomal RNA. *FEMS Microbiol. Lett.*, 113(1), 81-86, 1993. NCBI web page at http://www.ncbi.nlm.nih.gov/entrez/viewer.fcgi?db=nucleotide&val=415336, as available via the Internet and printed Mar. 10, 2005.
Entrez Nucleotide, NCBI Sequence, Accession No. AF064705, (Definition)—*Bacillus arsenicoselenatis*16S ribosomal RNA gene, partial sequence. *Arch. Microbiol.*, 171(1), 19-30, 1998. NCBI web page at http://www.ncbi.nlm.nih.gov/entrez/viewer.fcgi?db=nucleotide&val=4038083, as available via the Internet and printed Mar. 10, 2005.
Entrez Nucleotide, NCBI Sequence, Accession No. AF233412, (Definition)—Uncultured human fecal bacterium HF74 16S ribosomal RNA gene, partial sequence. *Appl. Environ. Microbiol.*, 66(4), 1587-1594, 2000. NCBI web page at http://www.ncbi.nlm.nih.gov/entrez/viewer.fcgi?db=nucleotide&val=7385167, as available via the Internet and printed Mar. 10, 2005.
Entrez Nucleotide, NCBI Sequence, Accession No. AF233408, (Definition)—Uncultured human fecal bacterium HF8 16S ribosomal RNA gene, partial sequence. *Appl. Environ. Microbiol.*, 66(4), 1587-1594, 2000. NCBI web page at http://www.ncbi.nlm.nih.gov/entrez/viewer.fcgi?db=nucleotide&val=7385163, as available via the Internet and printed Mar. 10, 2005.
Entrez Nucleotide, NCBI Sequence, Accession No. AF233413, (Definition)—Uncultured human fecal bacterium HF10 16S ribosomal RNA gene, partial sequence. *Appl. Environ. Microbiol.*, 66(4), 1587-1594, 2000. NCBI web page at http://www.ncbi.nlm.nih.gov/entrez/viewer.fcgi?db=nucleotide&val=7385168, as available via the Internet and printed Mar. 10, 2005.
Entrez Nucleotide, NCBI Sequence, Accession No. AB091761, (Definition)—*Burkholderia cepacia* gene for 16S rRNA, complete sequence. *Biosci. Biotechnol. Biochem.*, 67(9), 2026-2029, 2003. NCBI web page at http://www.ncbi.nlm.nih.gov/entrez/viewer.fcgi?db=nucleotide&val=23263363, as available via the Internet and printed Mar. 10, 2005.
Entrez Nucleotide, NCBI Sequence, Accession No. AF148556, (Definition)—*Burkholderia cepacia* genomovar III 16S ribosomal RNA gene, partial sequence. *Submitted* (May 5, 1999) *by Laboratorium voor Microbiologie, Universiteit Gent, K.L. Ledeganckstraat 35*, Gent 9000, Belgium, (unpublished). NCBI web page at http://www.ncbi.nlm.nih.gov/entrez/viewer.fcgi?db=nucleotide&val=8163584, as available via the Internet and printed Mar. 10, 2005.
Entrez Nucleotide, NCBI Sequence, Accession No. AE014075, (Definition)—*Escherichia coli* CFT073 complete genome. *Proc. Natl. Acad. Sci. USA*, 99(26), 17020-17024, 2002. NCBI web page at http://www.ncbi.nlm.nin.gov/entrez/viewer.fcgi?db=nucleotide&val=26111730, as available via the Internet and printed Mar. 10, 2005.
Entrez Nucleotide, NCBI Sequence, Accession No. U00096, (Definition)—*Escherichia coli* K-12 MG1655 partial genome. *Science*, 277(5331), 1453-1474, 1997. NCBI web page at http://www.ncbi.nlm.nih.gov/entrez/viewer.fcgi?db=nucleotide&val=48994873, as available via the Internet and printed Mar. 10, 2005.
Entrez Nucleotide, NCBI Sequence, Accession No. AJ301833, (Definition)—*Enterococcus gallinarm* 16S rRNA gene, strain LMG 13129. *Submitted* (Nov. 22, 2000) *by Ludwig W., Tu Muenchen, Lehrstuhl fuer Mikrobiologie, Am Hochanger 4*, Germany (unpublished). NCBI web page at http://www.ncbi.nlm.nih.gov/entrez/viewer.fcgi?db=nucleotide&val=11342559, as available via the Internet and printed Mar. 10, 2005.
Entrez Nucleotide, NCBI Sequence, Accession No. AF222998, (Definition)—*Cryptosporidium parvum* 18S ribosomal RNA gene and internal transcribed spacer 1, complete sequence; and 5.8S ribosomal RNA gene, partial sequence. Submitted (Jan. 11, 2000) by Biomedical Sciences, Tufts University School of Veterinary Medicine, 200 Westboro Road, North Grafton, MA 01536, USA (Unpubllished). NCBI web page at http://www.ncbi.nlm.nih.gov/entrez/viewer.fcgi?db=nucleotide&val=7530439, as available via the Internet and printed Aug. 9, 2005.
Entrez Nucleotide, NCBI Sequence, Accession No. AF351647, (Definition)—*Geochelone nigra vicina* isolate C8 NADH dehydrogenase subunit 4 (ND4) gene, partial cds; tRNA-His and tRNA-Ser genes, complete sequence; and tRNA-Leu gene, partial sequence; mitochondrial genes for mitochondrial products. Submitted (Feb. 21, 2001) by Center for Conservation and Research, Henry Doorly Zoo, 3701 South 10th Street, Omaha, NE 68107, USA. NCBI web page at http://www.ncbi.nlm.nih.gov/entrez/viewer.fcgi?db=nucleotide&val=22134763, as available via the Internet and printed Aug. 9, 2005.
Office Action mailed May 26, 2006 for U.S. Appl. No. 10/131,618.
Office Action mailed Dec. 5, 2005 for U.S. Appl. No. 10/131,618.
Office Action mailed Sep. 16, 2005 for U.S. Appl. No. 10/131,618.
Amendment and Response sent to USPTO on Mar. 6, 2006 for U.S. Appl. No. 10/131,618.
Election and Response sent to USPTO on Oct. 14, 2005 for U.S. Appl. No. 10/131,618.
Interview Summary sent to USPTO on Sep. 26, 2006 for U.S. Appl. No. 10/131,618.
Interview Summary mailed Jun. 28, 2006 for U.S. Appl. No. 10/131,618.
Supplemental Notice of Allowance mailed Dec. 22, 2006 for U.S. Appl. No. 11/071,849.
Notice of Allowance mailed Dec. 8, 2006 for U.S. Appl. No. 11/071,849.
Office Action mailed Oct. 31, 2005 for U.S. Appl. No. 11/071,849.
Office Action mailed Dec. 27, 2005 for U.S. Appl. No. 11/071,849.
Office Action mailed Apr. 17, 2006 for U.S. Appl. No. 11/071,849.
Amendment and response to first office action sent to USPTO on Sep. 15, 2006 for U.S. Appl. No. 11/071,849.
Response to Communication sent to USPTO on Jan. 27, 2006 for U.S. Appl. No. 11/071,849.
Election and Response sent to USPTO on Nov. 30, 2005 for U.S. Appl. No. 11/071,849.
Preliminary Amendment sent to USPTO on Mar. 3, 2005 for U.S. Appl. No. 11/071,849.
Interview Summary mailed Dec. 22, 2006 for U.S. Appl. No. 11/071,849.
Interview Summary mailed Dec. 8, 2006 for U.S. Appl. No. 11/071,849.
Interview Summary mailed Aug. 28, 2006 for U.S. Appl. No. 11/071,849.
Interview Summary mailed Apr. 17, 2006 for U.S. Appl. No. 11/071,849.
Election and Response filed with the USPTO on Apr. 21, 2009 for U.S. Appl. No. 11/527,129.
Schaefer, F., "Novel Mutation in the FGFR2 Gene at the Same Codon as the Crouzon Syndrome Mutations in a Severe Pfeiffer Syndrome Type 2 Case," Am. J. Med. Genet 75;252-255, 1998.
Morel et al., "The Chemical Cycle and Bioaccumulation of Mercury," Annu. Rev. Ecol. Syst., 29:543-66, 1998.
Kerin et al., "Mercury Methylation by Dissimilatory Iron-Reducing Bacteria," Appl. Environ. Microbiol, 72:7919-7921, 2006.
Osborn et al., "Distribution, diversity and evolution of the bacterial mercury resistance (*mer*) operon," FEMS Microbiol. Rev., 19:239-262, 1997.
Nascimento et al., "*Operon mer*. Bacterial resistance to mercury and potential for bioremediation of contaminated environments," Genet. Mol. Res., 2:92-101, 2003.
Picard et al., "Detection and Enumeration of Bacteria in Soil by Direct DNA Extraction and Polymerase Chain Reaction," App. Enviorn. Microbiol., 58:2717-2722, 1992.
Colinvaux, 1993, Ecology 2, John Wiley & Sons, Inc., New York.
Kemp et al., "Estimating prokaryotic diversity: When are 16S rDNA libraries large enough?", Limnol., Oceanogr.: Methods, 2:114-125, 2004.
Lincoln et al., 1998, A Dictionary of Ecology, Evolution, and Systematics, Cambridge University Press, New York.
Muller et al., "The effect of long-term mercury pollution on the soil microbial community," FEMS Microbiol. Ecology, 36:11-19, 2001.

Muller et al., "The Diversity and Function of Soil Microbial Communities Exposed to Different Disturbances," Microb. Ecol., 44:49-58, 2002.

Rasmussen et al., "The Effect of Longterm Exposure to Mercury on the Bacterial Community in Marine Sediment," Current Microbiology, 36:291-297, 1998.

Rasmussen et al., "Effects of mercury contamination on the culturable heterotrophic, functional and genetic diversity of the bacterial community in soil," FEMS Microbiology Ecology, 36:1-9, 2001.

Thayer, "Phytoplankton Production and the Distribution of Nutrients in a Shallow Unstratified Estuarine System Near Beaufort, N.C.," Chesapeake Science, 12:240-253, 1971.

Mallin, "Phytoplankton Ecology of North Carolina Estuaries," Estuaries, 17:561-574, 1994.

Bowers et al., "Development of Real-Time PCR Assays for Rapid Detection of *Pfiesteria piscicida* and Related Dinoflagellates," Applied and Environ. Microbiology, 66:4641-4648, 2000.

Griffin et al., "Detection of Viral Pathogens by Reverse Transcriptase PCR and of Microbial Indicators by Standard Methods in the Canals of the Florida Keys," Applied and Environ. Microbiology, 65:4118,4125, 1999.

Doyle et al., "DNA isolation from small amounts of plant tissue," 1987, available at http://ird.igd.cornell.edu/Protocols/DoyleProtocol.pdf.

Eilers, H. et al., "Culturability and in Situ Abundance of Pelagic Bacteria from the North Sea," 2000, Appl. Environ. Microbiol., 66:3044-3051.

Nickrent, D. and Sargent, M., "An overview of the secondary structure of the V4 region of eukaryotic small-subunit ribosomal RNA," 1991, Nucl. Acids Res., 19:227:235.

Office action mailed Oct. 14, 2010 corresponding to U.S. Appl. No. 11/716,450.

* cited by examiner

FIG. 12 A-1

```
                 ....|....| ....|....| ....|....| ....|....| ....|....| ....|....|
                      5         15        25        35        45        55
E. coli          aaattgaaga gtttgatcat ggctcagatt gaacgctggc ggcaggccta acacatgcaa ....|....| ....|....| ....|....| ....|....| ....|....| ....|....|
                      65        75        85        95       105       115
E. coli          gtcgaacggt aacaggaaga agcttgcttc tttgctgacg agtggcggac gggtgagtaa ....|....| ....|....| ....|....| ....|....| ....|....| ....|....|
                     125       135       145       155       165       175
E. coli          tgtctgggaa actgcctgat ggaggggat  aactactgga aacggtagct aataccgcat ....|....| ....|....| ....|....| ....|....| ....|....| ....|....|
                     185       195       205       215       225       235
E. coli          aacgtcgcaa gaccaaagag ggggaccttc gggcctcttg ccatcggatg tgcccagatg ....|....| ....|....| ....|....| ....|....| ....|....| ....|....|
                     245       255       265       275       285       295
E. coli          ggattagcta gtaggtgggg taacggctca cctaggcgac gatccctagc tggtctgaga ....|....| ....|....| ....|....| ....|....| ....|....| ....|....|
                     305       315       325       335       345       355
E. coli          ggatgaccag ccacactgga actgagacac ggtccagact cctacgggag gcagcagtgg ....|....| ....|....| ....|....| ....|....| ....|....| ....|....|
                     365       375       385       395       405       415
E. coli          ggaatattgc acaatgggcg caagcctgat gcagccatgc cgcgtgtatg aagaaggcct ....|....| ....|....| ....|....| ....|....| ....|....| ....|....|
                     425       435       445       455       465       475
E. coli          tcgggttgta aagtactttc agcggggagg aagggagtaa agttaatacc tttgctcatt ....|....| ....|....| ....|....| ....|....| ....|....| ....|....|
                     485       495       505       515       525       535
E. coli          gacgttaccc gcagaagaag caccggctaa ctccgtgcca gcagccgcgg taatacggag ....|....| ....|....| ....|....| ....|....| ....|....| ....|....|
                     545       555       565       575       585       595
E. coli          ggtgcaagcg ttaatcggaa ttactgggcg taaagcgcac gcaggcggtt tgttaagtca ....|....| ....|....| ....|....| ....|....| ....|....| ....|....|
                     605       615       625       635       645       655
E. coli          gatgtgaaat ccccgggctc aacctggaa  ctgcatctga tactggcaag cttgagtctc ....|....| ....|....| ....|....| ....|....| ....|....| ....|....|
                     665.      675       685       695       705       715
E. coli          gtagagggg  gtagaattcc aggtgtagcg gtgaaatgcg tagagatctg gaggaatacc ....|....| ....|....| ....|....| ....|....| ....|....| ....|....|
                     725       735       745       755       765       775
E. coli          ggtggcgaag gcggccccct ggacgaagac tgacgctcag gtgcgaaagc gtggggagca ....|....| ....|....| ....|....| ....|....| ....|....| ....|....|
                     785       795       805       815       825       835
E. coli          aacaggatta gataccctgg tagtccacgc cgtaaacgat gtcgacttgg aggttgtgcc ....|....| ....|....| ....|....| ....|....| ....|....| ....|....|
                     845       855       865       875       885       895
E. coli          cttgaggcgt ggcttccgga gctaacgcgt taagtcgacc gcctggggag tacggccgca
```

FIG. 12A-2

```
              ....|....| ....|....| ....|....| ....|....| ....|....| ....|....|
                  905        915        925        935        945        955
E. coli       aggttaaaac tcaaatgaat tgacgggggc ccgcacaagc ggtggagcat gtggtttaat ....|....| ....|....| ....|....| ....|....| ....|....| ....|....|
                  965        975        985        995       1005       1015
E. coli       tcgatgcaac gcgaagaacc ttacctggtc ttgacatcca cggaagtttt cagagatgag ....|....| ....|....| ....|....| ....|....| ....|....| ....|....|
                 1025       1035       1045       1055       1065       1075
E. coli       aatgtgcctt cgggaaccgt gagacaggtg ctgcatggct gtcgtcagct cgtgttgtga ....|....| ....|....| ....|....| ....|....| ....|....| ....|....|
                 1085       1095       1105       1115       1125       1135
E. coli       aatgttgggt taagtcccgc aacgagcgca acccttatcc tttgttgcca gcggtccggc ....|....| ....|....| ....|....| ....|....| ....|....| ....|....|
                 1145       1155       1165       1175       1185       1195
E. coli       cgggaactca aaggagactg ccagtgataa actggaggaa ggtggggatg acgtcaagtc ....|....| ....|....| ....|....| ....|....| ....|....| ....|....|
                 1205       1215       1225       1235       1245       1255
E. coli       atcatggccc ttacgaccag ggctacacac gtgctacaat ggcgcataca aagagaagcg ....|....| ....|....| ....|....| ....|....| ....|....| ....|....|
                 1265       1275       1285       1295       1305       1315
E. coli       acctcgcgag agcaagcgga cctcataaag tgcgtcgtag tccggattgg agtctgcaac ....|....| ....|....| ....|....| ....|....| ....|....| ....|....|
                 1325       1335       1345       1355       1365       1375
E. coli       tcgactccat gaagtcggaa tcgctagtaa tcgtggatca gaatgccacg gtgaatacgt ....|....| ....|....| ....|....| ....|....| ....|....| ....|....|
                 1385       1395       1405       1415       1425       1435
E. coli       tcccgggcct tgtacacacc gcccgtcaca ccatgggagt gggttgcaaa agaagtaggt ..
E. coli       ag
```

*E. coli* 16S rRNA gene (SEQ ID NO: 317)

FIG. 12B-1

```
                    ....|....| ....|....| ....|....| ....|....| ....|....| ....|....|
                        5         15         25         35         45         55
S. cerevis          tatctggttg atcctgccag tagtcatatg cttgtctcaa agattaagcc atgcatgtct ....|....| ....|....| ....|....| ....|....| ....|....| ....|....|
                        65        75         85         95        105        115
S. cerevis          aagtataagc aatttataca gtgaaactgc gaatggctca ttaaatcagt tatcgtttat ....|....| ....|....| ....|....| ....|....| ....|....| ....|....|
                       125        135        145        155        165        175
S. cerevis          ttgatagttc ctttactaca tggtataacc gtggtaattc tagagctaat acatgcttaa ....|....| ....|....| ....|....| ....|....| ....|....| ....|....|
                       185        195        205        215        225        235
S. cerevis          aatctcgacc ctttggaaga gatgtattta ttagataaaa aatcaatgtc ttcgcactct ....|....| ....|....| ....|....| ....|....| ....|....| ....|....|
                       245        255        265        275        285        295
S. cerevis          ttgatgattc ataataactt ttcgaatcgc atggccttgt gctggcgatg gttcattcaa ....|....| ....|....| ....|....| ....|....| ....|....| ....|....|
                       305        315        325        335        345        355
S. cerevis          atttctgccc tatcaacttt cgatggtagg atagtggcct accatggttt caacgggtaa ....|....| ....|....| ....|....| ....|....| ....|....| ....|....|
                       365        375        385        395        405        415
S. cerevis          cggggaataa gggttcgatt ccggagaggg agcctgagaa acggctacca catccaagga ....|....| ....|....| ....|....| ....|....| ....|....| ....|....|
                       425        435        445        455        465        475
S. cerevis          aggcagcagg cgcgcaaatt acccaatcct aattcaggga ggtagtgaca ataaataacg ....|....| ....|....| ....|....| ....|....| ....|....| ....|....|
                       485        495        505        515        525        535
S. cerevis          atacagggcc cattcgggtc ttgtaattgg aatgagtaca atgtaaatac cttaacgagg ....|....| ....|....| ....|....| ....|....| ....|....| ....|....|
                       545        555        565        575        585        595
S. cerevis          aacaattgga gggcaagtct ggtgccagca gccgcggtaa ttccagctcc aatagcgtat ....|....| ....|....| ....|....| ....|....| ....|....| ....|....|
                       605        615        625        635        645        655
S. cerevis          attaaagttg ttgcagttaa aaagctcgta gttgaacttt gggcccggtt ggccggtccg ....|....| ....|....| ....|....| ....|....| ....|....| ....|....|
                       665        675        685        695        705        715
S. cerevis          atttttcgt gtactggatt ccaacgggg cctttccttc tggctaacct tgagtccttg ....|....| ....|....| ....|....| ....|....| ....|....| ....|....|
                       725        735        745        755        765        775
S. cerevis          tggctcttgg cgaaccagga cttttacttt gaaaaaatta gagtgttcaa agcaggcgta ....|....| ....|....| ....|....| ....|....| ....|....| ....|....|
                       785        795        805        815        825        835
S. cerevis          ttgctcgaat atattagcat ggaataatag aataggacgt ttggttctat tttgttggtt ....|....| ....|....| ....|....| ....|....| ....|....| ....|....|
                       845        855        865        875        885        895
S. cerevis          tctaggacca tcgtaatgat taatagggac ggtcgggggc atcggtattc aattgtcgag
```

FIG. 12B-2

```
                    ....|....| ....|....| ....|....| ....|....| ....|....| ....|....|
                       905        915        925        935        945        955
        S. cerevis  gtgaaattct tggatttatt gaagactaac tactgcgaaa gcatttgcca aggacgtttt ....|....| ....|....| ....|....| ....|....| ....|....| ....|....|
                       965        975        985        995       1005       1015
        S. cerevis  cattaatcaa gaacgaaagt taggggatcg aagatgatct ggtaccgtcg tagtcttaac ....|....| ....|....| ....|....| ....|....| ....|....| ....|....|
                      1025       1035       1045       1055       1065       1075
        S. cerevis  cataaactat gccgactaga tcgggtggtg ttttttttaat gacccactcg gtaccttacg ....|....| ....|....| ....|....| ....|....| ....|....| ....|....|
                      1085       1095       1105       1115       1125       1135
        S. cerevis  agaaatcaaa gtctttgggt tctgggggga gtatggtcgc aaggctgaaa cttaaaggaa ....|....| ....|....| ....|....| ....|....| ....|....| ....|....|
                      1145       1155       1165       1175       1185       1195
        S. cerevis  ttgacggaag ggcaccacta ggagtggagc ctgcggctaa tttgactcaa cacggggaaa ....|....| ....|....| ....|....| ....|....| ....|....| ....|....|
                      1205       1215       1225       1235       1245       1255
        S. cerevis  ctcaccaggt ccagacacaa taaggattga cagattgaga gctctttctt gattttgtgg ....|....| ....|....| ....|....| ....|....| ....|....| ....|....|
                      1265       1275       1285       1295       1305       1315
        S. cerevis  gtggtggtgc atggccgttt ctcagttggt ggagtgattt gtctgcttaa ttgcgataac ....|....| ....|....| ....|....| ....|....| ....|....| ....|....|
                      1325       1335       1345       1355       1365       1375
        S. cerevis  gaacgagacc ttaacctact aaatagtggt gctagcattt gctggttatc cacttcttag ....|....| ....|....| ....|....| ....|....| ....|....| ....|....|
                      1385       1395       1405       1415       1425       1435
        S. cerevis  agggactatc ggtttcaagc cgatggaagt ttgaggcaat aacaggtctg tgatgccctt ....|....| ....|....| ....|....| ....|....| ....|....| ....|....|
                      1445       1455       1465       1475       1485       1495
        S. cerevis  agaacgttct gggccgcacg cgcgctacac tgacggagcc agcgagtcta accttggccg ....|....| ....|....| ....|....| ....|....| ....|....| ....|....|
                      1505       1515       1525       1535       1545       1555
        S. cerevis  agaggtcttg gtaatcttgt gaaactccgt cgtgctgggg atagagcatt gtaattattg ....|....| ....|....| ....|....| ....|....| ....|....| ....|....|
                      1565       1575       1585       1595       1605       1615
        S. cerevis  ctcttcaacg aggaattcct agtaagcgca agtcatcagc ttgcgttgat tacgtccctg ....|....| ....|....| ....|....| ....|....| ....|....| ....|....|
                      1625       1635       1645       1655       1665       1675
        S. cerevis  ccctttgtac acaccgcccg tcgctagtac cgattgaatg gcttagtgag gcctcaggat ....|....| ....|....| ....|....| ....|....| ....|....| ....|....|
                      1685       1695       1705       1715       1725       1735
        S. cerevis  ctgcttagag aaggggcaa ctccatctca gagcggagaa tttggacaaa cttggtcatt ....|....| ....|....| ....|....| ....|....| ....|....| ....|...
                      1745       1755       1765       1775       1785       1795
        S. cerevis  tagaggaact aaaagtcgta acaaggtttc cgtaggtgaa cctgcggaag gatcatta
```

*S. cerevisiae* 18S rRNA gene (SEQ ID NO: 318)

FIG. 12C-1

V1 region (SEQ ID NO: 319)

```
                                                           |....|....|
                                                                   55
E. coli                                                    a acacatgcaa ....|....| ....|....| ....|....| ....|....| ....|....| ....|....|
            65         75         85         95        105        115
E. coli gtcgaacggt aacaggaaga agcttgcttc tttgctgacg agtggcggac gggtgagtaa ....|....| ....|....| ....|....| ....|....| ....|....| ....|....|
           125        135        145        155        165        175
E. coli tgtctgggaa actgcctgat ggagggggat
```

V2 region (SEQ ID NO: 320)

```
                                                      |....|....| ....|....|
                                                              165        175
E. coli                                               a aacggtagct aataccgcat ....|....| ....|....| ....|....| ....|....| ....|....| ....|....|
           185        195        205        215        225        235
E. coli aacgtcgcaa gaccaaagag ggggaccttc gggcctcttg ccatcggatg tgcccagatg ....|....| ....|....| ....|....| ....|....| ....|....| ....|....|
           245        255        265        275        285        295
E. coli ggattagcta
```

V3 region (SEQ ID NO: 321)

```
        |....|....| ....|....| ....|....| ....|....| ....|....| ....|....|
           435        445        455        465        475
E. coli   a aagtactttc agcggggagg aagggagtaa agttaatacc tttgctcatt ....|....| ....|....| ....|....| ....|....| ....|....| ....|....|
           485        495        505        515        525        535
E. coli gacgttaccc gcagaagaag caccggctaa
```

FIG. 12C-2

V4 region (SEQ ID NO: 322)

```
                                         |....|....| ....|....|
                                            825         835
E. coli                                  t gtcgacttgg aggttgtgcc ....|....| ....|....| ....|....| ....|....| ....|....| ....|....|
           845        855        865        875        885        895
E. coli    cttgaggcgt ggcttccgga gctaacgcgt taagtcgacc
```

V6 region (SEQ ID NO: 323)

```
                              |....|....| ....|....| ....|....| ....|....|
                                 1105        1115        1125        1135
E. coli                       c aacgagcgca acccttatcc tttgttgcca gcggtccggc ....|....| ....|....| ....|....| ....|....| ....|....| ....|....|
           1145       1155       1165       1175       1185       1195
E. coli    cgggaactca aaggagactg
```

FIG. 12D-1

V1 plus flanking region (SEQ ID NO: 324)

```
                                                                    |....|....|
                                                                            55
S. cerevis                                                          c atgcatgtct ....|....| ....|....| ....|....| ....|....| ....|....| ....|....|
                  65         75         85         95        105        115
S. cerevis    aagtataagc aatttataca gtgaaactgc gaatggctca ttaaatcagt tatcgtttat ....|....| ....|....| ....|....| ....|....| ....|....| ....|....|
                 125        135        145        155        165        175
S. cerevis    ttgatagttc ctttactaca tggtataacc gtggtaattc tagagctaat acatgcttaa ....|....| ....|....| ....|....| ....|....| ....|....| ....|....|
                 185        195        205        215        225        235
S. cerevis    aatctcgacc ctttggaaga gatgtattta ttagataaaa aatcaatgtc ttcgcactct ....|....| ....|....| ....|....| ....|....| ....|....| ....|....|
                 245        255        265        275        285        295
S. cerevis    ttgatgattc ataataactt ttcgaatcgc atggccttgt gctggcgatg gttcattcaa ....|....| ....|....| ....|....| ....|....| ....|....| ....|....|
                 305        315        325        335        345        355
S. cerevis    atttctgccc tatcaacttt cgatggtagg atagtggcct accatggttt caacgggtaa ....|....| ....|....| ....|....| ....|....| ....|....| ....|....|
                 365        375        385        395        405        415
S. cerevis    cggggaataa gggttcgatt ccggagaggg agcctgagaa acggctacca catccaagga ....|....| ....|....| ....|....| ....|....| ....|....| ....|....|
                 425        435        445        455        465        475
S. cerevis    aggcagcagg cgcgcaaatt acccaatcct aattcaggga ggtagtgaca ataaataacg ....|....| ....|....| ....|....| ....|....| ....|....| ....|....|
                 485        495        505        515        525        535
S. cerevis    atacagggcc cattcgggtc ttgtaattgg aatgagtaca atgtaaatac cttaacgagg ....|....| ....|....| ....|....| ....|....| ....|....| ....|....|
                 545        555        565        575        585        595
S. cerevis    aacaattgga
```

FIG. 12D-2

V2 region (SEQ ID NO: 325)

```
S. cerevis                                                                    t ....|....| ....|....| ....|....| ....|....| ....|....| ....|....|
                605        615        625        635        645        655
S. cerevis    attaaagttg ttgcagttaa aaagctcgta gttgaacttt gggcccggtt ggccggtccg ....|....| ....|....| ....|....| ....|....| ....|....| ....|....|
                665        675        685        695        705        715
S. cerevis    atttttcgt gtactggatt tccaacgggg cctttccttc tggctaacct tgagtccttg ....|....| ....|....| ....|....| ....|....| ....|....| ....|....|
                725        735        745        755        765        775
S. cerevis    tggctcttgg cgaaccagga cttttacttt gaaaaaatta gagtgttcaa agcaggcgta ....|....| ....|....| ....|....| ....|....| ....|....| ....|....|
                785        795        805        815        825        835
S. cerevis    ttgctcgaat atattagcat
```

V3 region (SEQ ID NO: 326)

```
                         ....|....| ....|....| ....|....| ....|....| ....|....|
                            805        815        825        835
S. cerevis               t ggaataatag aataggacgt ttggttctat tttgttggtt ....|....| ....|....| ....|....| ....|....| ....|....| ....|....|
                845        855        865        875        885        895
S. cerevis    tctaggacca tcgtaatgat taatagggac
```

V4 region (SEQ ID NO: 327)

```
                                     ....|....| ....|....| ....|....|
                                        1005       1015
S. cerevis                            t ggtaccgtcg tagtcttaac ....|....| ....|....| ....|....| ....|....| ....|....| ....|....|
                1025       1035       1045       1055       1065       1075
S. cerevis    cataaactat gccgactaga tcgggtggtg ttttttaat gacccactcg gtaccttacg ....|....| ....|....| ....|....| ....|....| ....|....| ....|....|
                1085       1095       1105       1115       1125       1135
S. cerevis    agaaatcaaa gtctttgggt
```

V5 region (SEQ ID NO: 328)

```
                                     ....|....| ....|....| ....|....|
                                        1355       1365       1375
S. cerevis                            t gctagcattt gctggttatc cacttcttag ....|....| ....|....| ....|....| ....|....| ....|....| ....|....|
                1385       1395       1405       1415       1425       1435
S. cerevis    agggactatc ggtttcaagc cgatggaagt ttgaggcaat aacaggtctg tgatgccctt ....|....| ....|....| ....|....| ....|....| ....|....| ....|....|
                1445       1455       1465       1475       1485       1495
S. cerevis    agaacgttct
```

Fig. 14A-1     Fig. 14A-2     Fig. 14B
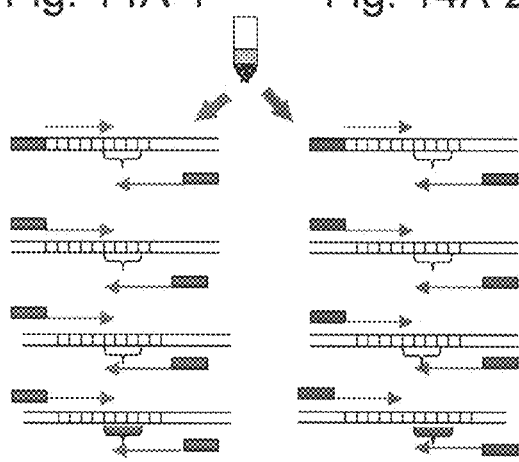

COMPOSITIONS, PRODUCTS, METHODS AND SYSTEMS TO MONITOR WATER AND OTHER ECOSYSTEMS

RELATED APPLICATIONS

This application is a continuation-in-part of currently pending U.S. patent application Ser. No. 11/716,450, filed on Mar. 9, 2007, and U.S. patent application Ser. No. 11/716,895, filed Mar. 12, 2007, which are both divisional applications of U.S. patent application Ser. No. 11/071,849 filed Mar. 3, 2005, now U.S. Pat. No. 7,214,492, which is a continuation-in-part of U.S. patent application Ser. No. 10/131,618, filed Apr. 24, 2002 now abandoned; and is also a continuation-in-part of U.S. patent application Ser. No. 11/527,129, filed on Sep. 26, 2006, which is a continuation of U.S. patent application Ser. No. 10/131,618, filed Apr. 24, 2002 now abandoned. The disclosures of U.S. patent application Ser. No. 10/131,618, U.S. patent application Ser. No. 11/071,849, patent application Ser. No. 11/716,450, and patent application Ser. No. 11/716,895 are hereby incorporated by reference in their entireties.

FEDERAL FUNDING

Parts of this work were supported by federal funding in the form of a Cooperative Agreement #82946501 with the Environmental Protection Agency to C. Neal Stewart, Vincent C. Henrich and Parke A. Rublee, an Environmental Protection Agency STAR Grant #R831627 to Parke A. Rublee, and a Small Business Innovation Research Grant awarded to Michael Marshall by the U.S Environmental Protection Agency. Thus, the government may have rights in this invention.

FIELD OF THE INVENTION

The present invention relates to compositions, products, methods and systems to monitor water and other ecosystems for parameters of interest.

BACKGROUND

Human development can result in chemicals, waste, and/or agricultural runoff being introduced into the ecosystem. Increases in population may lead to over-harvesting of marine resources, landscape alterations that alter the ecosystem, and the introduction of living and non-living contaminants into the ecosystem (Mallin, M. A, et al. 2000, *Marine Pollution Bulletin*, 41:56-75). Additionally, as the threat of bioterrorist activities has become evident in recent years, concern about the vulnerability of ecosystems such as municipal water supplies to deliberate contamination has grown.

For example, water and/or other ecosystems may be contaminated with heavy metals, such as mercury. Such contamination may enter water supplies through natural deposit erosion, factory and refinery discharges, landfill/cropland runoffs, and coal power plant emissions. Most of the mercury in lakes and sediments exists in the more reactive inorganic mercuric form Hg(II), which can be effectively transported across microbial membranes and subsequently converted to organic mercury compounds, or methyl mercury (MeHg) (Morel et al., 1998, *Ann. Rev. Ecol. Syst.* 29:543-66.). Although the conversion of inorganic mercury to organic mercury may occur under aerobic conditions, it is predominantly due to dissimilatory sulfate or iron reducing bacteria under anoxic conditions (Kerin et al., 2006, *Appl. Environ. Microbiol.* 72:7912-7921). MeHg is a highly toxic compound and may constitute up to 20% or more of the total mercury concentration in sediments (Osborne, et al., 1997, *FEMS Microbiol. Rev.* 19:239-262; Nascimento and Chartone-Souza, 2003, *Genet. Mol. Res.*, 2:92-101). Since mercury can accumulate in living tissues, its concentration tends to be greater at higher trophic levels of the natural food chain. Consequently, ongoing, low-level consumption of mercury-laden food poses a chronic health risk to humans. Other contaminants may be equally as problematic.

Reservoirs, recreational lakes, and coastal areas can be difficult to secure against accidental or intentional contamination. Further, the contamination of a water source has the propensity to impact a relatively large population, and water filtration systems may not sufficiently alleviate the threat. Also troubling is the lack of a real-time test to detect the agents that are most likely to contaminate water supplies. The turnaround times for culturing microbes and/or obtaining chemical test results is slow enough that consumption of contaminated water may occur before the test results are known. Also, the expense involved in frequent monitoring of the water supply with currently available laboratory tests can be prohibitive.

As yet, there has not been a large-scale, deliberate contamination of a municipal water source. However, sporadic and relatively confined natural contaminations have demonstrated the importance in being able to monitor the water supply. The number of outbreaks attributable to contaminated drinking water supplies more than doubled in 1999-2000 over the previous two-year period, with contamination of well water also on the rise. In addition, recreational water sources have also reported significant increases in contamination (Bowman, 2002, Outbreaks of waterborne illnesses on the rise in US, *Scripps-Howard News Service*, Nov. 23, 2002). These incidents of water contamination were exacerbated by the difficulty in pinpointing the cause of the outbreak and subsequent misdiagnosis of the symptoms, illustrating the importance of "early warning" diagnostics of water supplies.

A number of microbial genome sequencing projects have been initiated to characterize pathogenic organisms. Although identification and characterization of genomic sequence data for individual pathogens may provide for the identification of specific microbes, such targeted testing fails to provide a comprehensive, economically feasible system for monitoring ecosystems of interest, such as municipal water supplies. The accuracy of a molecular diagnostic test for a microbe may be compromised where the pathogenic agent is endemic, or possesses substantial genetic similarity to non-pathogenic organisms (Leff et al., 1995, *Appl. Environ. Microbiol.*, 61:1634-1636; Xiao et al, 1999, *Appl Environ. Microbiol.*, 65:3386-3391). Also, although some putative contaminants of water have been identified, anticipating all possible contaminants is not feasible, and thus, specific tests are inherently limited.

Thus, there is a need for devices and methods that enable real-time monitoring of water supplies and other ecosystems of interest. The monitoring system should allow for detection of known, as well as unknown, contaminants. The monitoring system should be available in a format that is accessible for routine monitoring, as well as for rapid testing in response to a specific event.

SUMMARY

The present invention provides compositions, products, methods and systems for monitoring aquatic ecosystems and other ecosystems. The present invention may be embodied in a variety of ways.

In certain embodiments, the present invention comprises a composition comprising an isolated oligonucleotide, wherein the nucleic acid sequence of the isolated oligonucleotide is specific to a single operational taxonomic unit in an ecosystem, and wherein the oligonucleotide comprises a bioindicator for one or more parameters in an ecosystem. In some embodiments, the ecosystem is an aquatic ecosystem. In some embodiments, the parameter is the presence or absence, or level of mercury in the ecosystem.

In other embodiments, the present invention comprises a product for monitoring an ecosystem, the product comprising an isolated oligonucleotide, wherein the nucleic acid sequence of the isolated oligonucleotide is specific to a single operational taxonomic unit in an ecosystem, and wherein the oligonucleotide comprises a bioindicator for one or more parameters in an ecosystem. In some embodiments, the ecosystem is an aquatic ecosystem. In certain embodiments, the product comprises a plurality of individual locations, the plurality of locations each comprising an oligonucleotide having a nucleic acid sequence that is derived from a single operational taxonomic unit in the ecosystem. For example, one embodiment of the present invention comprises an array for monitoring an ecosystem for a parameter such as the presence or absence of mercury, the array comprising a plurality of oligonucleotides immobilized at known locations on a substrate, such that the array comprises a plurality of locations each having at least one oligonucleotide having a sequence derived from a single, predetermined microbial operational taxonomic unit (OTU).

Another embodiment of the present invention may comprise a method to identify a bioindicator for an ecosystem. In some embodiments, the ecosystem is an aquatic ecosystem. The method may comprise the step of isolating a plurality of distinct DNA molecules from an ecosystem. The method may further comprise determining the sequence of at least some of the plurality of DNA molecules. Also, the method may comprise grouping the DNA sequences into operational taxonomic units; and identifying at least one nucleic acid sequence that is specific to a single operational taxonomic unit in the ecosystem. The method may also comprise correlating detection of a nucleic acid sequence that is specific to a single operational taxonomic unit to a parameter of the ecosystem, such that the nucleic acid sequence specific to the single operational taxonomic unit comprises a bioindicator of the parameter in an ecosystem.

Yet other embodiments of the present invention comprise methods for monitoring an ecosystem for one or more parameters of interest. In some embodiments, the ecosystem is an aquatic ecosystem. For example, in some embodiments, the present invention may comprise a method to monitor a parameter of an ecosystem comprising the step of obtaining a sample from an ecosystem. The method may also comprise using an oligonucleotide specific to a single operational taxonomic unit to determine whether a nucleic acid sequence specific to the operational taxonomic unit is present in the sample, and correlating detection of the nucleic acid sequence specific to the operational taxonomic unit to a parameter of the ecosystem.

Yet other embodiments may comprise a system for monitoring an ecosystem for one or more parameters of interest. The system may, in some embodiments, comprise a device for analysis of bioindicator profiles related to the one or more parameters of interest.

In some embodiments, the compositions, products, methods and systems of the present invention may comprise a bioindicator that provides information about a parameter of the ecosystem. In certain embodiments, the parameter may comprise the presence or absence of mercury, or the levels of mercury in the ecosystem. For example, certain embodiments of the compositions, products, methods, and systems of the present invention may comprise an isolated oligonucleotide having the sequence as set forth in SEQ ID NO: 329-SEQ ID NO: 340 or SEQ ID NO: 351-SEQ ID NO: 370, or the sequence as set forth in SEQ ID NO: 341-SEQ ID NO: 350 or SEQ ID NO: 371-SEQ ID NO: 388, wherein the oligonucleotide is a bioindicator for the presence or absence of mercury, or the levels of mercury in the ecosystem. Or the bioindicator may be specific for the presence and/or absence or levels of any other physical (e.g. temperature, pressure), chemical (e.g. alkalinity, pH, element or compound), or biological component (e.g. a virus, a bacterium, an algae, a protozoan, a fungus, or another flora or fauna) or characteristic of the ecosystem.

There may be certain advantages that may be realized with various embodiments of the present invention. By using compositions, products, methods and systems comprising nucleic acid sequences that are specific to microbial operational taxonomic units (OTUs) that are correlated with a parameter such as the presence or absence of mercury or other parameters, a wide variety of microbial taxa may be characterized in various ecosystems. Thus, the compositions, products, methods and systems of the present invention may provide a single test that provides substantially comprehensive information on community structure.

The compositions, products, methods and systems of the present invention may, in certain embodiments, provide quantitative data. For example, by using quantifiable labels to label individual samples, or to differentially label specific sequences in a single sample, the techniques of the present invention may provide information on the abundance of specific organisms of interest, such as key bioindicators, pathogens, or microbial contaminants in a water system.

Also, the compositions, products, methods and systems of the present invention, if applied to a number of samples over time, may be able to indicate the "trajectory" of the ecosystem as either improving or degrading, where probes associated with contamination of the ecosystem of interest with mercury and/or other contaminants are monitored.

For example, microorganisms generally respond rapidly to environmental changes. The compositions, products, methods and systems of the present invention may therefore provide results in near "real-time" (i.e., within hours) of an event occurring, such as a contamination of the ecosystem with mercury. Thus, the compositions, products, methods and systems of the present invention may detect changes in ecosystem perturbations early, so that potential problems may be quickly rectified.

There may be a large number of microorganisms specific to any one ecosystem of interest, such as a specific body of water. Also, the prevalence of particular microorganisms may vary depending upon the water source. Still, by prudent selection of the nucleic acid sequences used as part of the compositions, products, methods and systems of the present invention, it may be possible to detect and monitor a plurality of microorganisms that are specific to certain ecosystem parameters. Thus, once developed, the compositions, products, methods and systems of the present invention can be a highly cost-effective way to monitor a variety of ecosystems. Also, the compositions, products, methods and systems of the present invention may be easily modified and expanded to include new targets of interest as they are identified.

A microbial community may be affected by biological changes, physical changes, or chemical changes to the environment. Because the compositions, products, methods and systems of the present invention can provide a measure of the microbial community, the techniques of the present invention may be sensitive to a wide variety of changes that may occur as a result of changes in the ecosystem of interest.

The present invention may be better understood by reference to the description and figures that follow. It is to be understood that the invention is not limited in its application to the specific details as set forth in the following description and figures. The invention is capable of other embodiments and of being practiced or carried out in various ways.

BRIEF DESCRIPTION OF THE FIGURES

The file of this patent contains at least one drawing executed in color. Copies of this patent or patent application publication with color drawing(s) will be provided by the Office upon request and payment of the necessary fee. The present invention may be better understood by reference to the following figures.

FIG. 12 illustrates the sequences from prokaryotic rDNA (Panels A-1 and A-2), eukaryotic rDNA (Panels B-1 and B-2), prokaryotic variable regions (Panels C-1 and C-2), and prokaryotic variable regions (Panels D-1 and D-2), in accordance with an embodiment of the present invention.

FIG. 14 shows a schematic diagram of amplification and labeling of two DNA samples for array analysis with universal primers for 16S rDNA or 18S rDNA (Panel A); and results of one hybridization experiment (Panel B), where the eukaryotic and prokaryotic PCR products are detected on the microarray, in accordance with an embodiment of the present invention.

DETAILED DESCRIPTION

Figure 1:
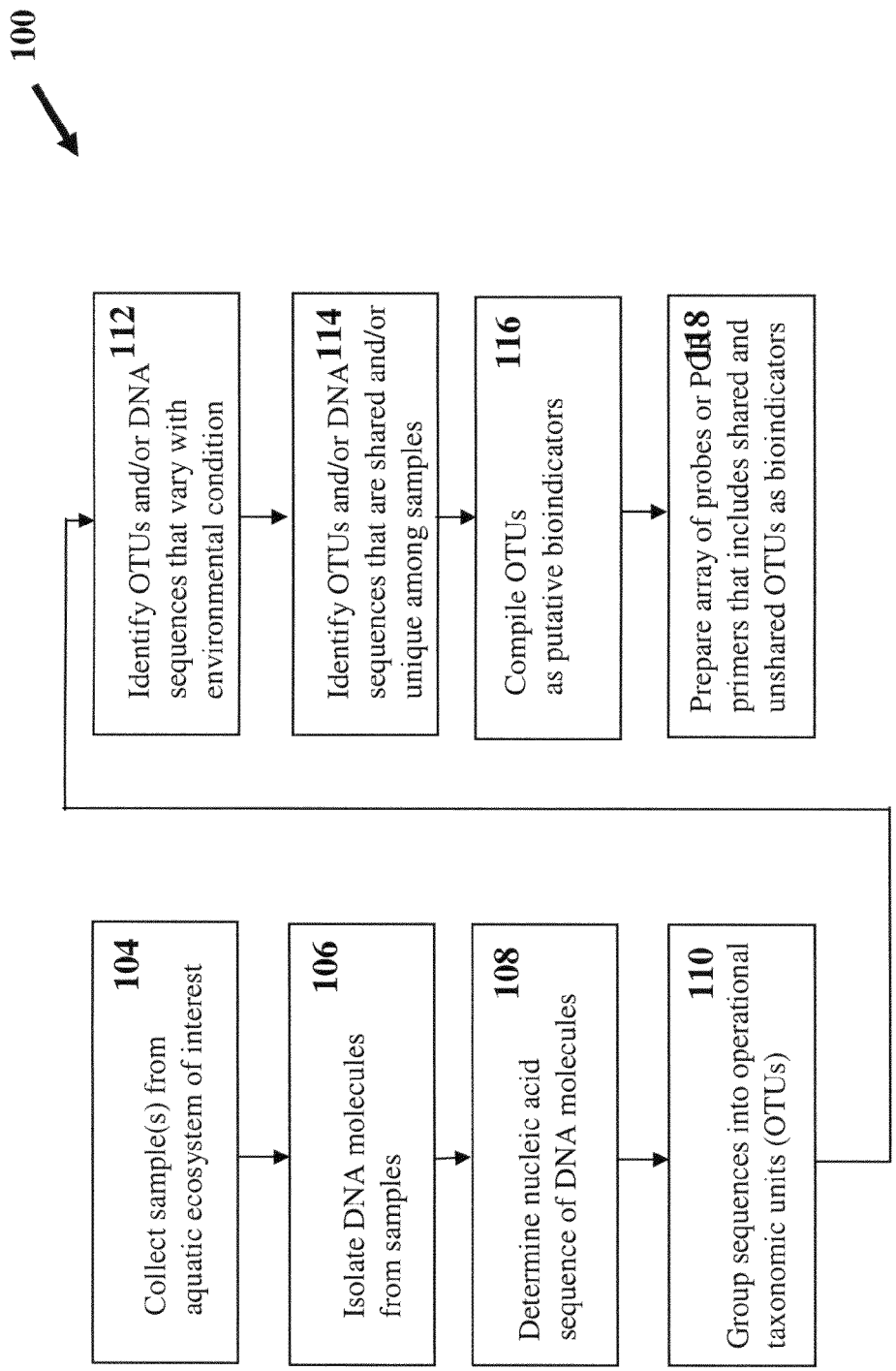
FIG. 1 shows a method for identification of a bioindicator and use of such bioindicators to monitor ecosystems in accordance with an example embodiment of the present invention.

Ecogenomics is the recovery, characterization, and analysis of genomes recovered from organisms living in the natural environment. Metagenomics is the recovery, characterization, and analysis of all, or at least a plurality, of the genomes of a community of organisms living in natural or artificial environments. Embodiments of the present invention utilize ecogenomics and metagenomics to develop nucleic acid based compositions, products, methods and systems for monitoring water supplies and other ecosystems. In certain embodiments, the nucleic acid based compositions, products, methods and systems for monitoring water supplies and other ecosystems comprise bioindicators for a parameter or parameters of an ecosystem.

Thus, embodiments of the present invention provide compositions, products, methods, and systems to monitor ecosystems. In at least some embodiments, the compositions, products, methods, and systems of the present invention comprise a bioindicator for one or more parameters of the ecosystem. For example, in certain embodiments, the bioindicator is informative about either the presence or absence of mercury, or the levels of mercury in the ecosystem. Or the bioindicator may be informative about the presence and/or absence or levels of any other physical (e.g. temperature, pressure), chemical (e.g. alkalinity, pH, element or compound), or biological component (e.g. viruses, bacteria, alga, protozoan, fungus, or other flora or fauna) or characteristic of the ecosystem.

The compositions, products, methods, and systems of the present invention may be used to monitor aqueous (i.e., aquatic) ecosystems such as a natural or anthropogenic body of water. Or, other aqueous, terrestrial and/or atmospheric ecosystems may be monitored. Thus, a variety of ecosystems may be monitored using the compositions, methods, products and systems of the present invention. In one embodiment, the ecosystem may comprise an aquatic ecosystem, such as a body of water. For example, the ecosystem may be a lake. Additionally or alternatively, the ecosystem may be an estuary, a tidal pool, a wetland, a stream, a river, ground-water, runoff water, flood water, standing water, wells, water distribution systems, and/or marine system. Or, the sample may be isolated from other ecosystems, e.g., terrestrial or atmospheric. Such aqueous, terrestrial and/or atmospheric ecosystems may comprise a variety of components, such as, but not limited to, soil, air, air venting systems and the atmosphere.

Where the ecosystem of interest comprises water, the parameter comprising at least part of the ecosystem may relate to the quality of the water. Thus, the parameter may relate to a quality that is important to evaluate if the water is suitable for drinking, cooking, bathing, agriculture, or other uses of water.

The bioindicator may comprise a biological system, such as a microorganism, or a molecule, such as a nucleic acid sequence, that changes in response to a parameter that is related to the ecosystem of interest. The bioindicators may comprise known microorganisms or unknown microorganisms. Rather than measuring the microorganism itself, embodiments of the present invention provide molecular bioindicators to monitor ecosystems of interest.

A bioindicator for the analysis of an ecosystem of interest may comprise an isolated nucleic acid having a sequence derived from a single operational taxonomic unit (OTU). In certain embodiments, the OTU is a microbial OTU. In certain embodiments, the OTU is associated with a known microbe. Or, the OTU may be associated with an unknown microbe(s). In other embodiments, the OTU is specific to other species (e.g., flora or fauna) that may be present in an ecosystem.

For each of the compositions, products, methods and systems of the present invention, at least some of the operational taxonomic units may utilize variable ribosomal DNA (rDNA) sequences as a means to detect specific organisms. For example, in certain embodiments, the OTU-specific oligonucleotides (e.g., primers and/or probes) may comprise eukaryotic ribosomal DNA sequences, and/or prokaryotic ribosomal DNA sequences. Additionally or alternatively, OTU-specific oligonucleotides may comprise pathogen-specific sequences. Additionally, or alternatively, the OTU-specific oligonucleotides may comprise novel sequences from as yet unidentified microbes.

In certain embodiments, the present invention may comprise an isolated oligonucleotide for use in monitoring an ecosystem, wherein the oligonucleotide is specific to a single operational taxonomic unit (OTU) in at least one ecosystem, and wherein the oligonucleotide is a bioindicator for one or more parameters of the ecosystem. In one embodiment, the ecosystem is an aquatic ecosystem. In other embodiments, terrestrial or atmospheric ecosystems may be monitored. For example, in certain embodiments, the present invention may comprise an isolated oligonucleotide for use in monitoring an aquatic ecosystem, wherein the oligonucleotide is specific to a single operational taxonomic unit (OTU) in at least one aquatic ecosystem, and wherein the oligonucleotide is a bioindicator for one or more parameters of the aquatic ecosystem. In certain embodiments, the parameter is the level of mercury. For example, where the ecosystem parameter is mercury, the isolated oligonucleotide may comprise the sequence as set forth in SEQ ID NO: 329-SEQ ID NO:340 or SEQ ID NO: 351-SEQ ID NO: 370, or the sequence as set forth in SEQ ID NO: 341-SEQ ID NO: 350 or SEQ ID NO: 371-SEQ ID NO: 388, or fragments of these sequences. Or, other oligonucleotides, identical to any one of SEQ ID NO: 5-SEQ ID NO: 113, or the reverse complement of SEQ ID NO: 5-SEQ ID NO: 113, and/or SEQ ID NO: 114-SEQ ID NO: 316, or a fragments of these sequences, may be used for detection of other parameters. Or a plurality (e.g., 2, 3, 4, 5, 6, 10, 15, 20, 25, 30, 35, 40, 50, 75, 100, or more than 100) of such oligonucleotides may be used.

In certain embodiments, the present invention comprises a composition comprising an isolated oligonucleotide, wherein the nucleic acid sequence of the isolated oligonucleotide is specific to a single operational taxonomic unit in an ecosystem, and wherein the oligonucleotide comprises a bioindicator for one or more parameters in an ecosystem. In an embodiment, the ecosystem is an aquatic ecosystem. Or, other ecosystems such as terrestrial or atmospheric ecosystems may be monitored. Thus, in certain embodiments, the present invention comprises a composition comprising an isolated oligonucleotide, wherein the nucleic acid sequence of the isolated oligonucleotide is specific to a single operational taxonomic unit in an aquatic ecosystem, and wherein the oligonucleotide comprises a bioindicator for one or more parameters in the aquatic ecosystem. In some embodiments, the parameter is the presence or absence, or the levels of mercury in the ecosystem. Or, the oligonucleotide may be a bioindicator for other parameters of the ecosystem. Where the parameter of interest is mercury, the isolated oligonucleotide may comprise the sequence as set forth in SEQ ID NO: 329-SEQ ID NO: 340 or SEQ ID NO: 351-SEQ ID NO: 370, or the sequence as set forth in SEQ ID NO: 341-SEQ ID NO: 350, or SEQ ID NO: 371-SEQ ID NO: 388, or fragments of these sequences. Or, other oligonucleotides, identical to any one of SEQ ID NO: 5-SEQ ID NO: 113, or the reverse complement of SEQ ID NO: 5-SEQ ID NO: 113, or SEQ ID NO: 114-SEQ ID NO: 316, or a fragments of these sequences may be used for detection of other parameters.

In certain embodiments, the compositions of the present invention may comprise a plurality of oligonucleotides that are each individually specific to a single operational taxonomic unit. For example, in alternate embodiments, the compositions of the present invention may comprise 2, 3, 4, 5, 6, 10, 16, 20, 25, 30, 36, 40, 50, 75, 100, or more than 100 of each of these oligonucleotides. Thus, in certain embodiments, the composition may comprise two distinct oligonucleotides, the two distinct oligonucleotides each comprising at least one of the sequences as set forth in SEQ ID NO: 341-SEQ ID NO: 350 or SEQ ID NO: 371-SEQ ID NO: 388. Additionally or alternatively, the composition may comprise two distinct oligonucleotides, the two distinct oligonucleotides each comprising at least one of the sequences as set forth in SEQ ID NO: 114-SEQ ID NO: 316. In some embodiments, the two oligonucleotides are derived from a single genomic target sequence such that the two oligonucleotides can be used as primers in a polymerase chain reaction to amplify DNA from the genomic target sequence. For example, in certain embodiments, the composition may comprise at least 2, 4, 6, 10, 20, 30, 40, 50, 80, or 100, distinct oligonucleotides each comprising one of the sequences as set forth in SEQ ID NO: 341-SEQ ID NO: 350 or SEQ ID NO: 371-SEQ ID NO: 388, or SEQ ID NO: 114 to SEQ ID NO: 316, or fragments of these sequences, wherein the oligonucleotides can be used as primers in a polymerase chain reaction to amplify DNA from a plurality of genomic target sequences. Such primer mixes may be used, for example, for multiplex PCR of DNA samples from ecosystems of interest.

In certain embodiments, the present invention comprises a product for monitoring an ecosystem, the product comprising an isolated oligonucleotide, wherein the nucleic acid sequence of the isolated oligonucleotide is specific to a single operational taxonomic unit (OTU) in an ecosystem, and wherein the oligonucleotide comprises a bioindicator for one or more parameters in an ecosystem. In an embodiment, the ecosystem is an aquatic ecosystem. Or, other ecosystems such as terrestrial or atmospheric ecosystems may be monitored. For example, in certain embodiments, the present invention comprises a product for monitoring an ecosystem, the product comprising an isolated oligonucleotide, wherein the nucleic acid sequence of the isolated oligonucleotide is specific to a single operational taxonomic unit (OTU) in an aquatic ecosystem, and wherein the oligonucleotide comprises a bioindicator for one or more parameters in an aquatic ecosystem. In an embodiment, the OTU is a microbial OTU. Or, OTUs from other sources (e.g., flora or fauna) may be used.

The product may comprise a single oligonucleotide that is specific to an OTU (an OTU-specific oligonucleotide) or may include multiple distinct OTU-specific oligonucleotides. As used herein, a distinct oligonucleotide is a oligonucleotide that has a different sequence than another oligonucleotide. Where the product comprises multiple OTU-specific oligonucleotides, the product may comprise individual locations for each of the OTU-specific oligonucleotides. For example, the product may comprise a plurality of individual locations, the plurality of locations each comprising a distinct oligonucleotide having a nucleic acid sequence that is derived from a single operational taxonomic unit in the ecosystem. In an embodiment, there is a plurality (i.e., more than one) of identical oligonucleotides at each location. Thus, the product may comprise a plurality of oligonucleotides each having the same sequence all located at a single location, but the different locations have oligonucleotides that have different sequences. For example, as discussed in more detail herein, such a product may comprise chip with a plurality of dried primer pairs or probes spotted as an array (e.g., nanoarray), a multiwell plate, or a collection of primer sets in individual tubes.

In at least some embodiments, at least one of the oligonucleotides of the product is a bioindicator for at least one parameter associated with the ecosystem. In certain embodiments, the bioindicator is informative about either the presence or absence of mercury, or the levels of mercury in the ecosystem. For example, in certain embodiments, the products of the present invention may comprise an isolated oligonucleotide having the sequence as set forth in SEQ ID NO: 329-SEQ ID NO: 340 or SEQ ID NO: 351-SEQ ID NO: 370, or the sequence as set forth in SEQ ID NO: 341-SEQ ID NO: 350 or SEQ ID NO: 371-SEQ ID NO: 388, or fragments of these sequences, where the oligonucleotide is a bioindicator for the presence or absence of mercury, or the levels of mercury in the ecosystem. Or the bioindicator may be specific for the presence and/or absence or levels of any other physical (e.g. temperature, pressure), chemical (e.g. alkalinity, pH, element or compound), or biological component (e.g. a virus, a bacterium, an algae, a protozoan, a fungus, or another flora or fauna) or characteristic of the ecosystem. Thus, the product may comprise other oligonucleotides, identical to any one of SEQ ID NO: 5-SEQ ID NO: 113, or the reverse complement of SEQ ID NO: 5-SEQ ID NO: 113, or SEQ ID NO: 114-SEQ ID NO: 316, or a fragments of these sequences for detection of other ecosystem parameters. Or a plurality (e.g., 2, 3, 4, 5, 6, 10, 15, 20, 25, 30, 35, 40, 50, 75, 100, or more than 100) of such oligonucleotides may be used.

The bioindicators of the present invention may be used to monitor water. Or, other aqueous, terrestrial or atmospheric ecosystems as described herein may be monitored.

In certain embodiments, the product may comprise the use of PCR amplification to detect nucleic acid sequences that are specific to a bioindicator OTU. For example, in certain embodiments, at least one the locations of the product comprises an oligonucleotide having the sequence as set forth in SEQ ID NO: 114-SEQ ID NO: 316, SEQ ID NO: 341-SEQ ID NO:350 or SEQ ID NO: 371-SEQ ID NO: 388. Or, fragments of these sequences may be used. In some embodiments, at least one of the locations comprises two oligonucleotides, the two oligonucleotides each comprising one of the sequences as set forth in SEQ ID NO: 114-SEQ ID NO: 316, SEQ ID NO: 341-SEQ ID NO: 350 or SEQ ID NO: 371-SEQ ID NO: 388, and wherein the two oligonucleotides at each location are derived from a single genomic target sequence such that the two oligonucleotides can be used as primers in a polymerase chain reaction to amplify DNA from the genomic target sequence. Or, the product may have a plurality of locations each comprising two oligonucleotides, the two oligonucleotides each comprising one of the sequences as set forth in SEQ ID NO: 114-SEQ ID NO: 316, SEQ ID NO: 341-SEQ ID NO: 350 or SEQ ID NO: 371-SEQ ID NO: 388. In certain embodiments, the primers are derived from variable regions of ribosomal DNA (rDNA).

In certain embodiments, the product is used to detect nucleic acid sequences that are specific to a bioindicator OTU by real-time PCR and/or quantitative PCR. For example, in certain embodiments, the product may comprise a plurality of primer sets at individual locations (e.g., assay wells or primers applied to a location on a substrate), where a primer set is two primers that can amplify a single genomic sequence. A sample from an ecosystem as well as PCR reagents and a *Thermus aquaticus* (Taq) polymerase enzyme may then be added at the location and the mixture subjected to thermal conditions such that PCR amplification can occur. In an embodiment, the production of a PCR product may be monitored using a dye (e.g., MOLECULAR PROBES SYBR® Green dye) that can intercalate in the double-stranded PCR product thereby indicating whether amplification has occurred, and in some embodiments, providing a level of amplification. As a PCR product labeled in this fashion will accumulate as the reaction proceeds, a growth curve can be generated in real time indicating the fluorescence signal that is produced by the PCR product.

In other embodiments, the product may comprise individual locations, wherein each location comprises a distinct OTU-specific oligonucleotide probe, and wherein the OTU-specific oligonucleotide probes comprise bioindicator sequences in at least one ecosystem. For example, in certain embodiments, the product may have at least one location that comprises an oligonucleotide comprising the sequence as set forth in SEQ ID NO: 329-SEQ ID NO: 340 or SEQ ID NO: 351- to SEQ ID NO: 370, or a fragment thereof, for the detection of mercury in an ecosystem. Or, the bioindicator may comprise a sequence identical to any one of SEQ ID NO: 5-SEQ ID NO: 113, or the complement of SEQ ID NO: 5-SEQ ID NO: 113, or a fragment thereof, for the detection of other ecosystem parameters.

In alternate embodiments, the product comprises a plurality of OTU-specific oligonucleotides. The plurality of OTU-specific oligonucleotides may comprise at least 2, or 3, or 4, or 5, or 6, or 10, or 16, or 20, or 24, or 30, or 40, or 50, or 75, or 100 distinct nucleic acid sequences included as part of the product.

The product or the present invention may comprise immobilization of the OTU-specific oligonucleotides at each of the locations. Immobilization of the OTU-specific oligonucleotides may utilize a variety of methods. For example, in certain embodiments, immobilization comprises formation of a chemical bond between the oligonucleotide at each location and a substrate comprising at least part of the location. Such chemical bonds may be formed by the use of chemical reagents or UV-induced cross-linking of the DNA to a substrate. Alternatively and/or additionally, immobilization may comprise evaporation of a plurality of solutions at each of the locations, wherein each of the solutions comprises the oligonucleotide to be immobilized at each of the locations. Or other methods known in the art may be used.

Thus, embodiments of the present invention may comprise arrays of oligonucleotides for monitoring an ecosystem of interest. For example, one embodiment of the present invention comprises a device comprising an array having a plurality of oligonucleotides located at known locations on a substrate, such that each location on the array comprises an oligonucleotide having a sequence that is derived from a single, predetermined microbial operational taxonomic unit (OTU). In at least some embodiments, at least one sequence on the array is a bioindicator for at least one specific parameter associated with the ecosystem. For example, in certain embodiments, the bioindicator is informative about either the presence or absence of mercury, or the levels of mercury in the ecosystem. Or, the bioindicator may be specific for other parameters. For example, in an embodiment the present invention comprises a device for monitoring water quality comprising an array, wherein the array comprises a plurality of oligonucleotides immobilized at known locations on a substrate, and wherein each location on the array comprises an oligonucleotide having a sequence that is derived from a single, predetermined microbial operational taxonomic unit (OTU), and wherein at least one sequence is associated with the presence or absence of mercury, and/or mercury levels in the ecosystem.

In other embodiments, the present invention comprises methods to identify a bioindicator. In this embodiment, the present invention may comprise a method to identify microbes that are able to modify, or adjust to, a particular ecosystem. In an embodiment, the ecosystem is an aquatic ecosystem. Or, other ecosystems such as terrestrial or atmospheric ecosystems may be monitored. In some embodiments, the ecosystem of interest comprises an ecosystem being monitored for the presence or absence of mercury.

The method to identify a bioindicator may comprise the steps of: (a) isolating a plurality of distinct DNA molecules from an ecosystem; (b) determining the sequence of at least some of the plurality of DNA molecules; (c) grouping the DNA sequences into operational taxonomic units; and (d) identifying at least one nucleic acid sequence that is specific to a single operational taxonomic unit in the ecosystem. The method may further comprise correlating detection of the nucleic acid sequence specific to the single operational taxonomic unit (OTU) to a parameter of the ecosystem, such that the nucleic acid sequence specific to the single operational taxonomic unit comprises a bioindicator of the parameter in the ecosystem. In an embodiment, the ecosystem is an aquatic ecosystem. Or, other ecosystems such as terrestrial or atmospheric ecosystems may be monitored. Thus, in certain embodiments, the method to identify a bioindicator may comprise the steps of: (a) isolating a plurality of distinct DNA molecules from an aquatic ecosystem; (b) determining the sequence of at least some of the plurality of DNA molecules; (c) grouping the DNA sequences into operational taxonomic units; and (d) identifying at least one nucleic acid sequence that is specific to a single operational taxonomic unit in the aquatic ecosystem. The method may further comprise correlating detection of the nucleic acid sequence specific to the single operational taxonomic unit (OTU) to a parameter of the aquatic ecosystem, such that the nucleic acid sequence specific to the single operational taxonomic unit comprises a bioindicator of the parameter in the aquatic ecosystem. In an embodiment, the OTU may comprise a microbial OTU. Or OTUs from other organisms (e.g., flora or fauna) may be used.

Thus, in one embodiment, the present invention may comprise a method for preparing a bioindicator for the analysis of an ecosystem comprising the steps of: preparing a nucleic acid sample comprising a plurality of DNA molecules from an ecosystem; determining the sequence of at least some of the plurality of DNA molecules in the isolated DNA sample; grouping the DNA sequences into operational taxonomic units (OTUs); and associating at least one OTU with an ecosystem parameter of interest. In an embodiment, each associated OTU can be distinguished by the presence of a least one bioindicator DNA sequence that is specific for the single OTU.

In another embodiment, the method may comprise the steps of: (a) identifying a bioindicator that is associated with a particular microbe; (b) identifying the bioindicator in at least one ecosystem; and (c) correlating the presence of the microbe with a parameter specific to the ecosystem. The method may further comprise identifying the nature of the ability of the microbe to modify, or adjust to, the ecosystem. For example, the identification of a microbe whose presence shows an association with a particular toxin may indicate that the microbe has the ability to modify the toxin and/or modify the effect of the toxin on the environment.

In certain embodiments, the ecosystem parameter may be the presence or absence, or levels of mercury in an ecosystem or the levels of mercury in an ecosystem. Or, the bioindicator may provide information about other ecosystem parameters as described herein.

DNA from a variety of ecosystems may be used to develop bioindicators. In one embodiment, the ecosystem may comprise an aquatic (or aqueous) ecosystem, such as a body of water. For example, the ecosystem may be a lake or sea. Additionally or alternatively, the ecosystem may be an estuary, a tidal pool, a wetland, a stream, a river, ground-water, runoff water, flood water, standing water, and/or salt water may be used. Additionally or alternatively, the bioindicator may be isolated from a terrestrial and/or atmospheric ecosystem such as those described herein.

The method may utilize bioindicators that are shared among ecosystems, and/or bioindicators that are specific to one, or a few, ecosystems. Thus, a plurality of bioindicators may be developed. The bioindicators may be used as a means to analyze a variety of ecosystems of interest. In one embodiment, the method may comprise the step of identifying the distribution of at least one of the OTUs in at least two ecosystems of interest.

Once the DNA molecules have been categorized and grouped by OTU, the sequences of the DNA molecules in each of the OTUs may be used to develop the collection of bioindicators as an assay system. Thus, the method may comprise preparing a collection of bioindicators wherein at least one of the OTUs comprises sequences that are unshared between at least two of the ecosystems of interest. Additionally and alternatively, the method may comprise preparing a collection of bioindicators wherein at least one of the OTUs comprises sequences that are shared between at least two of the ecosystems of interest.

The method may also include a step of applying a plurality of oligonucleotide bioindicators at known locations on a substrate to form an array, wherein each oligonucleotide has a sequence that is derived from a single, predetermined microbial operational taxonomic unit (OTU). In some embodiments, the oligonucleotides may be immobilized at these locations as discussed herein.

In certain embodiments, the array may comprise a plurality of oligonucleotides that can be used as probes to detect new bioindicators (e.g., new OTUs or new members of an OTU) in a sample from an ecosystem. In certain embodiments, the oligonucleotides are themselves bioindicators as a result of their ability to detect ecosystem bioindicator nucleic acid sequences.

In certain embodiments of the compositions, products, methods and systems of the present invention, where the OTU-specific oligonucleotides are used as probes to detect a DNA sequence from a sample by hybridization, the oligonucleotides should be of sufficient length to provide specific hybridization to nucleic acid molecules isolated from various ecosystem samples that are used to probe the array. The oligonucleotide probes may be at least 20 nucleotides in length. In alternate embodiments, oligonucleotide probes may range from about 30 to 200, or from 40 to 100, or from 45 to 80 nucleotides in length. Or ranges within these ranges may be used. In one example embodiment, the oligonucleotide probes are each about 50 nucleotides in length. Specific hybridization does not require a perfect match between the oligonucleotide and the ecosystem sample. As used herein, specific hybridization comprises hybridization such that a nucleic acid molecule isolated from the ecosystem of interest hybridizes to a single location (i.e., a single oligonucleotide sequence) on the array. In one embodiment, specific hybridization requires that the mismatch between two nucleic acid molecules is about 2.5% or less under high stringency hybridization conditions, which as described in more detail herein defines the specificity used to define an OTU. This may allow for a mismatch at one or more base pairs for a 50-mer probe.

Also, for detection of bioindicators by hybridization, the amount of the oligonucleotide should be sufficient to allow detection of complementary nucleic acid sequences by hybridization, but in an amount such that background hybridization to unrelated sequences is avoided. For example, where the oligonucleotides are immobilized at a plurality of locations as an array, the oligonucleotides immobilized on the array may range from about 1 femptogram (fg) to about 10 micrograms (μg), or from about 50 fg to about 10 nanograms (ng), or from about 0.5 picograms (pg) to 1,000 pg, or from about 2 pg to 200 pg, or from about 8 pg to about 50 pg, at each location.

Alternatively or additionally, the OTU-specific oligonucleotides may comprise primers for amplification of OTU-specific sequences that function as bioindicators. The primers may be used in a variety of ways.

Also, in certain embodiments of the compositions, products, methods and systems of the present invention, the primers are used in conjunction with probe OTUs such that DNA from an ecosystem sample may be amplified e.g., using PCR, and then the presence or absence of specific bioindicator DNA is detected by hybridization of the PCR products to OTU-specific probes. For example, the PCR product(s) comprising potential bioindicators may be used to probe an array comprising a plurality of oligonucleotides immobilized at known locations on a substrate, and wherein each location on the array comprises an oligonucleotide having a sequence that is derived from a single, predetermined microbial operational taxonomic unit (OTU). The samples that have DNA that hybridizes to certain of the OTU-specific probes on the array may comprise bioindicators that are the same, or that are different members of the OTU that includes the OTU-specific probes on the array. For example, if DNA isolated from the sample hybridizes to a variety of non-shared OTUs, the sample may comprise a new bioindicator(s) that can recognize several of the OTU-specific probes. Or, the sample may comprise bioindicators that are derived from the OTU-specific probes, but that are new members of the OTU.

Thus, in certain embodiments, a plurality of DNA molecules that may be generated from an ecosystem may tested to determine if the molecules are members of a previously characterized OTU, or have a new sequence that is not included in a previously characterized OTU. In this way, new OTU-specific probes may be derived.

Alternatively or additionally in certain embodiments of the compositions, products, methods and systems of the present invention, primer sets may provide for using a plurality of PCR amplification reactions as a means to characterize an ecosystem. For example, in certain embodiments, a plurality of primer sets are provided (e.g., assay wells or primers applied to a location on a substrate), where a primer set is two primers that can amplify a single genomic sequence. A sample from an ecosystem as well as PCR reagents and polymerase enzyme may then be added at the location and the mixture subjected to thermal conditions such that PCR amplification can occur. In an embodiment, the production of a PCR product may be monitored using a dye (e.g., SYBR® Green dye) that can intercalate in the double-stranded PCR product thereby indicating whether amplification has occurred, and in some embodiments, providing the level of PCR amplification.

In certain embodiments of the compositions, products, methods and systems of the present invention, the operational taxonomic units may utilize variable ribosomal DNA (rDNA) sequences as a means to detect specific organisms. Thus, the OTU-specific oligonucleotides (primers and/or probes) may comprise eukaryotic ribosomal DNA sequences, and/or prokaryotic ribosomal DNA sequences. Additionally, or alternatively, the OTU-specific oligonucleotides may comprise pathogen-specific sequences. Additionally, or alternatively, the OTU-specific oligonucleotides may comprise novel sequences from as yet unidentified microbes.

Once a collection of OTU-specific oligonucleotides has been generated, DNA isolated from an ecosystem sample of interest may be used to probe a product comprising a plurality of primers and/or probes comprising nucleic acid sequences that are specific to organisms of interest. In one embodiment, detection of bioindicator sequences in the sample may be evaluated to determine how the presence and/or absence of the bioindicator may correlate with a parameter of the ecosystem. In one embodiment, the parameter may comprise the presence or absence of mercury.

In other embodiments, the present invention may comprise a method for using a first bioindicator from a particular microbe as an "entry point" for isolating other bioindicators from the microbe. Thus, in one embodiment, a bioindicator isolated from a portion of the genome of a microbe is used to identify a second bioindicator nucleic acid sequence from the same microbe. For example, the sequence of a first bioindicator nucleic acid molecule may be used to identify and isolate contiguous DNA sequence from the microbe that can serve as a bioindicator.

The present invention also comprises methods to monitor ecosystem's. In some embodiments, the method comprises using a sequence that is a bioindicator for a specific parameter associated with the ecosystem. In an embodiment, the ecosystem is an aquatic ecosystem. Or, other ecosystems such as terrestrial or atmospheric ecosystems may be monitored. Thus, in certain embodiments, the present invention comprises a method to monitor a parameter of an ecosystem comprising the steps of: (a) obtaining a sample from an aqueous (or other) ecosystem; (b) using an oligonucleotide specific to a single operational taxonomic unit to determine whether nucleic acid sequences specific to the operational taxonomic unit are present in the sample; and (c) correlating detection of the nucleic acid sequence specific to the operational taxonomic unit to a parameter of the ecosystem.

The method may comprise generating a plurality of oligonucleotides each specific to a single operational taxonomic unit for use as biomarkers of an ecosystem parameter of interest. For example, the method may comprise generating a plurality of oligonucleotides each specific to a single operational taxonomic unit in at least one ecosystem and determining whether nucleic acid sequences specific to the operational taxonomic unit are present in the sample. Additionally or alternatively, the method may comprise identifying the oligonucleotide specific to a single operational taxonomic unit in a first ecosystem and using the oligonucleotide to determine whether nucleic acid sequences specific to the operational taxonomic unit are present in a second ecosystem.

The method may employ amplification of bioindicator DNA as a means to detect the presence or absence of certain bioindicators in an ecosystem. For example, in certain embodiments, the method may comprise using two oligonucleotides each specific to the single operational taxonomic unit as primers in a polymerase chain reaction to amplify DNA from a single genomic target sequence. The method may comprise performing a plurality of PCR amplification reactions as a means to detect a plurality of bioindicator sequences. Thus, in some embodiments, the method may comprise using a plurality of paired oligonucleotides, each pair of oligonucleotides being specific to a single operational taxonomic unit, as primers in a plurality of separate polymerase chain reactions to amplify DNA from a plurality of genomic target sequences.

Where the ecosystem parameter is mercury, oligonucleotide primers that are specific to the single operational taxonomic unit in the first ecosystem may comprise at least one oligonucleotide comprising the sequence as set forth in SEQ ID NO: 341-SEQ ID NO: 350 or SEQ ID NO: 371-SEQ ID NO: 388. In certain embodiments, these sequences may be used as primers for PCR amplification of intervening sequences that are bioindicators for mercury. Additionally or alternatively, the oligonucleotide specific to the single operational taxonomic unit may comprise at least one oligonucleotide comprising the sequence as set forth in SEQ ID NO: 329-SEQ ID NO: 340 or SEQ ID NO: 351-SEQ ID NO: 370.

In certain embodiments, these sequences may be used as probes for PCR amplification products that comprise intervening sequences that are bioindicators for mercury.

Or, other ecosystem parameters may be monitored. Thus, in alternate embodiments, the oligonucleotide primers that are specific to the single operational taxonomic unit in the first ecosystem may comprise at least one oligonucleotide comprising the sequence as set forth in SEQ ID NOS: 114-316. In certain embodiments, these sequences may be used as primers for PCR amplification of intervening sequences that are bioindicators. Additionally or alternatively, the oligonucleotide specific to the single operational taxonomic unit may comprise at least one oligonucleotide comprising the sequence as set forth in SEQ ID NO: 5 to SEQ ID NO: 113, or the reverse complement of SEQ ID NO: 5 to SEQ ID NO: 113. In certain embodiments, these sequences may be used as probes for PCR amplification products that comprise intervening sequences that are bioindicators.

In alternate embodiments, the method of monitoring an ecosystem comprises using a plurality of OTU-specific oligonucleotides. The plurality of OTU-specific oligonucleotides may comprise at least 2, or 3, or 4, or 5, or 6, or 10, or 16, or 20, or 26, or 30, or 40, or 50, or 75, or 100 distinct nucleic acid sequences. The oligonucleotides may be immobilized (e.g., as probes on an array) or may be combined as a single composition (e.g., primers for multiplex PCR).

Thus, the method may, in certain embodiments, comprise using an array of individual locations, each location comprising an oligonucleotide specific to a single operational taxonomic unit. In one embodiment, the method may comprise the steps of: generating an array comprising a plurality of oligonucleotides located (and in some cases immobilized) at known locations on a substrate, wherein each location on the array comprises an oligonucleotide having a sequence derived from a single, predetermined microbial operational taxonomic unit (OTU) and wherein at least one sequence is associated with at least one parameter of the ecosystem; preparing an ecosystem nucleic acid sample from the ecosystem of interest; hybridizing the ecosystem nucleic acid sample to the array; measuring hybridization of the ecosystem nucleic acid sample to the array; and correlating hybridization of the ecosystem nucleic acid sample to the array with a parameter that comprises at least part of the ecosystem.

In one approach, the oligonucleotides are each selected to comprise different taxonomic units. The oligonucleotides may be selected such that at least some are from a microbial operational taxonomic unit (OTU). Or, OTUs from other types of organisms (e.g., flora or fauna) may be used.

In certain embodiments, the OTU-specific oligonucleotides of the array are used as probes to detect whether the bioindicator is present or absent in a sample. In this embodiment, the oligonucleotides immobilized on the array should be of sufficient length to provide specific hybridization to nucleic acid molecules isolated from various ecosystem samples that are used to probe the array. The immobilized oligonucleotides may be at least 20 nucleotides in length. In alternate embodiments, the immobilized oligonucleotides may range from about 30 to 200, or from 40 to 100, or from 45 to 80, nucleotides in length. Or, ranges within these ranges may be used. In one example embodiment, the immobilized oligonucleotides are each about 50 nucleotides in length.

Also, the amount of the oligonucleotide immobilized on the array should be sufficient to allow detection of complementary nucleic acid sequences by the array, but in an amount such that background hybridization to unrelated sequences is avoided. In alternate embodiments of the methods of the present invention, the oligonucleotides immobilized on the array range from about 1 fg to about 10 µg, or from about 50 fg to about 10 ng, or from about 0.5 pg to 1,000 pg, or from about 2 pg to 200 pg, or from about 8 pg to about 50 pg, at each location.

The oligonucleotides used in the compositions, products, methods and systems of the present invention may be derived from sequences found by analysis of microbes present in various ecosystems of interest. In one embodiment, oligonucleotides having sequences specific to organisms found in lakes or seas may be used. Additionally or alternatively, oligonucleotides having sequences specific to organisms found in estuaries may be used. Additionally or alternatively, oligonucleotides having sequences specific to organisms found in other types of aquatic systems, such as tidal pools, wetlands, streams, rivers and marine systems may be used. Or, probes from a terrestrial and/or atmospheric ecosystem, such as those described herein, may be used to monitor an ecosystem by the methods of the present invention. As noted herein, the probes and/or primers used as OTU-specific oligonucleotides may be derived from a different ecosystem (e.g., a first ecosystem) than the ecosystem being monitored (e.g., a second ecosystem).

The array may be hybridized with a nucleic acid sample comprising at least one bioindicator that is isolated from the sample of interest. In at least some embodiments, at least one of the bioindicators is a bioindicator for a specific parameter associated with the ecosystem. For example, in certain embodiments, the bioindicator is informative about either the presence or absence of mercury, or the levels of mercury in the ecosystem. Or, the bioindicator may be specific for other ecosystem parameters.

For example, PCR may be used to amplify rDNA sequences from genomic DNA from a water sample of interest, and the amplified DNA can be used to probe an array of OTU-specific probes that comprise bioindicator sequences. Alternatively or additionally, PCR may be used to amplify known pathogen-specific sequences from a water sample of interest, and used to probe an array of OTU-specific probes that comprise bioindicator sequences. Alternatively and additionally, PCR may be used to amplify unidentified (i.e., novel) sequences specific to a water sample of interest, and the amplified DNA can be used to probe an array of OTU-specific probes that comprise bioindicator sequences. Alternatively or additionally, PCR may be used to amplify known non-pathogen specific sequences associated with a water sample of interest, and the amplified DNA can be used to probe an array of OTU-specific probes that comprise bioindicator sequences. Or, non-amplified genomic DNA may be used to probe the array.

The bioindicator isolated from the ecosystem of interest may comprise nucleic acid sequences isolated from rDNA. In one embodiment, the nucleic acid sample hybridized to an array of OTU-specific probe sequences sequence comprises a plurality of rDNA sequences. For example, the nucleic acid sequence hybridized to the array may be generated using PCR primers derived at least in part from a ribosomal variable region so as to specifically amplify rDNA sequences. For example, the primers may comprise at least one oligonucleotide molecule having a sequence identical to any one of SEQ ID NO: 114-SEQ ID NO: 316, and/or SEQ ID NO: 341-SEQ ID NO: 350 and/or SEQ ID NO: 371-SEQ ID NO: 388, or a fragment thereof. In separate and alternate embodiments, the primers used for amplification of DNA from a sample of interest may comprise at least 2, 4, 6, 8, 10, 20, 40 or 50 oligonucleotide molecules having a sequence identical to any one of SEQ ID NO: 114-SEQ ID NO: 316, and/or SEQ ID NO: 341-SEQ ID NO: 350 and/or SEQ ID NO: 371-SEQ ID NO: 388, or a fragment thereof.

In another embodiment, the method may comprise use of an array comprising PCR primers (rather than probes) at each of the locations. For example, in certain embodiments, the array may comprise a plurality of primer sets at individual locations, where a primer set is two primers that can amplify a single genomic sequence. Or a plurality of individual PCR reactions (e.g., individual tubes) may be used. A sample from an ecosystem as well as PCR reagents and polymerase enzyme may then be added at the location and the mixture subjected to thermal conditions such that PCR amplification can occur. In an embodiment, the production of a PCR product may be monitored using a dye (e.g., SYBR® Green dye) that can intercalate in the double-stranded PCR product thereby indicating whether amplification has occurred, and in some embodiments, providing a level of amplification.

In yet other embodiments, the present invention also provides methods for isolating samples from an ecosystem of interest that may be analyzed using molecular methods. In some embodiments, the ecosystem of interest is being monitored for a parameter of interest. The method may comprise isolating and/or identifying bioindicators that are informative about the ecosystem. In at least some embodiments, at least one of the bioindicators is a bioindicator for a specific parameter associated with the ecosystem. For example, in certain embodiments, the bioindicator is informative about either the presence or absence of mercury, or the levels of mercury in the ecosystem. Or, the bioindicator may be specific for other parameters as described herein.

Thus, in yet another embodiment, the present invention comprises a method to prepare a nucleic acid sample from a ecosystem of interest, the nucleic acid sample comprising one or a plurality of bioindicator DNA sequences, wherein the method comprises amplifying a DNA sample isolated from a ecosystem with a plurality of primers that have the ability to specifically amplify nucleic acid sequences comprising bioindicators. In one embodiment, at least one of the primers comprise at least a portion of a variable region of a ribosomal RNA. For example, the primers may comprise at least one oligonucleotide molecule having a sequence identical to any one of SEQ ID NO: 114-SEQ ID NO: 316, and/or SEQ ID NO: 329-SEQ ID NO: 340, and/or SEQ ID NO: 351-SEQ ID NO: 370, or a fragment thereof. In separate and alternative embodiments, the primers used for amplification of DNA from a sample of interest may comprise at least 2, 4, 6, 10, 20, 40, 50, 60, 70, 80, 90 or 100 oligonucleotide molecules having a sequence identical to any one of SEQ ID NO: 114-SEQ ID NO: 316, and/or SEQ ID NO: 329-SEQ ID NO: 340, and/or SEQ ID NO: 351-SEQ ID NO: 370, or a fragment thereof.

By measuring hybridization of the array of bioindicators to a sample from an ecosystem of interest, or by measuring changes in PCR amplification of certain OTUs, changes in at least one parameter that are indicative of a change in the ecosystem may be measured. In at least some embodiments, at least one of the bioindicators is a bioindicator for a specific parameter associated with the ecosystem. For example, in certain embodiments, the bioindicator is informative about either the presence or absence of mercury, or the levels of mercury in the ecosystem. Or, the bioindicator may be specific for other parameters. Thus, in one embodiment, the present invention comprises a method for analyzing a bioindicator profile or pattern of bioindicator profiles to evaluate the status of an ecosystem. For example, the method may comprise the step of measuring hybridization of a nucleic acid sample to an array of oligonucleotides immobilized at known locations on a substrate, or changes in a PCR abundance profile, wherein each location on the array, or primer set used for PCR, comprises an oligonucleotide having a sequence that is derived from a single, predetermined microbial operational taxonomic unit (OTU), and wherein at least one sequence is associated an ecosystem parameter (e.g., the presence, absence or levels of mercury in the ecosystem), and correlating the hybridization of the nucleic acid to the array, or the changes in a PCR abundance profile, with the ecosystem parameter.

In one embodiment, a single change in the pattern of a bioindicator abundance profile (e.g., provided by array hybridization data, PCR amplification or other methods of detection of the presence of bioindicator OTUs in a sample) for a first nucleic acid sample isolated from an ecosystem of interest as compared to a second nucleic acid sample isolated from an ecosystem of interest is associated with a change in a single parameter, such as the presence or absence of mercury. Or, a single change in the bioindicator abundance profile for a first nucleic acid sample isolated from an ecosystem of interest as compared to a second nucleic acid sample isolated from an ecosystem of interest may be associated with a change in a plurality of ecosystem parameters. In an embodiment, at least one of the plurality of ecosystem parameters is the presence or absence of mercury. Additionally or alternatively, a plurality of changes in the bioindicator abundance profile of a first nucleic acid sample isolated from an ecosystem of interest as compared to a second nucleic acid sample isolated from an ecosystem of interest is associated with a change in one ecosystem parameter, such as the presence or absence of mercury. Or, a plurality of changes in the bioindicator abundance profile of a first nucleic acid sample isolated from an ecosystem of interest as compared to a second nucleic acid sample isolated from an ecosystem of interest may be associated with a change in a plurality of parameters. In an embodiment, at least one of the plurality of ecosystem parameters is the presence or absence of mercury.

In one embodiment, the analysis of the bioindicator abundance profile may comprise using known bioindicator profiles such that changes in ecosystem parameters of a sample may be determined. Samples may vary by location of the ecosystem, the time of sampling of a single ecosystem, or the location of sampling within a single ecosystem. In an embodiment, the analysis may comprise using a computer program including known bioindicator profiles to identify profiles that are associated with certain parameters in an ecosystem sample.

Also included as part of the present invention are systems for monitoring ecosystems of interest. The systems of the present invention may comprise any of the compositions, methods or products as described herein. Thus, another embodiment of the present invention comprises a system for monitoring an ecosystem of interest comprising a product having a plurality oligonucleotides, such that each oligonucleotide comprises an oligonucleotide having a sequence that is derived from a single predetermined microbial operational taxonomic unit (OTU). In certain embodiments, the plurality of OTU-specific oligonucleotides comprise individual locations. For example, the plurality of OTU-specific oligonucleotides may be applied as probes or primers on a substrate as an array. The system may also comprise a device able to measure hybridization of a nucleic acid sample to the array and/or to measure the PCR profiles generated by OTU-specific primers for ecosystem samples.

Also, the system may comprise a computer for analysis of the results. For example, the computer may comprise an algorithm for compiling the data showing detection of bioindicators using the plurality of OTU-specific oligonucleotides and analyzing the data to determine the status of an ecosystem parameter.

DEFINITIONS

As used herein, the following terms shall have the definitions set out below. Also, in accordance with the present invention, conventional molecular biology, microbiology, and recombinant DNA techniques may be used that will be apparent to those skilled in the relevant art. Such techniques are explained fully in the literature (see, e.g., Maniatis, Fritsch & Sambrook, "Molecular Cloning: A Laboratory Manual (1982); "DNA Cloning: A Practical Approach," Volumes I and II (D. N. Glover ed. 1985).

Ecosystem as used herein follows a definition as generally used by ecologists—the biotic and abiotic components of a system defined by generally recognized boundaries, such as a lake, pond, river, wetland or reservoir. Aquatic ecosystems are characterized by being continuously or generally water saturated. Ecosystems may also be terrestrial ecosystems and/or atmospheric ecosystems. Ecosystems may be natural (e.g. lakes and/or their sediments, such as the Great Lakes, forested areas and/or soils) or anthropogenic (e.g., agricultural soils, ponds, reservoirs, or even water storage facilities). Laboratory scale containment (e.g. test tubes, flasks, carboys) are generally not considered ecosystems.

As used herein, the presence or absence of mercury includes measurements of both the presence of mercury, or the absence of mercury, or the presence and/or absence of mercury. The presence of mercury is used to describe a state comprising a level of mercury that can be measured by techniques known in the art. For example, mercury may be measured using approved EPA testing methods such as total mercury (THg) analyses using Method 7471, a cold-vapor atomic absorption method based on the absorption of radiation ($\lambda$=253.7 nm) by mercury vapor and/or monomethyl mercury (MMHg) analyses in accordance with EPA Method 1630.

As used herein, "taxonomic unit" is a group of organisms that are considered distinct enough to be treated as a separate unit. A taxonomic unit may comprise a family, genus or species but is not limited as such. Also as used herein, each "operational taxonomic unit (OTU)" comprises a group of one or more microorganisms that are treated as a unit based on a small sub-unit (SSU) rDNA sequence identity of $\geq$97.5% among members of the group.

As used herein, a bioindicator is an organism or part thereof, or a biological process, whose change in numbers, structure, or function points to a change, or a plurality of changes, in the environment. Generally, a bioindicator has a relatively high and easily identifiable sensitivity to selective environmental influences. The changes in the environment may relate to various changes in the ecosystem such as changes in a single chemical, physical or biological parameter, or changes in combinations of chemical, physical, or biological parameters in either absolute abundance or relative abundance to each other. Any microbe whose relative abundance depends upon a biotic and/or an abiotic aspect(s) of an ecosystem of interest, or whose appearance is restricted to a subset of ecosystems, can be a bioindicator. Moreover, a plurality of two or more bioindicators (two or more present or more abundant than in the absence of a condition, two or more absent or less abundant than in the absence of the condition, or combinations of two or more in abundance and/or presence) may together indicate a condition of the ecosystem of interest. A condition of an ecosystem may refer to either a single biotic or abiotic factor or a combination of such factors.

For example, a bioindicator for a parameter of interest can be a DNA sequence that can be used to monitor an ecosystem for that parameter. A bioindicator for mercury can be a DNA sequence that can be used to monitor an ecosystem for the absence or presence of mercury and/or levels of mercury. Similarly, a bioindicator for cadmium can be a DNA sequence that can be used to monitor an ecosystem for the absence or presence of cadmium and/or levels of cadmium, and a bioindicator for acidity can be a DNA sequence that can be used to monitor an ecosystem for the absence or presence of an acid environment and/or levels of acidity.

A "vector" is a replicon, such as plasmid, phage or cosmid, to which another DNA segment may be attached so as to bring about the replication of the attached segment.

As used herein, variable ribosomal DNA is a region within the small subunit ribosomal DNA (SSU rDNA) which can be used to derive OTU-specific primer and probe oligonucleotides as described herein. As used herein, variable ribosomal DNA comprises a contiguous sequence of 20 or more nucleotides in which 80% of the nucleotides are not represented more than 60% of the time by a single nitrogen base (i.e., A, C, G, or T) as assessed for sequences from all known rDNA molecules. For example, in certain embodiments, the V1 and V2 regions of rDNA are used as a source of variable ribosomal DNA. In certain embodiments, portions of other variable regions (e.g., V3-V6) may comprise variable rDNA. With reference to locations in *E. coli* (Prosius et al., 1981, *J. Mol. Biol.*, 148:107-127), variable 16S rDNA can include at least portions of the following sequence regions: 50-150, 160-263, 423-523, 806-906, 950-1050, 1110-1220 and 1409-1509. With reference to locations in *Saccharomyces cerevisiae* (Rubstov et al., 1980, *Nucl., Acids Res.*, 8: 5779-5794), variable 18S rDNA can include at least portions of the following sequence regions: 50-550, 600-750, 800-900, 970-1200, 1350-1600, and 1700-1800.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), microbes, viruses, plasmids, and chromosomes.

DNA molecules may be identified by their nucleic acid sequences, which are generally presented in the 5' to 3' direction, wherein 5' and 3' indicate the linkages formed between the 5'-phosphate group of one nucleotide and the 3'-hydroxyl group of the next. For a single stranded DNA molecule with the sequence presented in the 5'-3' direction, the reverse complement is the DNA sequence in the 5'-3' direction of the single-stranded DNA molecule that hybridizes to the first strand to form a double-stranded DNA molecule according to the Watson-Crick base pairing model. Thus, the sequence of the reverse complement is defined by the sequence of the original strand, such that adenine base-pairs with thymine, and cytosine base-pairs with guanine.

The term "gene" means a region of DNA encoding for the mRNA sequence that codes for a given protein/polypeptide along with elements regulating mRNA production, or a region of DNA encoding for a ribosomal RNA (rRNA) sequence that performs a structural function as a subunit of ribosomes along with elements regulating rRNA expression.

"Messenger RNA" or "mRNA" shall mean a RNA molecule that encodes for a polypeptide. "Ribosomal RNA" or "rRNA" shall mean a RNA molecule that performs a structural function in ribosomes.

"Complementary DNA" or "cDNA" shall mean the DNA molecule synthesized by polymerization of deoxyribonucleotides from an RNA template by an enzyme with reverse transcriptase activity and the subsequent double-stranded cDNA sequence.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as an oligonucleotide, a genomic fragment, a fragment produced by polymerase chain reaction (PCR), or a restriction fragment; and (d) a recombinant nucleotide sequence that is part of a hybrid gene, i.e., a gene encoding a fusion protein.

"Oligonucleotide", as used herein, is defined as a molecule comprised of two or more deoxy- or ribonucleotides, preferably more than eight. Its exact size will depend upon many factors which, in turn, depend upon the ultimate function and use of the oligonucleotide. As is known in the art, it is possible that each of the oligonucleotide molecules may vary by a few bases. For example, the synthesis of the oligonucleotide may result in a portion of the oligonucleotides being less than full length. Or, a portion of the oligonucleotides immobilized at a particular location may degrade by a small percentage over time. Such oligonucleotides are considered to be "fragments" of the original oligonucleotide. Thus, an oligonucleotide sequence that is derived from, and specific to, a single, individual OTU may include fragments of that oligonucleotide.

A "DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have non naturally-occurring portions. Thus, DNA fragments may have, altered sugar moieties or inter-sugar linkages. Exemplary among these are the phosphorothioate and other sulfur containing species. They may also contain altered base units or other modifications, provided that biological activity is retained. DNA fragments may also include species that include at least some modified base forms. Thus, purines and pyrimidines other than those normally found in nature may be so employed. Similarly, modifications on the cyclofuranose portions of the nucleotide subunits may also occur.

The term "identical" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, *Adv. Appl. Math.* 2:482 (1981); Needleman and Wunsch, *J. Mol. Biol.* 48:443 (1970); Pearson and Lipman, *Proc. Natl. Acad. Sci.* (*USA*), 85:2444 (1988)) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In one embodiment, percent identity of two nucleotide sequences may be determined using GCG with a gap weight of 1, such that each gap is weighted as if it were a single nucleotide mismatch between the two sequences.

"Primer" shall refer to an oligonucleotide, whether occurring naturally or produced synthetically, which is capable of acting as a point of initiation of DNA synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for multiplex PCR amplification of genomic DNA, the oligonucleotide primer typically contains 15-30 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

"Probe" shall refer to any oligonucleotide that can be used for detection of a nucleic acid molecule (e.g., RNA or DNA) that has a complementary sequence to the probe, wherein detection uses hybridization of the probe to the complementary nucleic acid sequence. Such probes include single-stranded DNA molecules. The act of "probing" as used herein describes the step of hybridizing a nucleic acid sample with a probe having a known sequence, or a plurality of probes having known sequences (i.e., an array), to determine whether any of the sequences in the sample are complementary to the probe sequence(s).

As used herein, the term "hybridization" refers generally to a technique wherein denatured RNA or DNA is combined with complementary nucleic acid sequence that is either free in solution or bound to a solid phase. As recognized by one skilled in the art, complete complementarity between the two nucleic acid sequences is not a pre-requisite for hybridization to occur. Hybridization conditions can be described as ranging from low to high stringency. Hybridization that occurs under high stringency conditions is specific in that a large percentage of complementarity between two nucleotide molecules is required for hybridization to occur under stringent conditions. Hybridization that occurs under low stringency conditions is less specific in that a lower percentage of complementarity between two nucleotide molecules is required for hybridization to occur under stringent conditions. Even under highly stringent conditions, there may not be perfect complementarity between two oligonucleotide molecules that hybridize, although conditions may be established that require perfect complementarity. Generally, highly stringent conditions refer to washing hybrids in low salt buffer at high temperatures. Hybridization may be to filter bound DNA using hybridization solutions standard in the art such as 0.5M NaHPO$_4$, 7% sodium dodecyl sulfate (SDS) at 65° C., and washing in 0.25 M NaHPO$_4$, 3.5% SDS followed by washing 0.1×SSC/0.1% SDS at a temperature ranging from room temperature to 68° C. depending on the length of the probe (see e.g. Ausubel, F. M. et al., *Short Protocols in Molecular Biology*, 4$^{th}$ Ed., Chapter 2, John Wiley & Sons, N.Y). For example, a high stringency wash comprises washing in 6×SSC/0.05% sodium pyrophosphate at 37° C. for a 14 base oligonucleotide, or at 48° C. for a 17 base oligonucleotide, or at 55° C. for a 20 base oligonucleotide, or at 60° C. for a 25 base oligonucleotide, or at 65° C. for a nucleotide probe about 250 nucleotides in length. Equivalent stringencies may be obtained with other wash solutions by varying the temperature as is known in the art. Nucleic acid probes may be labeled with radionucleotides by end-labeling with, for example, [γ-$^{32}$P]ATP, or by incorporation of radiolabeled nucleotides such as [α-$^{32}$P]dCTP by random primer labeling. Alternatively, probes may be labeled by incorporation of biotinylated or fluorescein labeled nucleotides, and the probe detected using antibodies to the label, or by chemical incorporation of cyanin dyes as described herein.

As used herein, "restriction endonucleases" and "restriction enzymes" shall refer to bacterial enzymes that cleave double-stranded DNA at or near a specific nucleotide sequence.

A polypeptide refers to any peptide generated from a protein or the full-length protein itself. A polypeptide may include the full-length protein or a fragment generated by proteolytic cleavage, chemical cleavage, or other means.

As used herein, an array or microarray comprises a substrate having a plurality of discrete locations. An array may comprise locations that have specific elements at each location. For example, one type of array is a solid-state grid containing short sequences of nucleic acid (usually DNA) of known sequence a particular position (i.e., location or address) on the grid. The DNA molecules may be immobilized at these positions (e.g., by UV-induced formation of chemical bonds between the DNA molecule and the substrate (i.e., UV cross-linking) or evaporation of the DNA onto the substrate. DNA arrays may be termed microarrays due to the small size of the grid and the small amounts of nucleotide (e.g., µM or nM amounts) present at each address.

As used herein, a computer program comprises a computer-encoded language that encodes the steps required for the computer to perform a specific task or tasks.

Also, as used herein, software comprises the computer program(s) used in conjunction with any other operating systems required for computer function.

As used herein, the singular forms "a", "an" and "the" include plural references unless the context clearly dictates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

Water Surveillance Using Nucleic Acid Based Arrays

The present invention recognizes that the abundance of certain microorganisms may be affected by local water conditions. These conditions may vary for individual species and strains. For example, whereas one species might proliferate in phosphate-rich water, another species may prefer low-phosphate water (Kilham et al, 1986, *Limnol. Oceanogr.*, 31:1169-1181; Siver et al., 1999, *Limnol. Oceanograph.*, 44:1928-1955). Also, phytoplankton and benthic algae may be used as indicators of eutrophication (Shubert, L. E. (ed.), 1984, *Algae as ecological indicators*. Academic Press, N.Y; Stoermer, E. F. and J. P. Smol, 1999, *The Diatoms: applications for the environmental and earth sciences*, Cambridge Univ. Press, Cambridge, UK). Or, the abundance of known microbial species can vary as a function of pollution levels (Lemke et al., 1997, *Microb. Ecol.*, 34:224-231). It has been shown that the presence of high levels of heavy metals in water may be reflected in the tissue of the marine limpet (Pérez-Lopez, M., et al., 2003, *Journal of Environmental Health, Part A—Toxic/Hazardous Substances and Environmental Engineering*, 38:2845-2856). Also, coliform bacteria may be used as an indicator of the presence of human sewage in aquatic systems.

Over the past decade, direct observation and culturing of microbes has been complemented by emerging molecular approaches, including: in situ hybridization (Schohuber, W., et al. 1991, *Appl. Environ. Microbiol.* 65:1258-1267), selective PCR detection of individual taxa (e.g. Oldach, D. W., et al. 2000, *Proc. Natl. Acad. Sci. USA*, 97:4303-4308; Rublee, P. A., et al. 2001, *Environ. Health Perspectives*, 109 [Supplement 5]:765-767), community assays such as Differential Gradient Gel Electrophoresis (DGGE) analyses (e.g., Diez, B., et al. 2001, *Appl. Environ. Microbiol.*, 67:2942-2951) and filter macroarray hybridization (e.g., Rudi, K., et al. 2000, *Appl. Environ. Microbiol.*, 66:4004-4011). In situ hybridization allows taxon-specific identification and enumeration of target organisms. Although highly specific, the method is time consuming as it generally involves microscopic observation of the sample. PCR, the polymerase chain reaction, may detect a targeted organism that exists in low abundance in the natural environment. Selective PCR detection of individual microbes is highly specific, rapid, and may even be quantitative (e.g., real-time quantitative PCR), but can be limited in that primers specific to the sequence to be amplified must be available. DGGE analysis has become a relatively common approach to community assessment of prokaryotic or even eukaryotic communities, but is limited in that it relies on the assumption that different nucleic acid sequences will display differential mobility in a gradient gel, which is not always the case.

From the standpoint of environmental investigations, recent microarray development efforts have increasingly focused on the identification of genes from specific microbial organisms associated with environmental processes, such as nitrogen fixation, or with the detection of specific microbes (Wu et al., 2001, *Appl Environ. Microbiol.*, 67:5780-5790). Most of the microbes that exist in freshwater sources, however, are unknown and/or unculturable (Kaeberlein et al., 2002, *Science*, 296:1127-1129; Hiorns et al., 1997, *Appl. Environ. Microbiol.*, 63: 2957-2960; Lopez-Garcia et al., 2001, *Nature*, 409:603-607).

The present invention uses a different approach. Instead of using DNA sequences from known microbes, the present invention uses bioindicator sequences that are specific to an operational taxonomic unit and that are derived from a specific ecosystem. These bioindicators are not only informative about parameters associated with the ecosystem from which the bioindicator is derived, but can provide information about other ecosystems. For example, a first step of developing methods and systems to monitor water may be the identification of suitable bioindicator molecules. Embodiments of the present invention provide compositions, products (e.g., devices), methods and systems to monitor a an aquatic ecosystem, such as a water supply by identifying nucleic acid sequences that are diagnostic of the aquatic microbial population. In at least some embodiments, at least one of the bioindicators is a bioindicator for a specific parameter associated with the ecosystem. For example, in certain embodiments, the bioindicator is informative about either the presence or absence of mercury, or the levels of mercury in the ecosystem. Or the bioindicator may be informative about the presence and/or absence or levels of any other physical (e.g. temperature, pressure), chemical (e.g. alkalinity, pH, element or compound), or biological component (e.g. viruses, bacteria, alga, protozoan, fungus, or other flora or fauna) or characteristics of the ecosystem. The compositions, products, methods, and systems of the present invention may be used to monitor water. Or, other ecosystems may be monitored.

FIG. 1 shows an embodiment of a method of the present invention that may be used to identify potential ecosystem biomarkers and to prepare a product or device that can be used to monitor an ecosystem or ecosystems. As shown in FIG. 1, the method 100 may comprise a first step of collecting a sample from an ecosystem of interest 104 (FIG. 1). The ecosystem may comprise an aquatic ecosystem such as a lake or other body of water. In alternate embodiments, water from a lake, a sea, an estuary, a tidal pool, wetlands, a stream, river, ground water, flood water, standing water, or marine systems may be used.

The bioindicator may comprise the microorganism itself, or a molecule that provides information about the microorganism. The bioindicator may comprise a nucleic acid molecule. Nucleic acid molecules may be useful as bioindicators as nucleic acid molecules comprise a source of qualitative and quantitative information. By analyzing the sequence of the DNA molecules in the water sample, information about the genetic make-up of the microbes present in the sample may be obtained. Also, by measuring the amount of DNA molecules in the water sample, information about the amount of specific microbes in the sample may be obtained. As described herein, nucleic acid molecules, such as DNA may be used to identify and classify microorganisms into operational taxonomic units (OTUs). Thus, the method may comprise the step of isolating nucleic molecules from the water sample 106 (FIG. 1).

The method may next comprise the step of determining the sequence of DNA molecules isolated from the sample of interest 108. In an embodiment, rDNA may be used as diagnostic sequences. Thus, to make an array for monitoring water, a first step may comprise the isolation and sequence characterization of 16S rDNA (prokaryotic) and 18S (eukaryotic) DNA species from selected water reservoir samples. The DNA molecules selected for analysis may comprise small subunit (SSU) ribosomal RNA genes (SSU rDNA). In this way, recovery of DNA sequences may be based on the endogenous abundance of individual microbes, and is not restricted to the recovery of known microorganisms.

The DNA sequences isolated from the ecosystem of interest may be used to generate bioindicator probes. As illustrated in FIG. 1, in one embodiment, the bioindicator probes are categorized into operational taxonomic units (OTUs) 110. Both prokaryotic and eukaryotic SSU rDNA can be useful targets for determination of operational taxonomic units because SSU rDNA sequences contain highly conserved nucleotide regions interspersed with variable regions. The conserved sequences provide an anchor by which a plurality of different rDNA sequences may be isolated from a sample. By using primers that hybridize to the conserved regions of either eukaryotic or prokaryotic rRNA genes, a library of amplified rDNA sequences that are different in the variable regions may be isolated from a single sample. Primers that can be used for amplification of prokaryotic rDNA sequences may comprise SEQ ID NOS: 1 and 2 (Table 1). Primers that can be used for amplification of eukaryotic rDNA sequences may comprise SEQ ID NOS: 3 and 4 (Table 1).

TABLE 1

Sequences and target positions of primers used to amplify rDNAs

| Primer | Sequence | SEQ ID NO: | Location |
|---|---|---|---|
| 16S Forward | AGAGTTTGATCCTGGCTCAG[1] | 1 | 8-27[2] |
| 16S Reverse | AAGGAGGTGATCCAGCCGCA[1] | 2 | 1541-1522[2] |
| 18S Forward | AACCTGGTTGATCCTGCCAGT[3] | 3 | 1-21[4] |
| 18S Reverse | TGATCCTTCTGCAGGTTCACCTAC[3] | 4 | 1795-1772[4] |

[1]Primers from Edwards et al., 1989, Nucleic Acids Res., 17, 7843-7853; Bruce et al., 1992, Appl. Environ. Microbiol., 58, 3413-3416.
[2]Position in *E. coli* (Brosius et al., 1981, J. Mol. Biol., 148, 107-127).
[3]Primers from Medlin et al., 1988, Gene 71, 491-499.
[4]Position in *S. cerevisiae* (Rubstov et al., 1980, Nucl. Acids Res., 8, 5779-5794).

The amplified rDNA products may be used to provide a foundation for phylogenetic classification and comparison of both prokaryotic and eukaryotic microbial species isolated from the water samples of interest (see e.g., McCaig, A. E., et al., 1999, *Appl. Environ. Microbiol.*, 65:1721-173036, Reysenbach, A. L., et al., 1992, *Appl. Environ. Microbiol.*, 58:3417-3418; Pace et al., 1986, *Adv. Microb. Ecol.*, 9:1-55; Sogin and Gunderson, 1987, *Annals. NY Acad. Sci.* 503:125-139). A level of 97.5% sequence identity is a generally accepted criterion by which rDNAs may be placed in the same operational taxonomic unit (OTU). Because multiple small subunit rDNAs may reside within a genome for any single species (Farrelly et al., 1995, *Appl. Environ. Microbiol.* 61:2798-2801), a 97.5% level of sequence identity generally allows for the possibility that sequences in the same species are recovered. In performing this type of analysis, it may be necessary to check for artifactual sequences resulting from the amplification protocol (e.g., CHIMERA-CHECK; Kopzcysnski et al., 1994, *Appl. Environ. Microbiol.*, 60:746-748; Wang and Wang, 1995, *Appl. Environ. Microbiol.*, 63:4645-4650; Qui et al., 2001, *App. Environ. Microbiol.*, 58: 2717-2722).

The present invention recognizes that the sequences of small subunit rDNAs in prokaryotes and eukaryotes may allow for phylogenetic classification of known and novel species as operational taxonomic units (OTUs). For example, as described in Example 2 and shown in FIGS. 2 and 3, rank-abundance curves were generated for 16S rDNA sequences, and 18S rDNA sequences, respectively, isolated from five separate samplings from three different lakes, and that were organized as operational taxonomic units. The water samples were taken from the following lakes: Lake Townsend, N.C., Station 1, in June; Lake Townsend, N.C., Station 2 in June; Lake Townsend, Station 1, in March; City Lake, N.C.; and Lake Toolik, Ak. It was found that some of the OTUs had multiple members (i.e., # clones>1), whereas many of the OTUs were represented by only one sequence. As described in Example 2, in certain embodiments, a sequence from a defined OTU can recognize (i.e., hybridize to) other members of the OTU under the conditions used for hybridization of the array. Thus, in one embodiment, an array may be made using unique OTUs as isolated from the various samples.

Figure 4A:
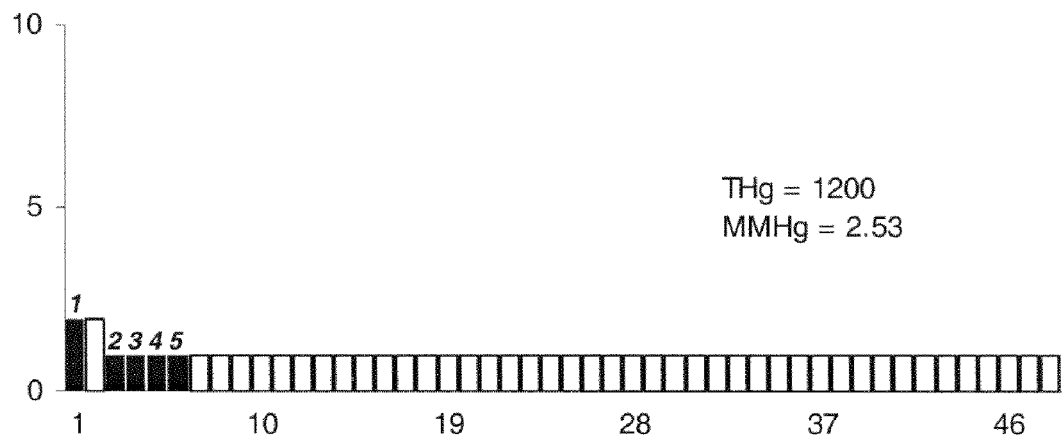
FIG. 4, Panels A-D, shows rank-abundance profiles for 16S rDNA libraries in accordance with alternate embodiments of the present invention, where Panel A is for samples from Holston River mile 77 (NFHR77), Panel B is for samples from Holston River mile 80.8 (NFHR80.8), Panel C is for samples from the Florida Everglades (FLWCA1), and Panel D is for samples from the Great Lakes/Detroit River (GLDRTC). Black bars represent candidate mercury (Hg) bioindicators. THg=total mercury (ng/g); MMHg=monomethyl mercury (ng/g); and BDL=below detection limit.
Figure 4B:
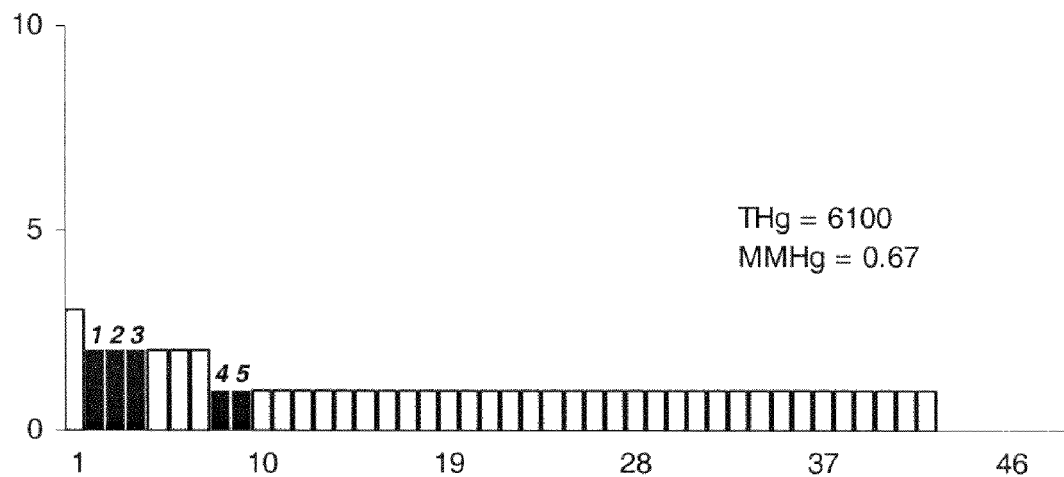
Figure 4C:
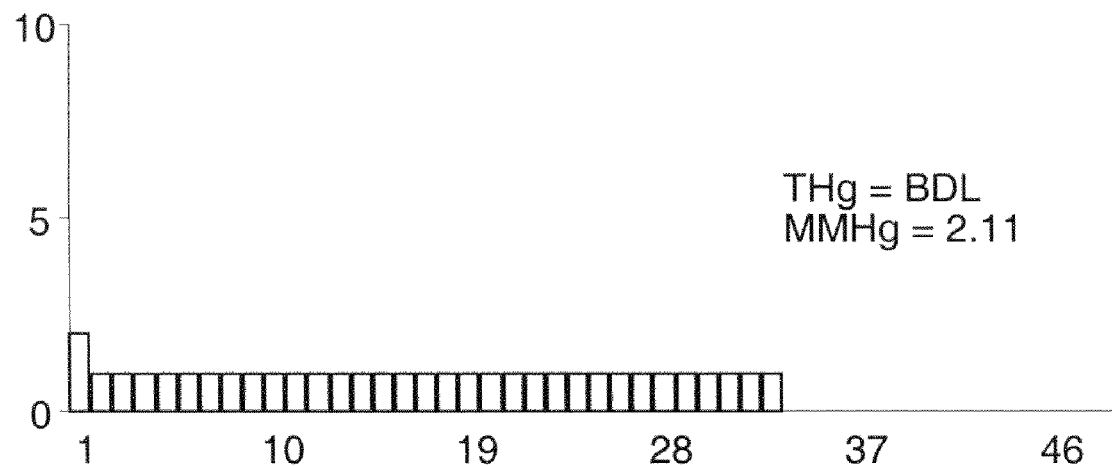
Figure 4D:
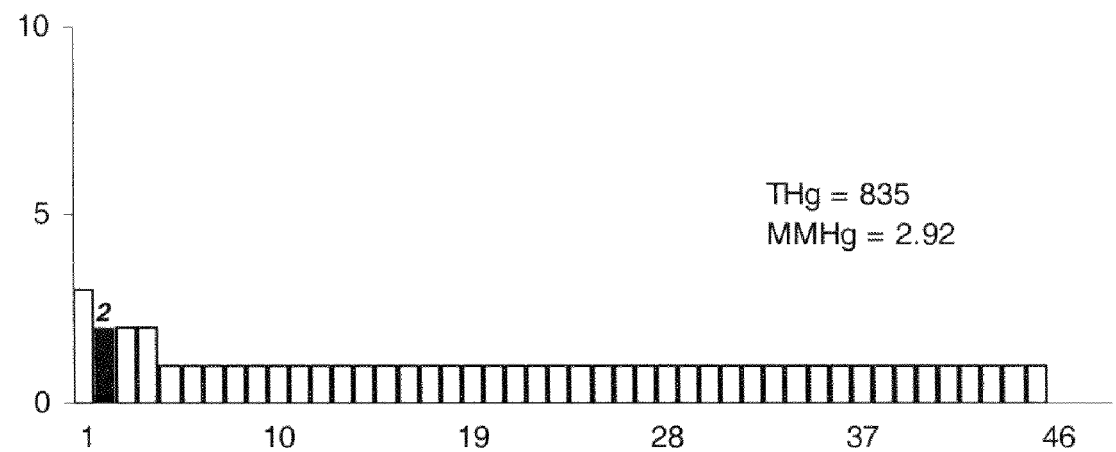
Figure 5A:
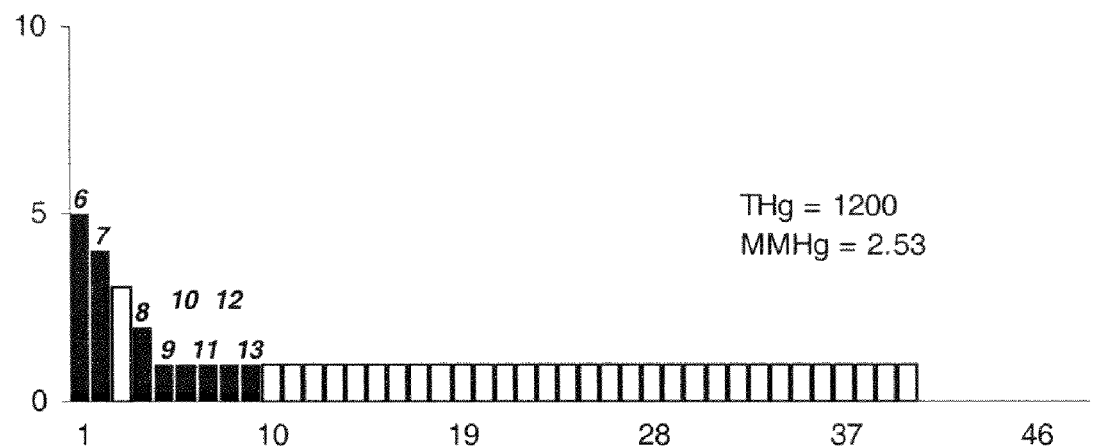
FIG. 5, Panels A-D, shows rank-abundance curves for 18S rDNA libraries in accordance with alternate embodiments of the present invention, where Panel A is for samples from Holston River mile 77 (NFHR77), Panel B is for samples from Holston River mile 80.8 (NFHR80.8), Panel C is for samples from the Florida Everglades (FLWCA1), and Panel D is for samples from the Great Lakes/Detroit River (GLDRTC). Black bars represent candidate mercury (Hg) bioindicators; stippled bars represent other shared OTUs. THg=total mercury (ng/g); MMHg=monomethyl mercury (ng/g); and BDL=below detection limit.
Figure 5B:
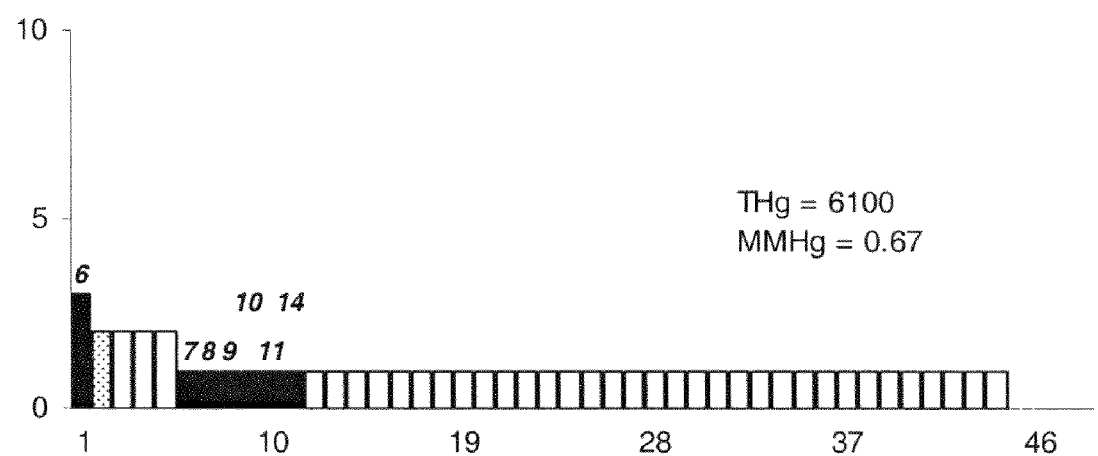
Figure 5C:
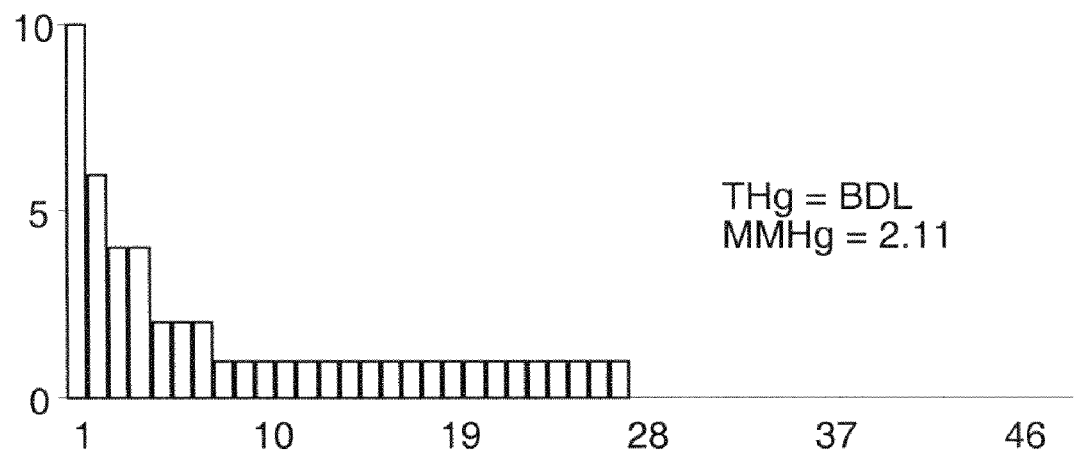
Figure 5D:
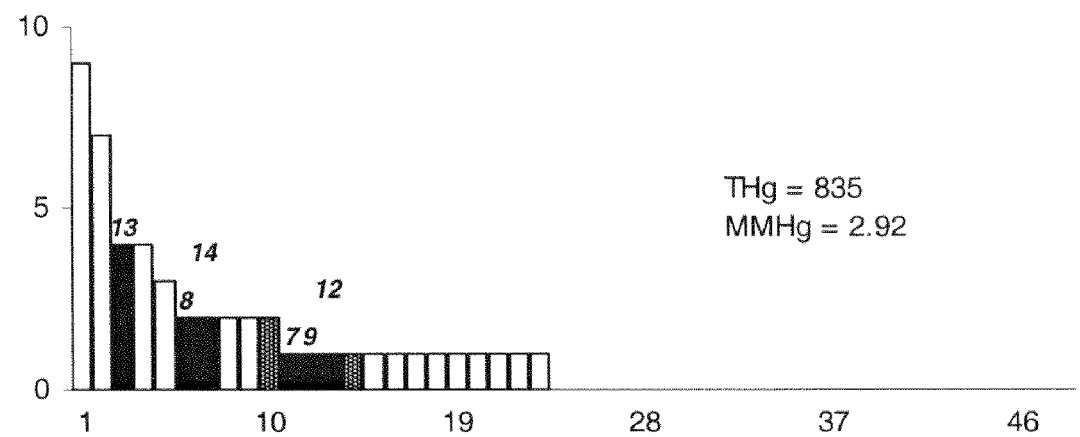

In certain embodiments, sequences specific to OTUs that are associated with the presence of mercury may be characterized. Thus, FIGS. 4 and 5, show rank abundance profiles for 16S prokaryotic rDNA libraries (FIG. 4) and for 18S eukaryotic rDNA libraries (FIG. 5) for four different bodies of water believed to be contaminated with mercury. The four samples were form three diverse sites where mercury contamination has been documented for several years. These locations included: (1) a hot spot for mercury contamination in the Great Lakes; (2) a Florida Everglades site that is part of the EPA National Atmospheric Deposition Network; and (3) two putative contamination sites in the North Fork of the Holston River (Saltville, Va.) (and one Holston River non-contaminated site not in figure). Specifically, the Great Lakes sample (GL-DRTC) (FIGS. 4D and 5D) was collected from bottom sediment in the Trenton-Riverview Channel of the Detroit River (N 42° 11.226', W 83° 9.188') and the Everglades sample (FL-WCA1) (FIGS. 4C and 5C) was collected from an area located within site WCA1. For the Holston River, bottom sediments were taken when river flow was at 1.54 ft and 302 ft$^3$/s: a reference (uncontaminated) sample at river mile 94 (NFHR 94), and a mercury-contaminated sample at river mi. 80.8 (NFHR 80.8) (FIGS. 4B and 5B). The third Holston River sample, also mercury-contaminated, was collected from a floodplain adjacent to the North Fork located at river mi. 77 (NFHR 77) (FIGS. 4A and 5A). River mile 80.8 and 77 sites are located at distinct mileage points along the river. The site at river mi. 80.8, in particular, is believed to be contaminated by mercury discharge from Pond 5 at river mi. 81.8 along the river.

Samples may be subjected to mercury analyses using approved EPA testing methods such as total mercury (THg) analyses using Method 7471, a cold-vapor atomic absorption method based on the absorption of radiation ($\lambda$=253.7 nm) by mercury vapor and/or monomethyl mercury (MMHg) analyses in accordance with EPA Method 1630. For the samples used for the OTU selection shown in FIGS. 4 and 5, Total Hg (THg) was positively identified in control sample NFHR 94, but the amount was estimated to be 22 ng/g, which is between the reporting limit and the minimum detection limit. MMHg in NFHR 94 was measured at 0.075 ng/g. By comparison, THg levels were at least 38 times greater in the other samples than in NFHR 94 (22 ng/g), except for FL-WCA1, which was below the minimum detection limit. For example, MMHg levels were at least 8.9 times greater in NFHR 80.8 and up to 39 times greater in GL-DRTC than in NFHR 94 (0.075 ng/g).

Figure 6:
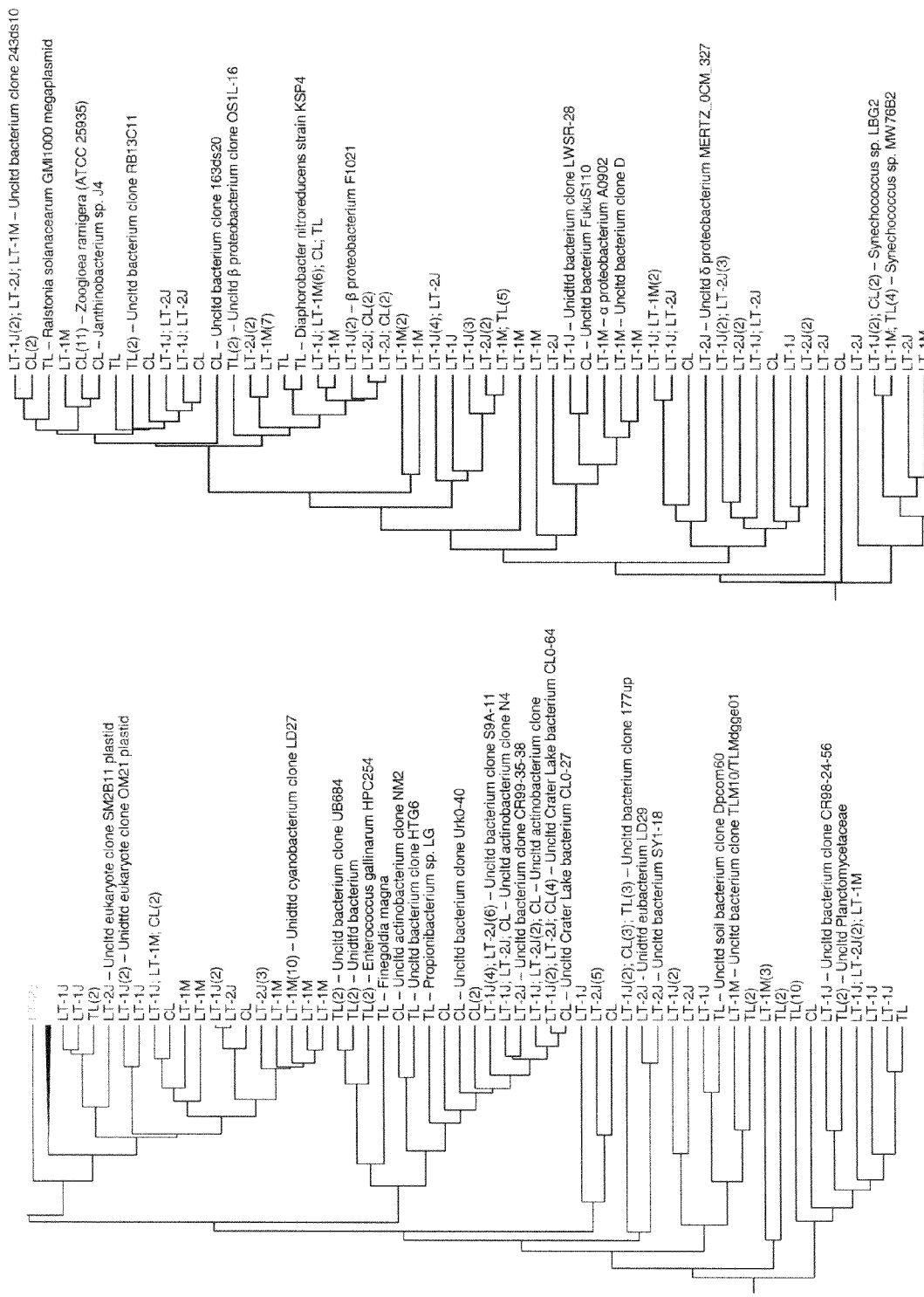
FIG. 6 shows a phylogenetic tree of 16S rDNA operational taxonomic units (OTUs) derived by an Unweighted Pair-Group Method with Arithmetic Mean (UPGMA) analysis using DNA isolated from three different lakes in accordance with an embodiment of the present invention. Numbers in parentheses designate the size of OTUs (i.e., the number of unique sequences per OTU). Identifications by BLAST analysis using the GenBank database are shown. Water samples from which the rDNA was isolated were as follows: LT-1J: Lake Townsend, station 1, June; LT-2J: Lake Townsend, station 2, June; LT-1M: Lake Townsend, station 1, March; CL: City Lake; TL: Toolik Lake.
Figure 7:
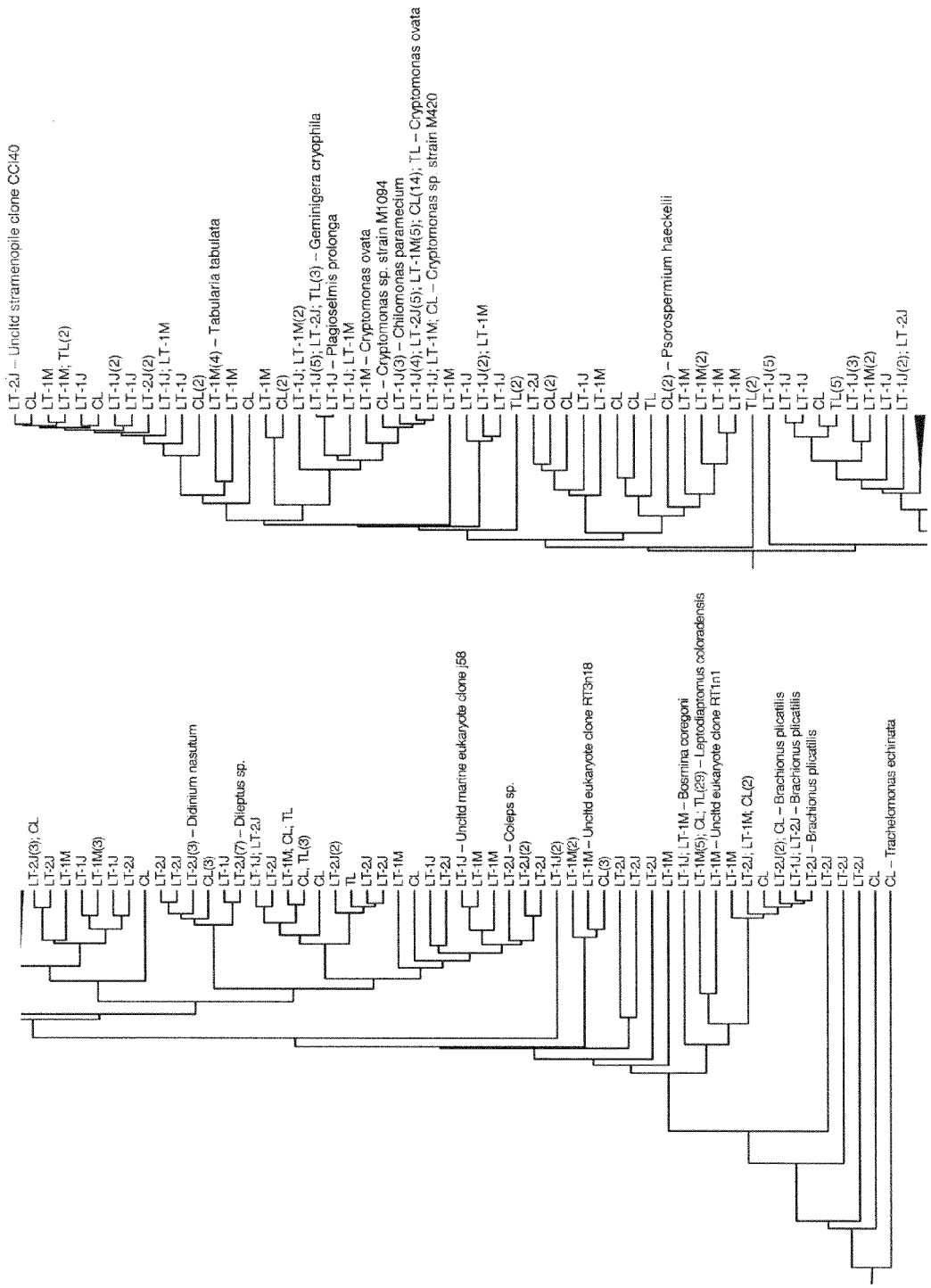
FIG. 7 shows a phylogenetic tree of 18S rDNA operational taxonomic units (OTUs) derived by an Unweighted Pair-Group Method with Arithmetic Mean (UPGMA) analysis using DNA isolated from three different lakes in accordance with an embodiment of the present invention. Numbers in parentheses designate the size of OTUs (i.e., the number of unique sequences per OTU). Identifications by BLAST analysis using the GenBank database are shown. Water samples from which the rDNA was isolated were as follows: LT-1J: Lake Townsend, station 1, June; LT-2J: Lake Townsend, station 2, June; LT-1M: Lake Townsend, station 1, March; CL: City Lake; TL: Toolik Lake.

The sequences of rDNAs from isolated samples may be also used to generate phylogenetic trees. In one embodiment, the Unweighted Pair Group Method with Arithmetic Mean (UPGMA) may be used to compare the sequence data from OTUs and to generate a phylogenetic tree. This type of analysis may be used to confirm the relationship between known sequences, and to order newly identified sequences and OTUs. For example, the data in FIGS. 6 and 7 show a prokaryote tree constructed using data from sequences isolated from Lake Townsend (Greensboro, N.C.), Toolik Lake (AL), and City Lake (High Point, N.C.) using 111 different 16S rDNA OTUs, including 40 OTUs that were based on known rDNA sequences (FIG. 6), and a eukaryote tree constructed using 109 18S rDNA OTUs, and including 22 known rDNA sequences (FIG. 7).

The sequence information may also permit the development of species specific primers. Species-specific primers may be used to characterize a variety of prokaryotic and eukaryotic microbes such as cyanobacteria, *Mycobacterium*, *Pfiesteria piscicida*, and other types of microbial species (see e.g., Edwards, U., et al., 1989, *Nucleic Acids Res.*, 17:7843-7853; Reysenbach, A. L., et al., 1992, *Appl. Environ. Microbiol.*, 58:3417-3418; Shi, W., et al., 2002, *Appl. Environ. Microbiol.*, 68:3859-3866; and Oldach, D. W., et al., 2000, *Proc. Natl. Acad. Sci., USA*, 97:43034308).

Bioindicators may be unique to a specific ecosystem, or may be shared among a plurality of ecosystems. A diversity of microbial species may be readily retrievable even from a single body of water. Also, while any one body of water may have several unique OTUs, it is highly likely that the sample will include OTUs that are common to other ecosystems. Such common OTUs may represent 10% or more of the rDNAs analyzed in the sample, and may be shared across water samples. Also, an environmental event that occurs in an environmental community, such as a contamination, may alter the abundance of individual microbial species and related bioindicators in that community. The method may therefore comprise the step of determining whether an operational taxonomic unit (OTU) and/or an individual or species-specific DNA sequence is specific to a particular ecosystem, or varies in abundance between ecosystems. For example, a bioindicator for assessing freshwater microbial communities may comprise nucleic acid sequences specific to microbes that are characteristic of the freshwater system, or that are diagnostic of the response of microbes to certain changes in the fresh water environment. Or, a bioindicator for assessing marsh water microbial communities may comprise nucleic acid sequences specific to microbes that are characteristic of the marsh environment, or that are diagnostic of the response of microbes found in the marsh environment to certain changes (e.g., change in abundance) in a marsh water environment. Thus, referring back to FIG. 1, the method may therefore comprise identifying bioindicators or OTUs that vary among ecosystems 112. The method may also comprise identifying bioindicators or OTUs that are shared among, and/or that are unique to, individual ecosystems 114 (FIG. 1). Note, steps 112 and 114 may be performed in the order indicated, in reverse order, or simultaneously.

To determine which OTUs, if any, appear in more than one ecosystem, the sequences from a library of DNA sequences isolated from a ecosystem of interest may be compared to those sequences in every other library from ecosystems of interest in pairwise library comparisons, and a similarity coefficient may be calculated for each pairing. For example, in an analysis of five different samplings of DNA molecules from three different lakes (Lake Townsend, N.C.; City Lake, N.C.; and Toolik Lake, Ak.) there was some overlap between every pair of samples. There were also notable differences between the lakes. For example, none of the prokaryotic sequences were shared between Lake Townsend, a mesotrophic lake in North Carolina, and Toolik Lake, an oligotrophic lake in Alaska.

Figure 8:
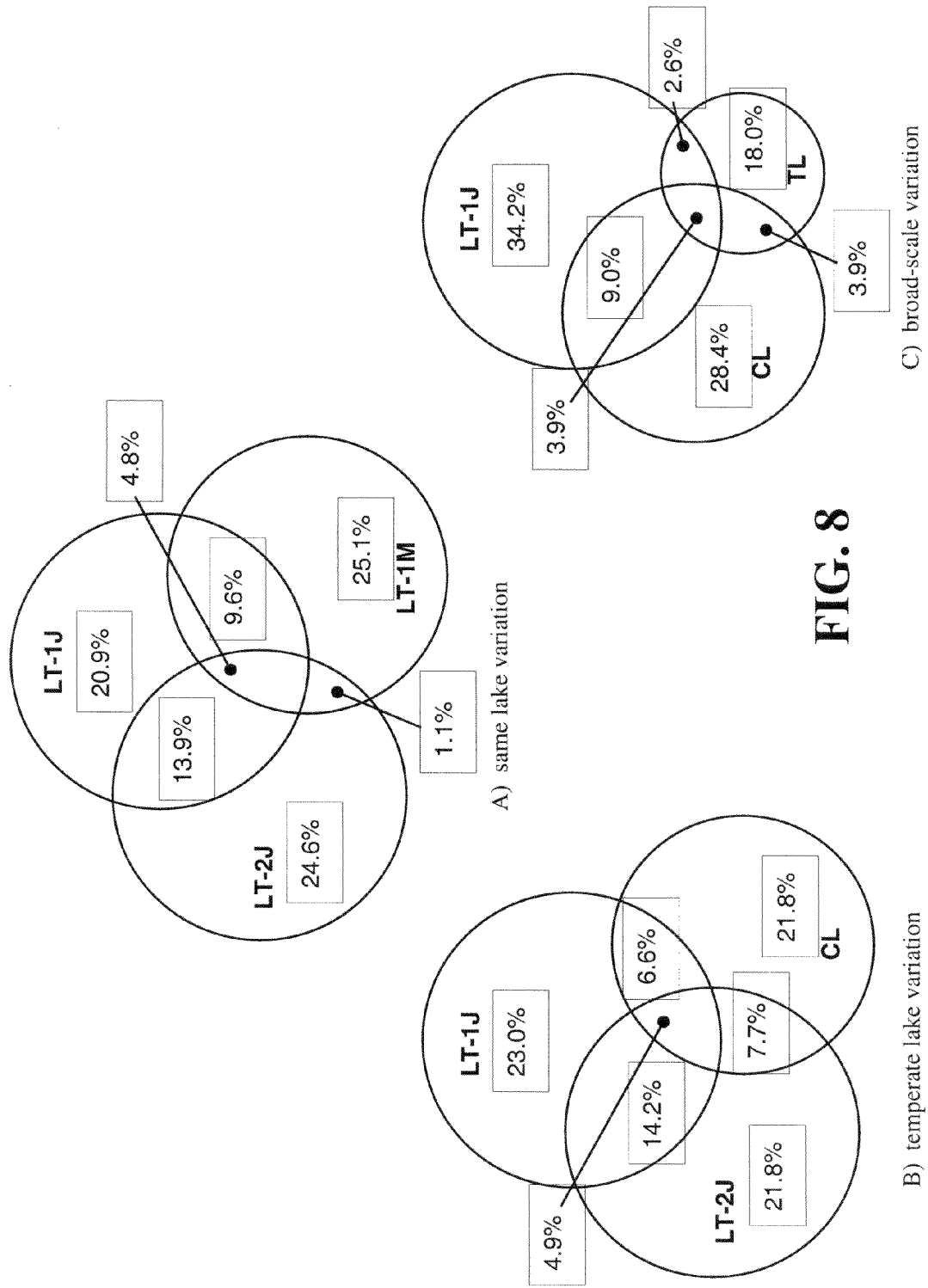
FIG. 8 shows Venn diagrams that illustrate the relative patterns of shared operational taxonomic units (OTUs) for five separate fresh water samples in accordance with an embodiment of the present invention. The size of each sample component is based on the total number of OTUs for that water sample relative to the other samples. Water samples from which the rDNA was isolated were as follows: LT-1J: Lake Townsend, station 1, June; LT-2J: Lake Townsend, station 2, June; LT-1M: Lake Townsend, station 1, March; CL: City Lake; TL: Toolik Lake.

Venn diagrams may be used depict sample comparisons at different spatial and temporal scales to identify sequences that may differ between ecosystems. Referring now to FIG. 8, in a fine-scale spatial comparison of samples taken in June from stations 1 and 2 at Lake Townsend, N.C. (LT-1J and LT-2J), it was found that even between samples that may be expected to be highly similar, differences in sequences may be found. For example, for LT-1J and LT-2J, there were two rDNA sequences that occurred four times as often in LT-2J as in LT-1J: an unidentified 16S rDNA OTU, and an 18S rDNA from *Geminigera cryophila*. Such unequal occurrences of an OTU between samples may signify a detectable difference in the relative abundance of a specific microbial population between samples, and OTUs that consistently vary in frequency among samples are potential bioindicators.

Once the nucleic acid sequences isolated from various ecosystems have been identified and compared, it may be possible to compile OTUs as putative bioindicators 116 (FIG. 1). For example, for five samplings from three different lakes (Lake Townsend, Greensboro, N.C.; City Lake, High Point, N.C.; and Toolik Lake, Ala.), 26 different eukaryotic OTUs represented by multiple copies, including 11 that are associated with known species, may be identified. Another 79 eukaryotic OTUs may be obtained as single copy clones, with many of the single-copy OTUs representing unidentified species (Marshall, 2002, Masters Thesis, University of North Carolina at Greensboro). Also, 45 different prokaryotic OTUs may be detected in multiple copies. Of these, 10 species are associated with a known species, and 19 species display substantial homology to reported sequences for as yet unidentified species. Another 92 single copy rDNA sequences, most from unidentified prokaryotes, may be recovered (Amos, 2002, Masters Thesis, University of North Carolina at Greensboro). As described in more detail herein, all of the sequences identified from the ecosystems of interest (e.g., water samples), whether derived from known or previously unidentified rDNA sequences, may be used as probes printed on an array of the present invention.

For example, for the four samplings of three lakes believed to be contaminated with mercury described herein, PCR amplicons may be used to generate 16S rDNA and 18S rDNA plasmid clone libraries (one library for each sampling). The libraries may then be sampled by randomly selecting 50 clones from each for sequence analyses. The resulting sequence data (~500 nucleotides for each clone) may be used to generate alignments so that sequences can be grouped into OTUs using a 97.5% sequence identity criterion. Samples may then be compared based on OTU composition so as to screen for candidate Hg bioindicators. Rank-abundance profiles may be assembled showing the number and relative abundance of OTUs found in each sample, as well as the OTUs that were designated as candidate Hg bioindicators (FIGS. 4 and 5).

It may be expected that three diverse samples would share approximately 4% of the OTUs recovered if 50 clones were sequenced from each sample. However, samples that have a higher chemical similarity (e.g., the presence of mercury) may also share a greater number of the same microbial sequences such that 10 or more candidate bioindicators might be expected to emerge from rDNA sequence analyses. This is consistent with previous work by Sorensen and colleagues (Muller, et al. 2001, 2002; Rasmussen and Sorensen 1998, 2001) who found rapid changes in community structure, including significant increases in the proportion of culturable mercury resistant bacteria. It may also be expected, that most of the unidentified rDNA sequences obtained from these samples would be novel. Therefore, the selection criteria may focus on direct associations between the presence of mercury and recovered sequences, rather than the specific identity of the microbial taxa associated with the various sequences.

For example, in certain embodiments, a microbial rDNA sequence may be established as a potential bioindicator for mercury if multiple copies were detected in three mercury-contaminated samples and it did not align with any other rDNA sequence in GenBank (unless known to be associated with mercury metabolism) or other databases.

Second, a sequence may designated as a potential bioindicator relating to mercury if multiple copies were found at two mercury-contaminated sites. If no sequences satisfy either of these criteria, then a sequence may be considered to be bioindicator for mercury if multiple copies are detected in at least one mercury-contaminated sample. Additionally or alternatively, a sequence may be considered to be mercury bioindicator if it grouped into one of the five most abundant mercury bioindicator OTUs. Using such criterion, candidate Hg bioindicators that meet the first two criteria, the samples that yielded them, and descriptions based on alignments with sequences reported in GenBank can be compiled (see e.g., Table 2).

TABLE 2

Abundance, distribution and BLAST identification of candidate mercury (Hg) bioindicators

| | NFHR 77 | NFHR 80.8 | FL-WCA1 | GL-DRTC | BLAST identification (≧97.5%) |
|---|---|---|---|---|---|
| Hg 1 | 2 | 2 | — | — | Uncultured bacterium clone P4T_162 (EF552046) |
| Hg 2 | 1 | 2 | — | 2 | Uncultured bacterium clone 170ds20 (AY212621) |
| Hg 3 | 1 | 2 | — | — | *Flavobacterium pectinovorum*, type strain DSM 6368 (AM230490) |
| Hg 4 | 1 | 1 | — | — | Uncultured bacterium clone Pia-s-4 (EF632936) |
| Hg 5 | 1 | 1 | — | — | No match |
| Hg 6 | 5 | 3 | — | — | Uncultured eukaryote clone Amb_18S_1283 (EF023834) |
| Hg 7 | 4 | 1 | — | 1 | Uncultured eukaryote clone: 18S-KM-B-35 (AB238192) |
| Hg 8 | 2 | 1 | — | 2 | Uncultured eukaryote clone: 18S-AK-B-23 (AB238131) |
| Hg 9 | 1 | 1 | — | 1 | No match |
| Hg 10 | 1 | 1 | — | — | Uncultured eukaryote clone: 18S-KM-B-21 (AB238178) |
| Hg 11 | 1 | 1 | — | — | No match |
| Hg 12 | 1 | — | — | 1 | *Staurosira construens* (AF525659) |
| Hg 13 | 1 | — | — | 4 | No match |
| Hg 14 | — | 1 | — | 2 | Uncultured Phaeosphaeriaceae clone Amb_18S_1368 (EF023910) |

Accession numbers in ( ).

In some cases, a majority of the candidates will not be identified based on BLAST alignments. This may be either because the candidate rDNA aligns with an uncultured microorganism as yet uncharacterized or because the candidate rDNA is unknown and fails to align with anything. Both cases present potential bioindicator opportunities since the vast majority of microbes have not been identified and their ecological functions remain unknown. Thus, in contrast to arrays that only use sequences specific to known microorganisms for the detection of biological changes, the arrays of the present invention may generally employ previously unidentified sequences as informative probes.

For example, Hg 1 is 99% identical to an uncultured bacterium reported as clone P4T_162 (Accession No. EF552046) and isolated during a study entitled "Microbial Community Analysis of Two Field-Scale Sulfate-Reducing Bioreactors Treating Mine Drainage" (publicly available on the NCBI database). Without more information, the ecological function of this organism remains unknown. However, although the identity of the microbe is unknown, the marker demonstrates potential dual applications as both bioindicator and bioremediator. In fact, many microbial bioindicators may also be bioremediators, but they have not been isolated and studied to establish their roles in overall community dynamics and their effects on the environment.

The method may next comprise the step of organizing a nucleic acid array of probes or an array of a plurality of assays (e.g., a plurality of probes or PCR assays) that can reflect microorganisms that are common to multiple communities, as well as organisms that are specific to one or only a few communities to thereby monitor the effect of an ecological change 118 (FIG. 1). Thus, the ability to assess environmental parameters of water quality may include a sufficient number of bioindicator species that have unique profiles in different ecosystems, but may also include species that are shared among samples to allow for general application.

The array may comprise nucleic acid probes and/or primers that are specific to known organisms. Additionally or alternatively, the array may comprise nucleic acids that are grouped to provide information about various taxonomic groups. For example, the array may comprise a plurality of prokaryotic and/or eukaryotic nucleic acid sequences derived from specific rDNAs. Or, the array may comprise a plurality of nucleic acid sequences organized by operational taxonomic unit. Notably, there is no requirement that the environmental DNA samples used to develop the array are the same as the environmental communities to be analyzed.

For example, in one embodiment, PCR primers derived from sequences specific to an OTU are used to amplify DNA from an ecosystem sample, and the amplified DNA is use to probe an array that includes oligonucleotide probes that are derived from the same OTU-specific nucleic acid molecules. If the ecosystem sample includes sequences that are specific to the OTU, the PCR product will hybridize to the array at the location of the correct probe. In certain embodiments, multiplex PCR is used for amplification of the sample DNA, such that a plurality of PCR primer sets, each set specific to a single OTU are used.

In another embodiment, the array may comprise PCR primers at each of the locations. For example, in certain embodiments, the array may comprises a plurality of primer sets at individual locations, where a primer set is two primers that can amplify a single genomic sequence. Or a plurality of individual PCR reactions may be used. A sample from an ecosystem as well as PCR reagents and polymerase enzyme may then be added at the location and the mixture subjected to thermal conditions such that PCR amplification can occur. In an embodiment, the production of a PCR product may be monitored using a dye (e.g., SYBR® Green dye) that can intercalate in the double-stranded PCR product thereby indicating whether amplification has occurred, and in some embodiments, providing a level of amplification.

Figure 9:
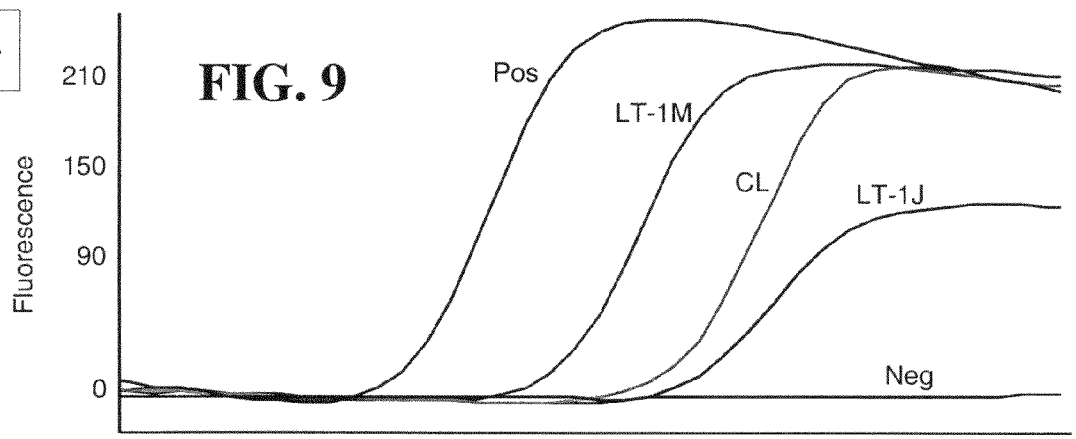
FIG. 9 shows quantitative PCR (Q-PCR) product accumulation curves generated using operational taxonomic unit (OTU)-specific primers and genomic DNA isolated from lake samples in accordance with an embodiment of the present invention where Panel (A) shows the relative abundance of the OTU for an unidentified cyanobacterium LD27 initially detected in Lake Townsend Station 1, March (LT-1M), panel (B) shows the relative abundance of OTU for *Zoogloea ramigera* initially detected in City Lake (CL), and panel (C) shows the relative abundance of OTU for *Asterionella formosa* initially detected in Lake Townsend Station 1, March (LT-1M). Pos: a positive control including a mixture of the three test DNAs; Neg: a negative control having no DNA; LT-1J: Lake Townsend, station 1, June; LT-1M: Lake Townsend, station 1, March; CL: City Lake.
Figure 9:
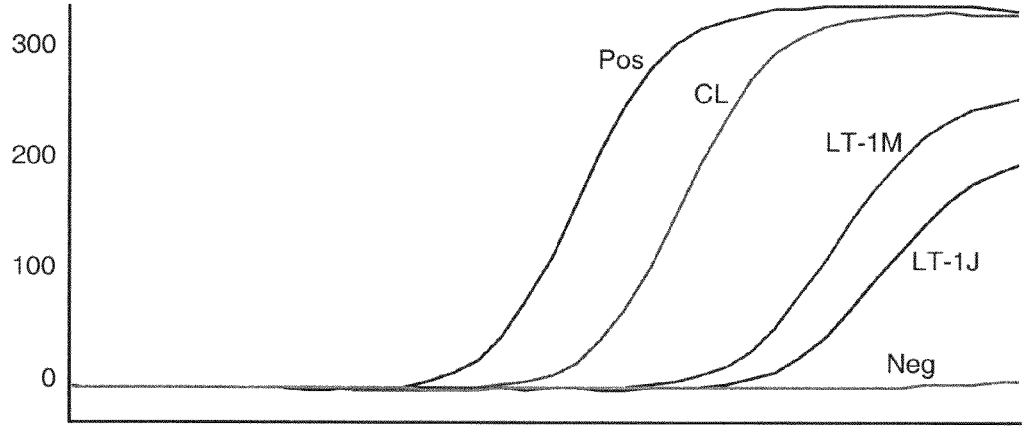
Figure 9:
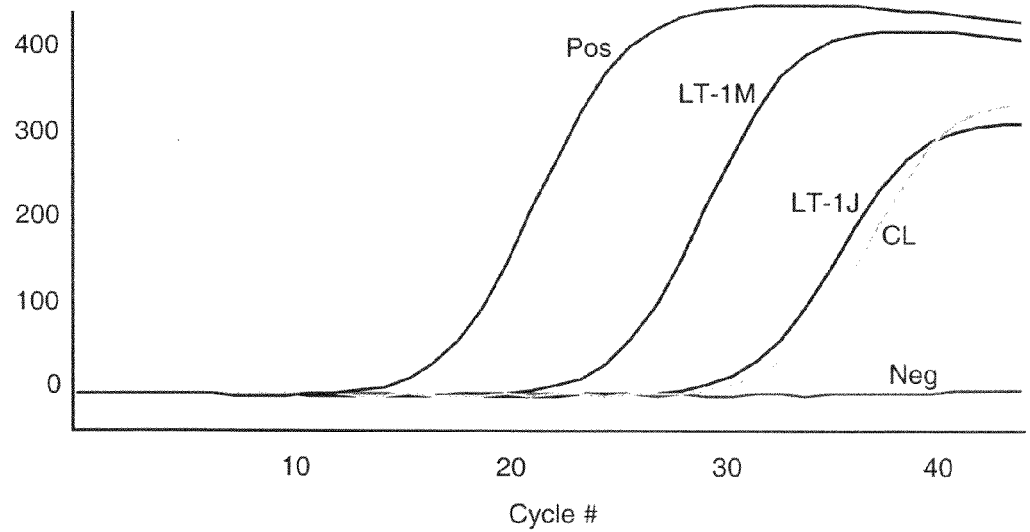

Samples that are derived from very different environmental communities may be expected to vary more than samples that are derived from similar communities, or the same community. Still, samples taken from a single lake, but either at a different location, or a different season, may also show variation. The variation may be qualitative, in that specific OTUs are either absent from, or present in, a water sample. Or, it may be that a certain OTU is much less abundant in one sample than another sample. For example, FIG. 9 illustrates a quantitative PCR determination of the relative amounts of three nucleic acid sequences found in each of three lake samples tested, but in highly varied amounts. For each of the curves shown in FIG. 9 (FIGS. 9A, 9B, and 9C) the second curve from the left represents the sample from which the nucleic acid of interest was detected in high abundance, and the third and fourth curves from the left represent other lake samples tested. Also, results for a positive control, including each of the test samples, and a negative control with no DNA, are shown. Such skewed amplification curves may be found where DNAs vary in quantity between samples. In alternate embodiments, the template DNAs may vary 10-fold, or 20-fold, or 50-fold, or more than 200-fold, between samples.

Figure 10A:
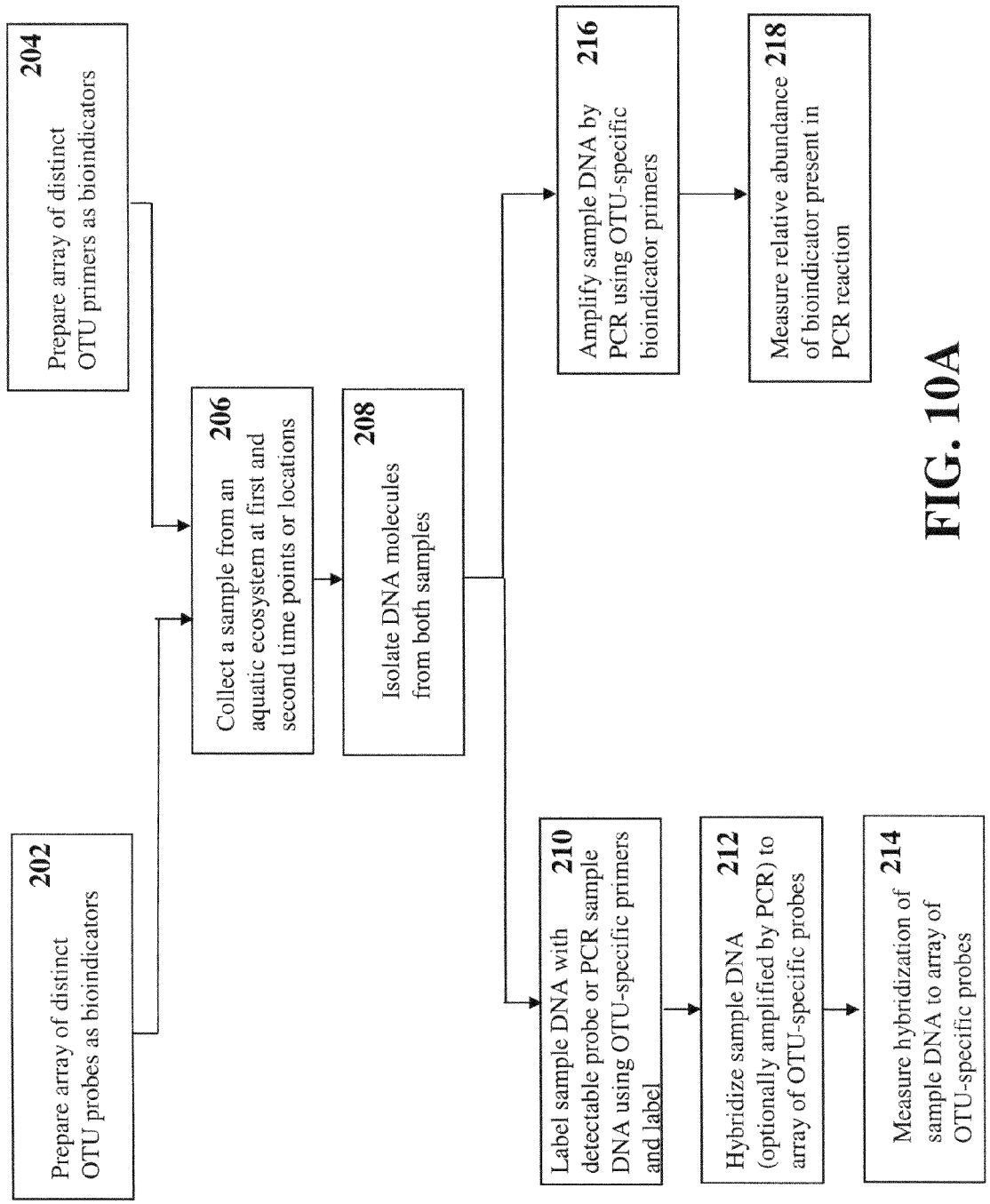
FIG. 10, Panels A and B, shows a method for monitoring water in accordance with alternate embodiments of the present invention wherein Panel A shows alternate methods to measure changes in a bioindicator in a ecosystem sample, and Panel B shows embodiments of how such data may be analyzed.

FIG. 10, panels A and B, provides a schematic representation of two embodiments of a method that may be used to monitor an aquatic ecosystem in accordance with an embodiment of the present invention. The method may comprise the first step 202 of generating an array comprising a plurality of oligonucleotides at known locations on a substrate, wherein each location on the array comprises an oligonucleotide probe having a sequence derived from a single, predetermined microbial operational taxonomic unit (OTU) as is described herein for FIG. 1. Alternatively, the method may comprise generating a plurality of individual primer sets, each primer set having at least one primer that has a sequence derived from a single, predetermined microbial operational taxonomic unit (OTU) 204. In certain embodiments, at least some of the OTU sequences used for the plurality of probes or primers are associated with the presence or absence of mercury. Also in certain embodiments, the array includes OTUs that are shared between ecosystems and/or unshared between ecosystems.

Next, the method may comprise the step of collecting a sample from an ecosystem of interest 206. In one embodiment, the ecosystem may comprise an aquatic ecosystem. For example, samples may be collected from a body of water at different levels, or at different locations, and/or during different times of the year. Also, samples from different aquatic ecosystems may be used. For example, samples may be collected from different lakes, pools, estuaries, or marshes. Or, aquatic ecosystems comprising different types of growth levels may be used (e.g., eutrophic, mesotrophic, or oligotrophic). Or, samples may be obtained from a body of water because there is a reason to suspect that the body of water has been contaminated in some way, as for example, with mercury. Additionally or alternatively, samples may be collected from a terrestrial and/or atmospheric ecosystem such as those described herein.

The method may next comprise the step of preparing a DNA sample from the ecosystem of interest 208. The nature of this step may vary depending upon whether DNA probes or primers or both will be used for detection of bioindicators in the sample.

For example, the polymerase chain reaction (PCR) may be used to amplify DNA sequences from a water sample of interest 210. The PCR amplification may use primers designed to amplify sequences which, if present in the sample and amplified, are complementary to the oligonucleotide probe or primer sequences on the array so as to generate a template for hybridization or PCR. In that way, if a sequence on the array is present in the sample of interest, it may be detected. In one example, a multiplex (i.e., multiple primer) PCR amplification is used to amplify multiple sequences from the sample of interest that are complementary to sequences immobilized on the array. Primer pairs that may be used for multiplex PCR may include a sequence selected from the group of SEQ ID NO: 114-SEQ ID NO: 316 or from the group of SEQ ID NO: 341-SEQ ID NO: 350 and/or SEQ ID NO: 371-SEQ ID NO: 388.

The sample genomic DNA or the PCR amplified DNA molecules from the sample of interest may be labeled in some manner 210. For example, the amplified DNA molecules may be labeled by the incorporation of a radiolabeled nucleotide, or a fluorescent dye(s) as described herein.

Next, the method may comprise the step of hybridizing the labeled DNA sample (i.e., either genomic or PCR amplified) from the ecosystem of interest to the array 214. In one embodiment, a high stringency hybridization is used. For example, the hybridization conditions may comprise the conditions as described herein.

Alternatively, the analysis may use a plurality of PCR primers in individual reactions and monitor whether amplification of a particular OTU-specific sequence occurs 216. In this case, the sample DNA may be directly used in the assay. Thus, as described above, in certain embodiments, the product comprises a plurality of primer sets at individual locations, where a primer set is two primers that can amplify a single genomic sequence. A sample from an ecosystem as well as PCR reagents and polymerase enzyme may then be added at the location and the mixture subjected to thermal conditions such that PCR amplification can occur. In an embodiment, the production of a PCR product may be monitored using a dye (e.g., SYBR® Green dye) that can intercalate in the double-stranded PCR product thereby indicating whether amplification has occurred, and in some embodiments, providing a level of amplification 218.

Figure 10B:
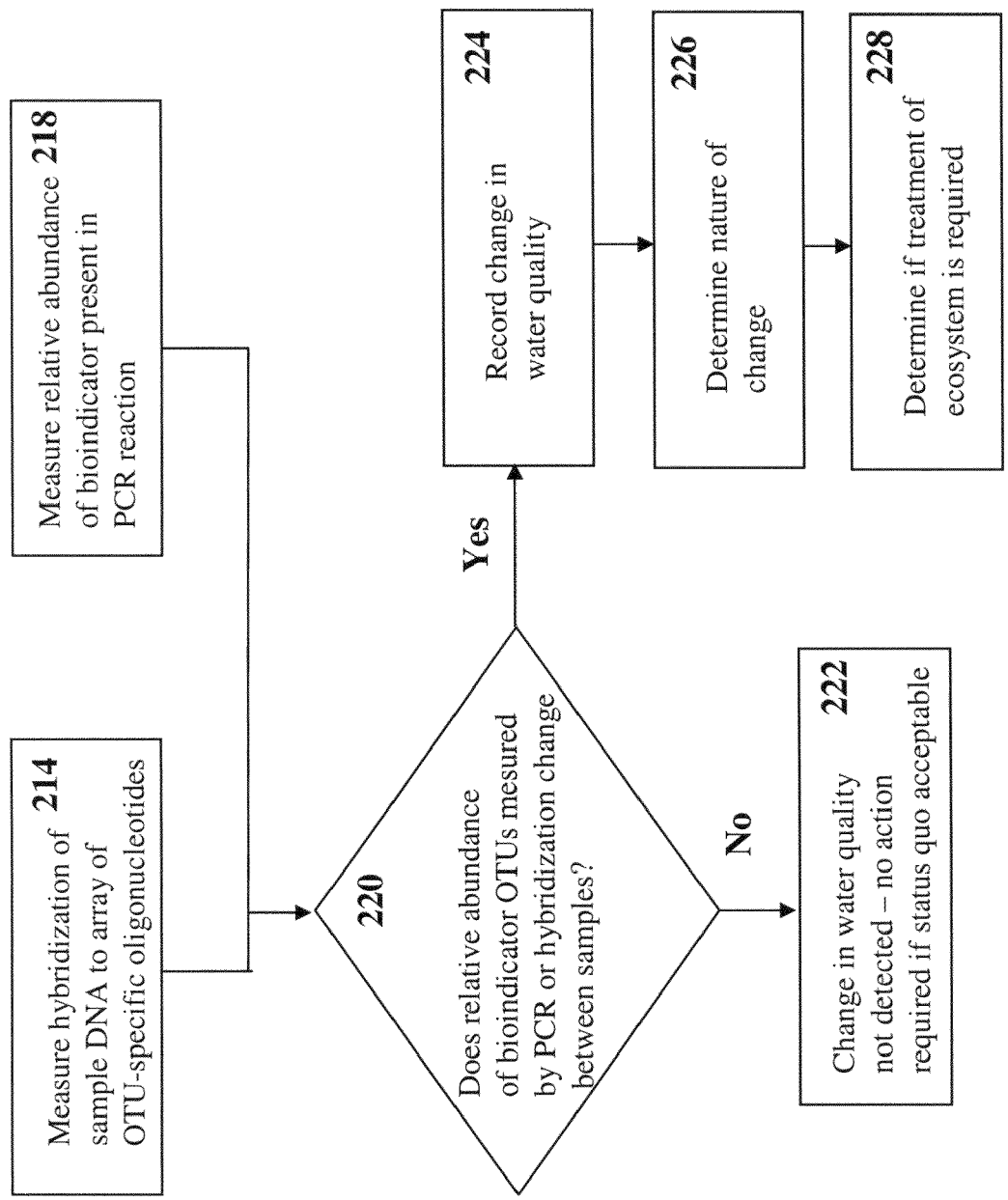

The method may then comprise the step of correlating hybridization of the DNA sample to the array with a parameter that comprises at least part of the ecosystem (FIG. 10B). The presence of sequences in the sample of interest that are complementary to putative bioindicator sequences on the array may be determined by measuring locations on the array that exhibit hybridization to the labeled probe 214. Or, the relative abundance of a bioindicator in a sample may be measured by real-time and/or quantitative PCR 218. In this way, the identity, and in some cases, the relative amounts, of sequences that are in the sample may be determined.

For example, if two samples of water (e.g., sample A and sample B) are hybridized to the same array, and different hybridization patterns result, or produce different amounts of an OTU-specific PCR product, than the oligonucleotide(s) on the array that displays a change in hybridization, or the primers that display changes in the levels of PCR product may correspond to a DNA sequence(s) that is diagnostic of a difference, or a plurality of differences, between the two samples. Thus, the method may comprise the step of determining whether the pattern of hybridization or PCR amplification at any one position or at a plurality of positions on the array changes 220. For example, in one embodiment, the pattern of hybridization may indicate a change in mercury levels in the sample.

In one embodiment, no change in the pattern of hybridization or PCR amplification at any one position or at a plurality of positions on the array is detected upon hybridization with two different samples. In this, case, no change in water quality is detected, and if the status quo is acceptable, no action is required 222. Alternatively, a change in the pattern of hybridization or PCR amplification at any one position or at a plurality of positions on the array is detected upon hybridization with two different samples. In this case the change in the water quality may be recorded 224 and the nature of the change determined 226. In an embodiment, the method may include the step of determining if treatment of the water is required 228.

Figure 11:
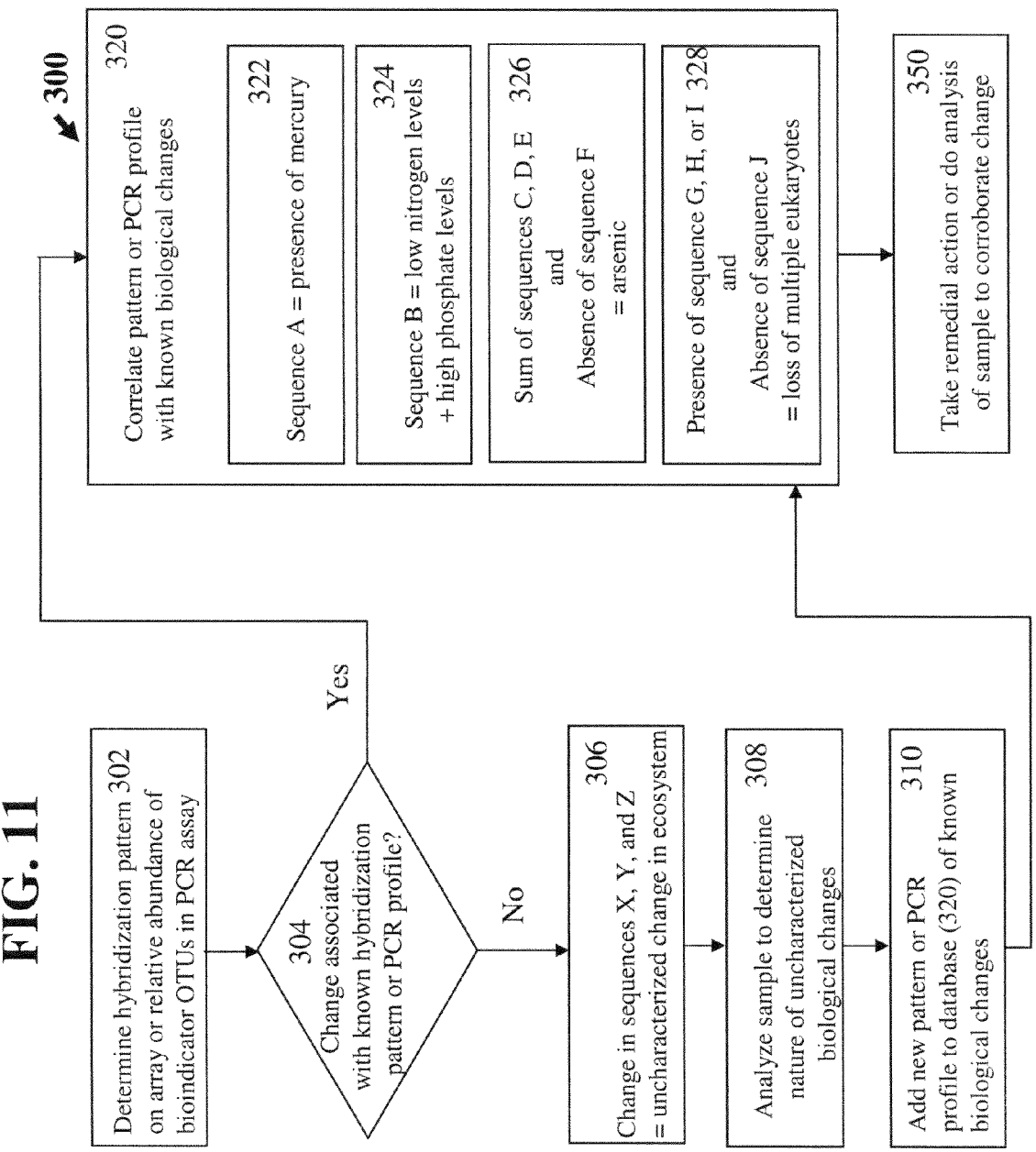
FIG. 11 illustrates the use of pattern analysis for assessing changes in an ecosystem in accordance with an embodiment of the present invention.

An example of the application of a method 300 of analysis of patterns, or changes in the patterns of bioindicator profiles to the evaluation of a ecosystem is shown in FIG. 11. As a first step, the method may include determining the pattern of hybridization or PCR amplification for an array of OTU-specific primers or probes 302. Methods for measuring hybridization may include use of a radiolabeled dNTP during amplification of the sample DNA such that DNA sequences that hybridize to an array of bioindicators such as OTU-specific oligonucleotides, may be detected by autoradiography. Or, the amplified PCR products hybridized to the probes may be labeled with a fluorescent dye and hybridization detected using a fluorometer. Once the pattern of hybridization and/or amplification has been measured and recorded, the pattern may be compared with the pattern of hybridization and/or amplification produced by a different sample (i.e., a sample from another ecosystem, or taken from the same ecosystem at a different time or location), such that any changes in hybridization and/or amplification between the two samples may be documented. Alternatively, the extent of PCR amplification using different primer sets may be monitored as a pattern of PCR amplification.

At this point, a determination may be made as to whether the new bioindicator profile(s) has a change that is associated with a known bioindicator profile(s) 304. If it is determined that the pattern of bioindicator profile(s) is not associated with a known biological change 306, the sample may be analyzed to determine the nature of the change 308. Once the nature of the change is known, the pattern of the bioindicator profile(s) may be added 310 to a database 320 of patterns associated with known biological changes.

Still referring to FIG. 11, in some cases, it may be possible to correlate the pattern of bioindicator profile(s), as detected by hybridization to OTU-specific oligonucleotides, or PCR amplification with OTU-specific oligonucleotides, to a known biological change(s) 320. For example, in one embodiment, the biological change may comprise a change in the levels of mercury in the sample. This may be possible even where at least some of the sequences on the array, or the changes in the hybridization pattern, arise from novel, or previously uncharacterized, organisms. For example, there may be a single change in the pattern of hybridization to an array, or a single change in one of a plurality of PCR amplification profiles, for two samples that is diagnostic of a single change between the two samples. Thus, as shown in FIG. 11, hybridization at the position corresponding to an oligonucleotide having the nucleic acid sequence of A may be associated with the presence of mercury 322. Again, it may not be necessary to identify or characterize the organism from which sequence A is derived as such information may be ascertained merely by prior characterization that sequence A is associated with chromium in a water sample.

Alternatively, a single change in the pattern of hybridization to an array or PCR amplification profiles for two samples may be diagnostic of a plurality of changes between the two samples. For example, a change in hybridization at sequence B may be associated with a change in the ratio of nitrogen to phosphate in a water sample 324. Or, there may be multiple changes in the pattern of hybridization to an array for two samples that are diagnostic of a single change between the two samples. For example, the presence of hybridization, or a particular level of PCR amplification, for oligonucleotide(s) having sequences from OTUs C, D, and E and the absence of hybridization, or a lack of PCR amplification, for oligonucleotide corresponding to sequence from OTU F may be diagnostic of the introduction of arsenic into the water system 326. In yet another embodiment, there may be multiple changes in the pattern of hybridization to an array for two samples that are diagnostic of multiple changes between the two samples. For example, the presence of hybridization, or PCR amplification, for oligonucleotides corresponding to sequences from OTU G, H, and I, in combination with the lack of hybridization, or PCR amplification, for sequences corresponding to OTU J, may be diagnostic of a loss of multiple eukaryotes from the system 328. The information provided by the array may be comprehensive and allow for any remedial steps that may be required to be taken 350. The analysis may be formatted as part of a computer program so as to be run on a computer. In one embodiment, known patterns for a bioindicator profile or profiles may be included as a part of the computer program. Alternatively, the information provided by the array may be considered to provide a preliminary screening which may then be verified by chemical and/or microbiological analysis of the sample.

Generation of Probes and Primers

As described herein, primers that may be used for amplification of bioindicator nucleic acid molecules from an ecosystem may be designed to amplify sequences from the variable regions of rDNA. Small subunit rRNA genes (SSU rDNA) are especially useful targets for the molecular identification of microbial species because these sequences contain highly conserved nucleotide regions interspersed with variable regions. The variable regions may be used as a foundation for phylogenetic classification and comparison of both prokaryotic and eukaryotic microbial species (e.g., Sogin and Gunderson, 1987, *Annals. NY Acad. Sci.,* 503:125-139). The sequence information also permits detection and quantification of microbial species by PCR amplification using species-specific primers.

Thus, in one embodiment, ribosomal DNA that includes highly conserved and highly variable regions is used to characterize the presence of microbial community members. Species-specific or OTU-specific primers that anneal to internal variable regions can then be used to test for the presence of individual species. For both eukaryotic and prokaryotic rDNA, the variable rDNA regions show sufficient variability to develop amplification primers and probes that may be sensitive and specific to the organism to be tested.

For increased specificity and sensitivity in microarray experiments, variable sequence regions within the SSU rDNA may be utilized in a two-tiered strategy: (1) species-specific or OTU-specific PCR primers (e.g., Tables 3-6) can be multiplexed in individual PCR reactions to selectively amplify individual species or OTUs; (2) PCR products may then be labeled and hybridized to corresponding species-specific or OTU-specific oligonucleotide probes (e.g., Tables 3-6) immobilized on a microarray, where the probes immobilized on the array have sequences that are included in the amplified DNA products. The process may provide improved specificity and sensitivity because each of the species-specific or OTU-specific primer pairs and probes are designed using the same rDNA sequence.

To determine nucleic acid sequences that are specific to a single OTU, and thus can be used to detect the presence of a specific OTU in an ecosystem of interest, samples from aquatic ecosystems (e.g., water) may be used to isolate DNA sequences derived from microbial ribosomal DNA. The individual ribosomal DNAs may be cloned and the nucleic acid sequence for each clone determined. Then, sequences from each rDNA clone are simultaneously aligned with either a prokaryotic rDNA sequence or a eukaryotic rDNA sequence to determine regions of variability for the cloned rDNAs. In this way, primers and probes (e.g., Tables 3-6) specific for a particular OTU (or microbe population) can be identified.

To ascertain the relative location and degree of variability among variable regions, rDNA sequences can be initially aligned using the multiple alignment computer program CLUSTAL W (Thompson et al., 1994, *Nucleic Acids Res.,* 22:4673-4680). Multiple alignment parameters including a gap initiation penalty of three, a gap extension penalty of one, a base match score of one, and a base mismatch penalty of one can be used. In some embodiments, transitions are not weighted and terminal gaps are not penalized. By aligning the cloned sequences with either the prokaryotic or eukaryotic rDNA, the SSU rDNA can be demarcated into conserved and variable sequence regions, which may be further aligned by hand to optimize the multiple alignment result where necessary. In certain embodiments, primers are designed that have at least 20 contiguous nucleotides with 80% or more of the nucleotides having 60% or more variability (i.e., the individual nucleotide is never represented more than 60% of the time by a single nitrogen base, A, C, G, or T) as assessed for sequences from all known rDNA molecules. In certain embodiments, primers from the V1 and V2 regions of either prokaryotic and/or eukaryotic rDNA are used. In some embodiments, for prokaryotic primer sequences and probes (Table 3), variable sequence regions may be used within nucleotides 50-880 (V1, V2, V3, and V4), based on alignments with *E. coli* rDNA (SEQ ID NO: 317) (FIG. 12A) (Brosius et al., 1981, J. Mol. Biol., 148:107-127; GenBank Accession No. V00348). Specifically, nucleotides 50-150 (V1 region) (SEQ ID NO: 319) or 160-250 (V2 region) (SEQ ID NO: 320) in the forward direction and nucleotides 430-510 (V3 region) (SEQ ID NO: 321) or 820-880 (V4 region) (SEQ ID NO: 322) (FIG. 12C) in the reverse direction allow for OTU-specific amplification by PCR that includes a region that complements microarray probes, which include nucleotides 160-250 (V2) (SEQ ID NO: 320) or 430-510 (V3) (SEQ ID NO: 321). Primer sequences within these regions can be selected to maximize specificity for each individual organism. Based on alignments with *S. cerevisiae* (Rubstov et al., 1980, Nucl. Acids Res., 8:5779-5794; GenBank Accession No. V01335) (SEQ ID NO: 318) (FIG. 12B) using the same alignment conditions, eukaryotic primer sequences and probes (Tables 2 and 4) included variable sequence regions within nucleotides 50-1100 (V1, V2, V3, and V4). Specifically, positions 50-550 (V1 plus flanking sequence region) (SEQ ID NO: 324) (FIGS. 12D-1) in the forward direction and positions 800-870 (V3) (SEQ ID NO: 326) or 1000-1100 (V4) (SEQ ID NO: 327) (FIGS. 12D-2) in the reverse direction allow for OTU-specific amplification of a region that includes a region that complements probes within nucleotides 600-800 (V2) (SEQ ID NO: 325) or 1000-1100 (V4). When the sequence regions specified for primer and probe design do not include OTU-specific sequences, such that primers designed for two microbes would be the same or substantially similar, other variable regions are used. For example, prokaryotic primer sequences may also include nucleotides 1100-1160 (V6) (SEQ ID NO: 323) in the reverse direction and eukaryotic primer sequences may also include nucleotides 1350-1450 (V5) (SEQ ID NO: 328) in the reverse direction, when necessary.

Thus, in one embodiment of the present invention, amplification of a genomic sample DNA may be performed by multiplex PCR using primers chosen to provide products that can hybridize to taxon-specific ribosomal DNAs. Using this protocol can dramatically reduce non-specific labeling, and eliminate the need for intermediate PCR reactions, which reduce sensitivity. Oligonucleotide probes that may be spotted to provide a taxon-specific array (e.g., SEQ ID NOS: 5-113 and/or SEQ ID NO: 329-SEQ ID NO: 340, and/or SEQ ID NO: 351-SEQ ID NO: 370), and the primers used to detect (i.e., amplify) such sequences in water samples (e.g., SEQ ID NOS. 114-316 and/or SEQ ID NO: 341-SEQ ID NO: 350 and/or SEQ ID NO: 371-SEQ ID NO: 388), are shown in Tables 3, 4, 5 and 6. For example, primers having the sequences SEQ ID NOS. 114 and 115 (1F and 1R, respectively) may be used to amplify DNA from a water sample such that the amplification product contains sequences that will hybridize with an oligonucleotide probe (1P) immobilized on an array, where probe 1P has the sequence described by SEQ ID NO: 5 (Table 3). Similarly, primers for Hg1 (SEQ ID NOS: 341 and 342) may be used to amplify DNA from a water sample such that the amplification product contains sequences that will hybridize with an oligonucleotide probe (Hg1) immobilized on an array (or its reverse complement Hg1rc), where probe Hg1 has the sequence described by SEQ ID NO: 329 and the reverse complement Hg1rc has the sequence described by SEQ ID NO: 330 (Table 5). In one embodiment, multiple primer pairs (e.g., SEQ ID NOS: 114-214) are used to amplify DNA sequences that include SEQ ID NOS: 5-60). In addition, as is known in the art, the reverse complementary sequence of each probe sequence in Tables 2 and 3 may also be spotted as an oligonucleotide on the array.

TABLE 3

Eukaryotic probes and primer pairs used for multiplex PCR

| Eukaryotic primer sequence (5'-3') | SEQ ID NO: | PCR No. | Template | GenBank Accession No. | Probe Sequence (5'-3') | SEQ ID NO: | Oligo No. |
|---|---|---|---|---|---|---|---|
| ATACAGGCGC TCGATAAGAG | 114 | 1F | Acanthamoeba mauritaniensis | AY35164 7 | ACTAACTCAATAGC AGGAACGGGAATC CAGAAGGAGGGA CGGGCGGGCC | 5 | 1P |
| AGCTGCTAGG GGAGTCATTC | 115 | 1R | | | | | |
| AACTCGACTTT ATGGAAGGG | 116 | 2F | Cryptosporidium parvum | AF22299 8 | GATTTCTCATAAGG TGCTGAAGGAG-TAAGGAACAACCT CCAATCTCTAGT | 6 | 2P |
| CAAAGTCCCTC TAAGAAGAC | 117 | 2R | | | | | |
| TTGGCTTTAGC CGGCGATAG | 118 | 3F | Cyclospora cayetanensis | AF11118 3 | AGTTCCGGAACACC AACGCACGCAGCG AAGCGCGGAAGGC TACCGGAAGA | 7 | 3P |
| AAGCCAAGGT AGGCGTTTCC | 119 | 3R | | | | | |
| GACGACACAT AACTCTAGAG | 120 | 4F | Entamoeba histolytica | X65163 | GAAATGTCTTATTG ACATCCCCTCAGCA TTGTCCCATGCTTG AATATTCA | 8 | 4P |
| TCATCCAATCC TTGGTTGAC | 121 | 4R | | | | | |
| AACTTGCCCAA TGCGCGG | 122 | 5F | Giardia intestinalis | AF19944 9 | CCCACGCGGCGGG TCCAACGGGCCTGC CTGGAGCGCTCCCG TTTCCTCGT | 9 | 5P |
| GGGAATACGG TGGTGTCTG | 123 | 5R | isolate Dog19 | | | | |
| GATTGGAATG ATGGGAATCC | 124 | 6F | Isospora belli | AF10693 5 | GAATTTCACCACGT ACACACCCCTAAG GGCGGACTGGCTG CTTCCAGCAG | 10 | 6P |
| AGGAGAAGTC AAGTATGACG | 125 | 6R | | | | | |
| GCGGTAGTAA GGAGACGTG | 126 | 7F | Microsporidium sp. STF | AY14064 7 | CTTTATCATCGGAC TCGCCCCTGGCCAG CGCTTTCGCCTCTG TCGCTCCT | 11 | 7P |
| GCATCGGCATC GTTTACTGC | 127 | 7R | | | | | |
| TTCGGTGGTGA GGTATTATC | 128 | 8F | Naegleria fowleri | AF33842 3 | CCTCCAACCATCTC CTGATGGAACTAGT TACCCCGTAAACAC TCTTAGGT | 12 | 8P |
| AAGATCGCTG GGATAGTGTC | 129 | 8R | | | | | |
| ATCGAGTATCA ATTGGAGGG | 130 | 9F | OTU LT3A27, multi-copy, | N/A | ACGGAGACAAACA AGCACCAACACAA GTGAAGGGCACGT TGCTCCAACCA | 13 | 9P |
| GACGGGGTCA ATACAACGAC | 131 | 9R | identified as Asterionella formosa | | | | |
| GCCAATGGTCT TCTTATTGG | 132 | 10F | OTU LT1A42, multi-copy, | N/A | CAAGCAGAAAGGC ACGCGCGCACCGTC CAACCAGAGGCTG ACAGTTCACA | 14 | 10P |
| GAGGTCGTAA ATTGACACTC | 133 | 10R | identified as Cryptomonas sp., strain M420 | | | | |
| TTCAAACCGGC CTCGTTCTG | 134 | 11F | OTU LT1A4, multi-copy, | N/A | GCACGCGCATGCC GTCCGACCAGAGG | 15 | 11P |

TABLE 3-continued

Eukaryotic probes and primer pairs used for multiplex PCR

| Eukaryotic primer sequence (5'-3') | SEQ ID NO: | PCR No. | Template | GenBank Accession No. | Probe Sequence (5'-3') | SEQ ID NO: | Oligo No. |
|---|---|---|---|---|---|---|---|
| CCCATAACCAACGAAATAGC | 135 | 11R | identified as *Cryptomonas ovata*, strain CCAP 979/61 | | CCGACAGCCCACACGCGCCCAAAA | | |
| TTAGCGAATCGTGGCACGTC | 136 | 12F | OTU LT2A7, multi-copy, | N/A | TAACTGTCCCTGATGGGACTAGTAGGGATTGGTTTAAAGCCTCTCCCTAG | 16 | 12P |
| AATGTATTCCTGCAAACGCC | 137 | 12R | identified as *Dileptus* sp. | | | | |
| GGGTTCTTACGAACTTTGGG | 138 | 13F | OTU LT2A19, single-copy, | N/A | TCTCAGACGGATGAACGCCTATACCTCGACCGGAGCCGCTGTACAAACGC | 17 | 13P |
| CTGATCGGGCTTGAAAGACC | 139 | 13R | identified as *Coleps* sp. | | | | |
| TATCGAGGACCAATTGGAGG | 140 | 14F | OTU LT3A2, single-copy, | N/A | ACCTAATGCCACACAGATTCCACCCAAGGATGGACGAGCTGCCCAAGTAC | 18 | 14P |
| GACGGAGTCAATACAACGAC | 141 | 14R | unidentified | | | | |
| TGGACTCTTTTGAGTCCGGC | 142 | 15F | OTU LT1A3, single-copy, | N/A | CCATCTGCGCCTCAACATGCAGGTAAATCGTAAAGAAAAGGCCAAATAGC | 19 | 15P |
| ATCAATACTAACACCCACCG | 143 | 15R | unidentified | | | | |
| TAACGATAGCGGGCTCGTTC | 144 | 16F | OTU LT1A10, multi-copy, | N/A | GTATCACACCAGGGAGGTTATTGAACGCAGACCACCTAGGAACACCTAA | 20 | 16P |
| CATAGGGTGCTGATAGAGTC | 145 | 16R | unidentified | | | | |
| CCGAGATTTCTCGGAAATTG | 146 | 17F | OTU LT2A12, multi-copy, | N/A | AAGGATGCTTTCAGGCACTGATCGCGCACACTGAGGTGGGAAGTGCCGTT | 21 | 17P |
| TTTCTCACGAGCTGCTGAGG | 147 | 17R | unidentified | | | | |
| ATGGTGGAGGTGATTCATTC | 148 | 18F | OTU TL1A16, multi-copy, | N/A | TAAGTGCAACGGGATCCTCATGCAGAAAGACCCGAGCCTGCCGTCCGACC | 22 | 18P |
| AATTGACATCCACTGATCCC | 149 | 18R | unidentified | | | | |
| GATACAGGACTCATCCGAGG | 150 | 19F | OTU TL1A1, multi-copy, | N/A | AAAGTAAACCTGCCAGCACAGACGGACACTCGGCGAAGAGCACCCGCCTG | 23 | 19P |
| AAACGCCTGCAGATCGCTAG | 151 | 19R | unidentified | | | | |
| ACAATGCCGGGCCTTTCAAG | 152 | 20F | OTU TL1A2, multi-copy, | N/A | TTAATGCCAGATATGCTCTCCCCGAGGATGGCTGCAGACACATAGTACAG | 24 | 20P |
| TGGAGTCGTTACAAACTTCC | 153 | 20R | unidentified | | | | |
| TCGGCGACGATGATTCATTC | 154 | 21F | OTU TL1A9, multi-copy, | N/A | AGTCGACCAGTTCTGACCCATGAGGCCGACCGGCTGAGCTCACTCTGAAC | 25 | 21P |
| TGAACAAACCACGCCCAATC | 155 | 21R | unidentified | | | | |
| CGGTTTACCGGCGATAGATC | 156 | 22F | OTU TL1A12, multi-copy, | N/A | TCAAACCTGATTCAAACCCGTATGGGTCGATCGGTCGTCCTCAGCAGAAA | 26 | 22P |
| TTCTCTCGAGGTGCTGAAGG | 157 | 22R | unidentified | | | | |
| AATCGGATCGCATGGGCTAG | 158 | 23F | OTU TL1A21, multi-copy, | N/A | TGGTAGGCTACCACTGCGCATCCACAAGGAGGCAGAAACTAGCCAACCAG | 27 | 23P |
| GAACGGGATAATTCTCGCCC | 159 | 23R | unidentified | | | | |
| CCCACTTATGTGGGTTTGAC | 160 | 24F | OTU CL1A3, single-copy, | N/A | GCTTCATGCAGGAGCATCTCAGCATCCAGTGTTGGGACCAGGACATACTG | 28 | 24P |
| GAAGTAGAGGATCTTGCCTC | 161 | 24R | unidentified | | | | |
| GACAGCTTCTTTAATGGAGG | 162 | 25F | OTU CL1A4, single-copy, | N/A | GTTATGATTCTATCTCAAGGAGGAGCGTCCTGTGCTCTCCCACTTCACTC | 29 | 25P |
| ATCTGTTGGTCCTCCAAATC | 163 | 25R | unidentified | | | | |

TABLE 3-continued

Eukaryotic probes and primer pairs used for multiplex PCR

| Eukaryotic primer sequence (5'-3') | SEQ ID NO: | PCR No. | Template | GenBank Accession No. | Probe Sequence (5'-3') | SEQ ID NO: | Oligo No. |
|---|---|---|---|---|---|---|---|
| AATACAGGGC TCTTTGAGTC AAGACGTACC ACCGATCCTG | 164 165 | 26F 26R | OTU CL1A5, single-copy, unidentified | N/A | TCCAGAAGGTGAG GCCGACGCAAAGA GTACTCACCGCTAG GTGGACCCTC | 30 | 26P |
| TAACAATGCG GAGCCTTCGG AAGAACGTCC GCCAATCCTG | 166 167 | 27F 27R | OTU CL1A6, single-copy, unidentified | N/A | ACAGTAAAGGACG CAGGTCCGGACGC CGACAAGTGAATG CCGACGCCTTC | 31 | 27P |
| TATCTGGCGCT TTTGCGTCG CAACGTCTACC CATCCCAAG | 168 169 | 28F 28R | OTU CL1A8, multi-copy, unidentified | N/A | TCTCTAGAAGGATG CCCAACCCGCACCG GCACTCACAGGCC AAAAAGGCC | 32 | 28P |
| ACTCGGGAAC CTAGTTCTAC TCTCTTACGGC GCCGAAAAG | 170 171 | 29F 29R | OTU LT2A20, single-copy, unidentified | N/A | CGAAGACGGATGA CTAACTATATACTG ACGTAAGCCAGCA TATAAATAGC | 33 | 29P |
| AGGGCCAACG GTCTTGTTAT TCGCAAATTGA CATCCACTG | 172 173 | 30F 30R | OTU LT1A5, multi-copy, unidentified | N/A | CACAATTAAGTGCA ACGGGATCCTCATG CAGAAAGACCCGA GCCTGCCGT | 34 | 30P |
| CTCTCTCCGAG TATCAATTG ACTTCCCTCAA TCGCTAGTC | 174 175 | 31F 31R | OTU LT1A8, multi-copy, unidentified | N/A | TATTAACGCACTAC GCCCTGGAAGGAT GCTTTCAGGCACTG ATCGCGCAC | 35 | 31P |
| GCAGAGCTTC ACAGTTTTGC AGACGTCTCCT GATCGCAAG | 176 177 | 32F 32R | OTU LT1A9, single-copy, unidentified | N/A | ACAGCTACCACCAC CCTAAGGTGGGA GGTCATCCCGATCA GAGATTCAA | 36 | 32P |
| N/A | | | OTU LT1A11, single-copy, unidentified | N/A | TTCCAAGAGGATGC CTCGGTCTAACCAG ACACAAACCCGTAT GGGTCGGT | 37 | 33P |
| N/A | | | OTU LT1A13, single-copy, unidentified | N/A | AAGTGTTTTCCGGA AGATGGACGCAAA CACCCGGTACACA GACCGCGAGT | 38 | 34P |
| ATACGTCCCGG GACTGCAAT CGAAGGCGGA TAATTCTCGC | 178 179 | 35F 35R | OTU LT3A5, multi-copy, unidentified | N/A | TAACAGAAGGATG GTAGGGCGGCTCA GCGCACTCAACTTG AGGGCAAAGT | 39 | 35P |
| ACAATGCAGG GCCTTTACGG GAATAACACT CACTGATCCC | 180 181 | 36F 36R | OTU LT3A6, multi-copy, unidentified | N/A | ACAGTACAAGTCTT GCGACTAGACCGTC CGGCCCAAAAACCT GAAATCCAA | 40 | 36P |
| ATACAGGACT CATCCGAGGC AAACGCCTGC AGATCGCTAG | 182 183 | 37F 37R | OTU LT3A7, multi-copy, unidentified | N/A | AAACAAGCCAGTA CCGAAAGCATTCG GACCGACTTCTGTC CGCCGAGATC | 41 | 37P |
| N/A | | | OTU LT3A11, single-copy, unidentified | N/A | GCAAGCGGATGAC TGTCAGAATCCCCG TCTAATGACTGAAG ACCTGAACA | 42 | 38P |
| CTTTACAGGTC TGGCAATTG CATACAGTGCT GACAGGGTC | 184 185 | 39F 39R | OTU LT3A13, single-copy, unidentified | N/A | ACCTAATGCCACAC AGATTCCACCCAAG GATGGACGAGCTG CCCAAGTAC | 43 | 39P |
| CAGGGCCTTTT CAGGTCTTG | 186 | 40F | OTU LT1A1, multi-copy, | N/A | TTCAGAAAAGAAG TGTCGTCCCGATCG | 44 | 40P |

TABLE 3-continued

Eukaryotic probes and primer pairs used for multiplex PCR

| Eukaryotic primer sequence (5'-3') | SEQ ID NO: | PCR No. | Template | GenBank Accession No. | Probe Sequence (5'-3') | SEQ ID NO: | Oligo No. |
|---|---|---|---|---|---|---|---|
| CACAAGGTGC CAACAGAGTC | 187 | 40R | unidentified | | CACTACCGTAAGGC GGCAAGCGT | | |
| AACAATGTCTG GCCCTACGG | 188 | 41F | OTU LT1A38, multi-copy, | N/A | AATGCCGCTGGTCA CACGGAAGAAAGA | 45 | 41P |
| GTAAACAACG CCCACCGATC | 189 | 41R | unidentified | | AGCCGACCAAACA GTGCGACTTG | | |
| GAGGGCAAGT CTGGTGCCAG | 190 | 42F | All LT1A & LT3A OTUs | N/A | N/A | | |

TABLE 4

Prokaryotic probes and primer pairs used for multiplex PCR

| Prokaryotic primer Sequence (5'-3') | SEQ ID NO: | PCR No. | Template | GenBank Accession No. | Prokaryotic probe Sequence (5'-3') | SEQ ID NO: | Oligo No. |
|---|---|---|---|---|---|---|---|
| CGAATGGATT AAGAGCTTGC | 191 | 43F | Bacillus anthracis strain: | AB116124 | GTGACAGCCGAA GCCGCCTTTCAAT | 46 | 43P |
| TGCCAGCTTAT TCAACTAGC | 192 | 43R | S51 | | TTCGAACCATGC GGTTCAAAATGT T | | |
| GAACGTACCA TTTGCTACGG | 193 | 44F | Brucella melitensis | AF220149 | CCAACGCGGGCC GATCATTTGCCG | 47 | 44P |
| ACCGTCATTAT CTTCACCGG | 194 | 44R | | | ATAAATCTTTCCC CCGAAGGGCACA T | | |
| ACGGGCTTCG GCCTGGTG | 195 | 45F | Burkholderia mallei strain | AY305760 | AGGCCCGAAGGT CCCCGCTTTCAT | 48 | 45P |
| TCCGGGTATTA GCCAGAATG | 196 | 45R | 2000031063 | | CCTCAGATCGTAT GCGGTATTAATC | | |
| GCTTGCTAGAA GTGGATTAG | 197 | 46F | Campylobacter jejuni strain | AF550630 | TCCTACACCGAA AAACTTTCCCTAC | 49 | 46P |
| CGTCAGAATTC TTCCCTAAG | 198 | 46R | B99/206 | | TCAACTTGTGTTA AGCAGGAGTATA | | |
| TTTAGTGGCGG AAGGGTTAG | 199 | 47F | Chlamydophila psittaci clone | AY334530 | GGTCCGAAGATC CCCTTCTTTAATA | 50 | 47P |
| ATCTCTCTTAT TCCCAAGCG | 200 | 47R | cvCps2 | | TGTTTTAGATGCC TAAACATACCAC | | |
| AAGCTTCCTTC GGGAAGTGG | 201 | 48F | Clostridium botulinum strain | AY303799 | CGCCGCGGGTCC ATCTCAAAGCAA | 51 | 48P |
| GGTACCGTCAT TATCGTCC | 202 | 48R | AIP 355.02 | | TAAATCTTTGATA AGAAAATCATGC G | | |
| ATAACCTGGG GAAACTCGGG | 203 | 49F | Coxiella burnetii strain Nine Mile | Y11502 | TCATCTTATAGCA CGAGGTCCGAAG | 52 | 49P |
| CCAAGGATATT ACCCTTGAG | 204 | 49R | | | ATCCCCCGCTTTG CTCCAAAGAGAT | | |
| AGAAGCTTGCT TCTTTGCTG | 205 | 50F | Escherichia coli O157:H7 | AB035920 | ACATCCGATGGC AAGAGGCCCGAA | 53 | 50P |
| TTCCTCCCCGC TGAAAGTAC | 206 | 50R | | | GGTCCCCCTCTTT GGTCTTGCGACG T | | |
| CAATTCTGGGA AGCGTGG | 207 | 51F | Escherichia coli O157:H7 | NC 002655 | CAATTCTGGGAA GCGTGGCATTAA | 54 | 51P |
| CGATGCATGAT GATGACA | 208 | 51R | EDL933 | | TACTGAATTGTCA TCATCATGCATCG | | |

TABLE 4-continued

Prokaryotic probes and primer pairs used for multiplex PCR

| Prokaryotic primer Sequence (5'-3') | SEQ ID NO: | PCR No. | Template | GenBank Accession No. | Prokaryotic probe Sequence (5'-3') | SEQ ID NO: | Oligo No. |
|---|---|---|---|---|---|---|---|
| N/A | | | Escherichia coli O157:H7 EDL933 | NC 002655 | GGTTGATGAAAA AGCATTTGGAGC CGCGAAATTTAC CAGTGTCTTAAA AC | 55 | 52P |
| N/A | | | Escherichia coli O157:H7 EDL933 | NC 002655 | TGTCCGATTCAGC ACGGGTAAATAG TCGTATTGTTAGT GGCCGAATTTAA | 56 | 53P |
| N/A | | | Escherichia coli O157:H7 EDL933 | NC 002655 | TTGCTGGAGAGT CCTTCTCGGGTAT CGATTGTCGAAG ATAAACATATTT A | 57 | 54P |
| GTGGTGGATTA CGCCATG GCTATTACTCC CCCCCGT | 209 210 | 55F 55R | Escherichia coli O157:H7 EDL933 | NC 002655 | GTGGTGGATTAC GCCATGACATGG GAGGATTAACGG GGGGGAGTAATA GC | 58 | 55P |
| TCTGGAGTATC AAGCACT CCAGGAAGAG GGTTTTGT | 211 212 | 56F 56R | Escherichia coli O157:H7 EDL933 | NC 002655 | TCTGGAGTATCA AGCACTTATAAC CTAATAACACAA AACCCTCTTCCTG G | 59 | 56P |
| GCCCTGACGTA TGGCGGG GTAATGGTCAC CGTCACT | 213 214 | 57F 57R | Escherichia coli O157:H7 EDL933 | NC 002655 | GCCCTGACGTAT GGCGGGTACGAA ATGAAGCCAGTG ACGGTGACCATT AC | 60 | 57P |
| N/A | | | Escherichia coli O157:H7 EDL933 | NC 002655 | ACTGGCGGAAC ACATGAAAACGT AACCACGCTACC AGTAGCCAGAAG AA | 61 | 58P |
| N/A | | | Escherichia coli O157:H7 EDL933 | NC 002655 | CCATTAAAACTA ATGCCTGTCATA ATGGAGGGGAT TCAGCGAAGTTA TT | 62 | 59P |
| AAGACATCTTC ACCGTTC TCAGATTTCCC CTCGTGC | 215 216 | 60F 60R | Escherichia coli K12 | NC 000913 | AAGACATCTTCA CCGTTCACGATAT TTTGAAAGCACG AGGGGAAATCTG A | 63 | 60P |
| N/A | | | Escherichia coli K12 | NC 000913 | CACCGTCGCTTTA AAACGCGCCCGG TGGGAGAATCGT CGTTGTACATTTA | 64 | 61P |
| N/A | | | Escherichia coli K12 | NC 000913 | TTTCTGATCGCGT TGCTGCGCTGATC AAAGAAGTAAAC AAAGCAGCTTAA | 65 | 62P |
| ATGGCATCCGT GGTATCC CACTTCACCGT TTTTGAA | 217 218 | 63F 63R | Escherichia coli K12 | NC 000913 | ATGGCATCCGTG GTATCCCGACTCT GCTGCTGTTCAA AAACGGTGAAGT G | 66 | 63P |
| AACAGCTTGCT GTTTCGCTG TTCCTCCCCGC TGAAAGTAC | 219 220 | 64F 64R | Shigella sonnei | X96964 | N/A | | |

TABLE 4-continued

Prokaryotic probes and primer pairs used for multiplex PCR

| Prokaryotic primer Sequence (5'-3') | SEQ ID NO: | PCR No. | Template | GenBank Accession No. | Prokaryotic probe Sequence (5'-3') | SEQ ID NO: | Oligo No. |
|---|---|---|---|---|---|---|---|
| CAGGTCTTAGG ATGCTGACG | 221 | 65F | Francisella tularensis strain 3523 | AY243028 | AGGCTCATCCAT CTGCGACACGCC GAAAGCCACCTT TAATCCACAGAT AT | 67 | 65P |
| AAGGCTATTA ACCTTGAGGC | 222 | 65R | | | | | |
| AGACTATCTAC TTCTGGTGC | 223 | 66F | Legionella pneumophila serogroup 6 | AJ496383 | AATCCTTAAAAG TCGGTCGTAGTCC GGATTGGAGTCT GCAACTCGACTC C | 68 | 66P |
| ATACAGGTGCT GCATGGCTG | 224 | 66R | | | | | |
| GAGTAGCAAT ACTCAGCGGC | 225 | 67F | Leptospira interrogans | Z12817 | ATCTCCGAGCAA TAAATCTTTACCC GAAAAATCTTAT GATCTCTCGGGA C | 69 | 67P |
| TACCATCATCA CATTGCTGC | 226 | 67R | | | | | |
| GAGCTTGCTCC TGGATTCAG | 227 | 68F | Pseudomonas aeruginosa strain WatG | AB117953 | TCATCTGATAGC GTGAGGTCCGAA GATCCCCCACTTT CTCCCTCAGGAC G | 70 | 68P |
| GTAACGTCAA AACAGCAAGG | 228 | 68R | | | | | |
| AGTTAATTAGT GGCAGACGG | 229 | 69F | Rickettsia prowazekii | M21789 | ATCTGACGCGGG CCCATCCATCAG CGATAAATCTTTC CTCCGTAGAGAA T | 71 | 69P |
| ACTAAACCGC CTACGCACTC | 230 | 69R | | | | | |
| AGCTTGCTGCT TTGCTGACG | 231 | 70F | Salmonella typhimurium | Z49264 | CTTGGTGAGCCG TTACCTCACCAAC AAGCTAATCCCA TCTGGGCACATCT | 72 | 70P |
| TAACCACAAC ACCTTCCTCC | 232 | 70R | | | | | |
| GAACTTGTTCC TTGGGTGGC | 233 | 71F | Vibrio cholerae CECT 514 T | X76337 | ATCCCACCTGGG CATATCCGGTAG CGCAAGGCCCGA AGGTCCCCTGCTT T | 73 | 71P |
| TTAACCACCTT CCTCCCTAC | 234 | 71R | | | | | |
| GTAGTTTACTA CTTTGCCGG | 235 | 72F | Yersinia pestis | AF366383 | TCTGGGTTCATCC GATGGCGTGAGG CCCTAAGGTCCC CCACTTTGCTCTT | 74 | 72P |
| GAGCGTATTA AACTCAACCC | 236 | 72R | | | | | |
| GCAAAGTGGC CCTCTGATTC | 237 | 73F | Arsenite-oxidizing bacterium MLHE-1 | AF406554 | TCAAGACCCACG GCTATTAACCGT AAGCTTTTCCTCC CTGCTGAAAGTG C | 75 | 73P |
| CCATAAATGA ACCCAACGGC | 238 | 73R | | | | | |
| ACCGGATACA CCTTCATACC | 239 | 74F | Thiomicrospira sp. CVO | U46506 | GCCGGTGCTTATT CATATGCTACCGT CATTTTCTTGACA TATAAAAGGAG | 76 | 74P |
| CCGCAATGAC AAGCATCACG | 240 | 74R | | | | | |
| ACGCTCCGATT TCACAGTTC | 241 | 75F | Desulfovibrio longreachii | Z24450 | GTACCGTCAGAC CATGGCTGATTA GCACCATGGCGG TTCTTCCCTCCTG A | 77 | 75P |
| AAGTCCAGCA GTATCAAGGG | 242 | 75R | | | | | |
| TGGGTTTACCT AACACTACG | 243 | 76F | Bacillus arsenicoselenatis | AF064705 | CAAGGTACCGCC CTATTTGAACGGT ACTTGTTCTTCCC TAGCAACAGAGC | 78 | 76P |
| TAGAGTCGAG TTACAGACCG | 244 | 76R | | | | | |
| ATCATGAGTTC ACATGTCCG | 245 | 77F | Uncultured human fecal bacterium HF74 | AF233412 | TATTCATAAGGT ACATACAAAACA CCACACGTGGCG AACTTTATTCCCT T | 79 | 77P |
| CAATCGGAGTT CTTCGTG | 246 | 77R | | | | | |

TABLE 4-continued

Prokaryotic probes and primer pairs used for multiplex PCR

| Prokaryotic primer Sequence (5'-3') | SEQ ID NO: | PCR No. | Template | GenBank Accession No. | Prokaryotic probe Sequence (5'-3') | SEQ ID NO: | Oligo No. |
|---|---|---|---|---|---|---|---|
| ATCATGAGTTC ACATGTCCG | 247 | 78F | Uncultured human fecal bacterium HF8 | AF233408 | TATTCATAAAGT ACATGCAAACGG GTATGCATACCC GACTTTATTCCTT T | 80 | 78P |
| CAATCGGAGTT CTTCGTG | 248 | 78R | | | | | |
| GCCGTCTACTC TTGGCC | 249 | 79F | Uncultured human fecal bacterium HF10 | AF233413 | TATTCATACGGTA CATACAAAAAGG CACACGTGCCTC ACTTTATTCCGT | 81 | 79P |
| CCTGCCTCTAC TGTACTC | 250 | 79R | | | | | |
| ACGGGTGCTTG CACCTGG | 251 | 80F | *Burkholderia cepacia* | AB091761 | AGGCCCGAAGGT CCCCCGCTTTCAT CCGTAGATCGTA TGCGGTATTAATC | 82 | 80P |
| CGACTGTATTA GAGCCAAGG | 252 | 80R | | | | | |
| GTTGGCCGATG GCTGATTAG | 253 | 81F | *Burkholderia cepacia* genomovar III | AF148556 | CGGTACCGTCAT CCCCCGACTGTAT TAGAGCCAAGGA TTTCTTTCCGGAC | 83 | 81P |
| TCTGCCATACT CTAGCCTGC | 254 | 81R | | | | | |
| ACATGCAAGT CGTACGAGAG | 255 | 82F | OTU LT3A11, multi-copy, identified as Unidentified cyanobacterium clone LD27 | N/A | AGCCGCAAGCTT CTCTTTAGGCGG AAATCCATTTCAC TCGAAAGCATAT G | 84 | 82P |
| ACACGTCATTT ATTCCTCCC | 256 | 82R | | | | | |
| ACGAACCTTCG GGTTAGTGG | 257 | 83F | OTU LT1A53-3A9, multi-copy, identified as *Synechococcus* sp. | N/A | AGACGCGAGCTC ATCCTCAGGCGA AATTCATTTCACC TCTCGGCATATG G | 85 | 83P |
| TCAAGTACCGT CAGATCTTC | 258 | 83R | | | | | |
| AAAGGCCTAC CAAGGCTTCG | 259 | 84F | OTU LT1A53, multi-copy, identified as *Synechococcus* sp. LBG2 | N/A | CCATCGCAGTAA TGGAGTTAAGCT CCACGCTTTGAC GACAGACTTAAA AG | 86 | 84P |
| GGCACTCTCTC GTTTCCAAG | 260 | 84R | | | | | |
| AAAGGCTTAC CAAGGCATTG | 261 | 85F | OTU LT3A9, multi-copy, identified as *Synechococcus* sp. LBP1 | N/A | CCATCGCTGAAA TGGAGTTGAGCT CCACGCTTTAAC GACAGACTTGTA AA | 87 | 85P |
| CCTCCGGTTTC CCAGAG | 262 | 85R | | | | | |
| GTAACAGGTCT TTCGGGATG | 263 | 86F | OTU TL1A7, multi-copy, identified as Uncultured beta proteobacterium clone OS1L-16 | N/A | CGCTCTAGTAGC ACAAGGCCCGAA GGTCCCCTGCTTT CATCCATAGATCT | 88 | 86P |
| CAAGACTTTTC GTTCCGTAC | 264 | 86R | | | | | |
| TCTTTCACCGG AGCTTGCTC | 265 | 87F | OTU TL1A9, multi-copy, identified as *Enterococcus gallinarum* strain LMG 13129 | N/A | TCAGTGACGCAA AAGCGCCTTTCA ACTTTCTTCCATG CGGAAAATAGTG T | 89 | 87P |
| CTCTCATCCTT GTTCTTCTC | 266 | 87R | | | | | |
| ACGGTCGCGT AACACGTAAG | 267 | 88F | OTU LT1A31, multi-copy, identified as Uncultured Crater Lake bacterium CL500-18 | N/A | TCCTGAAGCGAT AAATCTTTAGAC ACAAGTCGATGC CGACTCGTGACC AC | 90 | 88P |
| CGTCAAATTTC TTCCCACTC | 268 | 88R | | | | | |
| ATGAAGCTACT TCGGTAGTG | 269 | 89F | OTU CL1A15, single-copy, identified as Uncultured | N/A | AGGTCATCTTCA ACCGAAAAACTT TCCAGCCCCGAT CATGCGATCAGA | 91 | 89P |
| TGTAGGTACCG TCACTTTCG | 270 | 89R | | | | | |

TABLE 4-continued

Prokaryotic probes and primer pairs used for multiplex PCR

| Prokaryotic primer Sequence (5'-3') | SEQ ID NO: | PCR No. | Template | GenBank Accession No. | Prokaryotic probe Sequence (5'-3') | SEQ ID NO: | Oligo No. |
|---|---|---|---|---|---|---|---|
| | | | Crater Lake bacterium CL0-27 | | GC | | |
| ATGAAGCACC TTCGGGTGTG TGCAGGTACC GTCACTTTCG | 271 272 | 90F 90R | OTU LT1A54, multi-copy, identified as Uncultured Crater Lake bacterium CL0-64 | N/A | TCATCTTCAACCG AAAAACTTTCCA AACCCGCGGATG CCCGCAGGTTTC A | 92 | 90P |
| GATCTTTGATC TTAGTGGCG TCAAGTACCGT CAGAACTTC | 273 274 | 91F 91R | OTU LT1A55, multi-copy, identified as Uncultured freshwater bacterium LCK-26 | N/A | CAGACGCGAGCT CTTCCTAAGGTG GATAAATCCTTTT ACCTCTCGGCGT A | 93 | 91P |
| AACGTACCCA AGAGTGGG AAGGATATTA GCCTCTACCG | 275 276 | 92F 92R | OTU CL1A9, multi-copy, identified as Zoogloea ramigera | N/A | GGCCGCTCCAGG AGCACGAGGTCT TGCGATCCCCCG CTTTCATCCTTAG A | 94 | 92P |
| TGAAGTTCCTT CGGGAATGG TTCTTCCCTAC TGAAAGAGG | 277 278 | 93F 93R | OTU LT1A27, multi-copy, identified as Uncultured actinomycete clone SFD1-39 | N/A | ATCTTTCATCAAA ATTTTTTCCCGGC TCGGCGATGCCG CCAAGACGGAGT | 95 | 93P |
| CTCATCAGCAA TGGTGGGAG TCAACTCCGGA GGAGAACC | 279 280 | 94F 94R | OTU LT1A46, multi-copy, identified as Uncultured planctomycete clone CY0ARA-031E04 | N/A | TCATGTAAGCCG CTCCTCCGGCGG AATCACACCTTTG CTCCGCAGAGTT C | 96 | 94P |
| GGCAGCACGG TCTAGTTTAC TCAAATCCTCC TCCCCACTG | 281 282 | 95F 95R | OTU TL1A1, multi-copy, unidentified | N/A | TATTCTTAAAGCG CCAGGCCTTGCG GTCCCCAGCTTTT CTCCTCAGAGAT | 97 | 95P |
| GTCAGACTTCG GTCTGATTG GGTACTTCTTC CCGAGCAAC | 283 284 | 96F 96R | OTU TL1A2, multi-copy, unidentified | N/A | CTCCATCAGCGC CCTTGCGAGCTTT CATCCCTTCTGCG ACGAAGGGATCG | 98 | 96P |
| ATGTAGCAAT ACAGGACAGC CGTACATTTGA TTCCCTACG | 285 286 | 97F 97R | OTU TL1A6, single-copy, unidentified | N/A | GGGGCACGGGCT CATCTTGGGGCG GAATCACACCTTT GGTCCGCAAACA T | 99 | 97P |
| ATGAAGCTGG AGCTTGCTCC GCGAGCTCATC CTTGACC | 287 288 | 98F 98R | OTU CL1A2, multi-copy, unidentified | N/A | TCCTTGACCAAA ATTCTTTCCACGC CCGTGGGATGCC CCAAGGCGTCGT A | 100 | 98P |
| ACGGGAGCAA TCCTGGTG CCACTGTATTA GAGCAGACC | 289 290 | 99F 99R | OTU CL1A10, multi-copy, unidentified | N/A | TGATATCGGCCG CTCCAATCGCGC GAGGTCTTGCGA TCCCCCGCTTTCA T | 101 | 99P |
| ACGGCTTCGGC CTAGTAAAG AGGGCTGTTCA CCCTAATGG | 291 292 | 100F 100R | OTU LT2A3, multi-copy, unidentified | N/A | GCTCTTGCGAGCT CCCTTTCCCGAAA AACTCCTTACGA GTTCCGTCGCTC | 102 | 100P |

TABLE 4-continued

Prokaryotic probes and primer pairs used for multiplex PCR

| Prokaryotic primer Sequence (5'-3') | SEQ ID NO: | PCR No. | Template | GenBank Accession No. | Prokaryotic probe Sequence (5'-3') | SEQ ID NO: | Oligo No. |
|---|---|---|---|---|---|---|---|
| TTAACTTAAGT GGCGGACGG GGTACACGTC GTTTTATTCC | 293<br>294 | 101F<br>101R | OTU LT2A12, multi-copy, unidentified | N/A | AGACGCGAGCTT CTCTTTAGGCGG ATTACTCCATTTC ACTCGGAAGCAT A | 103 | 101P |
| TAACGCGGGG CAACCTGG GGGTATTAGCC CAGAGCG | 295<br>296 | 102F<br>102R | OTU LT2A16, multi-copy, unidentified | N/A | CGCTCCAATAGC GAGAGGTCTTGC GATCCCCCCCTTT CACCCGAAGGTC G | 104 | 102P |
| AGAGTTTGATC CTGGCTCAG ACGGAGGTAG CAATACCTTA GTGCTTCTTCT TCCGGTACC | 297<br>298<br>299 | 103F₁<br>103F₂<br>103R | OTU LT1A15, single-copy, unidentified | N/A | CGGTCCCAGCCTT TCCAGTAATCTCT CTCTAGACTACTG CTTACGACGTA | 105 | 103P |
| TTCGGTTATGT TGATGGCGA TCGGGTAACGT CAATAAACC | 300<br>301 | 104F<br>104R | OTU LT1A16, multi-copy, unidentified | N/A | TAATCCTAAAGC GCCAGGCCTTGC GGTCCCCAGCTTT CCTCCTAAGAGA T | 106 | 104P |
| AACCCCGGTG GCGAGTGG AACCCTGGTG GCGAGTGG TTCTTACGGTA CCGTCATG | 302<br>303<br>304 | 105F₁<br>105F₂<br>105R | OTU LT1A18, multi-copy, unidentified | N/A | GTCCCCGCTTTC ATCCATAGATCG TATGCGGTATTA GCGTAACTTTCGC | 107 | 105P |
| GAGCGATGAA GTTTCTTCGG AGCCGGTGCTT CTTTTGTAG | 305<br>306 | 106F<br>106R | OTU LT3A1, single-copy, unidentified | N/A | CAATATTCGGTAT TAGCACCGGTTTC CCGGTGTTATCCC AAAGTGGAGGG | 108 | 106P |
| GGTAACAGGT TAAGCTGACG CAGAGTATTA ATCCGAAGCG | 307<br>308 | 107F<br>107R | OTU LT3A2, multi-copy, unidentified | N/A | AGGTCTTGCGAT CCCCCCTTTCAC CCGTAGGTCGTA TGCGGTATTAATC | 109 | 107P |
| GGTCTAGTTTA CTAGATGGG TTCTTCTGTGG GTAACGTCC | 309<br>310 | 108F<br>108R | OTU LT3A7, multi-copy, unidentified | N/A | CAGCTTTTCTCCT CAGAGATTACGC GGTATTAGCCTG AGTTTCCCCAGGT | 110 | 108P |
| CATCGGAACG TACCTTATCG CGCAGTCTGTG TTAGAGCTG | 311<br>312 | 109F<br>109R | OTU LT1A35, multi-copy, unidentified | N/A | CTTTCCCCCTCAG GGCGTATGCGGT ATTAGCGCAACT TTCGCTGCGTTAT | 111 | 109P |
| CGTGAGAATCT ACCCTTAGG GCTTGCATCCT CTGTATTAC | 313<br>314 | 110F<br>110R | OTU LT1A55, multi-copy, unidentified | N/A | CAGACGCGAGCT CTTCCTAAGGTG GATAGATCCTTTT ACCTCTCGGCAT A | 112 | 110P |
| TGTCGTCAGCT CGTGTCG AAGGAGGTGA TCCAGCCG | 315<br>316 | 111F<br>111R | Control 1372 | N/A | TGACGGGCGGTG TGTACAAGGCCC G | 113 | 111P |

TABLE 5

Prokaryotic mercury probes and primer pairs used for multiplex PCR

| 16S Sequence ID | PCR Primer (5' to 3') | 60-mer Probe | SEQ ID NO: | OTU |
|---|---|---|---|---|
| 16S OTU 77 + 80.8_For | GTCACCAGTTTTACCCTAGG | | 341 | Hg 1 |
| 16S OTU 77 + 80.8_Rev | AACTGCCGTCGTAAGACGTG | | 342 | Hg 1 |
| 16S OTU 80.8_20 For | AGTCATCGGCCACACCGTGG | | 343 | Hg 2 |
| 16S OTU 80.8_20 Rev | AACTCTAAGGAGACTGCCGG | | 344 | Hg 2 |
| 16S OTU 80.8_26 For | CCTAGTTACCAGTTTTACCC | | 345 | Hg 3 |
| 16S OTU 80.8_26 Rev | AAGACTGCCAGTGCAAACTG | | 346 | Hg 3 |
| 16S OTU 80.8_2 For | ACGAACCCTGCCGTGGTAAT | | 347 | Hg 4 |
| 16S OTU 80.8_2 Rev | ATAAAGCCAGTCGTAGTCCG | | 348 | Hg 4 |
| 16S OTU 80.8_4 For | ACTTCATCCCAGTTACCAGC | | 349 | Hg 5 |
| 16S OTU 80.8_4 Rev | ACAATGAGAACCGATGCCGC | | 350 | Hg 5 |
| 16S OTU 77 + 80.8 | | TCACCAGTTTTACCCTAGGCGGCTCCTTAC-GGTTACCGACTTTAGGTACACCCGGCTTCC | 329 | Hg 1 |
| 16S OTU 77 + 80.8 rc | | GGAAGCCGGGTGTACCTAAAGTCGGTAACC-GTAAGGAGCCGCCTAGGGTAAAACTGGTGA | 330 | Hg 1 |
| 16S OTU 80.8_20 | | TCGGCCACACCGTGGCAAGCGCCCCCCTTG-CGGTTAAGCTACCTGCTTCTGGTGCAACAA | 331 | Hg 2 |
| 16S OTU 80.8_20 rc | | TTGTTGCACCAGAAGCAGGTAGCTTAACCG-CAAGGGGGCGCTTGCCACGGTGTGGCCGA | 332 | Hg 2 |
| 16S OTU 80.8_26 | | CTAGTTACCAGTTTTACCCTAGGCAGCTCC-TTGCGGTCACCGACTTCAGGCACCCCCAGC | 333 | Hg 3 |
| 16S OTU 80.8_26 rc | | GCTGGGGGTGCCTGAAGTCGGTGACCGCAA-GGAGCTGCCTAGGGTAAAACTGGTAACTAG | 334 | Hg 3 |
| 16S OTU 80.8_2 | | GAACCCTGCCGTGGTAATCGCCCTCCTTGC-GGTTAGGCTAACTACTTCTGGCAGAACCCG | 335 | Hg 4 |
| 16S OTU 80.8_2 rc | | CGGGTTCTGCCAGAAGTAGTTAGCCTAACC-GCAAGGAGGGCGATTACCACGGCAGGGTTC | 336 | Hg 4 |
| 16S OTU 80.8_4a | | ACCAGCCTTACCTTAGGACGCTGCCCCCTT-GCGGTTGGCGTGCATACTTCGGGTGCGACC | 337 | Hg 5 |
| 16S OTU 80.8_4a rc | | GGTCGCACCCGAAGTATGCACGCCAACCGC-AAGGGGGCAGCGTCCTAAGGTAAGGCTGGT | 338 | Hg 5 |
| 16S OTU 80.8_4b | | ACCAGCCTTACCTTAGGACGCTGCCCCCTT-GCGGTTGGCGCGCATACTTCGGGTGCGACC | 339 | Hg 5 |
| 16S OTU 80.8_4b rc | | GGTCGCACCCGAAGTATGCGCGCCAACCGC-AAGGGGGCAGCGTCCTAAGGTAAGGCTGGT | 340 | Hg 5 |

TABLE 6

Eukaryotic mercury probes and primer pairs used for multiplex PCR

| 18S Sequence ID | PCR Primer (5' to 3') | 60-mer Probe | SEQ ID NO: | OTU |
|---|---|---|---|---|
| 18S OTU 80.8_2 For | GCCATGCATGTCTAAGTATA | | 371 | Hg 6 |
| 18S OTU 80.8_2 Rev | TACACTACCGTCGAAAGCTG | | 372 | Hg 6 |
| 18S OTU 80.8_20 For | GTACACACTCTAGCAAAGTG | | 373 | Hg 7 |
| 18S OTU 80.8_20 Rev | ACCATGGTAGGCATATCACC | | 374 | Hg 7 |
| 18S OTU 77_54 For | CTAAGCATAGCTGGTGACAG | | 375 | Hg 8 |
| 18S OTU 77_54 Rev | AGGCACATAAACTACCATCG | | 376 | Hg 8 |
| 18S OTU 80.8_34 For | TGCAAGCATGCGCTGAAGTA | | 377 | Hg 9 |
| 18S OTU 80.8_34 Rev | ATGCATCGCCAGTGCTAGAC | | 378 | Hg 9 |
| 18S OTU 77_6 For | CATATGCTTTCCTCCTGGAG | | 379 | Hg 10 |
| 18S OTU 77_6 Rev | GTGATCGACTTGGTAGTCCA | | 380 | Hg 10 |
| 18S OTU 77_73 For | TGCATGTCTAAGCACATGCC | | 381 | Hg 11 |
| 18S OTU 77_73 Rev | ACCATGGTAGGCGTATAACC | | 382 | Hg 11 |
| 18S OTU GL_59 For | GATAGTCCCTTACTACTTGG | | 383 | Hg 12 |
| 18S OTU GL_59 Rev | AATTGCCAGACCTAAGAAGG | | 384 | Hg 12 |
| 18S OTU GL_8 For | GCTCATTACAACAGCCATAG | | 385 | Hg 13 |
| 18S OTU GL_8 Rev | TCGAGACCGTGCGATCTGCA | | 386 | Hg 13 |
| 18S OTU 80.8_66 For | GTATAAGCAATTATACCGTG | | 387 | Hg 14 |
| 18S OTU 80.8_66 Rev | TTACAAGACCCAAAAGAGCC | | 388 | Hg 14 |
| 18S OTU 80.8_2 | | CAACTCTCGCGGGGAGGGATGTATTTATTA-GATAAAAAACCAATGCGGGTTCTGCTCGCC | 351 | Hg 6 |
| 18S OTU 80.8_2 rc | | GGCGAGCAGAACCCGCATTGGTTTTTTATC-TAATAAATACATCCCTCCCCGCGAGAGTTG | 352 | Hg 6 |
| 18S OTU 80.8_20 | | ACTTTACGAAGGGGCGCTTTTATTAGATCA-AAATCAATCAGGAGCAATCCTGTTTTTGTG | 353 | Hg 7 |
| 18S OTU 80.8_20 rc | | CACAAAAACAGGATTGCTCCTGATTGATTT-TGATCTAATAAAAGCGCCCCTTCGTAAAGT | 354 | Hg 7 |
| 18S OTU 77_54 | | GACCCGACGCAAGGACGGTCGCATTTATTA-GAACAAAGCCATCCGGTCCCCGGGACCGTA | 355 | Hg 8 |
| 18S OTU 77_54 rc | | TACGGTCCCGGGGACCGGATGGCTTTGTTC-TAATAAATGCGACCGTCCTTGCGTCGGGTC | 356 | Hg 8 |
| 18S OTU 80.8_34 | | TGCGGGACGAGCGCATTTATTAGAACAAAA-CCATCCGGACTCTCGCGAGTCCGTTGCTGG | 357 | Hg 9 |

TABLE 6-continued

Eukaryotic mercury probes and primer pairs used for multiplex PCR

| 18S Sequence ID | PCR Primer (5' to 3') | 60-mer Probe | SEQ ID NO: | OTU |
|---|---|---|---|---|
| 18S OTU 80.8_34 rc | | CCAGCAACGGACTCGCGAGAGTCCGGATGG-TTTTGTTCTAATAAATGCGCTCGTCCCGCA | 358 | Hg 9 |
| 18S OTU 77_6 | | CATTTTGGGAAACTATGGCTAATACATGCT-TACAGACCTTCGGGTTGTATTTATTAGTTT | 359 | Hg 10 |
| 18S OTU 77_6 rc | | AAACTAATAAATACAACCCGAAGGTCTGTA-AGCATGTATTAGCCATAGTTTCCCAAAATG | 360 | Hg 10 |
| 18S OTU 77_73 | | GACCTTCGGAAAGAGCGCATTTATTAGACC-AAAACCAGTCGAGTTTCGGCTTGTTTGTTG | 361 | Hg 11 |
| 18S OTU 77_73 rc | | CAACAAACAAGCCGAAACTCGACTGGTTTT-GGTCTAATAAATGCGCTCTTTCCGAAGGTC | 362 | Hg 11 |
| 18S OTU GL_59 | | CAATACCCTTCTGGGGTAGTATTTATTAGA-AAGAAACCAACCCCTTCGGGGTGATGTGGT | 363 | Hg 12 |
| 18S OTU GL_59 rc | | ACCACATCACCCCGAAGGGGTTGGTTTCTT-TCTAATAAATACTACCCCAGAAGGGTATTG | 364 | Hg 12 |
| 18S OTU GL_8 | | ACGAACGAGCGCATTTATTAGAGCAAAACC-AATCAGGTTTCGGCCTGTCTTTTGGTGAAT | 365 | Hg 13 |
| 18S OTU GL_8 rc | | ATTCACCAAAAGACAGGCCGAAACCTGATT-GGTTTTGCTCTAATAAATGCGCTCGTTCGT | 366 | Hg 13 |
| 18S OTU 80.8_66a | | CCCCGACTTCGGAAGGGGTGTATTTATTAG-ATAAAAAACCAATGCCCTTCGGGGCTACTT | 367 | Hg 14 |
| 18S OTU 80.8_66a rc | | AAGTAGCCCCGAAGGGCATTGGTTTTTTAT-CTAATAAATACACCCCTTCCGAAGTCGGGG | 368 | Hg 14 |
| 18S OTU 80.8_66b | | CCCCAACTTCGGGAGGGGTGTATTTATTAG-ATAAAAAACCAACGCCCTTCGGGGCTTCTT | 369 | Hg 14 |
| 18S OTU 80.8_66b rc | | AAGAAGCCCCGAAGGGCGTTGGTTTTTTAT-CTAATAAATACACCCCTCCCGAAGTTGGGG | 370 | Hg 14 |

The PCR products in each reaction mixture (e.g., 16S rDNA and 18S rDNA) may be generated from dNTPs which contain a mixture of dATP, dGTP, dCTP, dTTP, and amino allyl-dUTP. The labeling step may employ dye incorporation resulting from a coupling reaction between a cyanine (Cy) and the PCR product. The pools of labeled PCR products may be hybridized with the array, whose immobilized oligonucleotides specify 50-mer sequences that are complementary to at least some of the individual rDNA sequences amplified from each sample. In some cases, the experiment may be replicated by performing a second "dye swap" experiment to minimize any false signals due to differential incorporation of the dye in the amplification products.

Also, probes that target taxa at different hierarchical levels may be included in the array in order to optimize detection of desired bioindicator organisms. For example, in addition to developing PCR primers that are specific to a single species, primers that are capable of detecting several species in a particular genus may be developed (e.g., Oldach, D. W., et al., 2000, *Proc. Natl. Acad. Sci. U.S.A.* 97:4303-4308). The more generic primers may be used both as a confirmation that a particular genus is present in any sample that tested positive with the more specific primers, and as an indicator that potentially unknown or undetected members of the genus are also present.

For example, in one embodiment, bioindicators in Table 2 may be screened by real-time quantitative PCR to measure the relative abundance of a subset of candidates across all samples. Thus, as described above, primer sequences may be designed using nonconserved rDNA regions flanking the V2 region of SSU rDNA (Sogin and Gunderson, 1987) so that a specific PCR product is generated. In these reactions, a fluorescent dye (SYBR® Green I) intercalates double-stranded DNA as it accumulates over the course of the reaction, providing a real-time "signal" that indicates the quantity of PCR product. The amount of starting rDNA template may be estimated by comparing the rate of accumulation to that of a known standard.

For the subset of bioindicators that appear to be most promising based on abundance profiles as being significantly more abundant in mercury-contaminated samples (e.g., Hg 1, Hg 2, Hg 3, Hg 7, Hg 8, and Hg 9 of Table 2), PCR testing may be performed to test for the presence and/or abundance of the specific rDNA in both mercury-contaminated and uncontaminated samples. The utility of these potential bioindicators may be established by demonstrating that the putative biomarkers are significantly (e.g., at least 2-fold, or 5-fold, or 10-fold or 20-fold) more abundant in the genomic DNA isolated from at least one of the mercury-contaminated samples than in the genomic DNA isolated from an uncontaminated sample. In this way, the bioindicator can provide a readily distinguishable level for purposes of microarray detection. In addition, the rDNA levels of each candidate may be evaluated in each of the samples to confirm that the selected bioindicators are consistently more abundant in mercury-contaminated samples.

In an embodiment, a subset of the bioindicators (e.g., Hg 1 and Hg 3) may be consistently more abundant in the presence of mercury and as such, are bioindicators of the presence or absence of mercury. In an embodiment, a different subset of the bioindicators may be consistently less abundant in the presence of mercury without qualification and as such, are bioindicators of the presence or absence of mercury. Or, there may be markers that are more abundant in the absence of mercury and so are bioindicators of the presence or absence of mercury. Or, there may be markers that are less abundant in the absence of mercury and so are bioindicators of the presence or absence of mercury. Additionally, there may be bioindicators that are sensitive to the same parameter (e.g., mercury) but that are specific to an ecosystem. For example, for the markers in Table 2, FL-WCA1 did not share any 16S rDNAs with any other sample.

Although many rDNAs may not meet all criteria, candidates (e.g., Hg 1-11 of Table 2) may be selected to develop a pilot mercury bioindicator microarray. For each candidate, a 50-mer oligonucleotide probe may be derived from the V2 region that lies between the Q-PCR primer sites and checked for uniqueness by aligning it with the other microarray probes (e.g., probes in Tables 3 and 4). For added quality control, redundancy may be built in by spotting a second 50-mer probe, complementary to the first, for each candidate.

Figure 13:
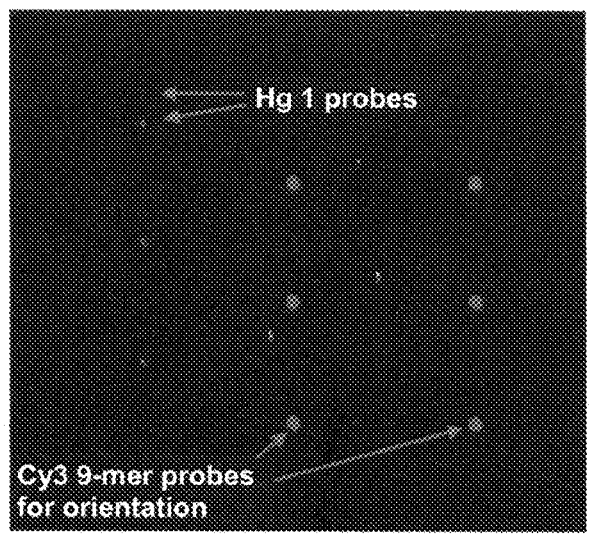
FIG. 13 shows microarray hybridization resulting from a multiplex PCR reaction containing about 250 pg of Hg1 plasmid clone DNA and 45 primer pairs plus Hg1 primers, where hybridization proceeded for 20 h at 48° C., and probes were printed in triplicate in accordance with an embodiment of the present invention.

Amplification/labeling protocols as described herein may then used to test the probe specificity of a single candidate (e.g., Hg 1), by preparing a multiplex reaction containing a solution of plasmid clones (diluted to 250 pg) corresponding to multiple (e.g., Hg 1 and 46) primer sets (i.e., including the same Hg 1 primers used in quantitative PCR. The other 45 primers may represent a diverse collection of rDNAs, including sequences for the following: known pathogens (GenBank), bacteria involved in arsenic oxidation/reduction pathways, and relatively common microbial species, both known and unknown, previously recovered from environmental samples. In an embodiment, the resulting reaction product only hybridizes at the appropriate locations on the microarray, corresponding to the two Hg 1 probes (FIG. 13). In a embodiment, a negative control reaction, prepared and carried out under identical conditions but without the primers for the bioindicator of interest results in no hybridization. Together, these results may indicate that the Hg 1 primers and probes are highly specific for the same rDNAs corresponding to the Hg 1 OTU.

The collection of OTU-specific oligonucleotides (e.g., array) may provide a qualitative result and/or a quantitative result. For example, as shown in FIG. 14, an array of prokaryotic rDNA sequences and/or an array of eukaryotic rDNA sequences may be probed using PCR amplified rDNA sequences amplified from genomic DNA from a water sample to provide qualitatively different patterns of hybridization. For example, DNA from a water sample may be amplified using prokaryotic specific primers and then labeled with a red dye (CY5) to provide a "red" prokaryotic probe (FIGS. 14A-1) that recognizes prokaryotic sequences immobilized at designated positions on an array (FIG. 14B). Alternatively or additionally, DNA from a water sample may be amplified using eukaryotic specific primers and then labeled with a green dye CY3) to provide a "green" eukaryotic probe (FIGS. 14A-2) that recognizes eukaryotic sequences immobilized at designated positions on an array (FIG. 14B).

Figure 15A:
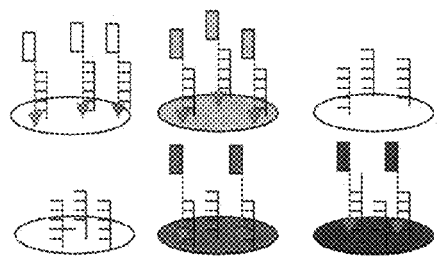
FIG. 15 shows a schematic diagram of hybridization of an array to two samples, in accordance with an embodiment of the present invention, where multiplex PCR reactions of each sample use the same primers, but the product of the amplification reaction from the first sample is labeled with CY3 dye (green) and the product of the amplification reaction from the second sample is labeled with CY5 dye (red). Panel A shows a schematic representation of the red (darkest arrowhead) and green (lighter arrowhead) amplified DNA hybridizing to immobilized DNA at an individual position on the array; Panel B shows a schematic representation of the color as viewed at each array position, wherein the overall color may comprise an average of the colors of the hybridizing probes; and Panel C shows an actual results of a hybridization experiment using red and green labeled probes, where the top panel shows PCR reactions using 16S primers, and the bottom panel shows the same samples amplified with 18S primers, and where prokaryotic oligonucleotides are spotted on the left side of each panel and eukaryotic oligonucleotides are spotted on the right side of each panel; green spots in lower right-hand position of each grid are for orientation.
Figure 15C:
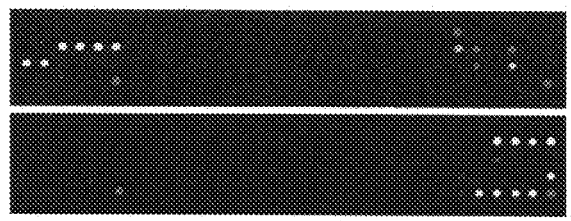
Figure 15B:
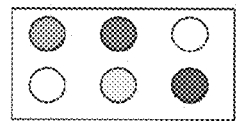

The collection of OTU-specific oligonucleotides (e.g., array) may also be used as a quantitative assessment tool, to monitor the change in various microbes over time, or to monitor the relative amounts of a microbe between two samples that vary in location (e.g., for two different bodies of water, or two locations in one body of water) or time of sampling (e.g., a single body of water sampled at two different seasons). Referring now to FIG. 15, an array may be probed with amplified DNA that corresponds to both 16S (prokaryotic) DNA sequences and/or 18S (eukaryotic) DNA sequences. To distinguish the two samples, amplification from the first sample may be labeled with a first dye (e.g., CY3, green), whereas the amplification from the second sample may be labeled with a second dye (e.g., CY5, red). As shown in FIG. 15A, the nucleic acids immobilized at a particular position (e.g., location or address) on the array, will bind to a complementary nucleic acid probe that is labeled either with the green dye (from the first sample), or the red dye (from the second sample). Upon hybridization, if hybridization is specific to probe from sample 1, a green spot will result; if hybridization is specific to probe from sample 2, a red spot will result; if hybridization occurs for probe molecules that are found in both samples, the color will vary dependent upon relative abundance of the amplified probe, and also the target, in each sample (FIGS. 15A and 15B). For example, FIG. 15A shows a proposed hybridization pattern for probes hybridized to an array where the top row is (from left to right): 2 red/1 green; 3 red; 3 non-labeled probes; and the bottom row is (from left to right): 3 non-labeled probes; 1 red/1 green/1 non-labeled; and 2 green/1 non-labeled. The colors as shown in FIG. 15B are thus (left to right) for the top row: orange, red, none; and for the bottom row: none, light green, dark green. FIG. 15C shows the results for this type of experiment for two lake samples amplified by PCR to generate either 16S probes (top panel) or 18S probes (bottom panel). In an embodiment, there may be at least one position per array for a known sequence that serves as a control to allow for orientation of the array (e.g., green spots in lower right hand position of each grid in FIG. 15C).

Figure 16:
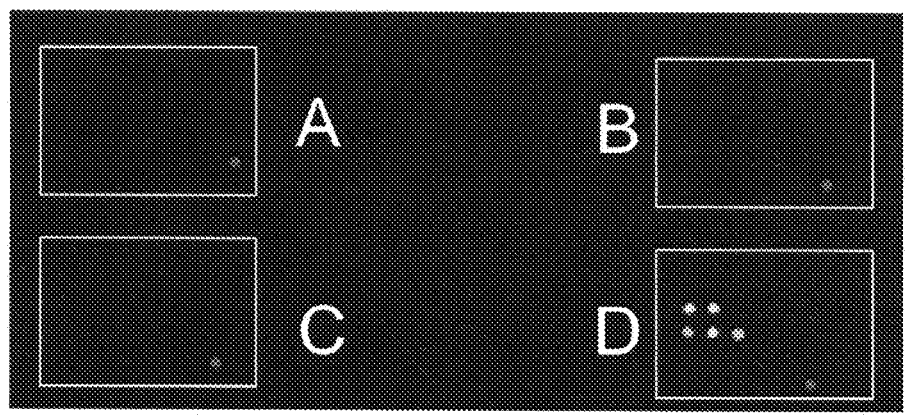
FIG. 16 shows an array that contains cyanobacteria sequences probed with amplification products generated using cyanobacteria multiplex primers from two water samples (one sample labeled in green and one sample labeled in red) that each contained cyanobacteria in accordance with an embodiment of the present invention, where oligonucleotide probes to 18S rDNA are spotted in Grid A and B, probes to 16S rDNA of *Escherichia coli* are spotted in Grid C, and twenty-one 16S rDNA probes containing cyanobacteria sequences, sequences associated with arsenic-responsive microbes, and other sequences identified in collected lake samples, are spotted in Grid D.

As described herein, the collection of OTU-specific oligonucleotides (e.g., array) may also be used to determine how chemical additions to water (e.g. mercury, cadmium, atrazine, perchlorate) may change the microbial community, and/or to detect known water pathogens. For example, a microarray of the present invention may include 16S rDNA sequences from several known pathogens. FIG. 16 shows results for such an experiment, where multiplex PCR amplification and direct labeling of cyanobacteria present in a water sample are detected using cyanobacterial sequences on the array (Panel 17D).

Figure 17:
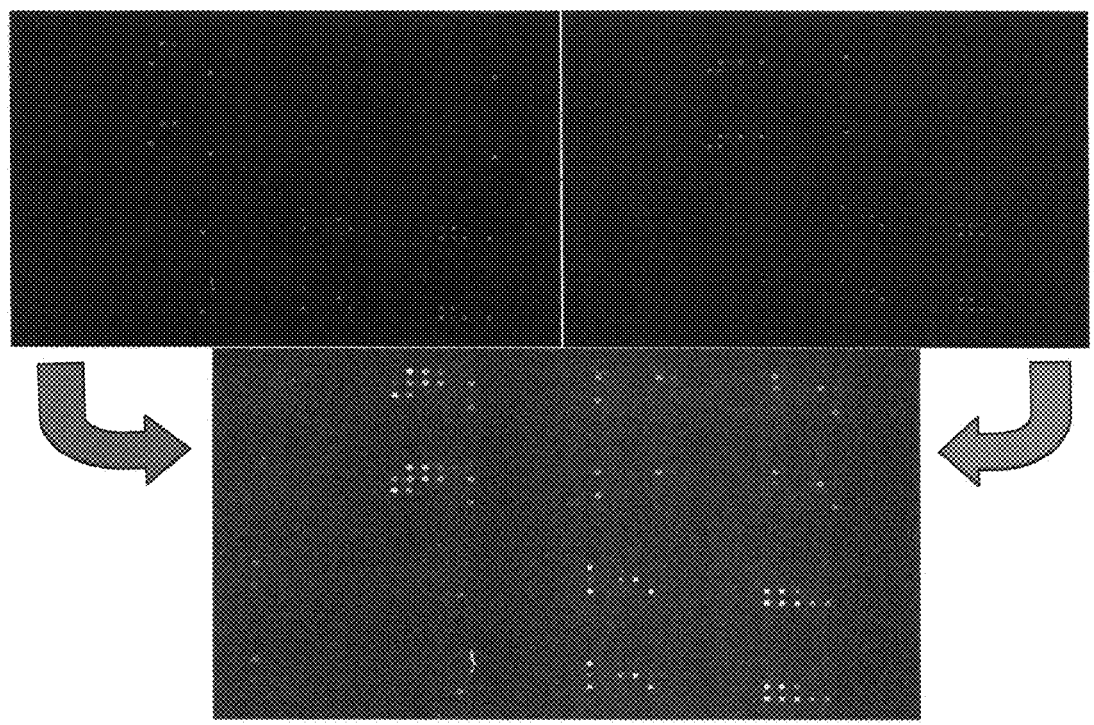
FIG. 17 shows hybridization of two samples to an array, where multiplex PCR reactions for both samples were identical and reaction products were either labeled with a red dye (CY5) or a green dye (CY3), allowing comparison of samples in accordance with an embodiment of the present invention. Shown are results from a test of two lake samples used to hybridize first singly (top panels) (left panel: CY3-labeled sample; right panel: CY5-labeled sample) and then together (bottom panel) to the same array of 105 oligonucleotide probes. As shown in the figure, the array is partitioned into duplicates of eight grids.

In one embodiment, a plurality of oligonucleotides that are isolated from known and unknown OTUs may be prepared. As used herein, known OTUs comprise sequences that are ≧97.5% identical to sequences that have been reported in public databases, whereas unknown OTUs comprise sequences that do not meet this criterion and are believed to represent as yet unknown organisms. FIG. 17 shows an array comprising 105 oligonucleotides isolated from predetermined known and unknown freshwater lake OTUs probed with amplified DNAs from two different lake samples, where multiplex PCR reactions of each sample were identical and products each reaction were either labeled with a red dye (CY5) or a green dye (CY3), allowing comparison of samples. Shown are results from a test of two lake samples used to hybridize first singly (top panels) (left panel: green probe, sample 1; right panel: red probe, sample 2) and then together (bottom panel) to the same array of 105 oligonucleotide probes.

Such taxon-specific arrays may be used to detect microbes that are known to be characteristic of a particular type of water system. For example, in one embodiment, the collection of OTU-specific oligonucleotides (e.g., array) may be formulated to detect microbes common to fresh water systems. Or, the collection of OTU-specific oligonucleotides (e.g., array) may be formulated to detect microbes common to marshlands or small tidal pools. Or, the collection of OTU-specific oligonucleotides (e.g., array) having nucleic acids derived from estuary water samples may be used to analyze water from various estuaries. The development of arrays that utilize OTU-specific nucleotide sequences to monitor ecosystems is described in more detail in the Examples, below.

EXAMPLES

Example 1

Materials and Methods

Sample Collection and DNA Extraction.
A. Freshwater Lakes—Set 1 (General Bioindicator Development)
To develop probes for an array, three lakes were sampled: Lake Townsend (LT) (Greensboro, N.C.); City Lake (CL) (High Point, N.C.); and Toolik Lake (T L) (Alaska). Lake Townsend and City Lake are temperate mesotrophic and eutrophic municipal drinking water reservoirs, respectively. Toolik Lake is a highly oligotrophic, glacial lake located in the Arctic Long Term Ecological Research Site above the Arctic Circle in Alaska (O'Brien, W. J., et al., 1997, The Limnology of Toolik Lake, p. 61-106, In: Freshwaters of Alaska—ecological syntheses, A. M. Milner and M. W. Oswood (eds), Springer-Verlag Publishers, New York, N.Y.).
Five samples of surface water were collected: (1) LT-1J—at an open water location in Lake Townsend (station 1), depth=8.3 m, on Jun. 14, 2000; (2) LT-2J—at a shallow, near shore location in Lake Townsend (station 2), depth=1.3 m, on Jun. 14, 2000; (3) LT-1M—at station 1 of Lake Townsend, on Mar. 28, 2001; (4) CL—at an artificially aerated location in City Lake near a subsurface water treatment system intake on May 22, 2001; and (5) TL—at a location near the main LTER sampling station in Toolik Lake on Aug. 11, 2000. Each sample (~100 ml) was drawn through GF/C and GF/F glass fiber filters that were placed in cetyltrimethylammonium bromide (CTAB) buffer for storage at room temperature until later DNA extraction. Other lake samples, such as water samples from lakes that may be diagnostic of deformities found in members of the ecosystem may be used. For example, tests have been conducted using a group of North Dakota lakes that were paired according to geographical proximity. Each pair of lakes includes one lake that has been associated with a high level of frog deformities and one lake that has not been associated with any known deformities in frogs or any other organism. Samples from the lakes were used to isolate DNA for array analysis to ascertain microbial bioindicators associated with conditions leading to such deformities.
B. Freshwater Lakes—Set 2 (Mercury Bioindicator Development)
Freshwater sediments were sampled at three diverse sites where mercury contamination has been documented for several years. These locations included: (1) a hot spot for mercury contamination in the Great Lakes (sampling arranged via D. Wethington, EPA, Great Lakes National Program Office); (2) a Florida Everglades site that is part of the EPA National Atmospheric Deposition Network; and (3) the North Fork of the Holston River (Saltville, Va.).
Specifically, the Great Lakes sample (GL-DRTC) was collected from bottom sediment in the Trenton-Riverview Channel of the Detroit River (N 42° 11.226', W 83° 9.188') and the Everglades sample (FL-WCA1) was collected from an area located within site WCA1. At two sites within the Holston River, bottom sediments were taken when river flow was at 1.54 ft and 302 ft$^3$/s: a reference (uncontaminated) sample at river mile 94 (NFHR 94) and a mercury-contaminated sample at river mi. 80.8 (NFHR 80.8). The third Holston River sample, also mercury-contaminated, was collected from a floodplain adjacent to the North Fork located at river mi. 77 (NFHR 77). River mi. 80.8 and 77 sites are located at distinct mileage sites (77 and 80.8 miles from a preset location) along the river. The site at river mi. 80.8, in particular, is believed to be contaminated by mercury discharge from Pond 5 at river mi. 81.8.
All samples were subjected to mercury analyses using approved EPA testing methods. Prism Laboratories (Charlotte, N.C.) conducted total mercury (THg) analyses using Method 7471, a cold-vapor atomic absorption method based on the absorption of radiation ($\lambda$=253.7 nm) by mercury vapor. Brooks Rand Labs (Seattle, Wash.) provided monomethyl mercury (MMHg) analyses in accordance with EPA Method 1630. Based on these analyses, Hg was positively identified in control sample NFHR 94, but the amount was estimated to be 22 ng/g, which is between the reporting limit and the minimum detection limit. MMHg in NFHR 94 was measured at 0.075 ng/g. By comparison, THg levels were at least 38 times greater in the other samples than in NFHR 94 (22 ng/g), except for FL-WCA1, which was below the minimum detection limit. MMHg levels were at least 8.9 times greater (NFHR 80.8) and up to 39 times greater (GL-DRTC) than in NFHR 94 (0.075 ng/g). Thus, a total of four samples were actually processed in the experiment (i.e., two Holston River samples were used).
Isolation of Genomic DNA Genomic. DNA was extracted from each water sample using a CTAB (cetyltrimethylammonium bromide) buffer DNA isolation technique (Rublee, P. A., et al., 1999, Va. J. Sci., 50:325-335). Briefly, the glass fiber filter was macerated in 2 ml CTAB in a 15 ml polypropylene conical tube using a sterile wooden applicator stick. After heating for 1 hr at 65° C., the mixture was extracted with 2 ml 24:1 (v/v) chloroform-isoamyl alcohol, and the DNA isolated from the aqueous portion by precipitation with 0.7 volumes 100% 2-propanol. The precipitate was pelleted, air-dried, and the DNA rehydrated in 25 µl TE buffer (pH 7.4) and stored at −20° C. For extraction from water suspected to have mercury contamination, genomic DNA was extracted from each river bottom (e.g., sediment) or flood plain (e.g., sediment/soil) sample using a DNA isolation kit (MO BIO POWERMAX SOIL DNA ISOLATION KIT) according to the manufacturer's instructions.
PCR amplification of genomic DNA from water samples for cloning rDNAs. SSU rDNA was amplified by PCR using prokaryotic-specific and eukaryotic-specific forward and reverse primers in 50 µl reactions (Table 1). Using the appropriate primer pairs, separate reactions were prepared for 16S rDNA and 18S rDNA. The amplification reactions consisted of: 5 µl 10×PCR Buffer; 5 µl PROMEGA 25 mM MgCl$_2$; 5 µl 100 mM BSA; 2.5 p. 116 mM dNTP stock (4 mM each of dATP, dCTP, dGTP and dTTP); 1 µl each of 10 µM forward and reverse primers; 1 U Taq DNA Polymerase; 30.2 µl sterile deionized H$_2$O; and 1 µl genomic DNA. An MJ RESEARCH PTC-100 Programmable Thermal Controller was used to amplify samples under the following conditions: 2 min initial denaturation at 94° C.; 30 cycles of 1 min denaturation at 94° C.; 1 min annealing at 56° C. for 16S primers or 58° C. for 18S primers; and 2 min extension at 72° C.; 5 min final extension at 72° C. PCR products were verified by gel electrophoresis.

Cloning and sequencing of amplified PCR products. Purified PCR products were subcloned in plasmid vectors using a cloning kit (INVITROGEN TOPO TA CLONING KIT) according to the manufacturer's protocol. Ligation reaction mixtures were then used to transform TOP 10 Chemically Competent *E. coli* cells and recombinant plasmids were identified by growth of bacterial colonies on LB agar plates containing 50 µg/ml ampicillin. Individual colonies from each plating were inoculated into LB liquid medium containing 50 µg/ml ampicillin and grown overnight with antibiotic selection. Inserts were purified from cultures using a miniprep kit (QIAGEN QIAPREP SPIN MINIPREP KIT) according to the manufacturer's protocol. After removal of the insert, gel electrophoresis was used to verify the presence of a DNA fragment corresponding in size to 16S rDNA or 18S rDNA.

Fifty verified clones from each library were sequenced using a DNA Analysis System (MEGABACE 1000) utilizing capillary electrophoresis. Sequencing reactions were prepared using a sequencing kit (DYENAMIC™ ET DYE TERMINATOR CYCLE SEQUENCING KIT; MEGABACE™) according to the manufacturer's protocol provided. Sequencing reactions included: DYENAMIC ET Dye Terminator Premix; M13-20 forward and reverse primers; purified DNA template—either cloned 16S rDNA or 18S rDNA; and sterile deionized $H_2O$. Using an MJ RESEARCH PTC-100 Programmable Thermal Controller, reactions were amplified by PCR using the following conditions: 25-30 cycles of the following: 20 sec denaturation at 95° C., 15 sec annealing at 50-51° C., and 1-2 min extension at 60° C. After amplification, post reaction clean-up steps are performed according to the manufacturer's protocol. During electrophoresis, reaction products are separated by size and detected using a fluorescence-based system. Sequencing of each clone resulted in sequence read lengths ranging from 400-700 by for each clone.

Sequence Alignments and Community Analyses. The sequences were submitted to the National Center for Biotechnology Information website for BLAST analysis (Altschul, S. F., et al., 1990, *J. Mol. Biol.*, 215:403410). Sequence alignments and analyses were performed using the BioEdit Sequence Alignment Editor and Analysis software (version 5.0.9; Department of Microbiology, North Carolina State University, available on-line), which includes CLUSTAL W as an accessory application for multiple alignments. Libraries were compared in pairwise fashion by combining and aligning two libraries at a time (100 sequences of 16S rDNA or 18S rDNA).

Taxonomic classifications were based on identity matrices generated using an analysis tool incorporated into the BIOEDIT sequence editor. Sequences having identity scores of 0.975 or greater were considered to be sufficiently similar to group them into the same operational taxonomic unit (OTU). After grouping clones into OTUs, several diversity indices were calculated for each library. These included: (1) species richness, or total number of OTUs; (2) Simpson's dominance index, used to describe the distribution of clones among OTUs, or evenness; and (3) the Shannon-Wiener index, which serves as a statistical measure of the probability of correctly guessing the OTU identity of a randomly selected clone (Colinvaux, P. 1993. Ecology 2. John Wiley & Sons, Inc., New York, U.S.A). In addition, Sorensen coefficients (Lemke, M. J., et al., 1997, *Microb. Ecol.*, 34:224-231) were calculated to measure the similarity in species composition between two communities, or the proportion of OTUs shared between two libraries.

Also total species richness (S) can be estimated using four methods based on the distribution of OTUs within a library. These include: $S_{cov}$, an estimate based on "coverage" (Finlay, B. J., 2002, *Science*, 296:1061-1063; Giovannoni, S. J., et al., 1990, *Nature*, 345:60-63); $S_{max}$, an estimate based on rarefaction analysis (Haldeman, D. L., et al, 1994, *Appl. Environ. Microbiol.*, 60:2697-2703; Methe, B. A., and J. P. Zehr, 1999, *Hydrobiologia*, 401:77-96), which can be performed using the program ANALYTIC RAREFACTION (version 1.3; Stratigraphy Lab, University of Georgia, available on-line); and $S_{ACE}$ and $S_{chao1}$, two estimates that can be evaluated using a form processor and spreadsheet available through a web-based interface (Kemp and Aller, 2004, *Limnol., Oceanogr. Methods*, 2:114-125).

Phylogenetic analyses can be conducted to assess molecular evolutionary relationships using MEGA software (version 2.1; Molecular Evolutionary Genetics Analysis, available online). All phylogenetic analyses are sensitive to alignment methods, assumptions regarding mutational rates, and the types and amount of sequence data used (Troesch, A., et al., 1999, *J. Clin. Microbiol.*, 37:49-55.). Trees may be constructed using the Unweighted Pair-Group Method with Arithmetic Mean (UPGMA) and distances were estimated according to the Kimura 2-parameter model for nucleotide exchange with a transition/transversion ratio of 2.0 (Hurlbert, S. H., 1971, *Ecology* 52:577-586).

Real-time Quantitative PCR. Real-time Quantitative PCR (Q-PCR) experiments were performed to analyze the relative abundance of the prospective 16S rDNA OTUs and 18S rDNA OTUs from both sets of water samples (i.e., set 1 and set 2 above) using a CEPHEID SMART CYCLER Cycler system. The presence and accumulation of fluorescence bound to each target OTU was measured directly and compared among LT-1J, LT-1M and CL. For samples from ecosystems believed to contain mercury, PCR was used to measure the relative abundance of 6 candidate mercury bioindicators (Hg 1, Hg 2, Hg 3, Hg 7, Hg 8, and Hg 9 of Table 2) across all samples. For each of these candidates, reactions were prepared to test for the presence and/or abundance of the specific bioindicator rDNA in both mercury-contaminated and uncontaminated samples.

For samples in set 1, individual 25 µl reactions included: 2.5 µl TAKARA 10×EX TAQ Taq Buffer; 1.25 µl TAKARA dNTP Mixture (2.5 mM each); 1.25 µl SYBR® Green I nucleic acid gel stain (10×); 0.25 µl TAKARA EX TAQ™ Taq polymerase; 1 µl OTU-specific forward and reverse primers (10 µM each); 16.75 µl sterile deionized $H_2O$; and 1 µl experimental template (genomic DNA sample –0.025 µg/µl), positive control (mixed clone standard –25 pg/µl each), or negative control (sterile deionized $H_2O$). The mixed clone standard was prepared by combining three clones representing three experimental samples used in the experiment (i.e., genomic DNA samples from three different OTUs). Relative abundance estimates can be calculated using a 1:10 dilution series of the mixed clone standard to determine cycle number differences between e.g., 25 pg, 2.5 pg, 0.25 pg, and 0.025 pg template concentrations.

For samples in set 2 (e.g., samples from lakes believed to contain mercury), individual 25 µl reactions included: 2.5 µl TAKARA 10×EX TAQ Taq Buffer; 1.25 µl TAKARA dNTP Mixture (2.5 mM each); 1.25 µl SYBR® Green I nucleic acid gel stain (10×); 0.25 µl TAKARA EX TAQ™ Taq polymerase; 1 µl OTU-specific forward and reverse primers (10 µM each) derived from candidate mercury bioindicators (i.e., Hg 1, Hg 2, Hg 3, Hg 7, Hg 8, and Hg 9 of Table 2); 16.75 µl sterile deionized $H_2O$; and 1 µl experimental template (genomic DNA sample—0.025 µg/µl), positive control (mixed clone standard—25 pg/µl each), or negative control (sterile deionized $H_2O$). Relative abundance estimates can be calculated using a 1:10 dilution series of the mixed clone standard to determine cycle number differences between e.g., 25 pg, 2.5 pg, 0.25 pg, and 0.025 pg template concentrations.

Multiplex PCR of probes for array. To generate the target sequences used for hybridization to the array, a multiplex PCR amplification using at least 45 primer pairs developed from an analysis of individual OTUs, may be performed. The identification of the eukaryotic primers and associated 50-mer probes are shown in Table 3 (for set 1) and Table 6 (for set 2). The sequences of the prokaryotic primers and associated 50-mer probes are shown in Table 4 (for set 1) and Table 5 (for set 2).

The conditions for multiplex PCR were as follows. Multiplexed PCR reactions containing ~250 ng genomic DNA are prepared in 0.5 ml thin-walled microcentrifuge tubes. The final reaction volume was 50 µl and contained a 200 nM final concentration of each primer, 5 µl 10× buffer, 5 µl BSA, 5 µl dNTPs, 1.25 U Taq, and sd $H_2O$ (remaining volume). Reactions were placed in a programmable thermal controller and DNA amplification by PCR is carried out under the following conditions: initial denaturation at 94° C. for 2 minutes; 30 cycles of denaturation at 94° C. for 1 minute, annealing at 1 to 3 degrees below lowest primer $T_m$, extension at 72° C. for 1 minute; final extension at 72° C. for 1 minute; and storage at 4° C. of reaction product until use. The dNTP mixture is prepared by adding 16.6 µl sd $H_2Od$ 20 to 2 µl 50× dNTP stock solution for an 8.33-fold dilution, where 50× dNTP stock solution is 10 µl each 100 mM dATP, dGTP, dCTP; 8 µl 100 mM amino allyl-dUTP; and 2 µl 100 mM dTTP.

The PCR products may, in some cases, be labeled using fluorescent dyes. For labeling with dyes, the PCR product was transferred to a 1.5 ml microcentrifuge tube and 5 µl 3 M sodium acetate and 500 µl 100% ethanol added. The contents were thoroughly mixed and stored overnight at −70° C. The samples were removed from −70° C. storage and spun in a microcentrifuge at 14,000 rpm for 20 minutes. After pouring off the supernatant, 500 µl 70% ethanol was added to wash the DNA pellet and this mixture was microcentrifuged at 14,000 rpm for 10 minutes. The supernatant was again poured off, the tube allowed to air dry to remove all ethanol, and the pellet then resuspended in 15 µl nuclease-free $H_2O$. The Cy dyes were removed from −20° C. storage and resuspended in 15 µl 0.1 M sodium bicarbonate, pH 9.0. The Cy dye and DNA resuspensions were combined, mixed well, and allowed to incubate for 1 hr at room temperature in the dark. To quench any unbound Cy dye after the dye coupling reaction, 15 µl 4 M hydroxylamine was added to each sample and these are incubated for 15 minutes at room temperature in the dark. Labeled samples are then purified using a PCR purification kit according to the manufacturer's protocol.

Spotting of oligonucleotides on the array. To immobilize nucleic acids on the array the following protocol was used. Each 50-mer oligonucleotide to be used as a probe sequence (i.e., sequences corresponding to SEQ ID NOS: 5-113, and/or the reverse complement of these sequences, and/or SEQ ID NO: 329-SEQ ID NO: 340, and/or SEQ ID NO: 351-SEQ ID NO: 370), on the array is diluted 1:10 with 3×SSC/0.1% sarkosyl in a 96-well microplate for a final oligonucleotide concentration of ~250 ng/µl. Epoxy-coated slides are secured in slide positions of arrayer for printing. After the oligonucleotides are printed, the slides are UV cross-linked at 60 mJoules, baked at 80° C. in an oven for 2 hours, and stored at room temperature. The 3×SSC is prepared using a 20×SSC concentrate containing 3 M NaCl and 0.3 M sodium citrate, pH 7.0.

Hybridization of DNA sample to array. After purification, the CY3 and CY5-labeled sample eluates may be combined and lyophilized until almost dry, leaving approximately 5-10 µl behind. The sample may be resuspended using 80 µl ROCHE DIG EASY HYB hybridization buffer and a clean lifterslip is placed on the microarray being used. The sample is heated at 95° C. for 2 minutes, cooled on ice for 1 minute, spun down to collect any condensation, and pipetted under the lifterslip. Next, the microarray is sealed within a hybridization cassette using the cassette lid and placed into a 45-55° C. water bath overnight. The next morning, three wash solutions are heated to 37° C., the hybridization cassette is removed from the water bath, and the microarray is removed from the cassette. The microarray with lifterslip is gently dipped into a staining dish containing wash buffer #1 (1×SSC, 0.1% SDS), to release the lifterslip. The microarray is then placed in a staining dish cassette and gently washed in wash buffer #1 for 5 minutes. Using the same technique, the microarray is next washed in wash buffer #2 (1×SSC), for 5 minutes. Finally, the microarray is washed in wash buffer #3 (0.05×SSC), by gently dipping it 5-10 times. The microarray is removed from the staining dish cassette and tapped on edge against the bench top to remove all solution droplets. Once dry, the microarray is scanned.

Example 2

Grouping rDNAs Into Operational Taxonomic Units for Five Samples From Three Different Lakes Analysis of Clones. Approximately 50 prokaryotic rDNA and 50 eukaryotic rDNA clones for each of the five lake samples from set 1 (i.e., Lake Townsend, Greensboro, N.C.; City Lake, High Point, N.C.; and Toolik Lake, Ala.) for a total of 500 rDNA sequences were sequenced through a 1700 by segment of the eukaryotic 18S rDNA, or a 1540 by segment of the prokaryotic 16S rDNA, to provide for phylogenetic classification of known and novel species (Pace et al., 1986, *Adv. Microb. Ecol.*, 9:1-55; Sogin and Gunderson, 1987, *Annals. NY Acad. Sci.*, 503:125-139). Based on the rDNA sequencing alignments, a level of 97.5% sequence identity was the criterion by which rDNAs were placed in the same operational taxonomic unit (OTU). Because multiple small subunit rDNA copies may reside within a species genome (Farrelly et al., 1995, *Appl. Environ. Microbiol.*, 61:2798-2801), a 97.5% level of sequence identity allows for the possibility that a different sequence in the same species was recovered. A software program (CHIMERA-CHECK; Kopzcysnski et al., 1994, *Appl. Environ. Microbiol.*, 60:746-748; Wang and Wang, 1995, *Appl. Environ. Microbiol.*, 63:4645-4650; Qui et al, 2001, *App. Environ. Microbiol.*, 58:2717-2722) was also employed to reduce the possibility of misidentifying a chimeric rDNA as an unique clone.

For each sample, libraries of SSU rDNA clones were produced, individual clones were sampled, sequences for each clone were generated, and standard diversity statistics were computed (Table 7). Based on a comparative analysis of all prokaryotic (16S) rDNA sequences, it was determined that 49 OTUs contained multiple sequences and that 62 OTUs were unique, each containing a single sequence. An analysis of all eukaryotic (18S) sequences resulted in 42 OTUs containing multiple sequences and 67 unique OTUs.

TABLE 7

Comparison of prokaryotic and eukaryotic diversity

| | LT-1J | | LT-2J | | LT-1M | | CL | | TL | |
|---|---|---|---|---|---|---|---|---|---|---|
| rDNA library | 16S | 18S | 16S | 18S | 16S | 18S | 16S | 18S | 16S | 18S |
| Number of clones | 50 | 50 | 50 | 50 | 50 | 50 | 49 | 50 | 50 | 50 |
| Number of OTUs | 33 | 31 | 31 | 32 | 26 | 34 | 28 | 28 | 23 | 12 |
| Evenness | 0.039 | 0.049 | 0.050 | 0.053 | 0.089 | 0.043 | 0.079 | 0.102 | 0.078 | 0.358 |
| Shannon-Wiener index | 3.38 | 3.24 | 3.24 | 3.24 | 2.84 | 3.35 | 3.00 | 2.90 | 2.86 | 1.62 |

LT-1J: Lake Townsend, station 1, June;
LT-2J: Lake Townsend, station 2, June;
LT-1M: Lake Townsend, station 1, March;
CL: City Lake;
TL: Toolik Lake.

Species Diversity Measures. Prokaryotic and eukaryotic species richness, evenness, and the Shannon-Wiener index differed among lakes. In general, Lake Townsend, N.C., contained more species and showed the most even distribution of species; consequently, its Shannon-Wiener index values were the highest. In contrast, Toolik Lake, Ak., had the lowest richness estimates, especially for eukaryotes, indicating that species diversity was much lower in Toolik Lake than in the temperate lakes and that a few successful competitors dominated the arctic community.

As a first indication of diversity, various statistical measurements of the recovered sequences were made to determine the species coverage, species evenness (Simpson's Index of Dominance; Colinvaux, 1993, *Ecology* 2, John Wiley & Sons, Inc. New York, N.Y.), species richness (the number of recovered species in a sample), species diversity (Shannon-Wiener index; Nubel et al., 1999, *Appl. Environ. Microbiol.*, 65:422-430) and the estimated proportion of shared OTUs between samples (Sorenson similarity coefficient; Lincoln et al, 1998, *A Dictionary of Ecology, Evolution, and Systematics*, Cambridge University Press, New York, N.Y.; McCaig et al., 1999, *Appl. Environ. Microbiol.*, 65:1721-1730). Coverage estimates of the percentage of OTUs recovered from a source were based on the relative abundance of the clones already obtained, and indicated that 48 to 76% of the prokaryotic rDNAs, and between 48 and 90% of the eukaryotic rDNAs, had been recovered from the samples. The highest coverage (i.e., 90%) was for Toolik Lake; apparently caused by the high level of recovery of a single rDNA. Not unexpectedly, the species evenness and richness was about the same for all the North Carolina lake samples, but the distribution of recovered species was much more skewed and lower in Toolik Lake, Ak. To generate a nucleic acid array for monitoring water, however, the purpose of the census is not necessarily to identify all the microbial species that exist in these samples, but rather to survey water sources for relatively common microbes whose appearance and abundance can be monitored on a microarray platform.

Rank-abundance curves for most samples (see e.g., FIGS. 2 and 3) showed that a few taxa were abundant and that many taxa were represented by a single clone. It is highly likely that the samples also contain several other clones at low frequencies. In Toolik Lake, fewer species were detected and these were more abundant relative to the other lakes tested, implying that Toolik Lale contained a smaller number of species. This was supported by the estimates of total taxonomic diversity using the four methods described above (Table 8).

TABLE 8

Estimates of species richness (S) for each prokaryotic and eukaryotic community

| | LT-1J | | LT-2J | | LT-1M | | CL | | TL | |
|---|---|---|---|---|---|---|---|---|---|---|
| rDNA library | 16S | 18S | 16S | 18S | 16S | 18S | 16S | 18S | 16S | 18S |
| Number of OTUs | 33 | 31 | 31 | 32 | 26 | 34 | 28 | 28 | 23 | 12 |
| Scov | 57 | 56 | 54 | 62 | 44 | 71 | 46 | 47 | 29 | 14 |
| $S_{max}$ | 93 | 72 | 73 | 74 | 40 | 53 | 47 | 40 | 12 |
| SACE | 61 | 80 | 77 | 110 | 110 | 106 | 67 | 65 | 38 | 17 |
| SChao1 | 54 | 77 | 63 | 88 | 91 | 99 | 54 | 60 | 28 | 14 |

LT-1J: Lake Townsend, station 1, June;
LT-2J: Lake Townsend, station 2, June;
LT-1M: Lake Townsend, station 1, March;
CL: City Lake;
TL: Toolik Lake.

Sequence Identifications and Library Comparisons. Clone sequences were submitted for BLAST analysis to assess phylogenetic affiliations with reported sequences in the GenBank database. Sequence alignments having ≧97.5% identity were used to propose OTU identifications and determine the proportion of known OTUs for each library (Table 9). The Lake Townsend March sample contained the lowest average proportion of known OTUs (24.8%), while Toolik Lake had the highest (43.0%). Identifications for clones within the same OTU were consistent, suggesting that a 97.5% identity threshold grouped individuals at the species level.

TABLE 9

Summary of prokaryotic and eukaryotic OTUs

|  | LT-1J | | LT-2J | | LT-1M | | CL | | TL | |
|---|---|---|---|---|---|---|---|---|---|---|
| rDNA library | 16S | 18S | 16S | 18S | 16S | 18S | 16S | 18S | 16S | 18S |
| No. known clones | 21 | 17 | 16 | 21 | 21 | 19 | 31 | 20 | 25 | 32 |
| Proportion known OTUs (%) | 12/33 (36.4) | 8/31 (25.8) | 10/31 (32.3) | 8/32 (25.0) | 6/26 (23.1) | 9/34 (26.5) | 13/28 (46.4) | 6/28 (21.4) | 14/23 (60.9) | 3/12 (25.0) |

LT-1J: Lake Townsend, station 1, June;
LT-2J: Lake Townsend, station 2, June;
LT-1M: Lake Townsend, station 1, March;
CL: City Lake;
TL: Toolik Lake.
Number of known OTUs = number of OTUs with clones having ≧97.5% sequence similarity to GenBank entries. Known clones refer to clones whose sequences correspond to known microbial species or unidentified species in the GenBank database.

Samples having similar estimates of species diversity were distinguished by differences in community composition. For instance, eight eukaryotic OTUs were identified in each Lake Townsend sample, but the species composition of this group varied between samples. Comparing only the OTUs with multiple sequences, the following observations were made: LT-1J species included *Chilomonas paramecium, Cryptomonas ovata,* and *Geminigera cryophila*; LT-2J species included *Brachionus plicatilis, Cryptomonas ovata, Didinium nasutum,* and *Dileptus* sp., and the LT-1M species included *Cryptomonas ovata* and *Tabularia tabulata*. A comparison of the unique OTUs distinguished these samples even more.

Based on sequence alignments and comparisons that included all OTUs, phylogenetic trees were generated according to the UPGMA method to show the overall distribution of OTUs among the five samples. The prokaryote tree in FIG. 6 was constructed using 111 different 16S rDNA OTUs, including 40 that are known rDNAs (about 36%). The eukaryote tree in FIG. 7 represents 109 18S rDNA OTUs and includes 22 known rDNA sequences (about 20%).

To determine which OTUs, if any, appeared in more than one library, the sequences from each library were compared to those in every other library in pairwise library comparisons and a similarity coefficient was calculated for each pairing (Table 7). Although no prokaryotic sequences were shared between LT-2J and TL, there was some overlap between every pair of samples and the degree of overlap varied considerably. In some comparisons, roughly equal proportions of prokaryotic and eukaryotic OTUs were shared, but other comparisons revealed different patterns.

TABLE 10

Sorensen coefficients for prokaryotic and eukaryotic sample comparisons

|  | LT-1J | | LT-2J | | LT-1M | | CL | | TL | |
|---|---|---|---|---|---|---|---|---|---|---|
| rDNA library | 16S | 18S | 16S | 18S | 16S | 18S | 16S | 18S | 16S | 18S |
| LT-1J | 1 | 1 | 0.344 (11) | 0.159 (5) | 0.169 (5) | 0.215 (7) | 0.230 (7) | 0.068 (2) | 0.071 (2) | 0.093 (2) |
| LT-2J |  |  | 1 | 1 | 0.070 (2) | 0.061 (2) | 0.169 (5) | 0.133 (4) | 0 (2) | 0.091 |
| LT-1M |  |  |  |  | 1 | 1 | 0.074 (2) | 0.161 (5) | 0.122 (3) | 0.174 (4) |
| CL |  |  |  |  |  |  | 1 | 1 | 0.039 (1) | 0.200 (4) |
| TL |  |  |  |  |  |  |  |  | 1 | 1 |

Coefficients were calculated as follows: $S = 2 \times C/(A + B)$, where A and B represent the numbers of OTUs in libraries A and B, respectively, and C represents the number of OTUs shared by A and B (34, 40).
( ) indicate the number of OTUs that were shared by the paired libraries.
LT-1J: Lake Townsend, station 1, June;
LT-2J: Lake Townsend, station 2, June;
LT-1M: Lake Townsend, station 1, March;
CL: City Lake;
TL: Toolik Lake.

Venn diagrams depict sample comparisons at different spatial and temporal scales (FIG. 8). In the fine-scale spatial comparison of LT-1J and LT-2J, each shared OTU contained nearly equal numbers of sequences from both samples, except for two sequences that occurred four times as often in LT-2J. One of these, a 16S rDNA OTU, was not identified, while the other 18S rDNA OTU aligned with *Geminigera cryophila*, and was also found in Toolik Lake (three copies). Such unequal occurrences of an OTU between samples may signify a detectable difference in the relative abundance of this particular microbial population between samples. OTUs that consistently vary in frequency among samples are potential bioindicators. For instance, one new bacterial species and the *Geminigera cryophila* OTU appear to be more abundant in temperate lakes, especially pelagic waters.

Thus, it was found that for the five lake samples analyzed from three lakes (Lake Townsend, City Lake, and Toolik Lake), 26 different eukaryotic OTUs were represented by multiple copies, including 11 that are associated with known species. Another 79 eukaryotic OTUs were obtained as single copy clones and almost all of these represent unidentified species (Marshall, 2002, Masters Thesis, University of North Carolina at Greensboro). Similarly, 45 different prokaryotic OTUs were found in multiple copies among the collection of samples, of which 10 are associated with a known species, and another 19 resemble reported sequences for as yet unidentified species. Another 92 single copy rDNA sequences, most from unidentified prokaryotes, were recovered from the samples (Amos, 2002, Masters Thesis, University of North Carolina at Greensboro). Both known and unidentified rDNA sequences may be used as probes printed on the assay matrix of the present invention.

The ability to assess environmental parameters of water quality may require a sufficient number of potential bioindicator species, but may also require sequences having sufficient similarity across samples to allow for some general application. As noted in Table 11, a diversity of microbial species may be readily retrievable from a single body of water for even an oligotrophic source such as Toolik Lake, Ak. While every sample produced several unique OTUs, all of the lakes produced multiply represented OTUs, and the most common OTU in each sample accounted for 10% or more of all the rDNAs analyzed in each of the samples.

acterized only in the designated sample either as a single copy, referred to as a unique OTU, or in multiple copies. It can be seen that the distribution of some OTUs is broad, while for others it is more localized (Table 12), suggesting that many microbial species exist across a range of watersheds and that a general purpose DNA microarray, that may be used for multiple watersheds, may be developed. An example analysis of specific OTUs is shown in Table 13.

A preliminary analysis of rDNA sequences from paired North Dakota lake samples (where one lake sample that exhibits substantial deformities in the frog population and one lake sample does not) acquired from the Fargo, N. Dak. USDA station indicates that some of the OTUs for unknown species are shared with sequences found in North Carolina lakes. Moreover, preliminary real-time PCR experiments suggest that at least some microbes exist at an endemic level

TABLE 11

Relative abundance of eukaryotic and prokaryotic OTUs

|  | Most abundant OTU | | 2X OTUs | | 1X OTUs | | Total OTUs | |
| --- | --- | --- | --- | --- | --- | --- | --- | --- |
|  | Eukary. | Prokary. | Eukary. | Prokary. | Eukary. | Prokary. | Eukary. | Prokary. |
| LT-1J | 10% | 8% | 9 | 10 | 23 | 26 | 32 | 36 |
| LT-2J | 14% | 10% | 9 | 8 | 22 | 26 | 31 | 34 |
| LT-1M | 10% | 14% | 8 | 7 | 26 | 23 | 34 | 30 |
| CL | 14% | 22% | 10 | 9 | 21 | 22 | 31 | 31 |
| TL | 58% | 20% | 7 | 12 | 5 | 12 | 12 | 24 |

LT-1J; Townsend, NC; June, Station 1;
LT-2J; Townsend, NC; June, Station 2;
LT-1M, Townsend, NC; March, Station 1;
CL, City Lake, NC May;
TL, Toolik Lake, AK; August.
2X represents OTUs with at least 2 members;
1X represents OTUs with only one member.

Table 12 shows the pattern of shared and unshared OTUs among the five freshwater lake samples of set 1. Unshared OTUs refer to rDNA sequences that were recovered and charin almost all freshwater lakes, suggesting that that relative abundance for these endemic microbes is primarily dictated by local water conditions.

TABLE 12

Shared and unshared OTUs among the five freshwater lake samples

|  | A | | B | | C | | D | | E | |
| --- | --- | --- | --- | --- | --- | --- | --- | --- | --- | --- |
|  | Euk. | Prok. | Euk. | Prok. | Euk. | Prok. | Euk. | Prok. | Euk. | Prok. |
| Unshared OTUs | 18 | 22 | 19 | 19 | 19 | 19 | 18 | 20 | 5 | 12 |
| OTUs in 2 samples only | 2 | 5 | 1 | 4 | 3 | 8 | 2 | 4 | 2 | 19 |
| Toolik only | 0 | 0 | 0 | 0 | 0 | 0 | 0 | 0 | — | — |
| Townsend only | 5 | 6 | 3 | 6 | 5 | 2 | — | — | — | — |
| Townsend or City | 2 | 2 | 1 | 3 | 2 | 1 | 5 | 6 | — | — |
| All lakes* | 4 | 0 | 3 | 0 | 5 | 0 | 5 | 0 | 5 | 0 |

*All lakes does not necessarily mean all samples.
A: Townsend, NC, June, Station 1;
B: Townsend, NC, June, Station 2;
C: Townsend, NC, March, Station 1;
D: City Lake, NC, May;
E, Toolik Lake, AK, August
Euk = Eukaryotic;
Prok = Prokaryotic

TABLE 13

Relative abundance of five eukaryotic rDNA species found in all three sampled lakes

| | A | B | C | D | E |
|---|---|---|---|---|---|
| *Cryptomonas ovata* | 30% | 12% | 20% | 30% | 8% |
| Unidentified 18s rDNA-1 | 0% | 0% | 10% | 6% | 58% |
| *Ochromonas tuberculata* | 12% | 6% | 6% | 8% | 4% |
| *Oxytricha longa* | 2% | 10% | 2% | 8% | 10% |
| Unidentified 18s rDNA-2 | 10% | 0% | 4% | 2% | 10% |

A: Townsend, NC, June, Station 1;
B: Townsend, NC, June, Station 2;
C: Townsend, NC, March, Station 1;
D: City Lake, NC, May;
E: Toolik Lake, AK, August Library Screening vs. Real-time Q-PCR. For the lake samples of set 1, it was found that several OTUs may be found at quantitatively different levels in different ecosystems. Three OTUs that appeared to be recovered differentially from one water sample were used in fluorescence detection real-time PCR experiments to determine if they were also present in other water samples (FIG. 9). It was found that each of the test OTUs was in fact present in all of the samples investigated. For example, two OTUs that appeared in LT-1M clone libraries at frequencies of 10 and four copies (out of 50), respectively. Another OTU in was originally recovered from a City Lake library (11 copies of 50).

The relative abundance of each of these OTUs was compared and estimated across the same three samples based on a dilution series of a known standard (data not shown). According to cycle threshold differences between growth curves in FIG. 9A, the amount of the LT-1M OTU product in the LT-1M sample was estimated to be 34 times greater than the amount of this product in LT-1J samples and 13 times greater than the amount in CL samples. For the experiment shown in FIG. 9B, it was found that the amount of product in CL was about 219 times greater than that found in LT-1J samples and 41 times greater than that found in LT-1M samples. For the experiment shown in FIG. 9C, it was found that the amount of product in LT-1M was about 29 times more abundant than in LT-1J and 55 times more abundant than in CL.

Real-time PCR assays also allowed for an estimation of the sensitivity of rDNA amplification for detecting community members. Based on four completed *E. coli* genomes from GenBank entries AE014075 (Venter, J. C., et al., 2004, *Science*, 304:66-74), U00096 (Blattner, F. R., et al., 1997, *Science*, 277:1453-1474), BA000007 (Lincoln, R., G. Boxshall, and P. Clark, 1998, A Dictionary of Ecology, Evolution and Systematics. Cambridge University Press, New York, N.Y.), and AE005174 (Pace, N. R., et al., 1986, *Adv. Microb. Ecol.*, 9: 1-55), it was estimated that 16S rDNA makes up about 0.206% of the *E. coli* genome, and therefore, about 52 pg of 16S rDNA should be present in 25 ng of genomic DNA material. Experiments indicated that Q-PCR detected a specific rDNA signal from as little as $3.6 \times 10^{-3}$ pg of genomic DNA, based on a comparison with the Q-PCR signal evoked by individual rDNA clones, indicating that clones occurring at a frequency as low as $6.9 \times 10^{-5}$ should be detectable by Q-PCR, and that a sampling of $14.5 \times 10^3$ clones would be required for a mean recovery of one target clone. Assuming a Poisson distribution of clones in a library, it was estimated that to ensure the recovery of any one clone at a probability of greater than 99%, a library screening method would require $66.7 \times 10^3$ clones.

Generally, the results indicated that the Toolik Lake microbial community differs more from the North Carolina lakes than the North Carolina lake communities differ from each other. The three Lake Townsend samples also showed variation as the samples differed with respect to the location and season of sampling. While the March and June collections at the same Lake Townsend location shared several OTUs with the other Lake Townsend and City lake samples, several multiple-copy OTUs were only found in the March collection, indicating that some microbial species thrive in the relatively cold waters of early Spring. Also, the two Lake Townsend samples collected on the same day showed the highest level of overall similarity. The library sampling method was able to detect similarities between samples, indicating that the microbial community is not too heterogeneous to analyze with molecular methods. In addition, the existence of unshared OTUs and the ability to detect quantitative differences between shared OTUs indicated differences between microbial communities that may be diagnostic of specific environmental conditions.

Example 3

Grouping rDNAs Into Operational Taxonomic Units for Ecosystems Believed to Contain Mercury Analysis of Clones. Clones for each of the four lake samples (i.e., NFHR 77; NFHR 80.8; WCA1; GLDRTC) were sequenced through a 1700 by segment of the eukaryotic 18S rDNA, or a 1540 by segment of the prokaryotic 16S rDNA, to provide for phylogenetic classification of known and novel species (Pace et al., 1986, *Adv. Microb. Ecol.*, 9:1-55; Sogin and Gunderson, 1987, *Annals. NY Acad. Sci.*, 503:125-139). Based on the rDNA sequencing alignments, a level of 97.5% sequence identity was the criterion by which rDNAs were placed in the same operational taxonomic unit (OTU). Because multiple small subunit rDNA copies may reside within a species genome (Farrelly et al., 1995, *Appl. Environ. Microbiol.*, 61:2798-2801), a 97.5% level of sequence identity allows for the possibility that a different sequence in the same species was recovered. A software program (CHIMERA-CHECK; Kopzcysnski et al., 1994, *Appl. Environ. Microbiol.*, 60:746-748; Wang and Wang, 1995, *Appl. Environ. Microbiol.*, 63:4645-4650; Qui et al, 2001, *App. Environ. Microbiol.*, 58:2717-2722) was also employed to reduce the possibility of misidentifying a chimeric rDNA as a naturally occurring sequence. For each sample, libraries of SSU rDNA clones were produced, individual clones were sampled, sequences for each clone were generated, and standard diversity statistics were computed.

Genomic DNA was extracted from each sample and amplified by PCR (except for control sample NFHR 94) using universal small-subunit ribosomal DNA (SSU rDNA) primers of Table 1. PCR amplicons were used to generate 16S rDNA and 18S rDNA plasmid clone libraries (four of each) and these were sampled by randomly selecting 50 clones from each for sequence analyses. The resulting sequence data (~500 nucleotides for each clone) were used to generate alignments so that sequences could be grouped into OTUs using a 97.5% sequence identity criterion. Samples were then compared based on OTU composition and this provided a mechanism for screening candidate Hg bioindicators. Rank-abundance profiles were assembled showing the number and relative abundance of OTUs found in each sample, as well as the OTUs that were designated as candidate Hg bioindicators (FIGS. 4 and 5).

Based on the data of Example 2, it was expected that three diverse samples would share approximately 4% of the OTUs recovered if 50 clones were sequenced from each sample. However, samples that have a higher chemical similarity (i.e. the presence or absence of mercury) may also share a greater number of the same microbial sequences such that 10 or more candidate bioindicators might be expected to emerge from rDNA sequence analyses. This is consistent with previous work by Sorensen and colleagues (Muller, et al. 2001, 2002; Rasmussen and Sorensen, 1998, *Current Microbiology* 36:291-297; Rasmussen and Sorensen, 2001, *FEMS Microbiology Ecology*. 36:1-9) who found rapid changes in community structure, including significant increases in the proportion of culturable mercury resistant bacteria. It was also expected that most of the unidentified rDNA sequences obtained from these samples would be novel. Therefore, the selection criteria utilized focused on direct associations between the presence or absence of mercury and recovered sequences, rather than microbial taxa.

First, a microbial rDNA sequence was established as a potential bioindicator if multiple copies were detected in three mercury-contaminated samples and the sequence did not align with any other rDNA sequence in GenBank (unless known to be associated with mercury metabolism) or the University of North Carolina at Greensboro (UNCG) database, which contains several thousand rDNA sequences. Second, a sequence was designated as a potential bioindicator if multiple copies were found at two mercury-contaminated sites. If no sequences satisfied either of these criteria, then a sequence would be considered if multiple copies were detected in at least one mercury-contaminated sample and if the sequence also grouped into one of the five most abundant OTUs. Due to the number of OTUs that met the first two criteria, the last criterion was not utilized. Table 2 lists candidate Hg bioindicators, the samples that yielded them, and descriptions based on alignments with sequences reported in GenBank.

As expected, most of the candidates could not be identified based on BLAST alignments. This was either because the candidate rDNA aligned with an uncultured microorganism as yet uncharacterized or because the candidate rDNA is unknown and failed to align with anything. Both cases present potential bioindicator opportunities since the vast majority of microbes have not been identified and their ecological functions remain unknown. For example, Hg 1 is 99% identical to an uncultured bacterium reported as clone P4T__162. Without more information, the ecological function of this organism remains unknown. However, this demonstrates potential dual applications as both bioindicator and bioremediator. In fact, most microbial bioindicators may also be bioremediators, but they have not been isolated and studied to establish their roles in overall community dynamics and their effects on the environment.

After screening candidate bioindicators in this fashion, real-time quantitative PCR was used to measure the relative abundance of six of these candidates across all samples. Following methods described herein, primer sequences were designed using nonconserved rDNA regions flanking the V2 region of SSU rDNA (Sogin and Gunderson, 1987) so that a specific PCR product would be generated. In these reactions, a fluorescent dye (SYBR® Green I) intercalates double-stranded DNA as it accumulates over the course of the reaction, providing a real-time "signal" that indicates the quantity of PCR product. The amount of starting rDNA template was estimated by comparing the rate of accumulation to that of a known standard.

The 6 bioindicator candidates that were tested included: Hg 1, Hg 2, Hg 3, Hg 7, Hg 8, and Hg 9 (Table 2). For each one, reactions were prepared to test for the presence and/or abundance of the specific rDNA in both mercury-contaminated and uncontaminated samples. The utility of these potential bioindicators was established by demonstrating that they were at least 5-fold more abundant in the genomic DNA isolated from at least one of the mercury-contaminated samples than in the genomic DNA isolated from an uncontaminated sample. This provides a readily distinguishable level for purposes of microarray detection. In addition, the rDNA levels of each candidate were inspected in each sample to confirm that they were consistently more abundant in mercury-contaminated samples generally.

Hg 1 and Hg 3 met this standard without qualification. Hg 2 was detected in greater abundance in NFHR 94 than in NFHR 80.8, but was over 10 times more abundant in GL-DRTC than any other sample. Hg 8 levels were over 6 times higher in NFHR 80.8 than NFHR 94, although Hg8 was not detected in GL-DRTC. Finally, Hg 7 and 9 were not amplified in any sample. In every case, a negative result was produced for both NFHR 77 and FL-WCA1, which were found to have much lower DNA concentrations of each of the probes than the other genomic samples based on a second trial of DNA quantifications. However, it seems likely that the negative Q-PCR results for FL-WCA1 represent real differences since mercury analyses suggested that FL-WCA1 may no longer be contaminated given that total Hg levels were below reporting limits. And, unlike NFHR 77, FL-WCA1 did not share any 16S rDNAs with any other sample. It should also be noted that positive and negative controls were run successfully with each panel of reactions. Positive controls contained plasmid clone dilutions (50-100 pg) of the candidate rDNA and yielded robust signals indicating DNA concentrations in excess of $10^4$ greater than in genomic samples.

Although many rDNAs did not meet all criteria, candidates Hg 1-11 were selected to develop a pilot mercury bioindicator microarray. For each candidate, a 50-mer oligonucleotide probe was derived from the V2 region that lies between the Q-PCR primer sites and checked for uniqueness by aligning it with the other microarray probes already developed (e.g., Example 2). For added quality control, redundancy was built in by spotting a second 50-mer probe, complementary to the first, for each candidate. The probe specificity of a single candidate, Hg 1, was tested by preparing a multiplex reaction containing a solution of plasmid clones (diluted to 250 pg) corresponding to Hg 1 and 46 primer sets, including the same Hg 1 primers used in Q-PCR. The other 45 primers represent a diverse collection of rDNAs, including sequences for the following: known pathogens (GenBank), bacteria involved in arsenic oxidation/reduction pathways, and relatively common microbial species, both known and unknown, previously recovered from environmental samples. The resulting reaction product only hybridized at the appropriate locations on the microarray, corresponding to the two Hg 1 probes (FIG. 13). In a negative control reaction, prepared and carried out under identical conditions, the Hg 1 primers were omitted from the multiplex reaction and no hybridization occurred (data not shown). A visual inspection of the microarray surface confirmed the presence of a dust particle, which became bound to unincorporated dye in the reaction product, shown as a "C-shaped" spot. Together, these results indicate that the Hg 1 primers and probes were highly specific for the same rDNAs corresponding to the Hg 1 OTU.

Example 4

Qualitative and Quantitative Analysis of Water Samples Using Microarrays

Based on the sequence information provided by the clones and information available in GenBank, two microarrays for testing water samples were made. The protocol for testing the microarray was as follows: appropriate prokaryotic and eukaryotic primers were used to amplify either 16S rDNA or 18S rDNA, respectively, from DNA that was extracted from the water samples as described above. The PCR products were then labeled by chemical attachment to either CY3 (green) or CY5 (red) dye, and upon denaturation, the labeled PCR products were hybridized to the array.

To make the arrays, 50-mer oligonucleotide sequences were spotted onto the surface of epoxy-coated glass slides. In Table 14, sequence identifications from Tables 3 and 4 are provided for each probe that was spotted to make the array shown in FIGS. 14 and 15. As indicated, there were some locations at which no probes were spotted.

TABLE 14

| Prokaryotic (16S rDNA) probes | | | | | | Eukaryotic (18S rDNA) probes | | | | | |
|---|---|---|---|---|---|---|---|---|---|---|---|
| 103P | | | 103P | | | 15P | 15P | 30P | 31P | 32P | 16P |
| 103P | 103P | 104P | 105P | 106P | 107P | 33P | 34P | 14P | 35P | 36P | 38P |
| 108P | 109P | 110P | 103F$_1$ | 103F$_1$* | 103F$_1$* | 39P | 40P | 41P | 37P | 42F | 42F** |
| | | | | | CY3 | | | | | | CY3 |
| | | | | | 9mer | | | | | | 9mer |

Figure 2:
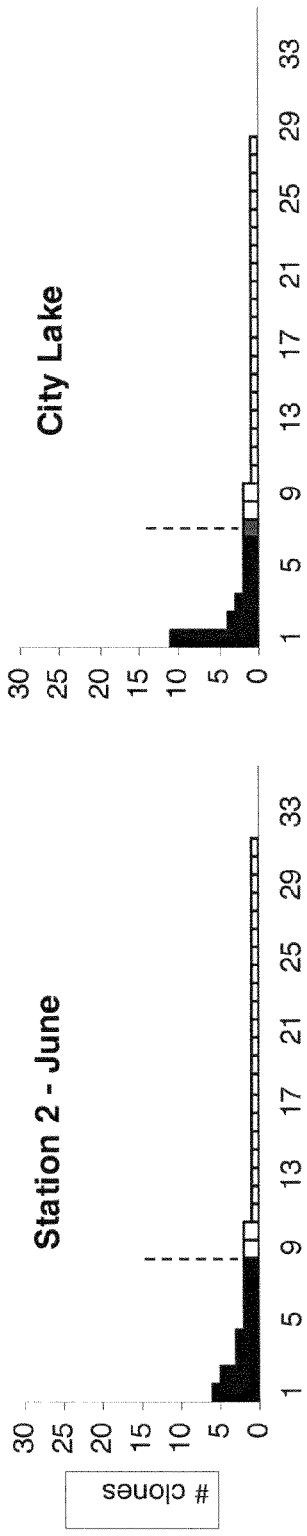
FIG. 2 shows rank-abundance curves for 16S rDNA libraries from three different lakes (Lake Townsend, N.C.; City Lake, N.C.; and Lake Toolik, Ak.) in accordance with an embodiment of the present invention. The curves on left-hand side represent Lake Townsend samples taken from different stations (Station 1 or Station 2) or at different times of the year (March or June). The median for each distribution partitions the operational taxonomic units (OTUs) into two groups shown in black and white; a stippled pattern is used where the median falls within an OTU.
Figure 2:
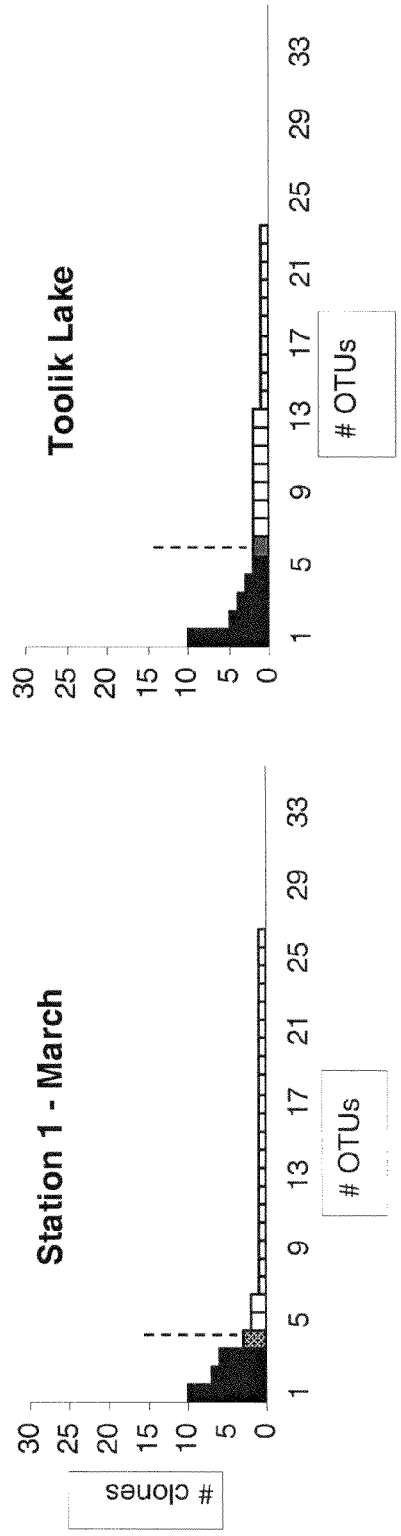
Figure 3:
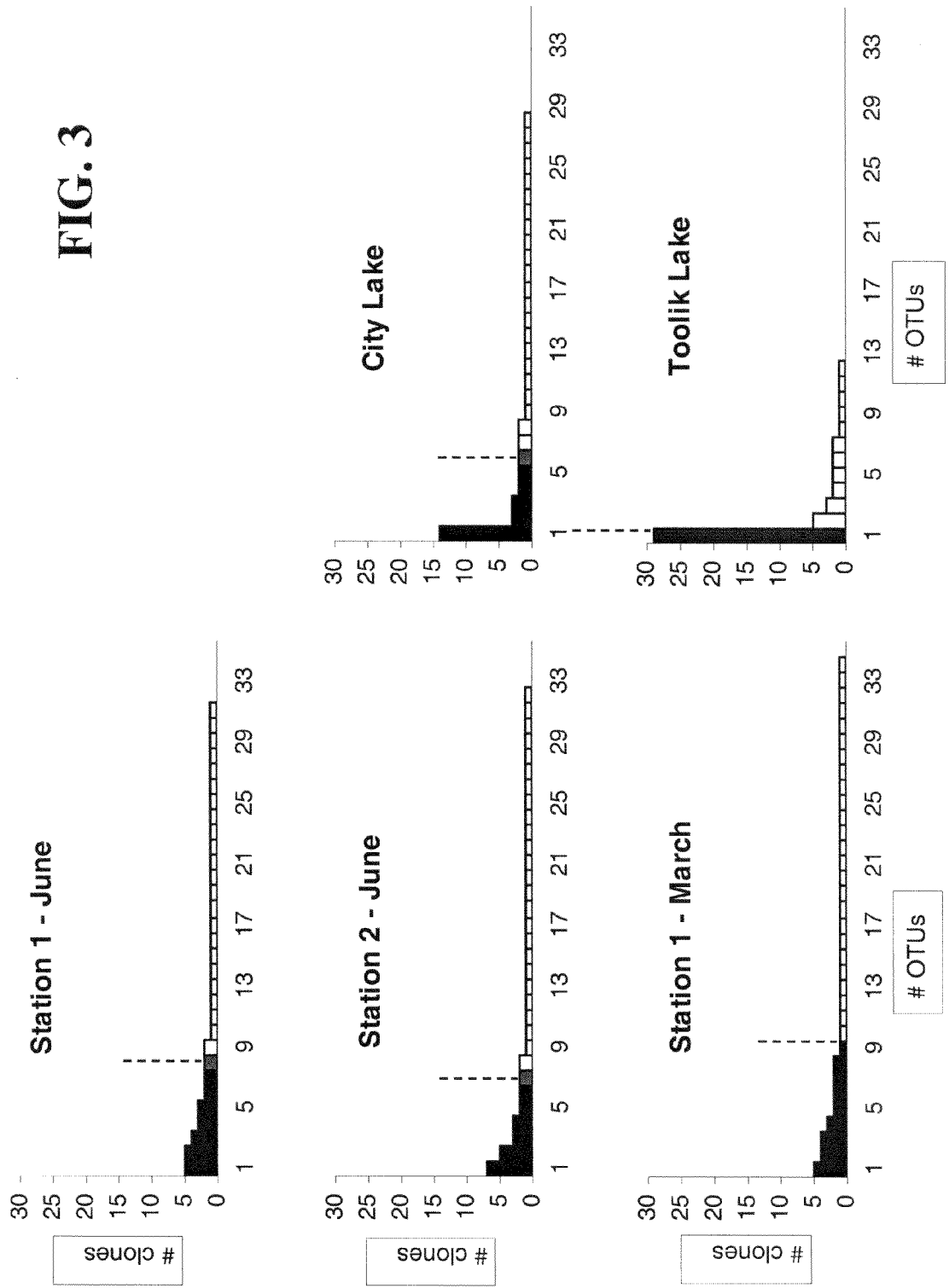
FIG. 3 shows rank-abundance curves for 18S rDNA libraries from three different lakes (Lake Townsend, N.C.; City Lake, N.C.; and Lake Toolik, Ak.) in accordance with an embodiment of the present invention. The curves on left-hand side represent Lake Townsend samples taken from different stations (Station 1 or Station 2) or at different times of the year (March or June). The median for each distribution partitions the operational taxonomic units (OTUs) into two groups shown in black and white; a stippled pattern is used for a median that falls within an OTU.

*reverse complementary sequence of 103F$_1$;
**reverse complementary sequence of 42F The experimental design is illustrated in FIG. 14A, showing labeling of a subset of sequences (e.g., prokaryotic) with red dye (FIGS. 14A-1) and labeling of a second subset of sequences (e.g., eukaryotic) with green dye (FIGS. 14A-2). Aligned sequences were used to design taxon-specific PCR primers (20-26-mer) and oligonucleotide probes (50-mers) to complementary variable regions. As a printing control and orientation marker, a CY3-labeled random 9-mer probe was also printed with each grouping of probes.

In the experiment shown in FIG. 14B, two aliquots drawn from a single genomic DNA sample (Lake Townsend, Station 1, June) were subjected to PCR with either a universal prokaryotic rDNA primer pair or a universal eukaryotic rDNA primer pair (Table 1) with dUTP added to the reaction mixture. The conditions for amplification were as described above for generation of the libraries. As described herein, the PCR reactions were then labeled with either CY5 (red, prokaryotic), or CY3 (green, eukaryotic) by chemically attaching the incorporated dUTP. The reactions were mixed and hybridized to a glass slide spotted with the oligonucleotide probes. As shown in FIG. 14B, the eukaryotic and prokaryotic PCR products are clearly detected on the prototype microarray. The scanned array image showed complete specificity of 12 of 12 prokaryotic probes and 19 of 21 eukaryotic probes. The green spot in the lower right of each sub-array was a CY3-labeled 9-mer marker for orientation. Also, locations at which no spots appear were printed with probes for sequences that were not experimental targets, thus acting as negative controls and, indicating that there was minimal DNA carryover during the array printing process. The actual array carried three sets of each grid, and scanned images of the replicate grids produced substantially identical images.

The experiment illustrated in FIG. 15C illustrated that the microarray may be used as a semi-quantitative assessment to compare two samples (for instance, the same location within a lake at two different times), or a sample and a standard. In this approach, two multiplex PCR amplifications were run—one for each lake sample. Both 16S and 18S rDNA were amplified together in a single reaction, and the amplified products from each sample were then labeled with either the red (Sample 1) or green (Sample 2) dye. When the amplified products were hybridized to a microarray, any resulting signal varied in color from red (target found in only sample 1) to yellow (target in both samples) to green (target found only in sample 2). The continuum from red to green is indicative of the relative abundance of the target in the samples.

Example 5

Testing For Specific Pathogens

The microarray is also capable of detecting known water pathogens and contaminants which affect water quality, thus raising the possibility of an "all in one" testing system. To test the feasibility of this additional feature, a microarray including 16S rDNA sequences from several cyanobacteria species was made. This microarray was tested with primers designed to amplify the rDNA of these species specifically, and the labeled products were hybridized to the microarray. As FIG. 16 shows, the multiplex/direct labeling methodology resulted in the appearance of signals specific for the cyanobacterial sequences from water samples known to contain cyanobacteria. For the experiment shown in FIG. 16, oligonucleotide probes to 18S rDNA are spotted in Grid A (16 probes) and B (15 probes). Twelve probes to 16S rDNA of *Escherichia coli* (strains K12 and O157:H7; Prena et al, 2001, *Nature*, 409: 465-466) are spotted in Grid C, and twenty one 16S rDNA probes are spotted in Grid D, which contains cyanobacteria sequences, sequences associated with arsenic-responsive microbes (Oremland and Stolz, 2003, *Science* 300:939-943), and sequences identified in collected samples. Grids A, B, C, and D from FIG. 16 are shown in Table 15, and the identity of each probe (Tables 3 and 4) is provided at its location on the array

TABLE 15

Oligonucleotide probes on array of FIG. 16

| A | | | | | | B | | | | | |
|---|---|---|---|---|---|---|---|---|---|---|---|
| 15P | 30P | 31P | 32P | 16P | 33P | 10P | 11P | 12P | 13P | | |
| 34P | 14P | 35P | 36P | 38P | 39P | 19P | 20P | 21P | 22P | 18P | 23P |
| 40P | 41P | | | | | 24P | 25P | 26P | 27P | 28P | |
| 17P | 29P | | | | CY3 9mer | | | | | | CY3 9mer |

| C | | | | | | D | | | | | |
|---|---|---|---|---|---|---|---|---|---|---|---|
| 51P | 52P | 53P | 54P | 55P | 56P | 83P | 81P | 73P | 74P | 75P | 76P |
| 57P | 58P | 60P | 61P | 62P | 63P | 84P | 85P | 82P | 80P | | |
| | | | | | | 103P | 104P | 105P | 106P | 107P | 108P |
| | | | | | CY3 9mer | 109P | 110P | 77P | 78P | 79P | CY3 9mer |

To generate the labeled probe for this experiment, Toolik Lake, Ak. and City Lake, N.C. genomic samples were amplified using cyanobacteria specific PCR primers in a multiplex format. Toolik Lake products were labeled with CY3 (green) and City Lake products were labeled with CY5 (red). The primer pairs were: *Synechococcus*. sp. LBP1, *Synechococcus* sp. LBG2, an unknown cyanobacteria clone LD27, and a degenerate *Synechococcus* primer set (Table 4). The four probes to cyanobacteria hybridized with amplicons from both lake samples as evidenced by the yellow signal in grid D (FIG. 16). The additional signal in Grid D resulted from a labeled product that recognized a probe corresponding to the bacterium *Burkholderia cepacia* genomovar III. Subsequent analysis revealed that at least one of the *Synechococus* primers resembled the *B. cepacia* sequence, and that it likely amplified *B. cepacia* rDNA in the sample, indicating the importance of designing primer pairs to prevent cross-reactivity.

Example 6

Taxon-Specific Arrays

Amplification of genomic sample DNA may be performed by multiplex PCR using primers chosen to provide products that can hybridize to taxon-specific DNAs. Using this protocol can dramatically reduce non-specific labeling, and eliminates the need for intermediate PCR reactions, which reduce sensitivity.

FIG. 17 shows a taxon-specific array comprising 105 oligonucleotides generated from known and unknown OTUs isolated from freshwater lakes and from GenBank pathogen sequences. DNA samples from two different lakes were amplified in identical multiplex PCR reactions and reaction products were either labeled with a red dye (CY5) or a green dye (CY3), allowing for comparison of samples. Shown are results from a test of two lake samples used to hybridize first singly (top panels) (left panel: CY3-labeled sample, sample 1; right panel: CY5-labeled sample) and then together (bottom panel) to the same array of 105 oligonucleotide probes.

The arrays included nucleic acid sequences from variable regions of individual eukaryotic and prokaryotic rDNAs. Sequences spotted on the arrays included 32 probes derived from the literature that target known pathogens or contaminant microbes and 73 probes to sequences derived from freshwater environmental samples, including both known and novel sequences, and four cyanobacteria. The actual probe sequences spotted on the array shown in FIG. 17 are provided in Table 16, and the location of each sequence on the array is provided in Table 17. See Tables 3 and 4 for SEQ ID NOS: that correspond to probe numbers; e.g., 43P is SEQ ID NO: 46 (Table 4).

TABLE 16

Primer/Probe combinations spotted on microarrays

| 16S rDNA sequence | GenBank accession no. | 18S rDNA sequence | GenBank accession no. |
|---|---|---|---|
| *Enterococcus gallinarum*, strain LMG 13129 | AJ301833 | *Cryptosporidium parvum* | AF222998 |
| *Burkholderia cepacia* | AB091761 | *Acanthamoeba mauritaniensis* | AY351647 |
| *Burkholderia cepacia* genomovar III | AF148556 | *Cyclospora cayetanensis* | AF111183 |
| Uncultured human fecal bacterium HF74 | AF233412 | *Entamoeba histolytica* | X65163 |
| Uncultured human fecal bacterium HF8 | AF233408 | *Giardia intestinalis* isolate | AF199449 |
| Uncultured human fecal bacterium HF10 | AF233413 | *Isospora belli* | AF106935 |
| *Bacillus anthracis* strain S51 | AB116124 | *Microsporidium* sp. STF | AY140647 |
| *Clostridium botulinum* strain AIP 355.02 | AY303799 | *Naegleria fowleri* | AF338423 |
| *Francisella tularensis* strain 3523 | AY243028 | OTU TL1A1, multi-copy, unidentified | |
| *Yersinia pestis* | AF366383 | OTU TL1A2, multi-copy, unidentified | |
| *Brucella melitensis* | AF220149 | OTU TL1A9, multi-copy, unidentified | |
| *Burkholderia mallei* strain 2000031063 | AY305760 | OTU TL1A12, multi-copy, unidentified | |
| *Chlamydophila psittaci* clone cvCps2 | AY334530 | OTU TL1A16, multi-copy, unidentified | |
| *Coxiella burnetii*, strain Nine Mile | Y11502 | OTU TL1A21, multi-copy, unidentified | |

TABLE 16-continued

Primer/Probe combinations spotted on microarrays

| 16S rDNA sequence | GenBank accession no. | 18S rDNA sequence | GenBank accession no. |
|---|---|---|---|
| *Escherichia coli* O157:H7 | AB035920 | OTU CL1A3, single-copy, unidentified | |
| *Escherichia coli* O157:H7 EDL933 | NC 002655 | OTU CL1A4, single-copy, unidentified | |
| *Escherichia coli* O157:H7 EDL933 | NC 002655 | OTU CL1A5, single-copy, unidentified | |
| *Escherichia coli* O157:H7 EDL933 | NC 002655 | OTU CL1A6, single-copy, unidentified | |
| *Escherichia coli* O157:H7 EDL933 | NC 002655 | OTU CL1A8, multi-copy, unidentified | |
| *Escherichia coli* O157:H7 EDL933 | NC 002655 | OTU LT2A12, multi-copy, unidentified | |
| *Escherichia coli* O157:H7 EDL933 | NC 002655 | OTU LT2A20, single-copy, unidentified | |
| *Escherichia coli* O157:H7 EDL933 | NC 002655 | OTU LT1A3, single-copy, unidentified | |
| *Escherichia coli* O157:H7 EDL933 | NC 002655 | OTU LT1A42, multi-copy, identified as *Cryptomonas* sp., strain M420 | |
| *Escherichia coli* K12 | NC 000913 | OTU LT1A5, multi-copy, unidentified | |
| *Escherichia coli* K12 | NC 000913 | OTU LT1A4, multi-copy, identified as *Cryptomonas ovata*, strain CCAP 979/61 | |
| *Escherichia coli* K12 | NC 000913 | OTU LT1A8, multi-copy, unidentified | |
| *Escherichia coli* K12 | NC 000913 | OTU LT2A7, multi-copy, identified as *Dileptus* sp. | |
| *Rickettsia prowazekii* | M21789 | OTU LT1A9, single-copy, unidentified | |
| *Salmonella typhimurium* | Z49264 | OTU LT2A19, single-copy, identified as *Coleps* sp. | |
| *Vibrio cholerae* (CECT 514 T) | X76337 | OTU LT1A10, multi-copy, unidentified | |
| *Campylobacter jejuni* strain B99/206 | AF550630 | OTU LT1A11, single-copy, unidentified | |
| *Legionella pneumophila* serogroup 6 | AJ496383 | OTU LT1A13, single-copy, unidentified | |
| *Leptospira interrogans* | Z12817 | OTU LT3A2, single-copy, unidentified | |
| *Pseudomonas aeruginosa*, strain WatG | AB117953 | OTU LT3A5, multi-copy, unidentified | |
| OTU TL1A1, multi-copy, unidentified | | OTU LT3A6, multi-copy, unidentified | |
| OTU TL1A2, multi-copy, unidentified | | OTU LT3A11, single-copy, unidentified | |
| OTU TL1A6, single-copy, unidentified | | OTU LT3A13, single-copy, unidentified | |
| OTU TL1A7, multi-copy, identified as Uncultured beta proteobacterium clone OS1L-16 | | OTU LT1A1, multi-copy, unidentified | |
| OTU LT1A31, multi-copy, identified as Uncultured Crater Lake bacterium CL500-18 | | OTU LT1A38, multi-copy, unidentified | |
| OTU LT1A55, multi-copy, identified as Uncultured freshwater bacterium LCK-26 | | | |
| OTU CL1A2, multi-copy, unidentified | | | |
| OTU CL1A9, multi-copy, identified as *Zoogloea ramigera* | | | |
| OTU CL1A10, multi-copy, unidentified | | | |
| OTU CL1A15, single-copy, identified as Uncultured Crater Lake bacterium CL0-27 | | | |
| OTU LT1A54, multi-copy, identified as Uncultured Crater Lake bacterium CL0-64 | | | |
| OTU LT1A27, multi-copy, identified as Uncultured actinomycete clone SFD1-39 | | | |
| OTU LT2A3, multi-copy, unidentified | | | |
| OTU LT1A46, multi-copy, identified as Uncultured planctomycete clone CY0ARA031E04 | | | |
| OTU LT2A12, multi-copy, unidentified | | | |
| OTU LT2A16, multi-copy, unidentified | | | |
| OTU LT1A53-3A9, multi-copy, identified as *Synechococcus* sp. | | | |
| OTU LT1A53, multi-copy, identified as *Synechococcus* sp. LBG2 | | | |
| OTU LT3A9, multi-copy, identified as *Synechococcus* sp. LBP1 | | | |
| OTU LT3A11, multi-copy, identified as Unidentified cyanobacterium clone LD27 | | | |

TABLE 16-continued

Primer/Probe combinations spotted on microarrays

| 16S rDNA sequence | GenBank accession no. | 18S rDNA sequence | GenBank accession no. |
|---|---|---|---|
| Arsenite-oxidizing bacterium MLHE-1 | | | |
| *Thiomicrospira* sp. CVO | | | |
| *Desulfovibrio longreachii* | | | |
| *Bacillus arsenicoselenatis* | | | |
| OTU LT3A1, single-copy, unidentified | | | |
| OTU LT3A2, multi-copy, unidentified | | | |
| OTU LT3A7, multi-copy, unidentified | | | |
| OTU LT1A15, single-copy, unidentified | | | |
| OTU LT1A16, multi-copy, unidentified | | | |
| OTU LT1A18, multi-copy, unidentified | | | |
| OTU LT1A35, multi-copy, unidentified | | | |
| OTU LT1A55, multi-copy, unidentified | | | |

TABLE 17

Oligonucleotide probes on array of FIG. 17

| A | | | | | | B | | | | | |
|---|---|---|---|---|---|---|---|---|---|---|---|
| | | | | | | 19P | 20P | 21P | 22P | 18P | 23P |
| | | | | | | 24P | 25P | 26P | 27P | 28P | |
| | | | | | | 17P | 29P | | | | |
| | | | | | | | | | | | CY3 9mer |

| C | | | | | | D | | | | | |
|---|---|---|---|---|---|---|---|---|---|---|---|
| 43P | 44P | 45P | 46P | 47P | 48P | 95P | 96P | 97P | 86P | 87P | 88P |
| 49P | 50P | 65P | 66P | 67P | 68P | 91P | 98P | 92P | 99P | 89P | 90P |
| 69P | 70P | 71P | 72P | | | 93P | 100P | 94P | 101P | 102P | |
| | | | | | | | | | | | CY3 9mer |

| E | | | | | | F | | | | | |
|---|---|---|---|---|---|---|---|---|---|---|---|
| 15P | 30P | 31P | 32P | 16P | 33P | 10P | 11P | 12P | 13P | 1P | 2P |
| 34P | 14P | 35P | 36P | 38P | 39P | 3P | 4P | 5P | 6P | 7P | 8P |
| 40P | 41P | | | | | | | | | | |
| | | | | | | | | | | | CY3 9mer |

| G | | | | | | H | | | | | |
|---|---|---|---|---|---|---|---|---|---|---|---|
| 51P | 52P | 53P | 54P | 55P | 56P | 83P | 81P | 73P | 74P | 75P | 76P |
| 57P | 58P | 60P | 61P | 62P | 63P | 84P | 85P | 82P | 80P | 77P | 78P |
| | | | | | | 79P | 106P | 107P | 108P | | |
| | | | | | | 103P | 104P | 105P | 109P | 110P | CY3 9mer |

Such taxon-specific arrays may be developed for specific bodies of water. For example, arrays may be developed for lakes, marshes, tidal pools, or estuaries. Such arrays may include probes developed for freshwater systems, as these may be diagnostic for known pathogens (e.g., coliform bacteria) or environmental conditions (e.g., eutrophication). Also, sequences specific to microbes known to be common in the body of water of interest may be used. For example, for estuaries, phytoplankton populations have been described (Williams, R. B. and M. B. Murdoch 1966, *Limnology and Oceanography* 11:73-82., Thayer, G. W., 1971 *Estuaries* 12:240-253; Mallin 1994, Mallin, et al. 2000). A review of the literature indicates that many of the sequences that may be used are known (Table 18). Using this information, primers and probes to these common organisms, may be designed. Finally, probes for the array may be derived by sequencing clonal libraries derived from field samples as described herein for the lake samples to develop additional OTUs. For example, to develop an estuary array, water samples may be collected every few months in estuarine tidal creeks at various sites representing a range of estuarine conditions. Specific sampling locations may be water quality monitoring stations, and samples may be taken late on the flooding tide and six hours later on the ebbing tide, to provide a representative sample of both the community that enters the estuarine site as well as the community that leaves the estuarine site with the falling tide.

TABLE 18

Examples of organisms of interest for North Carolina estuarine microarray targets based on literature reports[4]

Phytoplankton

| | |
|---|---|
| Cyclotella spp. | Melosira spp. |
| Nitzschia spp. | Navicula spp. |
| Psuedo-nitzschia australis[3] | Skeletonema costatum[1] |
| Thalassiosira spp. | |
| Amphidinium spp. | Ceratium spp. |
| Chattonella spp.[3] (C. antiqua, C. verruculosa) | Gymnodinium sanguineum |
| Heterocapsa triquetra[1] | Heterosgima akashiwo[3] |
| Hematodinium perezi[3] | Karenia brevis[3] |
| Karlodinium micrum[1] | Katodinium rotundatum[1] |
| Pfiesteria piscicida[3], P. shumwayae[3] | Prorocentrum minimum[1] |
| Calicomonas ovalis | Chlamydomonas spp. |
| Chroomonas spp. (C. minuta, C. amphioxiae) | Cyrptomonas testaceae |
| Hemiselmis virescens | Phaeocystis globosa |
| Pyramimonas | Eutreptia[1] |

Bacteria

| | |
|---|---|
| Acinetobcter spp. | Alcaligenes spp. |
| Bacteroides spp.[2] | Enterococcus spp.[2] (E. faecalis, E. faecium) |
| Escherichia spp.[2,3] (E. coli, E. coli O157H7) | Flavobacterium spp. |
| Oceanospirillum spp. | Salmonella spp.[2,3] (S. typhi, S. non-typhi) |
| Psuedomonas aeruginosa | Shigella sp.[2,3] |
| Clostridium sp.[2,3] (C. perfringens, C. botulinum Type E) | |
| Vibrio sp.[3] (V. anguillarum, V. cholerae 01, V. cholerae non 01, V. parahaemolyticus V. vulnificus) | |

Virus

| | |
|---|---|
| Hepatitis A[3] | Norwalk virus[3] |
| Adenovirus[3] | rotavirus[3] |

Protozoa

| | |
|---|---|
| Kudoa spp.[3] (K. clupeidae, K. fundulae) | Cryptosporidium spp.[2,3] |
| Giardia[2,3] | Perkinsus marinus[3] |
| Haplosporidium[3] | |

Fungi

Aphanomyces invadens[3]

[1]Genera or species referenced in the literature as commonly found in southeastern estuarine systems, and likely to be indicators of good ecosystem health (e.g. Campbell, 1973, Univ. of N.C. Sea Grant Publication, UNC-SG-73-07; Mallin, et al. 2000, American Scientist, 88: 26-37; Shubert, 1984, In Algae as Ecological Markers, Academic Press, NY, p. 434; Stoermer and Smol, 1999, In The Diatoms: Applications For the Environmental and Earth Sciences, Cambridge Univ. Press, Cambridge, UK, page 469; Thayer, 1971, Estuaries, 12: 240-253, Williams and Murdoch, 1966, Limnology and Oceanography, 11: 73-82;).
[2]Microbes linked to specific contamination sources (e.g. human sewage) which indicate point or non-point source pollution (e.g. Bernhard and Field, 2000, Applied and Environmental Microbiology, 66: 4641-4648; Lipp, et al. 2001, Marine Pollution Bull., 42: 286-293; Mallin, et al., 2000b, Ecological Applications, 10: 1047-1056' USEPA, 1985, Test methods for Escherichia coli and Enterococci in water by the membrane filter procedure, EPA600/4-85/076)
[3]Known human, fish, or shellfish pathogens or parasites (e.g. DeLeon, et al. 1990, In Proceeding of the Water Quality Conference, San Diego, CA, American Water Works Association, 18: 833-853; Grimes 1991, Estuaries, 14: 345-360; Kane, et al., 1998, Maryland Medical Journal, 37: 106-112; Lipp, 1999, Reed and Francis-Floyd, 1996, Vibrio Infections of Fish, Florida Cooperative Extension Service, Institute of Food and Agricultural Sciences, University of Florida web-site; Shields, 1997, An investigation into the epidemiology of Hematodinium perezi, a parasitic dinoflagellate in the blue crab, Callinectes sapidus, available on-line)
[4]Many of the taxa listed have GenBank sequence entries for one or more species.

It should be understood that various changes and modifications to the embodiments described herein will be apparent to those skilled in the art. Such changes and modifications can be made without departing from the spirit and scope of the present invention and without diminishing its attendant scope and/or advantages.

What is claimed is:

1. A method to monitor a parameter of an aquatic ecosystem comprising the steps of:
   (a) obtaining a sample from an aquatic ecosystem;
   (b) using at least one oligonucleotide specific to a single operational taxonomic unit to determine whether a nucleic acid sequence specific to the operational taxonomic unit is present in the sample wherein the at least one oligonucleotide specific to the single operational taxonomic unit comprises SEQ ID NO: 355 or SEQ ID NO: 356; and
   (c) correlating detection of the nucleic acid sequence specific to the operational taxonomic unit to a parameter of the ecosystem wherein the parameter is mercury.

2. The method of claim 1, further comprising generating a plurality of distinct oligonucleotides each specific to a single operational taxonomic unit in at least one aquatic ecosystem and determining whether nucleic acid sequences specific to each of the operational taxonomic units are present in the sample.

3. The method of claim 1, further comprising identifying the at least one oligonucleotide specific to a single operational taxonomic unit in a first aquatic ecosystem and using the at least one oligonucleotide specific to a single operational taxonomic unit to determine whether nucleic acid sequences specific to the operational taxonomic unit are present in a second aquatic ecosystem.

4. The method of claim 1, wherein step (b) comprises using two oligonucleotides as primers in a polymerase chain reaction to amplify DNA from a single genomic target sequence wherein the amplified product comprises the at least one oligonucleotide specific to a single operational taxonomic unit.

5. The method of claim 2, wherein step (b) comprises using a plurality of paired oligonucleotides as primers in a plurality of separate polymerase chain reactions to amplify DNA from a plurality of genomic target sequences wherein the amplified product comprises at least some of the plurality of the distinct oligonucleotides each specific to a single operational taxonomic unit.

6. The method of claim 1, wherein the at least one oligonucleotide specific to the single operational taxonomic unit further comprises an oligonucleotide comprising SEQ ID NO: 357 or 358.

7. The method of claim 2, wherein the plurality of distinct oligonucleotides comprises an array of individual locations, each location comprising at least one oligonucleotide specific to a single operational taxonomic unit.

8. The method of claim 1, wherein the at least one oligonucleotide specific to the single operational taxonomic unit further comprises an oligonucleotide having the sequence as set forth in any of SEQ ID NOs: 329-340 or SEQ ID NOs: 351-354 or SEQ ID NOs: 359-370.

9. The method of claim 1, wherein step (b) comprises using two oligonucleotides as primers in a polymerase chain reaction to amplify DNA from a single genomic target sequence wherein the amplified product comprises the oligonucleotide specific to a single operational taxonomic unit and wherein the primers comprise oligonucleotides comprising a first primer having the sequence as set forth in SEQ ID NO: 375 and a second primer having the sequence as set forth in SEQ ID NO: 376.

10. The method of claim 8, wherein step (b) comprises using two oligonucleotides as primers in a polymerase chain reaction to amplify DNA from a single genomic target sequence wherein the amplified product comprises the oligonucleotide specific to a single operational taxonomic unit and wherein the primers comprise oligonucleotides comprising the sequence as set forth in any of SEQ ID NOs: 341-350 or SEQ ID NOs: 371-374 or SEQ ID NOs: 377-388.

* * * * *

SEQUENCE LISTING

```
<160> NUMBER OF SEQ ID NOS: 388

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
agagtttgat cctggctcag                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
aaggaggtga tccagccgca                                                  20

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
```
aacctggttg atcctgccag t                                              21

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
tgatccttct gcaggttcac ctac                                           24

<210> SEQ ID NO 5
<211> LENGTH: 50
<212> TYPE: DNA
<213> ORGANISM: Artificial Sequence
<220> FEATURE:
<223> OTHER INFORMATION: Synthetic

<400> SEQUENCE: 5
actaactcaa tagcaggaac gggaatccag aaggagggga cgggcgggcc               50

<210> SEQ ID NO 6
<211> LENGTH: 50
<212> TYPE: DNA
<213> ORGANISM: Artificial Sequence
<220> FEATURE:
<223> OTHER INFORMATION: Synthetic

<400> SEQUENCE: 6
gatttctcat aaggtgctga aggagtaagg aacaacctcc aatctctagt               50

<210> SEQ ID NO 7
<211> LENGTH: 50
<212> TYPE: DNA
<213> ORGANISM: Artificial Sequence
<220> FEATURE:
<223> OTHER INFORMATION: Synthetic

<400> SEQUENCE: 7
agttccggaa caccaacgca cgcagcgaag cgcggaaggc taccggaaga               50

<210> SEQ ID NO 8
<211> LENGTH: 50
<212> TYPE: DNA
<213> ORGANISM: Artificial Sequence
<220> FEATURE:
<223> OTHER INFORMATION: Synthetic

<400> SEQUENCE: 8
gaaatgtctt attgacatcc cctcagcatt gtcccatgct tgaatattca               50

<210> SEQ ID NO 9
<211> LENGTH: 50
<212> TYPE: DNA
<213> ORGANISM: Artificial Sequence
<220> FEATURE:
<223> OTHER INFORMATION: Synthetic

<400> SEQUENCE: 9
cccacgcggc gggtccaacg ggcctgcctg gagcgctccc gtttcctcgt               50

<210> SEQ ID NO 10
<211> LENGTH: 50
<212> TYPE: DNA
<213> ORGANISM: Artificial Sequence
<220> FEATURE:

<223> OTHER INFORMATION: Synthetic

<400> SEQUENCE: 10
gaatttcacc acgtacacac ccctaagggc ggactggctg cttccagcag        50

<210> SEQ ID NO 11
<211> LENGTH: 50
<212> TYPE: DNA
<213> ORGANISM: Artificial Sequence
<220> FEATURE:
<223> OTHER INFORMATION: Synthetic

<400> SEQUENCE: 11
ctttatcatc ggactcgccc ctggccagcg ctttcgcctc tgtcgctcct        50

<210> SEQ ID NO 12
<211> LENGTH: 50
<212> TYPE: DNA
<213> ORGANISM: Artificial Sequence
<220> FEATURE:
<223> OTHER INFORMATION: Synthetic

<400> SEQUENCE: 12
cctccaacca tctcctgatg gaactagtta ccccgtaaac actcttaggt        50

<210> SEQ ID NO 13
<211> LENGTH: 50
<212> TYPE: DNA
<213> ORGANISM: Artificial Sequence
<220> FEATURE:
<223> OTHER INFORMATION: Synthetic

<400> SEQUENCE: 13
acggagacaa acaagcacca acacaagtga agggcacgtt gctccaacca        50

<210> SEQ ID NO 14
<211> LENGTH: 50
<212> TYPE: DNA
<213> ORGANISM: Artificial Sequence
<220> FEATURE:
<223> OTHER INFORMATION: Synthetic

<400> SEQUENCE: 14
caagcagaaa ggcacgcgcg caccgtccaa ccagaggctg acagttcaca        50

<210> SEQ ID NO 15
<211> LENGTH: 50
<212> TYPE: DNA
<213> ORGANISM: Artificial Sequence
<220> FEATURE:
<223> OTHER INFORMATION: Synthetic

<400> SEQUENCE: 15
gcacgcgcat gccgtccgac cagaggccga cagcccacac gcgcccaaaa        50

<210> SEQ ID NO 16
<211> LENGTH: 50
<212> TYPE: DNA
<213> ORGANISM: Artificial Sequence
<220> FEATURE:
<223> OTHER INFORMATION: Synthetic

<400> SEQUENCE: 16
taactgtccc tgatgggact agtagggatt ggtttaaagc ctctccctag        50

<210> SEQ ID NO 17

```
<211> LENGTH: 50
<212> TYPE: DNA
<213> ORGANISM: Artificial Sequence
<220> FEATURE:
<223> OTHER INFORMATION: Synthetic

<400> SEQUENCE: 17
tctcagacgg atgaacgcct atacctcgac cggagccgct gtacaaacgc          50

<210> SEQ ID NO 18
<211> LENGTH: 50
<212> TYPE: DNA
<213> ORGANISM: Artificial Sequence
<220> FEATURE:
<223> OTHER INFORMATION: Synthetic

<400> SEQUENCE: 18
acctaatgcc acacagattc cacccaagga tggacgagct gcccaagtac          50

<210> SEQ ID NO 19
<211> LENGTH: 50
<212> TYPE: DNA
<213> ORGANISM: Artificial Sequence
<220> FEATURE:
<223> OTHER INFORMATION: Synthetic

<400> SEQUENCE: 19
ccatctgcgc ctcaacatgc aggtaaatcg taaagaaaag gccaaatagc          50

<210> SEQ ID NO 20
<211> LENGTH: 50
<212> TYPE: DNA
<213> ORGANISM: Artificial Sequence
<220> FEATURE:
<223> OTHER INFORMATION: Synthetic

<400> SEQUENCE: 20
gtatcacacc agggaggtta ttgaacgcag accacctagg taacacctaa          50

<210> SEQ ID NO 21
<211> LENGTH: 50
<212> TYPE: DNA
<213> ORGANISM: Artificial Sequence
<220> FEATURE:
<223> OTHER INFORMATION: Synthetic

<400> SEQUENCE: 21
aaggatgctt tcaggcactg atcgcgcaca ctgaggtggg aagtgccgtt          50

<210> SEQ ID NO 22
<211> LENGTH: 50
<212> TYPE: DNA
<213> ORGANISM: Artificial Sequence
<220> FEATURE:
<223> OTHER INFORMATION: Synthetic

<400> SEQUENCE: 22
taagtgcaac gggatcctca tgcagaaaga cccgagcctg ccgtccgacc          50

<210> SEQ ID NO 23
<211> LENGTH: 50
<212> TYPE: DNA
<213> ORGANISM: Artificial Sequence
<220> FEATURE:
<223> OTHER INFORMATION: Synthetic

<400> SEQUENCE: 23
```
aaagtaaacc tgccagcaca gacggacact cggcgaagag cacccgcctg                50

<210> SEQ ID NO 24
<211> LENGTH: 50
<212> TYPE: DNA
<213> ORGANISM: Artificial Sequence
<220> FEATURE:
<223> OTHER INFORMATION: Synthetic

<400> SEQUENCE: 24
ttaatgccag atatgctctc cccgaggatg gctgcagaca catagtacag                50

<210> SEQ ID NO 25
<211> LENGTH: 50
<212> TYPE: DNA
<213> ORGANISM: Artificial Sequence
<220> FEATURE:
<223> OTHER INFORMATION: Synthetic

<400> SEQUENCE: 25
agtcgaccag ttctgaccca tgaggccgac cggctgagct cactctgaac                50

<210> SEQ ID NO 26
<211> LENGTH: 50
<212> TYPE: DNA
<213> ORGANISM: Artificial Sequence
<220> FEATURE:
<223> OTHER INFORMATION: Synthetic

<400> SEQUENCE: 26
tcaaacctga ttcaaacccg tatgggtcga tcggtcgtcc tcagcagaaa                50

<210> SEQ ID NO 27
<211> LENGTH: 50
<212> TYPE: DNA
<213> ORGANISM: Artificial Sequence
<220> FEATURE:
<223> OTHER INFORMATION: Synthetic

<400> SEQUENCE: 27
tggtaggcta ccactgcgca tccacaagga ggcagaaact agccaaccag                50

<210> SEQ ID NO 28
<211> LENGTH: 50
<212> TYPE: DNA
<213> ORGANISM: Artificial Sequence
<220> FEATURE:
<223> OTHER INFORMATION: Synthetic

<400> SEQUENCE: 28
gcttcatgca ggagcatctc agcatccagt gttgggacca ggacatactg                50

<210> SEQ ID NO 29
<211> LENGTH: 50
<212> TYPE: DNA
<213> ORGANISM: Artificial Sequence
<220> FEATURE:
<223> OTHER INFORMATION: Synthetic

<400> SEQUENCE: 29
gttatgattc tatctcaagg aggagcgtcc tgtgctctcc cacttcactc                50

<210> SEQ ID NO 30
<211> LENGTH: 50
<212> TYPE: DNA
<213> ORGANISM: Artificial Sequence
<220> FEATURE:

<223> OTHER INFORMATION: Synthetic

<400> SEQUENCE: 30
tccagaaggt gaggccgacg caaagagtac tcaccgctag gtggaccctc            50

<210> SEQ ID NO 31
<211> LENGTH: 50
<212> TYPE: DNA
<213> ORGANISM: Artificial Sequence
<220> FEATURE:
<223> OTHER INFORMATION: Synthetic

<400> SEQUENCE: 31
acagtaaagg acgcaggtcc ggacgccgac aagtgaatgc cgacgccttc            50

<210> SEQ ID NO 32
<211> LENGTH: 50
<212> TYPE: DNA
<213> ORGANISM: Artificial Sequence
<220> FEATURE:
<223> OTHER INFORMATION: Synthetic

<400> SEQUENCE: 32
tctctagaag gatgcccaac ccgcaccggc actcacaggc caaaaaggcc            50

<210> SEQ ID NO 33
<211> LENGTH: 50
<212> TYPE: DNA
<213> ORGANISM: Artificial Sequence
<220> FEATURE:
<223> OTHER INFORMATION: Synthetic

<400> SEQUENCE: 33
cgaagacgga tgactaacta tatactgacg taagccagca tataaatagc            50

<210> SEQ ID NO 34
<211> LENGTH: 50
<212> TYPE: DNA
<213> ORGANISM: Artificial Sequence
<220> FEATURE:
<223> OTHER INFORMATION: Synthetic

<400> SEQUENCE: 34
cacaattaag tgcaacggga tcctcatgca gaaagacccg agcctgccgt            50

<210> SEQ ID NO 35
<211> LENGTH: 50
<212> TYPE: DNA
<213> ORGANISM: Artificial Sequence
<220> FEATURE:
<223> OTHER INFORMATION: Synthetic

<400> SEQUENCE: 35
tattaacgca ctacgccctg gaaggatgct ttcaggcact gatcgcgcac            50

<210> SEQ ID NO 36
<211> LENGTH: 50
<212> TYPE: DNA
<213> ORGANISM: Artificial Sequence
<220> FEATURE:
<223> OTHER INFORMATION: Synthetic

<400> SEQUENCE: 36
acagctacca ccaccctaag gtggggaggt catcccgatc agagattcaa            50

<210> SEQ ID NO 37

-continued

```
<211> LENGTH: 50
<212> TYPE: DNA
<213> ORGANISM: Artificial Sequence
<220> FEATURE:
<223> OTHER INFORMATION: Synthetic

<400> SEQUENCE: 37
ttccaagagg atgcctcggt ctaaccagac acaaacccgt atgggtcggt        50

<210> SEQ ID NO 38
<211> LENGTH: 50
<212> TYPE: DNA
<213> ORGANISM: Artificial Sequence
<220> FEATURE:
<223> OTHER INFORMATION: Synthetic

<400> SEQUENCE: 38
aagtgttttc cggaagatgg acgcaaacac ccggtacaca gaccgcgagt        50

<210> SEQ ID NO 39
<211> LENGTH: 50
<212> TYPE: DNA
<213> ORGANISM: Artificial Sequence
<220> FEATURE:
<223> OTHER INFORMATION: Synthetic

<400> SEQUENCE: 39
taacagaagg atggtagggc ggctcagcgc actcaacttg agggcaaagt        50

<210> SEQ ID NO 40
<211> LENGTH: 50
<212> TYPE: DNA
<213> ORGANISM: Artificial Sequence
<220> FEATURE:
<223> OTHER INFORMATION: Synthetic

<400> SEQUENCE: 40
acagtacaag tcttgcgact agaccgtccg gcccaaaacc tgaaatccaa        50

<210> SEQ ID NO 41
<211> LENGTH: 50
<212> TYPE: DNA
<213> ORGANISM: Artificial Sequence
<220> FEATURE:
<223> OTHER INFORMATION: Synthetic

<400> SEQUENCE: 41
aaacaagcca gtaccgaaag cattcggacc gacttctgtc cgccgagatc        50

<210> SEQ ID NO 42
<211> LENGTH: 50
<212> TYPE: DNA
<213> ORGANISM: Artificial Sequence
<220> FEATURE:
<223> OTHER INFORMATION: Synthetic

<400> SEQUENCE: 42
gcaagcggat gactgtcaga atccccgtct aatgactgaa gacctgaaca        50

<210> SEQ ID NO 43
<211> LENGTH: 50
<212> TYPE: DNA
<213> ORGANISM: Artificial Sequence
<220> FEATURE:
<223> OTHER INFORMATION: Synthetic

<400> SEQUENCE: 43
```
acctaatgcc acacagattc cacccaagga tggacgagct gcccaagtac        50

<210> SEQ ID NO 44
<211> LENGTH: 50
<212> TYPE: DNA
<213> ORGANISM: Artificial Sequence
<220> FEATURE:
<223> OTHER INFORMATION: Synthetic

<400> SEQUENCE: 44
ttcagaaaag aagtgtcgtc ccgatcgcac taccgtaagg cggcaagcgt        50

<210> SEQ ID NO 45
<211> LENGTH: 50
<212> TYPE: DNA
<213> ORGANISM: Artificial Sequence
<220> FEATURE:
<223> OTHER INFORMATION: Synthetic

<400> SEQUENCE: 45
aatgccgctg gtcacacgga agaaagaagc cgaccaaaca gtgcgacttg        50

<210> SEQ ID NO 46
<211> LENGTH: 50
<212> TYPE: DNA
<213> ORGANISM: Artificial Sequence
<220> FEATURE:
<223> OTHER INFORMATION: Synthetic

<400> SEQUENCE: 46
gtgacagccg aagccgcctt tcaatttcga accatgcggt tcaaaatgtt        50

<210> SEQ ID NO 47
<211> LENGTH: 50
<212> TYPE: DNA
<213> ORGANISM: Artificial Sequence
<220> FEATURE:
<223> OTHER INFORMATION: Synthetic

<400> SEQUENCE: 47
ccaacgcggg ccgatcattt gccgataaat ctttcccccg aagggcacat        50

<210> SEQ ID NO 48
<211> LENGTH: 50
<212> TYPE: DNA
<213> ORGANISM: Artificial Sequence
<220> FEATURE:
<223> OTHER INFORMATION: Synthetic

<400> SEQUENCE: 48
aggcccgaag gtcccccgct ttcatcctca gatcgtatgc ggtattaatc        50

<210> SEQ ID NO 49
<211> LENGTH: 50
<212> TYPE: DNA
<213> ORGANISM: Artificial Sequence
<220> FEATURE:
<223> OTHER INFORMATION: Synthetic

<400> SEQUENCE: 49
tcctacaccg aaaactttc cctactcaac ttgtgttaag caggagtata        50

<210> SEQ ID NO 50
<211> LENGTH: 50
<212> TYPE: DNA
<213> ORGANISM: Artificial Sequence
<220> FEATURE:

<223> OTHER INFORMATION: Synthetic

<400> SEQUENCE: 50
ggtccgaaga tccccttctt taatatgttt tagatgccta aacataccac    50

<210> SEQ ID NO 51
<211> LENGTH: 50
<212> TYPE: DNA
<213> ORGANISM: Artificial Sequence
<220> FEATURE:
<223> OTHER INFORMATION: Synthetic

<400> SEQUENCE: 51
cgccgcgggt ccatctcaaa gcaataaatc tttgataaga aaatcatgcg    50

<210> SEQ ID NO 52
<211> LENGTH: 50
<212> TYPE: DNA
<213> ORGANISM: Artificial Sequence
<220> FEATURE:
<223> OTHER INFORMATION: Synthetic

<400> SEQUENCE: 52
tcatcttata gcacgaggtc cgaagatccc ccgctttgct ccaaagagat    50

<210> SEQ ID NO 53
<211> LENGTH: 50
<212> TYPE: DNA
<213> ORGANISM: Artificial Sequence
<220> FEATURE:
<223> OTHER INFORMATION: Synthetic

<400> SEQUENCE: 53
acatccgatg gcaagaggcc cgaaggtccc cctctttggt cttgcgacgt    50

<210> SEQ ID NO 54
<211> LENGTH: 50
<212> TYPE: DNA
<213> ORGANISM: Artificial Sequence
<220> FEATURE:
<223> OTHER INFORMATION: Synthetic

<400> SEQUENCE: 54
caattctggg aagcgtggca ttaatactga attgtcatca tcatgcatcg    50

<210> SEQ ID NO 55
<211> LENGTH: 50
<212> TYPE: DNA
<213> ORGANISM: Artificial Sequence
<220> FEATURE:
<223> OTHER INFORMATION: Synthetic

<400> SEQUENCE: 55
ggttgatgaa aaagcatttg gagccgcgaa atttaccagt gtcttaaaac    50

<210> SEQ ID NO 56
<211> LENGTH: 50
<212> TYPE: DNA
<213> ORGANISM: Artificial Sequence
<220> FEATURE:
<223> OTHER INFORMATION: Synthetic

<400> SEQUENCE: 56
tgtccgattc agcacgggta aatagtcgta ttgttagtgg ccgaatttaa    50

<210> SEQ ID NO 57

```
<211> LENGTH: 50
<212> TYPE: DNA
<213> ORGANISM: Artificial Sequence
<220> FEATURE:
<223> OTHER INFORMATION: Synthetic

<400> SEQUENCE: 57
ttgctggaga gtccttctcg ggtatcgatt gtcgaagata aacatattta          50

<210> SEQ ID NO 58
<211> LENGTH: 50
<212> TYPE: DNA
<213> ORGANISM: Artificial Sequence
<220> FEATURE:
<223> OTHER INFORMATION: Synthetic

<400> SEQUENCE: 58
gtggtggatt acgccatgac atgggaggat taacgggggg gagtaatagc          50

<210> SEQ ID NO 59
<211> LENGTH: 50
<212> TYPE: DNA
<213> ORGANISM: Artificial Sequence
<220> FEATURE:
<223> OTHER INFORMATION: Synthetic

<400> SEQUENCE: 59
tctggagtat caagcactta taacctaata acacaaaacc ctcttcctgg          50

<210> SEQ ID NO 60
<211> LENGTH: 50
<212> TYPE: DNA
<213> ORGANISM: Artificial Sequence
<220> FEATURE:
<223> OTHER INFORMATION: Synthetic

<400> SEQUENCE: 60
gccctgacgt atggcgggta cgaaatgaag ccagtgacgg tgaccattac          50

<210> SEQ ID NO 61
<211> LENGTH: 50
<212> TYPE: DNA
<213> ORGANISM: Artificial Sequence
<220> FEATURE:
<223> OTHER INFORMATION: Synthetic

<400> SEQUENCE: 61
actggcggga acacatgaaa acgtaaccac gctaccagta gccagaagaa          50

<210> SEQ ID NO 62
<211> LENGTH: 50
<212> TYPE: DNA
<213> ORGANISM: Artificial Sequence
<220> FEATURE:
<223> OTHER INFORMATION: Synthetic

<400> SEQUENCE: 62
ccattaaaac taatgcctgt cataatggag ggggattcag cgaagttatt          50

<210> SEQ ID NO 63
<211> LENGTH: 50
<212> TYPE: DNA
<213> ORGANISM: Artificial Sequence
<220> FEATURE:
<223> OTHER INFORMATION: Synthetic

<400> SEQUENCE: 63
```

-continued aagacatctt caccgttcac gatattttga aagcacgagg ggaaatctga　　　　　　　50

<210> SEQ ID NO 64
<211> LENGTH: 50
<212> TYPE: DNA
<213> ORGANISM: Artificial Sequence
<220> FEATURE:
<223> OTHER INFORMATION: Synthetic

<400> SEQUENCE: 64
caccgtcgct ttaaaacgcg cccggtggga gaatcgtcgt tgtacattta　　　　　　　50

<210> SEQ ID NO 65
<211> LENGTH: 50
<212> TYPE: DNA
<213> ORGANISM: Artificial Sequence
<220> FEATURE:
<223> OTHER INFORMATION: Synthetic

<400> SEQUENCE: 65
tttctgatcg cgttgctgcg ctgatcaaag aagtaaacaa agcagcttaa　　　　　　　50

<210> SEQ ID NO 66
<211> LENGTH: 50
<212> TYPE: DNA
<213> ORGANISM: Artificial Sequence
<220> FEATURE:
<223> OTHER INFORMATION: Synthetic

<400> SEQUENCE: 66
atggcatccg tggtatcccg actctgctgc tgttcaaaaa cggtgaagtg　　　　　　　50

<210> SEQ ID NO 67
<211> LENGTH: 50
<212> TYPE: DNA
<213> ORGANISM: Artificial Sequence
<220> FEATURE:
<223> OTHER INFORMATION: Synthetic

<400> SEQUENCE: 67
aggctcatcc atctgcgaca cgccgaaagc cacctttaat ccacagatat　　　　　　　50

<210> SEQ ID NO 68
<211> LENGTH: 50
<212> TYPE: DNA
<213> ORGANISM: Artificial Sequence
<220> FEATURE:
<223> OTHER INFORMATION: Synthetic

<400> SEQUENCE: 68
aatccttaaa agtcggtcgt agtccggatt ggagtctgca actcgactcc　　　　　　　50

<210> SEQ ID NO 69
<211> LENGTH: 50
<212> TYPE: DNA
<213> ORGANISM: Artificial Sequence
<220> FEATURE:
<223> OTHER INFORMATION: Synthetic

<400> SEQUENCE: 69
atctccgagc aataaatctt tacccgaaaa atcttatgat ctctcgggac　　　　　　　50

<210> SEQ ID NO 70
<211> LENGTH: 50
<212> TYPE: DNA
<213> ORGANISM: Artificial Sequence
<220> FEATURE:

```
<223> OTHER INFORMATION: Synthetic

<400> SEQUENCE: 70
tcatctgata gcgtgaggtc cgaagatccc ccactttctc cctcaggacg        50

<210> SEQ ID NO 71
<211> LENGTH: 50
<212> TYPE: DNA
<213> ORGANISM: Artificial Sequence
<220> FEATURE:
<223> OTHER INFORMATION: Synthetic

<400> SEQUENCE: 71
atctgacgcg ggcccatcca tcagcgataa atctttcctc cgtagagaat        50

<210> SEQ ID NO 72
<211> LENGTH: 50
<212> TYPE: DNA
<213> ORGANISM: Artificial Sequence
<220> FEATURE:
<223> OTHER INFORMATION: Synthetic

<400> SEQUENCE: 72
cttggtgagc cgttacctca ccaacaagct aatcccatct gggcacatct        50

<210> SEQ ID NO 73
<211> LENGTH: 50
<212> TYPE: DNA
<213> ORGANISM: Artificial Sequence
<220> FEATURE:
<223> OTHER INFORMATION: Synthetic

<400> SEQUENCE: 73
atcccacctg ggcatatccg gtagcgcaag gcccgaaggt ccnctgcttt        50

<210> SEQ ID NO 74
<211> LENGTH: 50
<212> TYPE: DNA
<213> ORGANISM: Artificial Sequence
<220> FEATURE:
<223> OTHER INFORMATION: Synthetic

<400> SEQUENCE: 74 tctggttca tccgatggcg tgaggcccta aggtccccca ctttgctctt         50

<210> SEQ ID NO 75
<211> LENGTH: 50
<212> TYPE: DNA
<213> ORGANISM: Artificial Sequence
<220> FEATURE:
<223> OTHER INFORMATION: Synthetic

<400> SEQUENCE: 75
tcaagaccca cggctattaa ccgtaagctt ttcctccctg ctgaaagtgc        50

<210> SEQ ID NO 76
<211> LENGTH: 50
<212> TYPE: DNA
<213> ORGANISM: Artificial Sequence
<220> FEATURE:
<223> OTHER INFORMATION: Synthetic

<400> SEQUENCE: 76
gccggtgctt attcatatgc taccgtcatt ttcttgacat ataaaggag         50

<210> SEQ ID NO 77
```

```
<211> LENGTH: 50
<212> TYPE: DNA
<213> ORGANISM: Artificial Sequence
<220> FEATURE:
<223> OTHER INFORMATION: Synthetic

<400> SEQUENCE: 77
gtaccgtcag accatggctg attagcacca tggcggttct tccctcctga                  50

<210> SEQ ID NO 78
<211> LENGTH: 50
<212> TYPE: DNA
<213> ORGANISM: Artificial Sequence
<220> FEATURE:
<223> OTHER INFORMATION: Synthetic

<400> SEQUENCE: 78
caaggtaccg ccctatttga acggtacttg ttcttcccta gcaacagagc                  50

<210> SEQ ID NO 79
<211> LENGTH: 50
<212> TYPE: DNA
<213> ORGANISM: Artificial Sequence
<220> FEATURE:
<223> OTHER INFORMATION: Synthetic

<400> SEQUENCE: 79
tattcataag gtacatacaa aacaccacac gtggcgaact ttattcccctt                 50

<210> SEQ ID NO 80
<211> LENGTH: 50
<212> TYPE: DNA
<213> ORGANISM: Artificial Sequence
<220> FEATURE:
<223> OTHER INFORMATION: Synthetic

<400> SEQUENCE: 80
tattcataaa gtacatgcaa acgggtatgc atacccgact ttattccttt                  50

<210> SEQ ID NO 81
<211> LENGTH: 50
<212> TYPE: DNA
<213> ORGANISM: Artificial Sequence
<220> FEATURE:
<223> OTHER INFORMATION: Synthetic

<400> SEQUENCE: 81
tattcatacg gtacatacaa aaaggcacac gtgcctcact ttattcccgt                  50

<210> SEQ ID NO 82
<211> LENGTH: 50
<212> TYPE: DNA
<213> ORGANISM: Artificial Sequence
<220> FEATURE:
<223> OTHER INFORMATION: Synthetic

<400> SEQUENCE: 82
aggcccgaag gtcccccgct ttcatccgta gatcgtatgc ggtattaatc                  50

<210> SEQ ID NO 83
<211> LENGTH: 50
<212> TYPE: DNA
<213> ORGANISM: Artificial Sequence
<220> FEATURE:
<223> OTHER INFORMATION: Synthetic

<400> SEQUENCE: 83
```

-continued cggtaccgtc atcccccgac tgtattagag ccaaggattt ctttccggac              50

<210> SEQ ID NO 84
<211> LENGTH: 50
<212> TYPE: DNA
<213> ORGANISM: Artificial Sequence
<220> FEATURE:
<223> OTHER INFORMATION: Synthetic

<400> SEQUENCE: 84
agccgcaagc ttctctttag gcggaaatcc atttcactcg aaagcatatg              50

<210> SEQ ID NO 85
<211> LENGTH: 50
<212> TYPE: DNA
<213> ORGANISM: Artificial Sequence
<220> FEATURE:
<223> OTHER INFORMATION: Synthetic

<400> SEQUENCE: 85
agacgcgagc tcatcctcag gcgaaattca tttcacctct cggcatatgg              50

<210> SEQ ID NO 86
<211> LENGTH: 50
<212> TYPE: DNA
<213> ORGANISM: Artificial Sequence
<220> FEATURE:
<223> OTHER INFORMATION: Synthetic

<400> SEQUENCE: 86
ccatcgcagt aatggagtta agctccacgc tttgacgaca gacttaaaag              50

<210> SEQ ID NO 87
<211> LENGTH: 50
<212> TYPE: DNA
<213> ORGANISM: Artificial Sequence
<220> FEATURE:
<223> OTHER INFORMATION: Synthetic

<400> SEQUENCE: 87
ccatcgctga atggagttg agctccacgc tttaacgaca gacttgtaaa              50

<210> SEQ ID NO 88
<211> LENGTH: 50
<212> TYPE: DNA
<213> ORGANISM: Artificial Sequence
<220> FEATURE:
<223> OTHER INFORMATION: Synthetic

<400> SEQUENCE: 88
cgctctagta gcacaaggcc cgaaggtccc ctgctttcat ccatagatct              50

<210> SEQ ID NO 89
<211> LENGTH: 50
<212> TYPE: DNA
<213> ORGANISM: Artificial Sequence
<220> FEATURE:
<223> OTHER INFORMATION: Synthetic

<400> SEQUENCE: 89
tcagtgacgc aaaagcgcct ttcaactttc ttccatgcgg aaaatagtgt              50

<210> SEQ ID NO 90
<211> LENGTH: 50
<212> TYPE: DNA
<213> ORGANISM: Artificial Sequence
<220> FEATURE:

<223> OTHER INFORMATION: Synthetic

<400> SEQUENCE: 90
tcctgaagcg ataaatcttt agacacaagt cgatgccgac tcgtgaccac    50

<210> SEQ ID NO 91
<211> LENGTH: 50
<212> TYPE: DNA
<213> ORGANISM: Artificial Sequence
<220> FEATURE:
<223> OTHER INFORMATION: Synthetic

<400> SEQUENCE: 91
aggtcatctt caaccgaaaa actttccagc cccgatcatg cgatcagagc    50

<210> SEQ ID NO 92
<211> LENGTH: 50
<212> TYPE: DNA
<213> ORGANISM: Artificial Sequence
<220> FEATURE:
<223> OTHER INFORMATION: Synthetic

<400> SEQUENCE: 92
tcatcttcaa ccgaaaaact ttccaaaccc gcggatgccc gcaggtttca    50

<210> SEQ ID NO 93
<211> LENGTH: 50
<212> TYPE: DNA
<213> ORGANISM: Artificial Sequence
<220> FEATURE:
<223> OTHER INFORMATION: Synthetic

<400> SEQUENCE: 93
cagacgcgag ctcttcctaa ggtggataaa tccttttacc tctcggcgta    50

<210> SEQ ID NO 94
<211> LENGTH: 50
<212> TYPE: DNA
<213> ORGANISM: Artificial Sequence
<220> FEATURE:
<223> OTHER INFORMATION: Synthetic

<400> SEQUENCE: 94
ggccgctcca ggagcacgag gtcttgcgat cccccgcttt catccttaga    50

<210> SEQ ID NO 95
<211> LENGTH: 50
<212> TYPE: DNA
<213> ORGANISM: Artificial Sequence
<220> FEATURE:
<223> OTHER INFORMATION: Synthetic

<400> SEQUENCE: 95
atctttcatc aaaattttt cccggctcgg cgatgccgcc aagacggagt    50

<210> SEQ ID NO 96
<211> LENGTH: 50
<212> TYPE: DNA
<213> ORGANISM: Artificial Sequence
<220> FEATURE:
<223> OTHER INFORMATION: Synthetic

<400> SEQUENCE: 96
tcatgtaagc cgctcctccg gcggaatcac acctttgctc cgcagagttc    50

<210> SEQ ID NO 97

```
<211> LENGTH: 50
<212> TYPE: DNA
<213> ORGANISM: Artificial Sequence
<220> FEATURE:
<223> OTHER INFORMATION: Synthetic

<400> SEQUENCE: 97
tattcttaaa gcgccaggcc ttgcggtccc cagcttttct cctcagagat         50

<210> SEQ ID NO 98
<211> LENGTH: 50
<212> TYPE: DNA
<213> ORGANISM: Artificial Sequence
<220> FEATURE:
<223> OTHER INFORMATION: Synthetic

<400> SEQUENCE: 98
ctccatcagc gcccttgcga gctttcatcc cttctgcgac gaagggatcg         50

<210> SEQ ID NO 99
<211> LENGTH: 50
<212> TYPE: DNA
<213> ORGANISM: Artificial Sequence
<220> FEATURE:
<223> OTHER INFORMATION: Synthetic

<400> SEQUENCE: 99
ggggcacggg ctcatcttgg ggcggaatca cacctttggt ccgcaaacat         50

<210> SEQ ID NO 100
<211> LENGTH: 50
<212> TYPE: DNA
<213> ORGANISM: Artificial Sequence
<220> FEATURE:
<223> OTHER INFORMATION: Synthetic

<400> SEQUENCE: 100
tccttgacca aaattctttc cacgcccgtg ggatgcccca aggcgtcgta         50

<210> SEQ ID NO 101
<211> LENGTH: 50
<212> TYPE: DNA
<213> ORGANISM: Artificial Sequence
<220> FEATURE:
<223> OTHER INFORMATION: Synthetic

<400> SEQUENCE: 101
tgatatcggc cgctccaatc gcgcgaggtc ttgcgatccc ccgctttcat         50

<210> SEQ ID NO 102
<211> LENGTH: 50
<212> TYPE: DNA
<213> ORGANISM: Artificial Sequence
<220> FEATURE:
<223> OTHER INFORMATION: Synthetic

<400> SEQUENCE: 102
gctcttgcga gctcccttc ccgaaaaact ccttacgagt tccgtcgctc         50

<210> SEQ ID NO 103
<211> LENGTH: 50
<212> TYPE: DNA
<213> ORGANISM: Artificial Sequence
<220> FEATURE:
<223> OTHER INFORMATION: Synthetic

<400> SEQUENCE: 103
```
agacgcgagc ttctctttag gcggattact ccatttcact cggaagcata          50

<210> SEQ ID NO 104
<211> LENGTH: 50
<212> TYPE: DNA
<213> ORGANISM: Artificial Sequence
<220> FEATURE:
<223> OTHER INFORMATION: Synthetic

<400> SEQUENCE: 104
cgctccaata gcgagaggtc ttgcgatccc cccctttcac ccgaaggtcg          50

<210> SEQ ID NO 105
<211> LENGTH: 50
<212> TYPE: DNA
<213> ORGANISM: Artificial Sequence
<220> FEATURE:
<223> OTHER INFORMATION: Synthetic

<400> SEQUENCE: 105
cggtcccagc ctttccagta atctctctct agactactgc ttacgacgta          50

<210> SEQ ID NO 106
<211> LENGTH: 50
<212> TYPE: DNA
<213> ORGANISM: Artificial Sequence
<220> FEATURE:
<223> OTHER INFORMATION: Synthetic

<400> SEQUENCE: 106
taatcctaaa gcgccaggcc ttgcggtccc cagctttcct cctaagagat          50

<210> SEQ ID NO 107
<211> LENGTH: 50
<212> TYPE: DNA
<213> ORGANISM: Artificial Sequence
<220> FEATURE:
<223> OTHER INFORMATION: Synthetic

<400> SEQUENCE: 107
gtcccccgct ttcatccata gatcgtatgc ggtattagcg taactttcgc          50

<210> SEQ ID NO 108
<211> LENGTH: 50
<212> TYPE: DNA
<213> ORGANISM: Artificial Sequence
<220> FEATURE:
<223> OTHER INFORMATION: Synthetic

<400> SEQUENCE: 108
caatattcgg tattagcacc ggtttcccgg tgttatccca aagtggaggg          50

<210> SEQ ID NO 109
<211> LENGTH: 50
<212> TYPE: DNA
<213> ORGANISM: Artificial Sequence
<220> FEATURE:
<223> OTHER INFORMATION: Synthetic

<400> SEQUENCE: 109
aggtcttgcg atccccccct ttcacccgta ggtcgtatgc ggtattaatc          50

<210> SEQ ID NO 110
<211> LENGTH: 50
<212> TYPE: DNA
<213> ORGANISM: Artificial Sequence
<220> FEATURE:

<223> OTHER INFORMATION: Synthetic

<400> SEQUENCE: 110
cagcttttct cctcagagat tacgcggtat tagcctgagt ttccccaggt             50

<210> SEQ ID NO 111
<211> LENGTH: 50
<212> TYPE: DNA
<213> ORGANISM: Artificial Sequence
<220> FEATURE:
<223> OTHER INFORMATION: Synthetic

<400> SEQUENCE: 111
ctttccccct cagggcgtat gcggtattag cgcaactttc gctgcgttat             50

<210> SEQ ID NO 112
<211> LENGTH: 50
<212> TYPE: DNA
<213> ORGANISM: Artificial Sequence
<220> FEATURE:
<223> OTHER INFORMATION: Synthetic

<400> SEQUENCE: 112
cagacgcgag ctcttcctaa ggtggataga tccttttacc tctcggcata             50

<210> SEQ ID NO 113
<211> LENGTH: 25
<212> TYPE: DNA
<213> ORGANISM: Artificial Sequence
<220> FEATURE:
<223> OTHER INFORMATION: Synthetic

<400> SEQUENCE: 113
tgacgggcgg tgtgtacaag gcccg                                       25

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
atacaggcgc tcgataagag                                             20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
agctgctagg ggagtcattc                                             20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
aactcgactt tatggaaggg                                             20

<210> SEQ ID NO 117

```
<211> LENGTH: 20
<212> TYPE: DNA
<213> ORGANISM: Artificial Sequence
<220> FEATURE:
<223> OTHER INFORMATION: Synthetic

<400> SEQUENCE: 117
caaagtccct ctaagaagac                                               20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
ttggctttag ccggcgatag                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
aagccaaggt aggcgtttcc                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
gacgacacat aactctagag                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
tcatccaatc cttggttgac                                               20

<210> SEQ ID NO 122
<211> LENGTH: 18
<212> TYPE: DNA
<213> ORGANISM: Artificial Sequence
<220> FEATURE:
<223> OTHER INFORMATION: Synthetic

<400> SEQUENCE: 122
aacttgccca atgcgcgg                                                 18

<210> SEQ ID NO 123
<211> LENGTH: 19
<212> TYPE: DNA
<213> ORGANISM: Artificial Sequence
<220> FEATURE:
<223> OTHER INFORMATION: Synthetic

<400> SEQUENCE: 123
```

```
gggaatacgg tggtgtctg                                                19

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
gattggaatg atgggaatcc                                               20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
aggagaagtc aagtatgacg                                               20

<210> SEQ ID NO 126
<211> LENGTH: 19
<212> TYPE: DNA
<213> ORGANISM: Artificial Sequence
<220> FEATURE:
<223> OTHER INFORMATION: Synthetic

<400> SEQUENCE: 126
gcggtagtaa ggagacgtg                                                19

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
gcatcggcat cgtttactgc                                               20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
ttcggtggtg aggtattatc                                               20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
aagatcgctg ggatagtgtc                                               20

<210> SEQ ID NO 130
<211> LENGTH: 20
<212> TYPE: DNA
<213> ORGANISM: Artificial Sequence
<220> FEATURE:
```

<223> OTHER INFORMATION: Synthetic

<400> SEQUENCE: 130
atcgagtatc aattggaggg                          20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
gacggggtca atacaacgac                          20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
gccaatggtc ttcttattgg                          20

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
gaggtcgtaa attgacactc                          20

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
ttcaaaccgg cctcgttctg                          20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
cccataacca acgaaatagc                          20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
ttagcgaatc gtggcacgtc                          20

<210> SEQ ID NO 137

```
<211> LENGTH: 20
<212> TYPE: DNA
<213> ORGANISM: Artificial Sequence
<220> FEATURE:
<223> OTHER INFORMATION: Synthetic

<400> SEQUENCE: 137
aatgtattcc tgcaaacgcc                                              20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
gggttcttac gaactttggg                                              20

<210> SEQ ID NO 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
ctgatcgggc ttgaaagacc                                              20

<210> SEQ ID NO 140
<211> LENGTH: 20
<212> TYPE: DNA
<213> ORGANISM: Artificial Sequence
<220> FEATURE:
<223> OTHER INFORMATION: Synthetic

<400> SEQUENCE: 140
tatcgaggac caattggagg                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
gacggagtca atacaacgac                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic

<400> SEQUENCE: 142
tggactcttt tgagtccggc                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
```
atcaatacta acacccaccg                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
taacgatagc gggctcgttc                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
catagggtgc tgatagagtc                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
ccgagatttc tcggaaattg                                              20

<210> SEQ ID NO 147
<211> LENGTH: 20
<212> TYPE: DNA
<213> ORGANISM: Artificial Sequence
<220> FEATURE:
<223> OTHER INFORMATION: Synthetic

<400> SEQUENCE: 147
tttctcacga gctgctgagg                                              20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
atggtggagg tgattcattc                                              20

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
aattgacatc cactgatccc                                              20

<210> SEQ ID NO 150
<211> LENGTH: 20
<212> TYPE: DNA
<213> ORGANISM: Artificial Sequence
<220> FEATURE:

<223> OTHER INFORMATION: Synthetic

<400> SEQUENCE: 150
gatacaggac tcatccgagg                                              20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
aaacgcctgc agatcgctag                                              20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
acaatgccgg gcctttcaag                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
tggagtcgtt acaaacttcc                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
tcggcgacga tgattcattc                                              20

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
tgaacaaacc acgcccaatc                                              20

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
cggtttaccg gcgatagatc                                              20

<210> SEQ ID NO 157

```
<211> LENGTH: 20
<212> TYPE: DNA
<213> ORGANISM: Artificial Sequence
<220> FEATURE:
<223> OTHER INFORMATION: Synthetic

<400> SEQUENCE: 157
ttctctcgag gtgctgaagg                                              20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
aatcggatcg catgggctag                                              20

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
gaacgggata attctcgccc                                              20

<210> SEQ ID NO 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
cccacttatg tgggtttgac                                              20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
gaagtagagg atcttgcctc                                              20

<210> SEQ ID NO 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
gacagcttct ttaatggagg                                              20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
```
atctgttggt cctccaaatc                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
aatacagggc tctttgagtc                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
aagacgtacc accgatcctg                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic

<400> SEQUENCE: 166
taacaatgcg gagccttcgg                                               20

<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
aagaacgtcc gccaatcctg                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
tatctggcgc ttttgcgtcg                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
caacgtctac ccatcccaag                                               20

<210> SEQ ID NO 170
<211> LENGTH: 20
<212> TYPE: DNA
<213> ORGANISM: Artificial Sequence
<220> FEATURE:

<223> OTHER INFORMATION: Synthetic

<400> SEQUENCE: 170
actcgggaac ctagttctac                                               20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
tctcttacgg cgccgaaaag                                               20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
agggccaacg gtcttgttat                                               20

<210> SEQ ID NO 173
<211> LENGTH: 20
<212> TYPE: DNA
<213> ORGANISM: Artificial Sequence
<220> FEATURE:
<223> OTHER INFORMATION: Synthetic

<400> SEQUENCE: 173
tcgcaaattg acatccactg                                               20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
ctctctccga gtatcaattg                                               20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
acttccctca atcgctagtc                                               20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
gcagagcttc acagttttgc                                               20

<210> SEQ ID NO 177

```
<211> LENGTH: 20
<212> TYPE: DNA
<213> ORGANISM: Artificial Sequence
<220> FEATURE:
<223> OTHER INFORMATION: Synthetic

<400> SEQUENCE: 177
agacgtctcc tgatcgcaag                                                    20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
atacgtcccg ggactgcaat                                                    20

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
cgaaggcgga taattctcgc                                                    20

<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
acaatgcagg gcctttacgg                                                    20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
gaataacact cactgatccc                                                    20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
atacaggact catccgaggc                                                    20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
```
aaacgcctgc agatcgctag 20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
ctttacaggt ctggcaattg 20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
catacagtgc tgacagggtc 20

<210> SEQ ID NO 186
<211> LENGTH: 20
<212> TYPE: DNA
<213> ORGANISM: Artificial Sequence
<220> FEATURE:
<223> OTHER INFORMATION: Synthetic

<400> SEQUENCE: 186 cagggcettt tcaggtcttg 20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
cacaaggtgc caacagagtc 20

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
aacaatgtct ggccctacgg 20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
gtaaacaacg cccaccgatc 20

<210> SEQ ID NO 190
<211> LENGTH: 20
<212> TYPE: DNA
<213> ORGANISM: Artificial Sequence
<220> FEATURE:

<223> OTHER INFORMATION: Synthetic

<400> SEQUENCE: 190
gagggcaagt ctggtgccag                                          20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
cgaatggatt aagagcttgc                                          20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
tgccagctta ttcaactagc                                          20

<210> SEQ ID NO 193
<211> LENGTH: 20
<212> TYPE: DNA
<213> ORGANISM: Artificial Sequence
<220> FEATURE:
<223> OTHER INFORMATION: Synthetic

<400> SEQUENCE: 193
gaacgtacca tttgctacgg                                          20

<210> SEQ ID NO 194
<211> LENGTH: 20
<212> TYPE: DNA
<213> ORGANISM: Artificial Sequence
<220> FEATURE:
<223> OTHER INFORMATION: Synthetic

<400> SEQUENCE: 194
accgtcatta tcttcaccgg                                          20

<210> SEQ ID NO 195
<211> LENGTH: 18
<212> TYPE: DNA
<213> ORGANISM: Artificial Sequence
<220> FEATURE:
<223> OTHER INFORMATION: Synthetic

<400> SEQUENCE: 195
acgggcttcg gcctggtg                                            18

<210> SEQ ID NO 196
<211> LENGTH: 20
<212> TYPE: DNA
<213> ORGANISM: Artificial Sequence
<220> FEATURE:
<223> OTHER INFORMATION: Synthetic

<400> SEQUENCE: 196
tccgggtatt agccagaatg                                          20

<210> SEQ ID NO 197

```
<211> LENGTH: 20
<212> TYPE: DNA
<213> ORGANISM: Artificial Sequence
<220> FEATURE:
<223> OTHER INFORMATION: Synthetic

<400> SEQUENCE: 197
gcttgctaga agtggattag                                               20

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
cgtcagaatt cttccctaag                                               20

<210> SEQ ID NO 199
<211> LENGTH: 20
<212> TYPE: DNA
<213> ORGANISM: Artificial Sequence
<220> FEATURE:
<223> OTHER INFORMATION: Synthetic

<400> SEQUENCE: 199
tttagtggcg gaagggttag                                               20

<210> SEQ ID NO 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
atctctctta ttcccaagcg                                               20

<210> SEQ ID NO 201
<211> LENGTH: 20
<212> TYPE: DNA
<213> ORGANISM: Artificial Sequence
<220> FEATURE:
<223> OTHER INFORMATION: Synthetic

<400> SEQUENCE: 201
aagcttcctt cgggaagtgg                                               20

<210> SEQ ID NO 202
<211> LENGTH: 19
<212> TYPE: DNA
<213> ORGANISM: Artificial Sequence
<220> FEATURE:
<223> OTHER INFORMATION: Synthetic

<400> SEQUENCE: 202
ggtaccgtca ttatcgtcc                                                19

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
```
ataacctggg gaaactcggg 20

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
ccaaggatat taccctttgag 20

<210> SEQ ID NO 205
<211> LENGTH: 20
<212> TYPE: DNA
<213> ORGANISM: Artificial Sequence
<220> FEATURE:
<223> OTHER INFORMATION: Synthetic

<400> SEQUENCE: 205
agaagcttgc ttctttgctg 20

<210> SEQ ID NO 206
<211> LENGTH: 20
<212> TYPE: DNA
<213> ORGANISM: Artificial Sequence
<220> FEATURE:
<223> OTHER INFORMATION: Synthetic

<400> SEQUENCE: 206
ttcctccccg ctgaaagtac 20

<210> SEQ ID NO 207
<211> LENGTH: 18
<212> TYPE: DNA
<213> ORGANISM: Artificial Sequence
<220> FEATURE:
<223> OTHER INFORMATION: Synthetic

<400> SEQUENCE: 207
caattctggg aagcgtgg 18

<210> SEQ ID NO 208
<211> LENGTH: 18
<212> TYPE: DNA
<213> ORGANISM: Artificial Sequence
<220> FEATURE:
<223> OTHER INFORMATION: Synthetic

<400> SEQUENCE: 208
cgatgcatga tgatgaca 18

<210> SEQ ID NO 209
<211> LENGTH: 18
<212> TYPE: DNA
<213> ORGANISM: Artificial Sequence
<220> FEATURE:
<223> OTHER INFORMATION: Synthetic

<400> SEQUENCE: 209
gtggtggatt acgccatg 18

<210> SEQ ID NO 210
<211> LENGTH: 18
<212> TYPE: DNA
<213> ORGANISM: Artificial Sequence
<220> FEATURE:

-continued

<223> OTHER INFORMATION: Synthetic

<400> SEQUENCE: 210
gctattactc cccccgt                                                      18

<210> SEQ ID NO 211
<211> LENGTH: 18
<212> TYPE: DNA
<213> ORGANISM: Artificial Sequence
<220> FEATURE:
<223> OTHER INFORMATION: Synthetic

<400> SEQUENCE: 211
tctggagtat caagcact                                                     18

<210> SEQ ID NO 212
<211> LENGTH: 18
<212> TYPE: DNA
<213> ORGANISM: Artificial Sequence
<220> FEATURE:
<223> OTHER INFORMATION: Synthetic

<400> SEQUENCE: 212
ccaggaagag ggttttgt                                                     18

<210> SEQ ID NO 213
<211> LENGTH: 18
<212> TYPE: DNA
<213> ORGANISM: Artificial Sequence
<220> FEATURE:
<223> OTHER INFORMATION: Synthetic

<400> SEQUENCE: 213
gccctgacgt atggcggg                                                     18

<210> SEQ ID NO 214
<211> LENGTH: 18
<212> TYPE: DNA
<213> ORGANISM: Artificial Sequence
<220> FEATURE:
<223> OTHER INFORMATION: Synthetic

<400> SEQUENCE: 214
gtaatggtca ccgtcact                                                     18

<210> SEQ ID NO 215
<211> LENGTH: 18
<212> TYPE: DNA
<213> ORGANISM: Artificial Sequence
<220> FEATURE:
<223> OTHER INFORMATION: Synthetic

<400> SEQUENCE: 215
aagacatctt caccgttc                                                     18

<210> SEQ ID NO 216
<211> LENGTH: 18
<212> TYPE: DNA
<213> ORGANISM: Artificial Sequence
<220> FEATURE:
<223> OTHER INFORMATION: Synthetic

<400> SEQUENCE: 216
tcagatttcc cctcgtgc                                                     18

<210> SEQ ID NO 217

```
<211> LENGTH: 18
<212> TYPE: DNA
<213> ORGANISM: Artificial Sequence
<220> FEATURE:
<223> OTHER INFORMATION: Synthetic

<400> SEQUENCE: 217
atggcatccg tggtatcc                                                 18

<210> SEQ ID NO 218
<211> LENGTH: 18
<212> TYPE: DNA
<213> ORGANISM: Artificial Sequence
<220> FEATURE:
<223> OTHER INFORMATION: Synthetic

<400> SEQUENCE: 218
cacttcaccg tttttgaa                                                 18

<210> SEQ ID NO 219
<211> LENGTH: 20
<212> TYPE: DNA
<213> ORGANISM: Artificial Sequence
<220> FEATURE:
<223> OTHER INFORMATION: Synthetic

<400> SEQUENCE: 219
aacagcttgc tgtttcgctg                                               20

<210> SEQ ID NO 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
ttcctccccg ctgaaagtac                                               20

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
caggtcttag gatgctgacg                                               20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
aaggctatta accttgaggc                                               20

<210> SEQ ID NO 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
```

```
agactatcta cttctggtgc                                               20

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
atacaggtgc tgcatggctg                                               20

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
gagtagcaat actcagcggc                                               20

<210> SEQ ID NO 226
<211> LENGTH: 20
<212> TYPE: DNA
<213> ORGANISM: Artificial Sequence
<220> FEATURE:
<223> OTHER INFORMATION: Synthetic

<400> SEQUENCE: 226
taccatcatc acattgctgc                                               20

<210> SEQ ID NO 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
gagcttgctc ctggattcag                                               20

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
gtaacgtcaa aacagcaagg                                               20

<210> SEQ ID NO 229
<211> LENGTH: 20
<212> TYPE: DNA
<213> ORGANISM: Artificial Sequence
<220> FEATURE:
<223> OTHER INFORMATION: Synthetic

<400> SEQUENCE: 229
agttaattag tggcagacgg                                               20

<210> SEQ ID NO 230
<211> LENGTH: 20
<212> TYPE: DNA
<213> ORGANISM: Artificial Sequence
<220> FEATURE:
```

```
<223> OTHER INFORMATION: Synthetic

<400> SEQUENCE: 230
actaaaccgc ctacgcactc                                               20

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
agcttgctgc tttgctgacg                                               20

<210> SEQ ID NO 232
<211> LENGTH: 20
<212> TYPE: DNA
<213> ORGANISM: Artificial Sequence
<220> FEATURE:
<223> OTHER INFORMATION: Synthetic

<400> SEQUENCE: 232
taaccacaac accttcctcc                                               20

<210> SEQ ID NO 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
gaacttgttc cttgggtggc                                               20

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
ttaaccacct tcctccctac                                               20

<210> SEQ ID NO 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
gtagtttact actttgccgg                                               20

<210> SEQ ID NO 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
gagcgtatta aactcaaccc                                               20

<210> SEQ ID NO 237
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 237
gcaaagtggc cctctgattc                                               20

<210> SEQ ID NO 238
<211> LENGTH: 20
<212> TYPE: DNA
<213> ORGANISM: Artificial Sequence
<220> FEATURE:
<223> OTHER INFORMATION: Synthetic

<400> SEQUENCE: 238
ccataaatga acccaacggc                                               20

<210> SEQ ID NO 239
<211> LENGTH: 20
<212> TYPE: DNA
<213> ORGANISM: Artificial Sequence
<220> FEATURE:
<223> OTHER INFORMATION: Synthetic

<400> SEQUENCE: 239
accggataca ccttcatacc                                               20

<210> SEQ ID NO 240
<211> LENGTH: 20
<212> TYPE: DNA
<213> ORGANISM: Artificial Sequence
<220> FEATURE:
<223> OTHER INFORMATION: Synthetic

<400> SEQUENCE: 240
ccgcaatgac aagcatcacg                                               20

<210> SEQ ID NO 241
<211> LENGTH: 20
<212> TYPE: DNA
<213> ORGANISM: Artificial Sequence
<220> FEATURE:
<223> OTHER INFORMATION: Synthetic

<400> SEQUENCE: 241
acgctccgat ttcacagttc                                               20

<210> SEQ ID NO 242
<211> LENGTH: 20
<212> TYPE: DNA
<213> ORGANISM: Artificial Sequence
<220> FEATURE:
<223> OTHER INFORMATION: Synthetic

<400> SEQUENCE: 242
aagtccagca gtatcaaggg                                               20

<210> SEQ ID NO 243
<211> LENGTH: 20
<212> TYPE: DNA
<213> ORGANISM: Artificial Sequence
<220> FEATURE:
<223> OTHER INFORMATION: Synthetic

<400> SEQUENCE: 243
```
tgggtttacc taacactacg                                              20

<210> SEQ ID NO 244
<211> LENGTH: 20
<212> TYPE: DNA
<213> ORGANISM: Artificial Sequence
<220> FEATURE:
<223> OTHER INFORMATION: Synthetic

<400> SEQUENCE: 244
tagagtcgag ttacagaccg                                              20

<210> SEQ ID NO 245
<211> LENGTH: 20
<212> TYPE: DNA
<213> ORGANISM: Artificial Sequence
<220> FEATURE:
<223> OTHER INFORMATION: Synthetic

<400> SEQUENCE: 245
atcatgagtt cacatgtccg                                              20

<210> SEQ ID NO 246
<211> LENGTH: 18
<212> TYPE: DNA
<213> ORGANISM: Artificial Sequence
<220> FEATURE:
<223> OTHER INFORMATION: Synthetic

<400> SEQUENCE: 246
caatcggagt tcttcgtg                                                18

<210> SEQ ID NO 247
<211> LENGTH: 20
<212> TYPE: DNA
<213> ORGANISM: Artificial Sequence
<220> FEATURE:
<223> OTHER INFORMATION: Synthetic

<400> SEQUENCE: 247
atcatgagtt cacatgtccg                                              20

<210> SEQ ID NO 248
<211> LENGTH: 18
<212> TYPE: DNA
<213> ORGANISM: Artificial Sequence
<220> FEATURE:
<223> OTHER INFORMATION: Synthetic

<400> SEQUENCE: 248
caatcggagt tcttcgtg                                                18

<210> SEQ ID NO 249
<211> LENGTH: 17
<212> TYPE: DNA
<213> ORGANISM: Artificial Sequence
<220> FEATURE:
<223> OTHER INFORMATION: Synthetic

<400> SEQUENCE: 249
gccgtctact cttggcc                                                 17

<210> SEQ ID NO 250
<211> LENGTH: 18
<212> TYPE: DNA
<213> ORGANISM: Artificial Sequence
<220> FEATURE:

```
<223> OTHER INFORMATION: Synthetic

<400> SEQUENCE: 250
cctgcctcta ctgtactc                                                18

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
acgggtgctt gcacctgg                                                18

<210> SEQ ID NO 252
<211> LENGTH: 20
<212> TYPE: DNA
<213> ORGANISM: Artificial Sequence
<220> FEATURE:
<223> OTHER INFORMATION: Synthetic

<400> SEQUENCE: 252
cgactgtatt agagccaagg                                              20

<210> SEQ ID NO 253
<211> LENGTH: 20
<212> TYPE: DNA
<213> ORGANISM: Artificial Sequence
<220> FEATURE:
<223> OTHER INFORMATION: Synthetic

<400> SEQUENCE: 253
gttggccgat ggctgattag                                              20

<210> SEQ ID NO 254
<211> LENGTH: 20
<212> TYPE: DNA
<213> ORGANISM: Artificial Sequence
<220> FEATURE:
<223> OTHER INFORMATION: Synthetic

<400> SEQUENCE: 254
tctgccatac tctagcctgc                                              20

<210> SEQ ID NO 255
<211> LENGTH: 20
<212> TYPE: DNA
<213> ORGANISM: Artificial Sequence
<220> FEATURE:
<223> OTHER INFORMATION: Synthetic

<400> SEQUENCE: 255
acatgcaagt cgtacgagag                                              20

<210> SEQ ID NO 256
<211> LENGTH: 20
<212> TYPE: DNA
<213> ORGANISM: Artificial Sequence
<220> FEATURE:
<223> OTHER INFORMATION: Synthetic

<400> SEQUENCE: 256
acacgtcatt tattcctccc                                              20

<210> SEQ ID NO 257
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 257
acgaaccttc gggttagtgg                                              20

<210> SEQ ID NO 258
<211> LENGTH: 20
<212> TYPE: DNA
<213> ORGANISM: Artificial Sequence
<220> FEATURE:
<223> OTHER INFORMATION: Synthetic

<400> SEQUENCE: 258
tcaagtaccg tcagatcttc                                              20

<210> SEQ ID NO 259
<211> LENGTH: 20
<212> TYPE: DNA
<213> ORGANISM: Artificial Sequence
<220> FEATURE:
<223> OTHER INFORMATION: Synthetic

<400> SEQUENCE: 259
aaaggcctac caaggcttcg                                              20

<210> SEQ ID NO 260
<211> LENGTH: 20
<212> TYPE: DNA
<213> ORGANISM: Artificial Sequence
<220> FEATURE:
<223> OTHER INFORMATION: Synthetic

<400> SEQUENCE: 260
ggcactctct cgtttccaag                                              20

<210> SEQ ID NO 261
<211> LENGTH: 20
<212> TYPE: DNA
<213> ORGANISM: Artificial Sequence
<220> FEATURE:
<223> OTHER INFORMATION: Synthetic

<400> SEQUENCE: 261
aaaggcttac caaggcattg                                              20

<210> SEQ ID NO 262
<211> LENGTH: 17
<212> TYPE: DNA
<213> ORGANISM: Artificial Sequence
<220> FEATURE:
<223> OTHER INFORMATION: Synthetic

<400> SEQUENCE: 262
cctccggttt cccagag                                                 17

<210> SEQ ID NO 263
<211> LENGTH: 20
<212> TYPE: DNA
<213> ORGANISM: Artificial Sequence
<220> FEATURE:
<223> OTHER INFORMATION: Synthetic

<400> SEQUENCE: 263
```
gtaacaggtc tttcgggatg 20

<210> SEQ ID NO 264
<211> LENGTH: 20
<212> TYPE: DNA
<213> ORGANISM: Artificial Sequence
<220> FEATURE:
<223> OTHER INFORMATION: Synthetic

<400> SEQUENCE: 264
caagactttt cgttccgtac 20

<210> SEQ ID NO 265
<211> LENGTH: 20
<212> TYPE: DNA
<213> ORGANISM: Artificial Sequence
<220> FEATURE:
<223> OTHER INFORMATION: Synthetic

<400> SEQUENCE: 265
tctttcaccg gagcttgctc 20

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266
ctctcatcct tgttcttctc 20

<210> SEQ ID NO 267
<211> LENGTH: 20
<212> TYPE: DNA
<213> ORGANISM: Artificial Sequence
<220> FEATURE:
<223> OTHER INFORMATION: Synthetic

<400> SEQUENCE: 267
acggtcgcgt aacacgtaag 20

<210> SEQ ID NO 268
<211> LENGTH: 20
<212> TYPE: DNA
<213> ORGANISM: Artificial Sequence
<220> FEATURE:
<223> OTHER INFORMATION: Synthetic

<400> SEQUENCE: 268
cgtcaaattt cttcccactc 20

<210> SEQ ID NO 269
<211> LENGTH: 20
<212> TYPE: DNA
<213> ORGANISM: Artificial Sequence
<220> FEATURE:
<223> OTHER INFORMATION: Synthetic

<400> SEQUENCE: 269
atgaagctac ttcggtagtg 20

<210> SEQ ID NO 270
<211> LENGTH: 20
<212> TYPE: DNA
<213> ORGANISM: Artificial Sequence
<220> FEATURE:

<223> OTHER INFORMATION: Synthetic

<400> SEQUENCE: 270
tgtaggtacc gtcactttcg                                               20

<210> SEQ ID NO 271
<211> LENGTH: 20
<212> TYPE: DNA
<213> ORGANISM: Artificial Sequence
<220> FEATURE:
<223> OTHER INFORMATION: Synthetic

<400> SEQUENCE: 271
atgaagcacc ttcgggtgtg                                               20

<210> SEQ ID NO 272
<211> LENGTH: 20
<212> TYPE: DNA
<213> ORGANISM: Artificial Sequence
<220> FEATURE:
<223> OTHER INFORMATION: Synthetic

<400> SEQUENCE: 272
tgcaggtacc gtcactttcg                                               20

<210> SEQ ID NO 273
<211> LENGTH: 20
<212> TYPE: DNA
<213> ORGANISM: Artificial Sequence
<220> FEATURE:
<223> OTHER INFORMATION: Synthetic

<400> SEQUENCE: 273
gatctttgat cttagtggcg                                               20

<210> SEQ ID NO 274
<211> LENGTH: 20
<212> TYPE: DNA
<213> ORGANISM: Artificial Sequence
<220> FEATURE:
<223> OTHER INFORMATION: Synthetic

<400> SEQUENCE: 274
tcaagtaccg tcagaacttc                                               20

<210> SEQ ID NO 275
<211> LENGTH: 18
<212> TYPE: DNA
<213> ORGANISM: Artificial Sequence
<220> FEATURE:
<223> OTHER INFORMATION: Synthetic

<400> SEQUENCE: 275
aacgtaccca agagtggg                                                 18

<210> SEQ ID NO 276
<211> LENGTH: 20
<212> TYPE: DNA
<213> ORGANISM: Artificial Sequence
<220> FEATURE:
<223> OTHER INFORMATION: Synthetic

<400> SEQUENCE: 276
aaggatatta gcctctaccg                                               20

<210> SEQ ID NO 277

```
<211> LENGTH: 20
<212> TYPE: DNA
<213> ORGANISM: Artificial Sequence
<220> FEATURE:
<223> OTHER INFORMATION: Synthetic

<400> SEQUENCE: 277
tgaagttcct tcgggaatgg                                              20

<210> SEQ ID NO 278
<211> LENGTH: 20
<212> TYPE: DNA
<213> ORGANISM: Artificial Sequence
<220> FEATURE:
<223> OTHER INFORMATION: Synthetic

<400> SEQUENCE: 278
ttcttcccta ctgaaagagg                                              20

<210> SEQ ID NO 279
<211> LENGTH: 20
<212> TYPE: DNA
<213> ORGANISM: Artificial Sequence
<220> FEATURE:
<223> OTHER INFORMATION: Synthetic

<400> SEQUENCE: 279
ctcatcagca atggtgggag                                              20

<210> SEQ ID NO 280
<211> LENGTH: 19
<212> TYPE: DNA
<213> ORGANISM: Artificial Sequence
<220> FEATURE:
<223> OTHER INFORMATION: Synthetic

<400> SEQUENCE: 280
tcaactccgg aggagaacc                                               19

<210> SEQ ID NO 281
<211> LENGTH: 20
<212> TYPE: DNA
<213> ORGANISM: Artificial Sequence
<220> FEATURE:
<223> OTHER INFORMATION: Synthetic

<400> SEQUENCE: 281
ggcagcacgg tctagtttac                                              20

<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282
tcaaatcctc ctccccactg                                              20

<210> SEQ ID NO 283
<211> LENGTH: 20
<212> TYPE: DNA
<213> ORGANISM: Artificial Sequence
<220> FEATURE:
<223> OTHER INFORMATION: Synthetic

<400> SEQUENCE: 283
```

| | |
|---|---|
| gtcagacttc ggtctgattg | 20 |

<210> SEQ ID NO 284
<211> LENGTH: 20
<212> TYPE: DNA
<213> ORGANISM: Artificial Sequence
<220> FEATURE:
<223> OTHER INFORMATION: Synthetic

<400> SEQUENCE: 284

| | |
|---|---|
| ggtacttctt cccgagcaac | 20 |

<210> SEQ ID NO 285
<211> LENGTH: 20
<212> TYPE: DNA
<213> ORGANISM: Artificial Sequence
<220> FEATURE:
<223> OTHER INFORMATION: Synthetic

<400> SEQUENCE: 285

| | |
|---|---|
| atgtagcaat acaggacagc | 20 |

<210> SEQ ID NO 286
<211> LENGTH: 20
<212> TYPE: DNA
<213> ORGANISM: Artificial Sequence
<220> FEATURE:
<223> OTHER INFORMATION: Synthetic

<400> SEQUENCE: 286

| | |
|---|---|
| cgtacatttg attccctacg | 20 |

<210> SEQ ID NO 287
<211> LENGTH: 20
<212> TYPE: DNA
<213> ORGANISM: Artificial Sequence
<220> FEATURE:
<223> OTHER INFORMATION: Synthetic

<400> SEQUENCE: 287

| | |
|---|---|
| atgaagctgg agcttgctcc | 20 |

<210> SEQ ID NO 288
<211> LENGTH: 18
<212> TYPE: DNA
<213> ORGANISM: Artificial Sequence
<220> FEATURE:
<223> OTHER INFORMATION: Synthetic

<400> SEQUENCE: 288

| | |
|---|---|
| gcgagctcat ccttgacc | 18 |

<210> SEQ ID NO 289
<211> LENGTH: 18
<212> TYPE: DNA
<213> ORGANISM: Artificial Sequence
<220> FEATURE:
<223> OTHER INFORMATION: Synthetic

<400> SEQUENCE: 289

| | |
|---|---|
| acgggagcaa tcctggtg | 18 |

<210> SEQ ID NO 290
<211> LENGTH: 20
<212> TYPE: DNA
<213> ORGANISM: Artificial Sequence
<220> FEATURE:

<223> OTHER INFORMATION: Synthetic

<400> SEQUENCE: 290
ccactgtatt agagcagacc                                                    20

<210> SEQ ID NO 291
<211> LENGTH: 20
<212> TYPE: DNA
<213> ORGANISM: Artificial Sequence
<220> FEATURE:
<223> OTHER INFORMATION: Synthetic

<400> SEQUENCE: 291
acggcttcgg cctagtaaag                                                    20

<210> SEQ ID NO 292
<211> LENGTH: 20
<212> TYPE: DNA
<213> ORGANISM: Artificial Sequence
<220> FEATURE:
<223> OTHER INFORMATION: Synthetic

<400> SEQUENCE: 292
agggctgttc accctaatgg                                                    20

<210> SEQ ID NO 293
<211> LENGTH: 20
<212> TYPE: DNA
<213> ORGANISM: Artificial Sequence
<220> FEATURE:
<223> OTHER INFORMATION: Synthetic

<400> SEQUENCE: 293
ttaacttaag tggcggacgg                                                    20

<210> SEQ ID NO 294
<211> LENGTH: 20
<212> TYPE: DNA
<213> ORGANISM: Artificial Sequence
<220> FEATURE:
<223> OTHER INFORMATION: Synthetic

<400> SEQUENCE: 294
ggtacacgtc gttttattcc                                                    20

<210> SEQ ID NO 295
<211> LENGTH: 18
<212> TYPE: DNA
<213> ORGANISM: Artificial Sequence
<220> FEATURE:
<223> OTHER INFORMATION: Synthetic

<400> SEQUENCE: 295
taacgcgggg caacctgg                                                      18

<210> SEQ ID NO 296
<211> LENGTH: 18
<212> TYPE: DNA
<213> ORGANISM: Artificial Sequence
<220> FEATURE:
<223> OTHER INFORMATION: Synthetic

<400> SEQUENCE: 296
gggtattagc ccagagcg                                                      18

<210> SEQ ID NO 297

```
<211> LENGTH: 20
<212> TYPE: DNA
<213> ORGANISM: Artificial Sequence
<220> FEATURE:
<223> OTHER INFORMATION: Synthetic

<400> SEQUENCE: 297
agagtttgat cctggctcag                                               20

<210> SEQ ID NO 298
<211> LENGTH: 20
<212> TYPE: DNA
<213> ORGANISM: Artificial Sequence
<220> FEATURE:
<223> OTHER INFORMATION: Synthetic

<400> SEQUENCE: 298
acggaggtag caatacctta                                               20

<210> SEQ ID NO 299
<211> LENGTH: 20
<212> TYPE: DNA
<213> ORGANISM: Artificial Sequence
<220> FEATURE:
<223> OTHER INFORMATION: Synthetic

<400> SEQUENCE: 299
gtgcttcttc ttccggtacc                                               20

<210> SEQ ID NO 300
<211> LENGTH: 20
<212> TYPE: DNA
<213> ORGANISM: Artificial Sequence
<220> FEATURE:
<223> OTHER INFORMATION: Synthetic

<400> SEQUENCE: 300
ttcggttatg ttgatggcga                                               20

<210> SEQ ID NO 301
<211> LENGTH: 20
<212> TYPE: DNA
<213> ORGANISM: Artificial Sequence
<220> FEATURE:
<223> OTHER INFORMATION: Synthetic

<400> SEQUENCE: 301
tcgggtaacg tcaataaacc                                               20

<210> SEQ ID NO 302
<211> LENGTH: 18
<212> TYPE: DNA
<213> ORGANISM: Artificial Sequence
<220> FEATURE:
<223> OTHER INFORMATION: Synthetic

<400> SEQUENCE: 302
aaccccggtg gcgagtgg                                                 18

<210> SEQ ID NO 303
<211> LENGTH: 18
<212> TYPE: DNA
<213> ORGANISM: Artificial Sequence
<220> FEATURE:
<223> OTHER INFORMATION: Synthetic

<400> SEQUENCE: 303
```

-continued aaccctggtg gcgagtgg                                                     18

<210> SEQ ID NO 304
<211> LENGTH: 19
<212> TYPE: DNA
<213> ORGANISM: Artificial Sequence
<220> FEATURE:
<223> OTHER INFORMATION: Synthetic

<400> SEQUENCE: 304
ttcttacggt accgtcatg                                                    19

<210> SEQ ID NO 305
<211> LENGTH: 20
<212> TYPE: DNA
<213> ORGANISM: Artificial Sequence
<220> FEATURE:
<223> OTHER INFORMATION: Synthetic

<400> SEQUENCE: 305
gagcgatgaa gtttcttcgg                                                   20

<210> SEQ ID NO 306
<211> LENGTH: 20
<212> TYPE: DNA
<213> ORGANISM: Artificial Sequence
<220> FEATURE:
<223> OTHER INFORMATION: Synthetic

<400> SEQUENCE: 306
agccggtgct tcttttgtag                                                   20

<210> SEQ ID NO 307
<211> LENGTH: 20
<212> TYPE: DNA
<213> ORGANISM: Artificial Sequence
<220> FEATURE:
<223> OTHER INFORMATION: Synthetic

<400> SEQUENCE: 307
ggtaacaggt taagctgacg                                                   20

<210> SEQ ID NO 308
<211> LENGTH: 20
<212> TYPE: DNA
<213> ORGANISM: Artificial Sequence
<220> FEATURE:
<223> OTHER INFORMATION: Synthetic

<400> SEQUENCE: 308
cagagtatta atccgaagcg                                                   20

<210> SEQ ID NO 309
<211> LENGTH: 20
<212> TYPE: DNA
<213> ORGANISM: Artificial Sequence
<220> FEATURE:
<223> OTHER INFORMATION: Synthetic

<400> SEQUENCE: 309
ggtctagttt actagatggg                                                   20

<210> SEQ ID NO 310
<211> LENGTH: 20
<212> TYPE: DNA
<213> ORGANISM: Artificial Sequence
<220> FEATURE:

```
<223> OTHER INFORMATION: Synthetic

<400> SEQUENCE: 310
ttcttctgtg ggtaacgtcc                                              20

<210> SEQ ID NO 311
<211> LENGTH: 20
<212> TYPE: DNA
<213> ORGANISM: Artificial Sequence
<220> FEATURE:
<223> OTHER INFORMATION: Synthetic

<400> SEQUENCE: 311
catcggaacg taccttatcg                                              20

<210> SEQ ID NO 312
<211> LENGTH: 20
<212> TYPE: DNA
<213> ORGANISM: Artificial Sequence
<220> FEATURE:
<223> OTHER INFORMATION: Synthetic

<400> SEQUENCE: 312
cgcagtctgt gttagagctg                                              20

<210> SEQ ID NO 313
<211> LENGTH: 20
<212> TYPE: DNA
<213> ORGANISM: Artificial Sequence
<220> FEATURE:
<223> OTHER INFORMATION: Synthetic

<400> SEQUENCE: 313
cgtgagaatc taccettagg                                              20

<210> SEQ ID NO 314
<211> LENGTH: 20
<212> TYPE: DNA
<213> ORGANISM: Artificial Sequence
<220> FEATURE:
<223> OTHER INFORMATION: Synthetic

<400> SEQUENCE: 314
gcttgcatcc tctgtattac                                              20

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
tgtcgtcagc tcgtgtcg                                                18

<210> SEQ ID NO 316
<211> LENGTH: 18
<212> TYPE: DNA
<213> ORGANISM: Artificial Sequence
<220> FEATURE:
<223> OTHER INFORMATION: Synthetic

<400> SEQUENCE: 316
aaggaggtga tccagccg                                                18

<210> SEQ ID NO 317
```

```
<211> LENGTH: 1442
<212> TYPE: DNA
<213> ORGANISM: Escherichia coli

<400> SEQUENCE: 317
aaattgaaga gtttgatcat ggctcagatt gaacgctggc ggcaggccta acacatgcaa      60
gtcgaacggt aacaggaaga agcttgcttc tttgctgacg agtggcggac gggtgagtaa     120
tgtctgggaa actgcctgat ggaggggat  aactactgga aacggtagct aataccgcat     180
aacgtcgcaa gaccaaagag ggggacccttc gggcctcttg ccatcggatg tgcccagatg    240
ggattagcta gtaggtgggg taacggctca cctaggcgac gatccctagc tggtctgaga     300
ggatgaccag ccacactgga actgagacac ggtccagact cctacgggag gcagcagtgg     360
ggaatattgc acaatgggcg caagcctgat gcagccatgc cgcgtgtatg aagaaggcct     420
tcgggttgta aagtactttc agcggggagg aagggagtaa agttaatacc tttgctcatt     480
gacgttaccc gcagaagaag caccggctaa ctccgtgcca gcagccgcgg taatacggag     540
ggtgcaagcg ttaatcggaa ttactgggcg taaagcgcac gcaggcggtt tgttaagtca     600
gatgtgaaat ccccgggctc aacctggaa  ctgcatctga tactggcaag cttgagtctc     660
gtagaggggg gtagaattcc aggtgtagcg gtgaaatgcg tagagatctg gaggaatacc     720
ggtggcgaag gcggccccct ggacgaagac tgacgctcag gtgcgaaagc gtggggagca     780
aacaggatta gataccctgg tagtccacgc cgtaaacgat gtcgacttgg aggttgtgcc     840
cttgaggcgt ggcttccgga gctaacgcgt taagtcgacc gcctggggag tacggccgca     900
aggttaaaac tcaaatgaat tgacggggc  ccgcacaagc ggtggagcat gtggtttaat     960
tcgatgcaac gcgaagaacc ttacctggtc ttgacatcca cggaagtttt cagagatgag    1020
aatgtgcctt cgggaaccgt gagacaggtg ctgcatggct gtcgtcagct cgtgttgtga    1080
aatgttgggt taagtcccgc aacgagcgca accctatcc  tttgttgcca gcggtccggc    1140
cgggaactca aaggagactg ccagtgataa actggaggaa ggtgggatg  acgtcaagtc    1200
atcatggccc ttacgaccag ggctacacac gtgctacaat ggcgcataca agagaagcg     1260
acctcgcgag agcaagcgga cctcataaag tgcgtcgtag tccggattgg agtctgcaac    1320
tcgactccat gaagtcggaa tcgctagtaa tcgtggatca gaatgccacg gtgaatacgt    1380
tcccgggcct tgtacacacc gcccgtcaca ccatgggagt gggttgcaaa agaagtaggt    1440
ag                                                                   1442

<210> SEQ ID NO 318
<211> LENGTH: 1798
<212> TYPE: DNA
<213> ORGANISM: Saccharomyces cerevisiae

<400> SEQUENCE: 318
tatctggttg atcctgccag tagtcatatg cttgtctcaa agattaagcc atgcatgtct      60
aagtataagc aatttataca gtgaaactgc gaatggctca ttaaatcagt tatcgtttat     120
ttgatagttc ctttactaca tggtataacc gtggtaattc tagagctaat acatgcttaa     180
aatctcgacc ctttggaaga gatgtattta ttagataaaa aatcaatgtc ttcgcactct     240
ttgatgattc ataataactt ttcgaatcgc atggccttgt gctggcgatg gttcattcaa     300
atttctgccc tatcaacttt cgatggtagg atagtggcct accatggttt caacgggtaa     360
cggggaataa gggttcgatt ccggagaggg agcctgagaa acggctacca catccaagga     420
aggcagcagg cgcgcaaatt acccaatcct aattcaggga ggtagtgaca ataaataacg     480
```

```
atacagggcc cattcgggtc ttgtaattgg aatgagtaca atgtaaatac cttaacgagg    540
aacaattgga gggcaagtct ggtgccagca gccgcggtaa ttccagctcc aatagcgtat    600
attaaagttg ttgcagttaa aaagctcgta gttgaacttt gggcccggtt ggccggtccg    660
attttttcgt gtactggatt tccaacgggg cctttccttc tggctaacct tgagtccttg    720
tggctcttgg cgaaccagga cttttacttt gaaaaaatta gagtgttcaa agcaggcgta    780
ttgctcgaat atattagcat ggaataatag aataggacgt ttggttctat tttgttggtt    840
tctaggacca tcgtaatgat taatagggac ggtcgggggc atcggtattc aattgtcgag    900
gtgaaattct tggatttatt gaagactaac tactgcgaaa gcatttgcca aggacgtttt    960
cattaatcaa gaacgaaagt taggggatcg aagatgatct ggtaccgtcg tagtcttaac   1020
cataaactat gccgactaga tcgggtggtg tttttttaat gacccactcg gtaccttacg   1080
agaaatcaaa gtctttgggt tctgggggga gtatggtcgc aaggctgaaa cttaaaggaa   1140
ttgacgaaag ggcaccacta ggagtggagc ctgcggctaa tttgactcaa cacggggaaa   1200
ctcaccaggt ccagacacaa taaggattga cagattgaga gctctttctt gattttgtgg   1260
gtggtggtgc atggccgttt ctcagttggt ggagtgattt gtctgcttaa ttgcgataac   1320
gaacgagacc ttaacctact aaatagtggt gctagcattt gctggttatc cacttcttag   1380
agggactatc ggtttcaagc cgatggaagt ttgaggcaat aacaggtctg tgatgccctt   1440
agaacgttct gggccgcacg cgcgctacac tgacggagcc agcgagtcta accttggccg   1500
agaggtcttg gtaatcttgt gaaactccgt cgtgctgggg atagagcatt gtaattattg   1560
ctcttcaacg aggaattcct agtaagcgca agtcatcagc ttgcgttgat tacgtccctg   1620
ccctttgtac acaccgcccg tcgctagtac cgattgaatg gcttagtgag gcctcaggat   1680
ctgcttagag aagggggcaa ctccatctca gagcggagaa tttggacaaa cttggtcatt   1740
tagaggaact aaaagtcgta acaaggtttc cgtaggtgaa cctgcggaag gatcatta    1798
```

<210> SEQ ID NO 319
<211> LENGTH: 101
<212> TYPE: DNA
<213> ORGANISM: Escherichia coli

<400> SEQUENCE: 319

```
aacacatgca agtcgaacgg taacaggaag aagcttgctt ctttgctgac gagtggcgga     60
cgggtgagta atgtctggga aactgcctga tggaggggga t                        101
```

<210> SEQ ID NO 320
<211> LENGTH: 91
<212> TYPE: DNA
<213> ORGANISM: Escherichia coli

<400> SEQUENCE: 320

```
aaacggtagc taataccgca taacgtcgca agaccaaaga ggggaccctt cgggcctctt     60
gccatcggat gtgcccagat gggattagct a                                    91
```

<210> SEQ ID NO 321
<211> LENGTH: 81
<212> TYPE: DNA
<213> ORGANISM: Escherichia coli

<400> SEQUENCE: 321

```
aaagtacttt cagcggggag gaagggagta aagttaatac ctttgctcat tgacgttacc     60
cgcagaagaa gcaccggcta a                                               81
```

```
<210> SEQ ID NO 322
<211> LENGTH: 61
<212> TYPE: DNA
<213> ORGANISM: Escherichia coli

<400> SEQUENCE: 322
tgtcgacttg gaggttgtgc ccttgaggcg tggcttccgg agctaacgcg ttaagtcgac    60
c                                                                   61

<210> SEQ ID NO 323
<211> LENGTH: 61
<212> TYPE: DNA
<213> ORGANISM: Escherichia coli

<400> SEQUENCE: 323
caacgagcgc aacccttatc ctttgttgcc agcggtccgg ccgggaactc aaaggagact    60
g                                                                   61

<210> SEQ ID NO 324
<211> LENGTH: 501
<212> TYPE: DNA
<213> ORGANISM: Saccharomyces cerevisiae

<400> SEQUENCE: 324
catgcatgtc taagtataag caatttatac agtgaaactg cgaatggctc attaaatcag    60
ttatcgttta tttgatagtt cctttactac atggtataac cgtggtaatt ctagagctaa   120
tacatgctta aaatctcgac cctttggaag agatgtattt attagataaa aaatcaatgt   180
cttcgcactc tttgatgatt cataataact tttcgaatcg catggccttg tgctggcgat   240
ggttcattca aatttctgcc ctatcaactt tcgatggtag gatagtggcc taccatggtt   300
tcaacgggta acggggaata agggttcgat tccggagagg gagcctgaga aacggctacc   360
acatccaagg aaggcagcag gcgcgcaaat tacccaatcc taattcaggg aggtagtgac   420
aataaataac gatacagggc ccattcgggt cttgtaattg gaatgagtac aatgtaaata   480
ccttaacgag gaacaattgg a                                             501

<210> SEQ ID NO 325
<211> LENGTH: 201
<212> TYPE: DNA
<213> ORGANISM: Saccharomyces cerevisiae

<400> SEQUENCE: 325
tattaaagtt gttgcagtta aaaagctcgt agttgaactt tgggcccggt tggccggtcc    60 gatttttttcg tgtactggat ttccaacggg gcctttcctt ctggctaacc ttgagtcctt   120
gtggctcttg gcgaaccagg acttttactt tgaaaaaatt agagtgttca aagcaggcgt   180
attgctcgaa tatattagca t                                             201

<210> SEQ ID NO 326
<211> LENGTH: 71
<212> TYPE: DNA
<213> ORGANISM: Saccharomyces cerevisiae

<400> SEQUENCE: 326
tggaataata gaataggacg tttggttcta ttttgttggt ttctaggacc atcgtaatga    60
ttaataggga c                                                        71

<210> SEQ ID NO 327
```

```
<211> LENGTH: 101
<212> TYPE: DNA
<213> ORGANISM: Saccharomyces cerevisiae

<400> SEQUENCE: 327
tggtaccgtc gtagtcttaa ccataaacta tgccgactag atcgggtggt gtttttttaa    60
tgacccactc ggtaccttac gagaaatcaa agtctttggg t                       101

<210> SEQ ID NO 328
<211> LENGTH: 101
<212> TYPE: DNA
<213> ORGANISM: Saccharomyces cerevisiae

<400> SEQUENCE: 328
tgctagcatt tgctggttat ccacttctta gagggactat cggtttcaag ccgatggaag    60
tttgaggcaa taacaggtct gtgatgccct tagaacgttc t                       101

<210> SEQ ID NO 329
<211> LENGTH: 60
<212> TYPE: DNA
<213> ORGANISM: Artificial Sequence
<220> FEATURE:
<223> OTHER INFORMATION: Synthetic

<400> SEQUENCE: 329
tcaccagttt taccctaggc ggctccttac ggttaccgac tttaggtaca cccggcttcc    60

<210> SEQ ID NO 330
<211> LENGTH: 60
<212> TYPE: DNA
<213> ORGANISM: Artificial Sequence
<220> FEATURE:
<223> OTHER INFORMATION: Synthetic

<400> SEQUENCE: 330
ggaagccggg tgtacctaaa gtcggtaacc gtaaggagcc gcctagggta aaactggtga    60

<210> SEQ ID NO 331
<211> LENGTH: 60
<212> TYPE: DNA
<213> ORGANISM: Artificial Sequence
<220> FEATURE:
<223> OTHER INFORMATION: Synthetic

<400> SEQUENCE: 331
tcggccacac cgtggcaagc gccccccttg cggttaagct acctgcttct ggtgcaacaa    60

<210> SEQ ID NO 332
<211> LENGTH: 60
<212> TYPE: DNA
<213> ORGANISM: Artificial Sequence
<220> FEATURE:
<223> OTHER INFORMATION: Synthetic

<400> SEQUENCE: 332
ttgttgcacc agaagcaggt agcttaaccg caagggggc gcttgccacg gtgtggccga    60

<210> SEQ ID NO 333
<211> LENGTH: 60
<212> TYPE: DNA
<213> ORGANISM: Artificial Sequence
<220> FEATURE:
<223> OTHER INFORMATION: Synthetic

<400> SEQUENCE: 333
```

```
ctagttacca gttttaccct aggcagctcc ttgcggtcac cgacttcagg cacccccagc    60

<210> SEQ ID NO 334
<211> LENGTH: 60
<212> TYPE: DNA
<213> ORGANISM: Artificial Sequence
<220> FEATURE:
<223> OTHER INFORMATION: Synthetic

<400> SEQUENCE: 334 gctggggtg cctgaagtcg gtgaccgcaa ggagctgcct agggtaaaac tggtaactag    60

<210> SEQ ID NO 335
<211> LENGTH: 60
<212> TYPE: DNA
<213> ORGANISM: Artificial Sequence
<220> FEATURE:
<223> OTHER INFORMATION: Synthetic

<400> SEQUENCE: 335
gaaccctgcc gtggtaatcg ccctccttgc ggttaggcta actacttctg gcagaacccg    60

<210> SEQ ID NO 336
<211> LENGTH: 60
<212> TYPE: DNA
<213> ORGANISM: Artificial Sequence
<220> FEATURE:
<223> OTHER INFORMATION: Synthetic

<400> SEQUENCE: 336
cgggttctgc cagaagtagt tagcctaacc gcaaggaggg cgattaccac ggcagggttc    60

<210> SEQ ID NO 337
<211> LENGTH: 60
<212> TYPE: DNA
<213> ORGANISM: Artificial Sequence
<220> FEATURE:
<223> OTHER INFORMATION: Synthetic

<400> SEQUENCE: 337
accagcctta ccttaggacg ctgcccccett gcggttggcg tgcatacttc gggtgcgacc    60

<210> SEQ ID NO 338
<211> LENGTH: 60
<212> TYPE: DNA
<213> ORGANISM: Artificial Sequence
<220> FEATURE:
<223> OTHER INFORMATION: Synthetic

<400> SEQUENCE: 338
ggtcgcaccc gaagtatgca cgccaaccgc aaggggcag cgtcctaagg taaggctggt    60

<210> SEQ ID NO 339
<211> LENGTH: 60
<212> TYPE: DNA
<213> ORGANISM: Artificial Sequence
<220> FEATURE:
<223> OTHER INFORMATION: Synthetic

<400> SEQUENCE: 339
accagcctta ccttaggacg ctgcccccctt gcggttggcg cgcatacttc gggtgcgacc    60

<210> SEQ ID NO 340
<211> LENGTH: 60
<212> TYPE: DNA
<213> ORGANISM: Artificial Sequence
<220> FEATURE:
```

<223> OTHER INFORMATION: Synthetic

<400> SEQUENCE: 340
ggtcgcaccc gaagtatgcg cgccaaccgc aagggggcag cgtcctaagg taaggctggt    60

<210> SEQ ID NO 341
<211> LENGTH: 20
<212> TYPE: DNA
<213> ORGANISM: Artificial Sequence
<220> FEATURE:
<223> OTHER INFORMATION: Synthetic

<400> SEQUENCE: 341
gtcaccagtt ttaccctagg    20

<210> SEQ ID NO 342
<211> LENGTH: 20
<212> TYPE: DNA
<213> ORGANISM: Artificial Sequence
<220> FEATURE:
<223> OTHER INFORMATION: Synthetic

<400> SEQUENCE: 342
aactgccgtc gtaagacgtg    20

<210> SEQ ID NO 343
<211> LENGTH: 20
<212> TYPE: DNA
<213> ORGANISM: Artificial Sequence
<220> FEATURE:
<223> OTHER INFORMATION: Synthetic

<400> SEQUENCE: 343
agtcatcggc cacaccgtgg    20

<210> SEQ ID NO 344
<211> LENGTH: 20
<212> TYPE: DNA
<213> ORGANISM: Artificial Sequence
<220> FEATURE:
<223> OTHER INFORMATION: Synthetic

<400> SEQUENCE: 344
aactctaagg agactgccgg    20

<210> SEQ ID NO 345
<211> LENGTH: 20
<212> TYPE: DNA
<213> ORGANISM: Artificial Sequence
<220> FEATURE:
<223> OTHER INFORMATION: Synthetic

<400> SEQUENCE: 345
cctagttacc agttttaccc    20

<210> SEQ ID NO 346
<211> LENGTH: 20
<212> TYPE: DNA
<213> ORGANISM: Artificial Sequence
<220> FEATURE:
<223> OTHER INFORMATION: Synthetic

<400> SEQUENCE: 346
aagactgcca gtgcaaactg    20

<210> SEQ ID NO 347

```
<211> LENGTH: 20
<212> TYPE: DNA
<213> ORGANISM: Artificial Sequence
<220> FEATURE:
<223> OTHER INFORMATION: Synthetic

<400> SEQUENCE: 347
acgaaccctg ccgtggtaat                                                     20

<210> SEQ ID NO 348
<211> LENGTH: 20
<212> TYPE: DNA
<213> ORGANISM: Artificial Sequence
<220> FEATURE:
<223> OTHER INFORMATION: Synthetic

<400> SEQUENCE: 348
ataaagccag tcgtagtccg                                                     20

<210> SEQ ID NO 349
<211> LENGTH: 20
<212> TYPE: DNA
<213> ORGANISM: Artificial Sequence
<220> FEATURE:
<223> OTHER INFORMATION: Synthetic

<400> SEQUENCE: 349
acttcatccc agttaccagc                                                     20

<210> SEQ ID NO 350
<211> LENGTH: 20
<212> TYPE: DNA
<213> ORGANISM: Artificial Sequence
<220> FEATURE:
<223> OTHER INFORMATION: Synthetic

<400> SEQUENCE: 350
acaatgagaa ccgatgccgc                                                     20

<210> SEQ ID NO 351
<211> LENGTH: 60
<212> TYPE: DNA
<213> ORGANISM: Artificial Sequence
<220> FEATURE:
<223> OTHER INFORMATION: Synthetic

<400> SEQUENCE: 351
caactctcgc ggggagggat gtatttatta gataaaaaac caatgcgggt tctgctcgcc         60

<210> SEQ ID NO 352
<211> LENGTH: 60
<212> TYPE: DNA
<213> ORGANISM: Artificial Sequence
<220> FEATURE:
<223> OTHER INFORMATION: Synthetic

<400> SEQUENCE: 352
ggcgagcaga acccgcattg gttttttatc taataaatac atccctcccc gcgagagttg         60

<210> SEQ ID NO 353
<211> LENGTH: 60
<212> TYPE: DNA
<213> ORGANISM: Artificial Sequence
<220> FEATURE:
<223> OTHER INFORMATION: Synthetic

<400> SEQUENCE: 353
```
actttacgaa ggggcgcttt tattagatca aaatcaatca ggagcaatcc tgtttttgtg    60

<210> SEQ ID NO 354
<211> LENGTH: 60
<212> TYPE: DNA
<213> ORGANISM: Artificial Sequence
<220> FEATURE:
<223> OTHER INFORMATION: Synthetic

<400> SEQUENCE: 354
cacaaaaaca ggattgctcc tgattgattt tgatctaata aaagcgcccc ttcgtaaagt    60

<210> SEQ ID NO 355
<211> LENGTH: 60
<212> TYPE: DNA
<213> ORGANISM: Artificial Sequence
<220> FEATURE:
<223> OTHER INFORMATION: Synthetic

<400> SEQUENCE: 355
gacccgacgc aaggacggtc gcatttatta gaacaaagcc atccggtccc cgggaccgta    60

<210> SEQ ID NO 356
<211> LENGTH: 60
<212> TYPE: DNA
<213> ORGANISM: Artificial Sequence
<220> FEATURE:
<223> OTHER INFORMATION: Synthetic

<400> SEQUENCE: 356
tacggtcccg gggaccggat ggctttgttc taataaatgc gaccgtcctt gcgtcgggtc    60

<210> SEQ ID NO 357
<211> LENGTH: 60
<212> TYPE: DNA
<213> ORGANISM: Artificial Sequence
<220> FEATURE:
<223> OTHER INFORMATION: Synthetic

<400> SEQUENCE: 357
tgcgggacga gcgcatttat tagaacaaaa ccatccggac tctcgcgagt ccgttgctgg    60

<210> SEQ ID NO 358
<211> LENGTH: 60
<212> TYPE: DNA
<213> ORGANISM: Artificial Sequence
<220> FEATURE:
<223> OTHER INFORMATION: Synthetic

<400> SEQUENCE: 358
ccagcaacgg actcgcgaga gtccggatgg ttttgttcta ataaatgcgc tcgtcccgca    60

<210> SEQ ID NO 359
<211> LENGTH: 60
<212> TYPE: DNA
<213> ORGANISM: Artificial Sequence
<220> FEATURE:
<223> OTHER INFORMATION: Synthetic

<400> SEQUENCE: 359
cattttggga aactatggct aatacatgct tacagacctt cgggttgtat ttattagttt    60

<210> SEQ ID NO 360
<211> LENGTH: 60
<212> TYPE: DNA
<213> ORGANISM: Artificial Sequence
<220> FEATURE:

<223> OTHER INFORMATION: Synthetic

<400> SEQUENCE: 360
aaactaataa atacaacccg aaggtctgta agcatgtatt agccatagtt tcccaaaatg    60

<210> SEQ ID NO 361
<211> LENGTH: 60
<212> TYPE: DNA
<213> ORGANISM: Artificial Sequence
<220> FEATURE:
<223> OTHER INFORMATION: Synthetic

<400> SEQUENCE: 361
gaccttcgga aagagcgcat ttattagacc aaaaccagtc gagtttcggc ttgtttgttg    60

<210> SEQ ID NO 362
<211> LENGTH: 60
<212> TYPE: DNA
<213> ORGANISM: Artificial Sequence
<220> FEATURE:
<223> OTHER INFORMATION: Synthetic

<400> SEQUENCE: 362
caacaaacaa gccgaaactc gactggtttt ggtctaataa atgcgctctt tccgaaggtc    60

<210> SEQ ID NO 363
<211> LENGTH: 60
<212> TYPE: DNA
<213> ORGANISM: Artificial Sequence
<220> FEATURE:
<223> OTHER INFORMATION: Synthetic

<400> SEQUENCE: 363
caataccctt ctggggtagt atttattaga aagaaaccaa ccccttcggg gtgatgtggt    60

<210> SEQ ID NO 364
<211> LENGTH: 60
<212> TYPE: DNA
<213> ORGANISM: Artificial Sequence
<220> FEATURE:
<223> OTHER INFORMATION: Synthetic

<400> SEQUENCE: 364
accacatcac cccgaagggg ttggtttctt tctaataaat actacccag aagggtattg    60

<210> SEQ ID NO 365
<211> LENGTH: 60
<212> TYPE: DNA
<213> ORGANISM: Artificial Sequence
<220> FEATURE:
<223> OTHER INFORMATION: Synthetic

<400> SEQUENCE: 365
acgaacgagc gcatttatta gagcaaaacc aatcaggttt cggcctgtct tttggtgaat    60

<210> SEQ ID NO 366
<211> LENGTH: 60
<212> TYPE: DNA
<213> ORGANISM: Artificial Sequence
<220> FEATURE:
<223> OTHER INFORMATION: Synthetic

<400> SEQUENCE: 366
attcaccaaa agacaggccg aaacctgatt ggttttgctc taataaatgc gctcgttcgt    60

<210> SEQ ID NO 367

```
<211> LENGTH: 60
<212> TYPE: DNA
<213> ORGANISM: Artificial Sequence
<220> FEATURE:
<223> OTHER INFORMATION: Synthetic

<400> SEQUENCE: 367
ccccgacttc ggaaggggtg tatttattag ataaaaaacc aatgcccttc ggggctactt    60

<210> SEQ ID NO 368
<211> LENGTH: 60
<212> TYPE: DNA
<213> ORGANISM: Artificial Sequence
<220> FEATURE:
<223> OTHER INFORMATION: Synthetic

<400> SEQUENCE: 368
aagtagcccc gaagggcatt ggttttttat ctaataaata caccccttcc gaagtcgggg    60

<210> SEQ ID NO 369
<211> LENGTH: 60
<212> TYPE: DNA
<213> ORGANISM: Artificial Sequence
<220> FEATURE:
<223> OTHER INFORMATION: Synthetic

<400> SEQUENCE: 369
ccccaacttc gggaggggtg tatttattag ataaaaaacc aacgcccttc ggggcttctt    60

<210> SEQ ID NO 370
<211> LENGTH: 60
<212> TYPE: DNA
<213> ORGANISM: Artificial Sequence
<220> FEATURE:
<223> OTHER INFORMATION: Synthetic

<400> SEQUENCE: 370
aagaagcccc gaagggcgtt ggttttttat ctaataaata caccccctccc gaagttgggg    60

<210> SEQ ID NO 371
<211> LENGTH: 20
<212> TYPE: DNA
<213> ORGANISM: Artificial Sequence
<220> FEATURE:
<223> OTHER INFORMATION: Synthetic

<400> SEQUENCE: 371
gccatgcatg tctaagtata                                                20

<210> SEQ ID NO 372
<211> LENGTH: 20
<212> TYPE: DNA
<213> ORGANISM: Artificial Sequence
<220> FEATURE:
<223> OTHER INFORMATION: Synthetic

<400> SEQUENCE: 372
tacactaccg tcgaaagctg                                                20

<210> SEQ ID NO 373
<211> LENGTH: 20
<212> TYPE: DNA
<213> ORGANISM: Artificial Sequence
<220> FEATURE:
<223> OTHER INFORMATION: Synthetic

<400> SEQUENCE: 373
```

```
gtacacactc tagcaaagtg                                              20

<210> SEQ ID NO 374
<211> LENGTH: 20
<212> TYPE: DNA
<213> ORGANISM: Artificial Sequence
<220> FEATURE:
<223> OTHER INFORMATION: Synthetic

<400> SEQUENCE: 374
accatggtag gcatatcacc                                              20

<210> SEQ ID NO 375
<211> LENGTH: 20
<212> TYPE: DNA
<213> ORGANISM: Artificial Sequence
<220> FEATURE:
<223> OTHER INFORMATION: Synthetic

<400> SEQUENCE: 375
ctaagcatag ctggtgacag                                              20

<210> SEQ ID NO 376
<211> LENGTH: 20
<212> TYPE: DNA
<213> ORGANISM: Artificial Sequence
<220> FEATURE:
<223> OTHER INFORMATION: Synthetic

<400> SEQUENCE: 376
aggcacataa actaccatcg                                              20

<210> SEQ ID NO 377
<211> LENGTH: 20
<212> TYPE: DNA
<213> ORGANISM: Artificial Sequence
<220> FEATURE:
<223> OTHER INFORMATION: Synthetic

<400> SEQUENCE: 377
tgcaagcatg cgctgaagta                                              20

<210> SEQ ID NO 378
<211> LENGTH: 20
<212> TYPE: DNA
<213> ORGANISM: Artificial Sequence
<220> FEATURE:
<223> OTHER INFORMATION: Synthetic

<400> SEQUENCE: 378
atgcatcgcc agtgctagac                                              20

<210> SEQ ID NO 379
<211> LENGTH: 20
<212> TYPE: DNA
<213> ORGANISM: Artificial Sequence
<220> FEATURE:
<223> OTHER INFORMATION: Synthetic

<400> SEQUENCE: 379
catatgcttt cctcctggag                                              20

<210> SEQ ID NO 380
<211> LENGTH: 20
<212> TYPE: DNA
<213> ORGANISM: Artificial Sequence
<220> FEATURE:
```

<223> OTHER INFORMATION: Synthetic

<400> SEQUENCE: 380
gtgatcgact tggtagtcca                                               20

<210> SEQ ID NO 381
<211> LENGTH: 20
<212> TYPE: DNA
<213> ORGANISM: Artificial Sequence
<220> FEATURE:
<223> OTHER INFORMATION: Synthetic

<400> SEQUENCE: 381
tgcatgtcta agcacatgcc                                               20

<210> SEQ ID NO 382
<211> LENGTH: 20
<212> TYPE: DNA
<213> ORGANISM: Artificial Sequence
<220> FEATURE:
<223> OTHER INFORMATION: Synthetic

<400> SEQUENCE: 382
accatggtag gcgtataacc                                               20

<210> SEQ ID NO 383
<211> LENGTH: 20
<212> TYPE: DNA
<213> ORGANISM: Artificial Sequence
<220> FEATURE:
<223> OTHER INFORMATION: Synthetic

<400> SEQUENCE: 383
gatagtccct tactacttgg                                               20

<210> SEQ ID NO 384
<211> LENGTH: 20
<212> TYPE: DNA
<213> ORGANISM: Artificial Sequence
<220> FEATURE:
<223> OTHER INFORMATION: Synthetic

<400> SEQUENCE: 384
aattgccaga cctaagaagg                                               20

<210> SEQ ID NO 385
<211> LENGTH: 20
<212> TYPE: DNA
<213> ORGANISM: Artificial Sequence
<220> FEATURE:
<223> OTHER INFORMATION: Synthetic

<400> SEQUENCE: 385
gctcattaca acagccatag                                               20

<210> SEQ ID NO 386
<211> LENGTH: 20
<212> TYPE: DNA
<213> ORGANISM: Artificial Sequence
<220> FEATURE:
<223> OTHER INFORMATION: Synthetic

<400> SEQUENCE: 386
tcgagaccgt gcgatctgca                                               20

<210> SEQ ID NO 387

```
<211> LENGTH: 20
<212> TYPE: DNA
<213> ORGANISM: Artificial Sequence
<220> FEATURE:
<223> OTHER INFORMATION: Synthetic

<400> SEQUENCE: 387
gtataagcaa ttataccgtg                                               20

<210> SEQ ID NO 388
<211> LENGTH: 20
<212> TYPE: DNA
<213> ORGANISM: Artificial Sequence
<220> FEATURE:
<223> OTHER INFORMATION: Synthetic

<400> SEQUENCE: 388
ttacaagacc caaaagagcc                                               20
```